US008846867B2

(12) United States Patent
Payne et al.

(10) Patent No.: US 8,846,867 B2
(45) **Date of Patent: *Sep. 30, 2014**

(54) ISOLATION OF ANTI-DESMOGLEIN 1 ANTIBODIES BY PHAGE DISPLAY OF PEMPHIGUS FOLIACEUS AUTOANTIBODIES

(75) Inventors: Aimee S. Payne, Merion Station, PA (US); John R. Stanley, Gladwyne, PA (US); Donald L. Siegel, Lansdale, PA (US); Jun Yamagami, Philadelphia, PA (US); Ken Ishii, Tokyo (JP)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1196 days.

This patent is subject to a terminal disclaimer.

(21) Appl. No.: 12/666,265

(22) PCT Filed: May 9, 2008

(86) PCT No.: PCT/US2008/005924

§ 371 (c)(1), (2), (4) Date: Dec. 16, 2010

(87) PCT Pub. No.: WO2009/002380
PCT Pub. Date: Dec. 31, 2008

(65) Prior Publication Data

US 2011/0091449 A1 Apr. 21, 2011

Related U.S. Application Data

(60) Provisional application No. 60/929,405, filed on Jun. 26, 2007.

(51) Int. Cl.
*C07K 16/00* (2006.01)

(52) U.S. Cl.
USPC .................................... 530/387.1; 424/130.1

(58) Field of Classification Search
None
See application file for complete search history.

(56) References Cited

FOREIGN PATENT DOCUMENTS

WO WO2004/009618 1/2004

OTHER PUBLICATIONS

Payne et al. (J. Invest. Dermatol. Jul. 2007, 127(7):168-1691).*
Payne et al. (Journal of Investigative Dermatology, vol. 127, pp. 1681-1691, published online Mar. 29, 2007).*
Payne et al. (Journal of Clinical Investigation, vol. 115, No. 4 pp. 888-899, Apr. 2005).*
Brauninger et al., (Accession No. CAD88666).
Payne et al., "Cloning and genetic characterization of human pemphigus autoantibodies." 2006, J Am Acad Dermatol 55(2):e2 abstract.
Payne et al., "Genetic and functional characterization of human pemphigus vulgaris monoclonal autoantibodies isolated by phage display." 2005 J.Clin. Invest 115:888-899.
Payne et al., Targeting pemphigus autoantibodies through their heavy-chain variable region genes. 2007 , J Invest Dermatol 127(7):1681-91.

* cited by examiner

*Primary Examiner* — Laura B Goddard
*Assistant Examiner* — Meera Natarajan
(74) *Attorney, Agent, or Firm* — Kathryn Doyle; Saul Ewing, LLP

(57) ABSTRACT

This invention relates to compositions and methods for the use of anti-autoimmune reagents that specifically bind to anti-desmoglein antibodies, which are responsible for pemphigus foliaceus. In addition, the invention relates to methods and compositions for inhibiting the expression or function of a variable region of an anti-desmoglein (anti-Dsg) pathogenic autoantibody.

17 Claims, 32 Drawing Sheets

| | EC1 | EC2 | EC3 | EC4 | EC5 | 1-18/L12 | 1-18/L2 | 3-08/O12O2 | 3-09/O18O8 | 3-09/O18O8 | 3-09/1c | 3-07/1e | 3-30/6h |
|---|---|---|---|---|---|---|---|---|---|---|---|---|---|
| Dsg1-Ighis | | | | | | + | + | + | + | + | + | + | + |
| Dsg3-Ighis | | | | | | − | − | − | − | − | − | − | − |
| Dsg1(1-161)/Dsg3(163-566) | | | | | | − | − | + | + | + | + | + | + |
| Dsg1(1-401)/Dsg3(405-566) | | | | | | + | + | + | + | + | + | + | + |
| Dsg3(1-161)/Dsg1(164-496) | | | | | | + | + | − | − | − | − | − | − |
| Dsg3(1-403)/Dsg1(404-496) | | | | | | − | − | − | − | − | − | − | − |
| Deduced Epitope | | | | | | (164-401) | (164-401) | (1-161) | (1-161) | (1-161) | (1-161) | (1-161) | (1-161) |

| scFv name(s) | Desmoglein Specificity | DNA Seq ID | AA Seq ID | Heavy chain genes (V/D/J) | Light chain genes (V/J) |
|---|---|---|---|---|---|
| PF1-2-7, 1-18/B3 | Dsg-1 | #1 | #44 | VH1-18/D3-10/JH4b | B3/JK4 |
| PF1-2-1, 1-18/L8 | Dsg-1 | #2 | #45 | VH1-18/D3-10/JH4b | L8/JK2 |
| PF1-2-5, 1-18/L1 | Dsg-1 | #3 | #46 | VH1-18/D3-10/JH4b | L1/JK3 |
| PF1-2-6, 1-18/L12 | Dsg-1 | #4 | #47 | VH1-18/D3-10/JH4b | L12/JK4 |
| PF1-3-K11, 1-18/L2 | Dsg-1 | #5 | #48 | VH1-18/D3-10/JH4b | L2/JK2 |
| PF1-2-15, 1-18/LFVK431 | Dsg-1 | #6 | #49 | VH1-18/D3-10/JH4b | LFVK431/JK4 |
| PF1-2-22, 1-08/O1202 | Dsg-1 | #7 | #50 | VH1-08/D3-3/JH6b | O12/JK4 |
| PF1-2-11, 3-09³/O1202 | Dsg-1 | #8 | #51 | VH3-09/D2-2/JH6b | O12/JK5 |
| PF1-2-17, 3-09³/O1808 | Dsg-1 | #9 | #52 | VH3-09/D2-2/JH6b | O18/JK4 |
| PF1-29, 3-09³/L11 | Dsg-1 | #10 | #53 | VH3-09/D2-2/JH6b | L11/JK1 |
| PF1-1-35, PF1-35, 3-09³/A30 | Dsg-1 | #11 | #54 | VH3-09/D2-2/JH6b | A30/JK1 |
| PF1-2-L19, 3-09³/1c | Dsg-1 | #12 | #55 | VH3-09/D2-2/JH6b | 1c/JL2 |
| PF1-2-L32, 3-09³/1e | Dsg-1 | #13 | #56 | VH3-09/D2-2/JH6b | 1e/JL2 |
| PF1-2-L4, 3-09³/1g | Dsg-1 | #14 | #57 | VH3-09/D2-2/JH6b | 1g/JL2 |
| PF1-2-L10, 3-09³/6a | Dsg-1 | #15 | #58 | VH3-09/D2-2/JH6b | 6a/JL3b |
| PF1-2-10, 3-09⁴/O1808 | Dsg-1 | #16 | #59 | VH3-09/D3-3/JH3a | O18/JK3 |
| PF1-2-9, 3-09⁵/O1808 | Dsg-1 | #17 | #60 | VH3-09/D3-3/JH3a | O18/JK3 |
| PF1-3-K6, 3-09⁵/L11 | Dsg-1 | #18 | #61 | VH3-09/D3-3/JH3a | L11/JK2 |
| PF1-26, 3-09⁶/L12 | Dsg-1 | #19 | #62 | VH3-09/D3-3/JH3a | L12/JK1 |
| PF1-22, 3-09⁶/O1808 | Dsg-1 | #20 | #63 | VH3-09/D3-3/JH3a | O18/JK3 |
| PF1-2-L02, 3-09⁶/1c | Dsg-1 | #21 | #64 | VH3-09/D3-3/JH3a | 1c/JL2 |
| PF1-2-3, PF1-2-03, 3-09⁷/1c | Dsg-1 | #22 | #65 | VH3-09/D3-3/JH3b | 1c/JL2 |
| PF1-2-18, 3- | Dsg-1 | #23 | #66 | VH3-09/D3-22/JH4b | L11/JK3 |

| 09⁸/L11 | | | | | |
|---|---|---|---|---|---|
| PF1-1-7, PF1-07, 3-09⁹/L8 | Dsg-1 | #24 | #67 | VH3-09/D2-8/JH2 | L8/JK1 |
| PF1-19, 3-09⁹/L2 | Dsg-1 | #25 | #68 | VH3-09/D2-8/JH2 | L2/JK5 |
| PF1-8-2, PF1-8-5, 3-07/1e | Dsg-1 | #26 | #69 | VH3-07/D3-10/JH4b | 1e/JL3b |
| PF1-8-15, 3-30/3h | Dsg-1 | #27 | #70 | VH3-30/D5-24/JH4b | 3h/JL2 |
| | | | | | |
| F24-1 | Dsg-1 | #28 | #71 | VH4-b/D3-10/JH3b | 3r/JL3b |
| F24-2, F24-6, F24-13, F24-16 | Dsg-1 | #29 | #72 | VH3-30/D6-13/JH4d | 3j/JL2 |
| F24-3, F24-7, F23-1, | Dsg-1 | #30 | #73 | VH3-09/D3-3/JH3b | 1c/JL7 |
| F24-4, F23-4 | Dsg-1 | #31 | #74 | VH3-09/D3-3/JH3a | L5/JK5 |
| F24-5, F24-8, F24-14, F23-2, F23-3, F23-10, F23-12, F23-13 | Dsg-1 | #32 | #75 | VH3-09/D3-3/JH3b | O18/JK4 |
| F24-9 | Dsg-1 | #33 | #76 | VH3-53/D4/JH4b | 1c/JL3b |
| F24-11 | Dsg-1 | #34 | #77 | VH3-09/D3-3/JH3b | 1c/JL3b |
| F24-15 | Dsg-1 | #35 | #78 | VH3-66/D7-27/JH4b | 1c/JL3b |
| F23-5 | Dsg-1 | #36 | #79 | VH1-08/D3-10/JH6b | 4b/JL3b |
| F23-6 | Dsg-1 | #37 | #80 | VH3-09/D3-22/JH3b | L11/JK4 |
| F23-7 | Dsg-1 | #38 | #81 | VH3-09/D3-3/JH3a | 1e/JL3b |
| F23-8 | Dsg-1 | #39 | #82 | VH3-09/D3-3/JH3b | O12/JK5 |
| F23-9 | Dsg-1 | #40 | #83 | VH3-09/D2-8/JH2 | 1c/JL2 |
| F23-14 | Dsg-1 | #41 | #84 | VH3-09/D3-3/JH3b | 1c/JL2 |
| F23-15 | Dsg-1 | #42 | #85 | VH3-30/D4-b/JH4b | O12/JK5 |
| F23-16 | Dsg-1 | #43 | #86 | VH3-09/D3-3/JH3b | 1c/JL3b |

Figure 9A-2

Figure 9B-1: SEQ ID #1
GAGCTCGTGTTGACACAGTCTCCAGACTCCCTGTCTGTGTCTCTGGGCGAGAGGGCC
ACCATCAACTGCAAGTCCAGCCAGACTGTTTTATACAACTCCGACAATAAGAACTAC
TTAAGTTGGTACCAGCAGAAACCAGGACAGCCTCCTAAGTTGATCATGAACTGGGCA
TCTATCCGGGCATCCGGGGTCCCTGACCGATTCAGTGGCAGCGGGTCTGGGACAGAT
TTCACTCTCACCATCAACAGCCTGCAGGCTGAAGATGTGGCAATTTATTACTGTCAGC
AATATTATAGTACTCCGCTCACCTTCGGCGGAGGGACCAAGGTGGAAATCAAA**GGT
GGTTCCTCTAGATCTTCCTCCTCTGGTGGCGGTGGCTCGGGCGGTG
GTGGG**CAGGTGCAGCTGGTGCAGTCTGGGGCTGAGGTGAAGAAGCCTGGGGCCTT
AGTGAAGGTCTCCTGCAAGGCTTCTGGTTACACGTTTACCAATTATGGTATCACCTGG
GTGCGACAGGCCCCTGGACAAGGGCTTGAGTGGATGGGATGGATCAGTGTTTATAAT
GGTGACACAAAGTATGCACAGAAGCTCCAGGGCAGAGTCACCATGACCACAGACAC
GCCCACGAACACAGTGTATATGGAGTTGAGGAGCCTGAGATCTGACGACACGGCCG
TGTATTATTGTGCGAGAGGTTATGGTTCGGGGAATTGGGACTACTGGGGCCAGGGAA
CCCTGGTCACCGTCTCCTCAG Figure 9B-2: SEQ ID #2
GAGCTCACACTCACGCAGTCTCCATCCTCCCTGTCTGCATCTGTAGGAGACAGAGTC
ACCATCACTTGCCGGGCCAGTCAGGGCATTGCCAGTTATTTAGCCTGGTATCAGCAA
AAACCAGGGAAAGCCCCTAAGCTCCTGATCTATGGTGCATCCACTTTGCAAAGTGGG
GTCCCATCAAGGTTCAGCGGCCGTAGATCTGGGACAGATTTCACTCTCACCATCAGC
AGCCTGCAGCCTGAAGATGCTGCAACTTATTACTGCCAACAATATAGTAATTACCCT
CTGACTTTTGGCCAGGGGACCAAGCTGGAGATCAAA**GGTGGTTCCTCTAGATC
TTCCTCCTCTGGTGGCGGTGGCTCGGGCGGTGGTGGG**CAGGTGCAGC
TGGTGCAGTCTGGAGCTGAGATGAAGAAGCCTGGGGCCTCAGTGAAGGTCTCCTGCA
AGGCTTCTGGTTACACCTTTACCAATTATGGTATCACCTGGGTGCGACAGGCCCCTGG
ACAAGGGCTTGAGTGGATGGGATGGATCAGTGTTTATAATGGTGACACAAAGTATGC
ACAGAAGCTCCAGGGCAGAGTCACTATGACCACAGACACACCCACGAGCACAGTCT
ACATGGAATTGAGGAGCCTGACATCTGACGACACGGCCGTGTATTATTGTGTGAGAG
GTTATGGTTCGGGGAATTGGGACTACTGGGGCCAGGGAACCCTGGTCACCGTCTCCT
CAG Figure 9B-3: SEQ ID #3
GAGCTCCAGATGACCCAGTCTCCATCCTCACTGTCTGCATCTGTAGGAGACAGAGTC
ACCATCACTTGTCGGGCGAGTCAGGGCATTAACAATTATTTAGCCTGGTTTCAGCAG
AAACCAGGGAAAGCCCCTAAGCTCCTGATCTATAAGGCGTCTAGTTTAGAAAGTGGG
GTCCCATCAAGGTTCAGCGGCAGTGGATCTGGGACAGAATTCACTCTCACCATCAGC
AGCCTGCAGCCTGATGATTTTGCAACTTATTACTGCCAACAGTATAATAGTTACCCAT
TCACTTTCGGCCCTGGGACCAAAGTGGATATCAAA**GGTGGTTCCTCTAGATCT
TCCTCCTCTGGTGGCGGTGGCTCGGGCGGTGGTGGG**CAGGTGCAGCTG
GTGCAGTCTGGGGCTGAGGTGAAGAAGCCTGGGGCCTCAGTGAAGGTCTCCTGCAA
GGCTTCTGGTTACACGTTTACCAATTATGGTATCACCTGGGTGCGACAGGCCCCTGG
ACAAGGGCTTGAGTGGATGGGATGGATCAGTGTTTATAATGGTGACACAAAGTATGC
ACAGAAGCTCCAGGGCAGAGTCACCATGACCACAGACACGCCCACGAACACAGTGT
ATATGGAGTTGAGGAGCCTGAGATCTGACGACACGGCCGTGTATTATTGTGCGAGAG
GTTATGGTTCGGGGAATTGGGACTACTGGGGCCAGGGAACCCTGGTCACCGTCTCCT
CAG Figure 9B-4: SEQ ID #4
GAGCTCCAGATGACCCAGTCTCCTTCCACCCTGTCTGCATCTGTAGGAGACAGAGTC
ACCATCACTTGTCGGGCGAGTCAGGGTATTAGCAACTGGTTAGCCTGGTATCAGCAG
AAACCAGGAAAAGCCCCTAAGCTCCTGATCCATAAGGCATCTAGTTTAGAAAGTGGG
GTCCCATCAAGGTTCAGCGGCAGTGGATCTGGGACAGAATTCACTCTCACCATCAGC
AGCCTGCAGCCTGATGATTTTGCAACTTATTACTGCCAACAGTATTATACTTACCCGC
TCACTTTCGGCGGAGGGACCAAGGTGGAAATCAAA**GGTGGTTCCTCTAGATC
TTCCTCCTCTGGTGGCGGTGGCTCGGGCGGTGGTGGG**CAGGTGCAGC
TGGTGCAGTCTGGGGCTGAGGTGAAGAAGCCTGGGGCCTCAGTGAAGGTCTCCTGCA
AGGCTTCTGGTTACACGTTTACCAATTATGGTATCACCTGGGTGCGACAGGCCCCTG
GACAAGGGCTTGAGTGGATGGGATGGATCAGTGTTTATAATGGTGACACAAAGTATG
CACAGAAGCTCCAGGGCAGAGTCACCATGACCACAGACACGCCCACGAACACAGTG
TATATGGAGTTGAGGAGCCTGAGATCTGACGACACGGCCGTGTATTATTGTGCGAGA
GGTTATGGTTCGGGGAATTGGGACTACTGGGGCCAGGGAACCCTGGTCACCGTCTCC
TCAG Figure 9B-5: SEQ ID #5
GAGCTCGTGTTGACGCAGTCTCCAGCCACCCTGTCTGTGTCTCCAGGGGAAAGAGCC
ACCCTCTCCTGCAGGGCCAGTCAGAGTGTTAGCAGCAATTTAGCCTGGTACCAGCAG
AAACCTGGCCAGGCTCCCAGGCTCCTCATCAAAGGAGCATCCACCAGGGCCACTGGT
ATCCCAGACAGGTTCAGTGGCAGCGGGTCTGGGACAGATTTCACTCTCACCATCAGC
AGCCTGCAGGCTGAAGATGTGGCAGTTTACTACTGTCACCAGTATTATGGTCCTTACT
CTTTTGGCCAGGGGACCAAGGTGGAAATCAAA**GGTGGTTCCTCTAGATCTTC
CTCCTCTGGTGGCGGTGGCTCGGGCGGTGGTGGG**CAGGTGCAGCTGGT
GCAGTCTGGGGCTGAGGTGAAGAAGCCTGGGTCCTCGGTGAAGGTCTCCTGCAAGGC
TTCTGGTTACACGTTTACCAATTATGGTATCACCTGGGTGCGACAGGCCCCTGGACA
AGGGCTTGAGTGGATGGGATGGATCAGTGTTTATAATGGTGACACAAAGTATGCACA
GAAGCTCCAGGGCAGAGTCACCATGACCACAGACACGCCCACGAACACAGTGTATA
TGGAGTTGAGGAGCCTGAGATCTGACGACACGGCCGTGTATTATTGTGCGAGAGGTT
ATGGTTCGGGGAATTGGGACTACTGGGGCCAGGGAACCCTGGTCACCGTCTCCTCAG Figure 9B-6: SEQ ID #6
GAGCTCCAGATGACCCAGTCTCCATCCTCACTGTCTGCATCTGTTGGAGACAGAGTC
ACCATCACTTGTCGGGCGACTCAGGGCATTAGTAATTATTTAGCCTGGTTTCAGCAG
AAACCAGGGAAAGCCCCTAAGTTGCTGATCTATGCTGCATCCAGTTTGCAAAGTGGG
GTCCCATCAAAGTTCAGCGGCAGTGGATCTGGGACAGATTTCACTCTCACCATCAGC
AGCCTGCAGCCTGAAGATTTTGCAACTTATTACTGCCAACAGTATAATAGTTATCCTC
TCACTTTCGGCGGAGGGACCAAGGTGGAAATCAAA**GGTGGTTCCTCTAGATC
TTCCTCCTCTGGTGGCGGTGGCTCGGGCGGTGGTGGG**CAGGTGCAGC
TGGTGCAGTCTGGGGCTGAGGTGAAGAAGCCTGGGGCCTCAGTGAAGGTCTCCTGCA
AGGCTTCTGGTTACACGTTTACCAATTATGGTATCACCTGGGTGCGACAGGCCCCTG
GACAAGGGCTTGAGTGGATGGGATGGATCAGTGTTTATAATGGTGACACAAAGTATG
CACAGAAGCTCCAGGGCAGAGTCACCATGACCACAGACACGCTCACGAACACAGTG
TATATGGAGTTGAGGAGCCTGAGATCTGACGACACGGCCGTGTATTATTGTGCGAGA
GGTTATGGTTCGGGGAATTGGGACTACTGGGGCCAGGGAACCCCGGTCACCGTCTCC
TCAG Figure 9B-7: SEQ ID #7
GAGCTCCAGATGACCCAGTCTCCATCCTCCCTGTCTGCATCTGTAGGAGACAGAGTC
ACCATCACTTGCCGGGCAAGTCAGAGCATTAGCAGCTATTTAAATTGGTATCAGCAG
AAACCAGGGAAAGCCCCTAAGCTCCTGATCTATGCTGCATCCAGTTTGCAAAGTGGG
GTCCCATCAAGGTTCAGTGGCAGTGGATCTGGGACAGATTTCACTCTCACCATCAGC
AGTCTGCAACCTGAAGATTTTGCAACTTACTACTGTCAACAGAGTTACAGTACCCCTC
GCACTTTCGGCGGAGGGACCAAGCTGGAGATCAAA**GGTGGTTCCTCTAGATC
TTCCTCCTCTGGTGGCGGTGGCTCGGGCGGTGGTGGG**CAGGTGCAGC
TGGTGCAGTCTGGGGCTGAGGTGAGGAAGCCTGGGGCCTCAGTGAGGGTCTCCTGCA
AGGCTTCTGGATACACCCTCACCACTTATGATATCAACTGGGTGCGACAGGCTACTG
GACAAGGGCTTGAGTGGATGGGATGGATGAACCCTACCAGTGGTAACACAGCCTAC
GCACAGAAGTTCCAGGGCAGAGTCACCATGACCAGGAACACCTCCATAAGCACAGC
CTACATGGAGCTGAGCAGCCTGAGATCTGAGGACACGGCCGTTTACTACTGTGCGAG
AGGCCTGTTTTTTGGAGTGGTTACAAAACCCAACTACTACTACTACGCTATGGACGTC
TGGGGCCAAGGGACCACGGTCACCGTCTCCTCAG Figure 9B-8: SEQ ID #8
GAGCTCCAGATGACCCAGTCTCCATCCTCCCTGTCTGTATCAGTAGGAGACAGAGTC
ACCATCACTTGCCGGGCAAGTCAGAGCATTAGCGGCTATTTAAATTGGTATCAGCAG
AAACCAGGGAAAGCCCCTAAACTGCTGATCTATGGTGCATCCAGTTTGCAAAGTGGG
GTCCCATCAAGGTTCAGTGGCAGTGGATCTGGGACAGATTTCGCTCTCACCATCAGC
AGTGTGCAACCTGAAGATTTTGCAAGTTACTTCTGTCAACAGAGTCACAGCGTCCCG
ATCAACTTCGGCCAAGGGACACGACTGGAGATTAAA**GGTGGTTCCTCTAGATC
TTCCTCCTCTGGTGGCGGTGGCTCGGGCGGTGGTGGG**CAGGTGCAGC
TGGTGCAGTCTGGGGGAGGCTTGGCACAGCCTGGCAAGTCCCTGAGACTCTCCTGTG
TAGCCTCTGGATTCACCTTTGATGATTATGCCATGCACTGGGTCCGGCAAGCTCCAGG
GAAGGGCCTGGAGTGGGTCTCAGGTATTAATTGGAATAGTGGTAGCATTGGTTATGC
GGACTCTGTGAAGGGCCGATTCACCATCTCCAGAGACAACGCCAAGAACTCCCTGTA
TCTGCAAATGAACAGTCTGAGAGCTGAGGACACGGCCTTGTATTACTGTGCAAAAGA
GCAAGGATATTGTGATAGTACCGGCTGCCAGAGGGGATCCGGAATGGACGTCTGGG
GCCAAGGGACCACGGTCACCGTCTCCTCAG Figure 9B-9: SEQ ID #9
GAGCTCCAGATGACCCAGTCTCCATCCTCCCTGTCTGCATCTGTAGGAGACAGAGTC
ACCATCACTTGCCAGGCGAGTCAGGACATTAGCAACTATTTAAATTGGTATCAGCAG
AAACCAGGGAAAGCCCCTAAGCTCCTGATCTACGATGCATCCAATTTGGAAACAGGG
GTCCCATCAAGGCTCAGTGGAAGTGGATCTGGGACAGATTTTACTTTCACCATCAGC
AGCCTGCAGCCTGAAGATATTGCAACATATTACTGTCAACAGTATGATGATCTCCCC
CTCACTTTCGGCGGAGGGACCAAGCTGGAGATCAAA**GGTGGTTCCTCTAGATC
TTCCTCCTCTGGTGGCGGTGGCTCGGGCGGTGGTGGG**CAGGTGCAGC
TGGTGCAGTCTGGGGGAGGCTTGGCACAGCCTGGCAAGTCCCTGAGACTCTCCTGTG
TAGCCTCTGGATTCACCTTTGATGATTATGCCATGCACTGGGTCCGGCAAGCTCCAGG
GAAGGGCCTGGAGTGGGTCTCAGGTATTAATTGGAATAGTGGTAGCATTGGTTATGC
GGACTCTGTGAAGGGCCGATTCACCATCTCCAGAGACAACGCCAAGAACTCCCTGTA
TCTGCAAATGAACAGTCTGAGAGCTGAGGACACGGCCTTGTATTACTGTGCAAAAGA
GCAAGGATATTGTGATAGTACCGGCTGCCAGAGGGGATCCGGAATGGACGTCTGGG
GCCAAGGGACCACGGTCACCGTCTCCTCAG Figure 9B-10: SEQ ID #10
GAGCTCCAGATGACCCAGTCTCCATCGTCCCTGGCTGCATCTGTGGGAGACAGAGTC
ACCATCACTTGCCGGGCAAGTCACGACATTAAAAATGATTTAGGCTGGTATCAGCAT
CAACCAGGGAAAGCCCCTAAGCTCCTGATCTATGCTGCATCCAGTTTACAAAGTGGG
GTCCCGTCAAGATTCAGCGGCAGTGGATCCGGCACAAATTTCACCCTCACCATCAAT
AGCCTGCAGCCTGAAGATTTTGCAACTTATTACTGTCTACATGATTACACTTACCCTC
GCACGTTCGGCCAAGGGACCAAGGTGGAAATCAAA**GGTGGTTCCTCTAGATC
TTCCTCCTCTGGTGGCGGTGGCTCGGGCGGTGGTGGG**CAGGTGCAGC
TGGTGCAGTCTGGGGGAGGCTTGGCACAGCCTGGCAAGTCCCTGAGACTCTCCTGTG
TAGCCTCTGGATTCACCTTTGATGATTATGCCATGCACTGGGTCCGGCAAGCTCCAGG
GAAGGGCCTGGAGTGGGTCTCAGGTATTAATTGGAATAGTGGTAGCATTGGTTATGC
GGACTCTGTGAAGGGCCGATTCACCATCTCCAGAGACAACGCCAAGAACTCCCTGTA
TCTGCAAATGAACAGTCTGAGAGCTGAGGACACGGCCTTGTATTACTGTGCAAAAGA
GCAAGGATATTGTGATAGTACCGGCTGCCAGAGGGGATCCGGAATGGACGTCTGGG
GCCAAGGGACCACGGTCACCGTCTCCTCAG Figure 9B-11: SEQ ID #11
GAGCTCCAGATGACCCAGTCTCCATCCTCCCTGTCTGCATCTGTAGGAGACAGAGTC
ACCATCACTTGCCGGGCAAGTCAGGGCATTAGATATGATGTAGGCTGGTATCAGCAG
AAACCAGGGAAAGCCCCTAAGCTCCTGATCTATGCTGCATCCACCTTGCAAAGTGGG
GTCCCATCAAGGTTCAGTGGCAGCGGATCTGAGACAGATTTCACTCTCACCATCAAC
AGTCTGCAGCCTGAAGATTCTGCAACTTACTACTGTCAACAGAGTTACAGTATCCCTT
CGACGTTCGGCCAGGGGACCAAGGTGGAGATCAAA**GGTGGTTCCTCTAGATC
TTCCTCCTCTGGTGGCGGTGGCTCGGGCGGTGGTGGG**GAGGTGCAGC
TGTTGGAGTCTGGGGGAGGCTTGGCACAGCCTGGCAAGTCCCTGAGACTCTCCTGTG
TAGCCTCTGGATTCACCTTTGATGATTATGCCATGCACTGGGTCCGGCAAGCTCCAGG
GAAGGGCCTGGAGTGGGTCTCAGGTATTAATTGGAATAGTGGTAGCATTGGTTATGC
GGACTCTGTGAAGGGCCGATTCACCATCTCCAGAGACAACGCCAAGAACTCCCTGTA
TCTGCAAATGAACAGTCTGAGAGCTGAGGACACGGCCTTGTATTACTGTGCAAAAGA
GCAAGGATATTGTGATAGTACCGGCTGCCAGAGGGGATCCGGAATGGACGTCTGGG
GCCAAGGGACCACGGTCACCGTCTCCTCAG Figure 9B-12: SEQ ID #12
GAGCTCGAGCTGACTCAGCCACCCTCAGTGTCTGGGACCCCCGGGCAGAGGGTCACC
ATCTCTTGTTCTGGAAGCAGCTCCAACATCGGAAGTGATACTGTAAACTGGTACCAG
CAGCTCCCAGGAACGGCCCCCAAACTCCTCATCTATAGTAATAATCAGCGGCCCTCA
GGGGTCCCTGACCGATTCTCTGGCTCCAAGTCTGGCACCTCAGCCTCCCTGGCCATCA
GTGGGCTCCAGTCTGAGGATGAGGCTGACTATTACTGTGCAACATGGGATGACGGCC
TGCGTGGCATGGTGTTCGGCGAAGGCACCAAGCTGACCGTCCTAGGC**GGTGGTTC
CTCTAGATCTTCCTCCTCTGGTGGCGGTGGCTCGGGCGGTGGTGGG**
CAGGTGCAGCTGCAGGAGTCGGGGGGAGGCTTGGCACAGCCTGGCAAGTCCCTGAG
ACTCTCCTGTGTAGCCTCTGGATTCACCTTTGATGATTATGCCATGCACTGGGTCCGG
CAAGCTCCAGGGAAGGGCCTGGAGTGGGTCTCAGGTATTAATTGGAATAGTGGTAGC
ATTGGTTATGCGGACTCTGTGAAGGGCCGATTCACCATCTCCAGAGACAACGCCAAG
AACTCCCTGTATCTGCAAATGAACAGTCTGAGAGCTGAGGACACGGCCTTGTATTAC
TGTGCAAAAGAGCAAGGATATTGTGATAGTACCGGCTGCCAGAGGGGATCCGGAAT
GGACGTCTGGGGCCAAGGGACCACGGTCACCGTCTCCTCAG Figure 9B-13: SEQ ID #13
GAGCTCGTGTTGACGCAGCCGCCCTCAGTGTCTGGGGCCCCAGGGCGGAGGGTCACC
ATCTCCTGCACTGGGAGCAGCTCCAACATCGGGGCTGCTTATGATGTACACTGGTAC
CAGCAGCTTCCAGGAACAGCCCCCAAACTCCTCATCTTTGGTAACACCAATCGGCCC
TCAGGGGTCCCTGACCGATTCTCTGGCTCCAAGTCTGGCACCTCAGCCTCCCTGGCCA
TCACTGGGCTCCAGTCTGAGGATGAGGCTGACTATTACTGTGCAACATGGGATGACA
GCCGGGATGGTCCGGAAGTGGTGTTCGGCGGAGGCACCGAGCTGACCGTCCTCGGT
**GGTGGTTCCTCTAGATCTTCCTCCTCTGGTGGCGGTGGCTCGGGCG
GTGGTGGG**GAGGTGCAGCTGGTGGAGTCTGGGGGAGGCTTGGCACAGCCTGGCA
AGTCCCTGAGACTCTCCTGTGTAGCCTCTGGATTCACCTTTGATGATTATGCCATGCA
CTGGGTCCGGCAAGCTCCAGGGAAGGGCCTGGAGTGGGTCTCAGGTATTAATTGGAA
TAGTGGTAGCATTGGTTATGCGGACTCTGTGAAGGGCCGATTCACCATCTCCAGAGA
CAACGCCAAGAACTCCCTGTATCTGCAAATGAACAGTCTGAGAGCTGAGGACACGG
CCTTGTATTACTGTGCAAAAGAGCAAGGATATTGTGATAGTACCGGCTGCCAGAGGG
GATCCGGAATGGACGTCTGGGGCCAAGGGACCACGGTCACCGTCTCCTCAG Figure 9B-14: SEQ ID #14
GAGCTCGTGCTGACTCAGCCACCTTCGGCGTCTGGGACCCCCGGACAGAGGGTCACC
ATCTCTTGTTCTGGAAGCAACTCCAACATCGGAAGTGATTATGTGTACTGGTATCAGC
GGTTCCCAGGAACGGCCCCCAAACTTCTCATCTATAGTAATAATCAGCGGCCCTCAG
GGGTCCCTGACCGATTCTCTGGCTCCAAGTCTGGCACCTCAGCCTCCCTGGCCATCAG
TGGACTCCAGTCTGAGGATGAGGCTGAGTATTACTGTGCAACATGGGATGACGCCCT
GCGTGGCATGGTGTTCGGCGAAGGCACCAAGCTGACCGTCCTAGGT**GGTGGTTCC
TCTAGATCTTCCTCCTCTGGTGGCGGTGGCTCGGGCGGTGGTGGG**G
AGGTGCAGCTGGTGGAGTCTGGGGGAGGCTTGGCACAGCCTGGCAAGTCCCTGAGA
CTCTCCTGTGTAGCCTCTGGATTCACCTTTGATGATTATGCCATGCACTGGGTCCGGC
AAGCTCCAGGGAAGGGCCTGGAGTGGGTCTCAGGTATTAATTGGAATAGTGGTAGC
ATTGGTTATGCGGACTCTGTGAAGGGCCGATTCACCATCTCCAGAGACAACGCCAAG
AACTCCCTGTATCTGCAAATGAACAGTCTGAGAGCTGAGGACACGGCCTTGTATTAC
TGTGCAAAAGAGCAAGGATATTGTGATAGTACCGGCTGCCAGAGGGGATCCGGAAT
GGACGTCTGGGGCCAAGGGACCACGGTCACCGTCTCCTCAG Figure 9B-15: SEQ ID #15
GAGCTCATGCTGACTCAGCCCCACTCTGTGTCGGAGTCTCCGGGGAAGACGGTAACC
ATCTCCTGCACCCGCAGCAGTGGCAGCATTGCCAGCAACTTTGTCCAGTGGTACCAG
CAGCGCCCGGGCAAGTCCCCCACCACTGTAATTTATGAGGACAACCAAAGACCGTCT
GGGGTACCTGATCGGTTCTCTGGCTCCGTCGACAGGTCCTCCAACTCTGCCTCCCTCA
CCATCTCTGGACTGCAGACTGAGGACGAGGCTGACTATTACTGTCAGTCTTTTTATGA
CGGCGTCCCTTCTTGGGTGTTCGGCGGAGGCACCGAGCTGACCGTCCTCGGC**GGTG
GTTCCTCTAGATCTTCCTCCTCTGGTGGCGGTGGCTCGGGCGGTGG
TGGG**GAGGTGCAGCTGGTGGAGTCTGGGGGAGGCGTGGTCCAACCTGGGGGGTCC
CTAAGACTCTCCTGTGTAGCCTCTGGATTCACCTTTGATGATTATGCCATGCACTGGG
TCCGGCAAGCTCCAGGGAAGGGCCTGGAGTGGGTCTCAGGTATTAATTGGAATAGTG
GTAGCATTGGTTATGCGGACTCTGTGAAGGGCCGATTCACCATCTCCAGAGACAACG
CCAAGAACTCCCTGTATCTGCAAATGAACAGTCTGAGAGCTGAGGACACGGCCTTGT
ATTACTGTGCAAAAGAGCAAGGATATTGTGATAGTACCGGCTGCCAGAGGGGATCC
GGAATGGACGTCTGGGGCCAAGGGACCACGGTCACCGTCTCCTCAG Figure 9B-16: SEQ ID #16
GAGCTCATGCTGACTCAGCCCCACTCTGTGTCGGAGTCTCCGGGGAAGACGGTAACC
ATCTCCTGCACCCGCAGCAGTGGCAGCATTGCCAGCAACTTTGTCCAGTGGTACCAG
CAGCGCCCGGGCAAGTCCCCCACCACTGTAATTTATGAGGACAACCAAAGACCGTCT
GGGGTACCTGATCGGTTCTCTGGCTCCGTCGACAGGTCCTCCAACTCTGCCTCCCTCA
CCATCTCTGGACTGCAGACTGAGGACGAGGCTGACTATTACTGTCAGTCTTTTTATGA
CGGCGTCCCTTCTTGGGTGTTCGGCGGAGGCACCGAGCTGACCGTCCTCGGC**GGTG
GTTCCTCTAGATCTTCCTCCTCTGGTGGCGGTGGCTCGGGCGGTGG
TGGG**CAGGTGCAGCTGGTGCAGTCTGGGGGAGGCGTGGTCCAGCCTGGGGGGTCC
CTGAGACTCTCCTGTGTAGCCTCTGGATTCACCTTTGATGATTATGCCATGCACTGGG
TCCGGCAAGCTCCAGGGAAGGGCCTGGAGTGGGTCTCAGGTATTAGTTGGAATAGTG
GTGCCATAGGCTATGCAGACTCTGTGAAGGGCCGATTCACCATCTCCAGAGACAACG
CCAAGAACTCCCTGTATCTGCAAATGAACAGTCTGAGAACTGAGGACACGGCCGTGT
ATTACTGTGCAAAAGATGGGATTACAATTTTTGGAGTGGGCGACGGTCTGGATGTCT
GGGGCCAAGGGACAATGGTCACCGTCTCTTCAG Figure 9B-17: SEQ ID #17
GAGCTCCAGATGACCCAGTCTCCATCCTCCCTGTCTGCATCTGTAGGAGACAGAGTC
ACCATCACTTGCCAGGCGAGTCAGGACATTGGCAACTATTTAAATTGGTATCAGCAG
AAACCAGGGAAAGCCCCTAAACTCCTGATCTACGATGCATCCTATTTGGAAACAGGG
GTCCCATCAAGGTTCAGTGGAAGTGGATCTGGGACAGATTTTACTTTCACCATCAGC
AGCCTACAGCCTGAAGATATTGCAACATATTACTGTCAACAGTATGATAATCTCCCG
TTCACTTTCGGCCCTGGGACCAAAGTGGATATCAAA**GGTGGTTCCTCTAGATC
TTCCTCCTCTGGTGGCGGTGGCTCGGGCGGTGGTGGG**GAGGTGCAGC
TGGTGGAGTCTGGGGGAGGCTTGGTACAGCCTGGCAGGTCCCTGAGACTCTCCTGTG
CAGCCTCTGGATTCACCTTTGATGATTATGCCATGCACTGGGTCCGGCAAGCTCCAG
GGAAGGGCCTGGAGTGGGTCTCAGGTATTAGTTGGAATAGTGGTAGCATAGACTATG
CGGACTCTGTGAAGGGCCGATTCACCATCTCCAGAGACAACGCCAAGAACTCCCTGT
ATCTGCAAATGAACAGTCTGAGAGTTGAGGACACGGCCTTGTATTATTGTGCAAAAG
ATGGGAGTAGGGTTTTGGAGTGGGCGGTGGTTTTGATTTCTGGGGCCAAGGGACAA
TGGTCACCGTCTCTTCAG Figure 9B-18: SEQ ID #18
GAGCTCGTGATGACTCAGTCTCCATCCTCCCTGTCTGCATCTGTAGGAGACAGAGTC
ACCATCACTTGCCGGGCAAGTCAGGGCATTACCGATGACTTAGGGTGGTATCAGCAG
AAGCCAGGGAAAGCCCCTAAGCTCCTGATCTATGCCACATCCAATTTAGAAAGTGGG
GTCCCATCAAGGTTCAGCGGCAGTGGATCTGACACAGAATTCACTCTCACCATCAGT
AGCCTGCAGCCTGAAGATCTTGCAACTTATTACTGTCTACAAGATTACAGTTACCCGT
ACACTTTTGGCCAGGGGACCAAGGTGGAGATCAAA**GGTGGTTCCTCTAGATC
TTCCTCCTCTGGTGGCGGTGGCTCGGGCGGTGGTGGG**GAGGTGCAGC
TAGTGGAGTCTGGGGGAGGCTTGGTACAGCCTGGCAGGTCCCTGAGACTCTCCTGTG
CAGCCTCTGGATTCACCTTTGATGATTACGCCATGCACTGGGTCCGGCAAGCTCCAG
GGAAGGGCCTGGAGTGGGTCTCAGGTATTAGTTGGAATAGTGGTAGCATAGACTATG
TGGACTCTGTGAAGGGCCGATTCACCATCTCCAGAGACAACGCCAAGAACTACCTGT
ATCTGCAAATGAACAGTCTGAGAGTTGAGGACACGGCCTTATATTATTGTGCAAAAG
ATGGCAGTAGGGTTTTGGAGTGGGCGGTGGTTTTGATTTCTGGGGCCAAGGGACAA
TGGTCACCGTCTCTTCAG Figure 9B-19: SEQ ID #19
GAGCTCCAGATGACCCAGTCTCCTTCCACCCTGTCTGCATCTGTAGGAGACAGAGTC
ACCATCACTTGCCGGGCCAGTCAGAGTATTAGTAGTTGGTTGGCCTGGTATCAGCAG
AAACCAGGGAAAGCCCCTAAGCTCCTGATCTATAAGGCGTCTAGTTTAGAAAGTGGG
GTCCCATCAAGGTTCAGCGGCAGTGGATCTGGGACAGAATTCACTCTCACCATCAGC
AGCCTGCAGCCTGATGATTTTGCAACTTATTACTGCCAACAGTATAATACTTATTCGA
GGACGTTCGGCCAAGGGACCAAGGTGGAAATCAAA**GGTGGTTCCTCTAGATC
TTCCTCCTCTGGTGGCGGTGGCTCGGGCGGTGGTGGG**GAGGTGCAGC
TGGTGGAGTCTGGGGGAGGCTTGGTACAGCCTGGCAGGTCCCTGAGACTCTCCTGTG
CAGCCTCTGGATTCACCTTTGATGATTATTCCATGCACTGGGTCCGGCAAGCTCCAGG
GAAGGGCCTGGAGTGGGTCTCAGGTATCAGTTGGAACAGTGGTGGCATAGGCTATGC
GGACTCTGTGAGGGGCCGATTCACCATCTCCAGAGACAACGCCAAGAACTCCCTGTA
TCTGCAAATGAACAGTCTGAGAGCTGAGGACACGGCCTTGTATTATTGTGCAAAAGA
TGGGATGAGGGTTTTTGGAGTGGGCGGTGGTTTTGATTTCTGGGGCCAAGGGACAAT
GGTCACCGTCTCTTCAG Figure 9B-20: SEQ ID #20
GAGCTCCAGATGACCCAGTCTCCATCCTCCCTGTCTGCATCTGTTGGAGACAGAGTC
ACCATCACTTGCCAGGCGAGTCGTGACATTAGCAACTATTTAAATTGGTATCAACAC
ATTCCAGGAAAGGCCCCTAAGCTCCTCATATTCCATGCATCCACTTTGGAAGCAGGG
ATCCCATCAAGGTTCAGTGGAAGTGGATCAGAGACATCTTTTACTTTCACCATAAGA
AGCCTACAGCCTGAAGATGTTGCAACATATTACTGTCAACAATATGATAATCTCCCC
TTCACTTTCGGCCCTGGGACCAAAGTGGATATCAAA**GGTGGTTCCTCTAGATC
TTCCTCCTCTGGTGGCGGTGGCTCGGGCGGTGGTGGG**GAGGTGCAGC
TGGTGGAGTCTGGGGGAGGCTTGGTACAGCCTGGCAGGTCCCTGAGACTCTCCTGTG
CAGCCTCTGGATTCACCTTTGATGATTATGCCATGTACTGGGTCCGGCAAGCTCCAGG
GAAGGGCCTGGAGTGGGTCTCAGGTATTAGTTGGAATAGTGGTAGCATAGACTATGC
GGACTCTGTGAAGGGCCGATTCACCATCTCCAGAGACAACGCCAAGAACTCCCTGTA
TCTGCAAATGAACAGTCTGAGAGCTGAGGACACGGCCTTGTATTATTGTGCAAAAGA
TGGGATGAGGGTTTTTGGAGTGGGCGGTGGTTTTGATTTCTGGGGCCAAGGGACAAT
GGTCACCGTCTCTTCAG Figure 9B-21: SEQ ID #21
GAGCTCATGCTGACTCAGCCCCACTCAGCGTCTGGGACCCCCGGGCAGAGGGTCACC
ATCTCTTGTTCTGGAAGCAGCTCCAACATCGGAAGTAATACTGTAAACTGGTACCAG
CAGCTCCCAGGAACGGCCCCCAAACTCCTCATCTATAGTAATAATCAGCGGCCCTCA
GGGGTCCCTGACCGATTCTCTGGCTCCAAGTCTGGCACCTCAGCCTCCCTGGCCATCA
GTGGGCTCCAGTCTGAGGATGAGGCTGATTATTACTGTGCAGCATGGGATGACAGCC
TGAATGGTCCGGTATTCGGCGGAGGCACCAAGGTGACCGTCCTAGGC**GGTGGTTC
CTCTAGATCTTCCTCCTCTGGTGGCGGTGGCTCGGGCGGTGGTGGG**
GAGGTGCAGCTGGTGGAGTCTGGGGGAGGCTTGGTACAGCCTGGCAGGTCCCTGAG
ACTCTCCTGTGCAGCCTCTGGATTCACCTTTGATGATTATGCCATGTACTGGGTCCGG
CAAGCTCCAGGGAAGGGCCTGGAGTGGGTCTCAGGTATTAGTTGGAATAGTGGTAGC
ATAGACTATGCGGACTCTGTGAAGGGCCGATTCACCATCTCCAGAGACAACGCCAAG
AACTCCCTGTATCTGCAAATGAACAGTCTGAGAGCTGAGGACACGGCCTTGTATTAT
TGTGCAAAAGATGGGATGAGGGTTTTTGGAGTGGGCGGTGGTTTTGATTTCTGGGGC
CAAGGGACAATGGTCACCGTCTCTTCAG Figure 9B-22: SEQ ID #22
GAGCTCGTGGTGACGCAGCCGCCCTCAGCGTCTGGGACCCCCGGGCAGAGGGTCACC
ATCTCTTGTTCTGGAAGCAGCTCCAACATCGGAAGTAATACTGTAAACTGGTACCAG
CAGCTCCCAGGAACGGCCCCCAAACTCCTCATCTATAGTAATAATCAGCGGCCCTCA
GGGGTCCCTGACCGATTCTCTGGCTCCAAGTCTGGCACCTCAGCCTCCCTGGCCATCA
GTGGGCTCCAGTCTGAGGATGAGGCTGATTATTACTGTGCAACGTGGGATGACGGCC
TGAATGGCATGGTGTTCGGCGGAGGGACCAAGCTGACCGTCCTAGGC**GGTGGTTC
CTCTAGATCTTCCTCCTCTGGTGGCGGTGGCTCGGGCGGTGGTGGG**
GAGGTGCAGCTGGTGGAGTCTGGGGGAGGCTTGGTACAGCCTGGCAGGTCCCTGAG
ACTCTCCTGTGCAGCCTCTGGATTCACCTTTGATGATTATGCCATGCACTGGGTCCGG
CAAGCTCCAGGGAAGGGCCTGGAGTGGGTCTCAGGTATTAGTTGGAATAGTGGGAC
CATAGGCTATGCGGACTCTGTGAAGGGCCGATTCACCATCTCCAGAGACAACGCCAA
GAACTCCCTGTATCTGCAAATGAACAGTCTGAGAGCTGAGGACACGGCCGTGTATTA
CTGTGCAAAAGATGGGATTACGGTTTTTGGAGTGGGCGATGGTTTGGATATCTGGGG
CCAAGGGACAATGGTCACCGTCTCTTCAG Figure 9B-23: SEQ ID #23
GAGCTCCAGATGACCCAGTCTCCTTCCTCCCTGTCTGCATCTGTAGGAGACAGAGTC
ACCATCACTTGCCGGGCAAGTCAGGGCATTGGAAATGATTTAGGCTGGTATCAGCAG
AAACCAGGGAAAGCCCCTAAGCTCCTGATCTATGCTGCATCCAGTTTACAAAGTGGG
GTCCCATCAAGGTTCAGCGGCAGTGGATCTGGCACAGATTTCACTCTCACCATCGGC
AGCCTGCAGCCTGAAGATTTTGCAACTTATTACTGTCTACAAGATTACAATTACCCAT
TCACTTTCGGCCCTGGGACCAAAGTGGATATCAAA**GGTGGTTCCTCTAGATCT
TCCTCCTCTGGTGGCGGTGGCTCGGGCGGTGGTGGG**GAGGTGCAGCT
GGTGGAGTCTGGGGGAACCTTGGTACAGCCTGGCAGGTCCCTGAGACTCTCCTGTGC
AGCCTCTGGATTCAGCTTTGATGATTATGCCATGCAGTGGGTCCGGCAAGCTCCAGG
GAAGGGCCTGGAGTGGGTCTCAGGTATTAGCTGGAATAGTGGTAGCATAGCCTATGC
GGACTCTGTGAAGGGCCGATTCACCATCTCCAGAGACAACGCCAAGAGCTCCCTGTA
TCTGCTAATGAACAGTCTGAGAGCTGAGGACACGGCCTTGTATTACTGTGCAAAAGC
GGGCACAGATTATTATGATAGTAGTGCTTCCGAACTTCCTGACTACTGGGGCCAGGG
AACCCTGGTCACCGTCTCCTCAG Figure 9B-24: SEQ ID #24
GAGCTCCAGATGACCCAGTCTCCATCCTTCCTGTCTGCATCTGTAGGAGACAGAGTC
ACCATCACTTGCCGGGCCAGTCAGGGCATTAGCAGTTATTTAGCCTGGTATCAGCAA
AAACCGGGGAAAGCCCCTAAACTCCTGATCTATGGTGCATCTACTTTGCAAAGTGGG
GTCCCATCAAGGTTCAGCGGCAGTGGATCTGGGACAGAATTCACTCTCACCATCAGC
AGCCTGCAGCCTGATGATTTTGCAACTTATTACTGCCAACAGTATAATAGTTATCCGT
GGACGTTCGGCCAAGGGACCAAGGTGGAAATCAAA**GGTGGTTCCTCTAGATC
TTCCTCCTCTGGTGGCGGTGGCTCGGGCGGTGGTGGG**CAGGTGCAGC
TGCAGGAGTCGGGGGAGGCTTGGTACAGCCTGGCAGGTCCCTGAGACTCTCCTGTG
CAGCCTCTGGATTCACCTTTGATGATTATGCCATGCACTGGGTCCGGCAAGCTCCAG
GGAAGGGCCTGGAGTGGGTCTCAGGTATTAGTTGGAATAGTGGTAGCATAGCCTATG
CGGACTCTGTGAAGGGCCGATTCACCATCTCCAGAGACAACGCCAAGAACTCCCTGT
ATCTGCAAATGAACAGTCTGAGAGCTGAGGACACGGCCTTCTATTACTGTGCGAAAG
TGGGCGGGGATACCTATGATATTACAAGTGGGGCGGATTACTTCGATCTCTGGGGCC
GTGGCGCCCTGGTCACTGTCTCCTCAG Figure 9B-25: SEQ ID #25
GAGCTCGTGATGACCCAGTCTCCAGCCACCCTGTCTGTGTCTCCAGGGGAAAGAGCC
ACCCTCTCCTGCAGGGCCAGTCAGAGTGTTAGCAGCAACTTAGCCTGGTACCAGCAG
AAACCTGGCCAGGCTCCCAGGCTCCTCATCTATGGTGCATCCACCAGGGCCACTGGT
ATCCCAGCCAGGTTCAGTGGCAGTGGGTCTGGGACAGAGTTCACTCTCACCATCAGC
AGCCTGCAGTCTGAAGATTTTGCAGTTTATTACTGTCAGCAGTATAATAACTGGCCCT
CGATCACCTTCGGCCAAGGGACACGACTGGAGATTAAA**GGTGGTTCCTCTAGA
TCTTCCTCCTCTGGTGGCGGTGGCTCGGGCGGTGGTGGG**CAGGTGCA
GCTGGTGCAGTCTGGGGGAGGCTTGGTACAGCCTGGCAGGTCCCTGAGACTCTCCTG
TGCAGCCTCTGGATTCACCTTTGATGATTATGCCATGCACTGGGTCCGGCAAGCTCCA
GGGAAGGGCCTGGAGTGGGTCTCAGGTATTAGTTGGAATAGTGGTAGCATAGCCTAT
GCGGACTCTGTGAAGGGCCGATTCACCATCTCCAGAGACAACGCCAAGAACTCCCTG
TATCTGCAAATGAACAGTCTGAGAGCTGAGGACACGGCCTTCTATTACTGTGCGAAA
GTGGGCGGGGATACCTATGATATTACAAGTGGGGCGGATTACTTCGATCTCTGGGGC
CGTGGCGCCCTGGTCACTGTCTCCTCAG Figure 9B-26: SEQ ID #26
GAGCTCGTGGTGACGCAGCCGCCCTCAGTGTCTGGGGCCCCAGGGCAGAGGGTCACC
ATCTCCTGCACTGGGAGCAGCTCCAACATCGGGGCAGGTTATGATGTACACTGGTAC
CAGCAGCTTCCAGGAACAGCCCCCAAACTCCTCATTTATGGTAACAAAAATCGGCCC
TCAGGGGTCCCTGACCGGTTCTCTGGCTCCAAGTCTGGCACCTCAGCCTCCCTGGCCA
TCACTGGGCTCCGGGCTGAGGATGAGGCTGATTACTACTGCCAGTCCTTCGACAGCA
GCCTGGGGTGGGTGTTCGGCGGAGGGACCCAGCTGACCGTCCTCGGC**GGTGGTTC
CTCTAGATCTTCCTCCTCTGGTGGCGGTGGCTCGGGCGGTGGTGGG**
CAGGTGCAGCTGGTGCAGTCTGGGGGAGGCTTGGTCCAGCCTGGGGGTCCCTGAGA
GTCTCCTGCGCAGCCTCTGGATTCACCTCTAATATCTTTGGATGAGTTGGGTCCGCC
AGGCTCCAGGTAAGGGGCTGGAGTGGGTGGCCAACATAGACGAAGATGGAAGTGAG
AAAAACTATGTGGACTCTGTGAAGGGCCGATTCACCATCTCCAGAGACAACGCCAAG
AACTCACTGTATCTGCAAATGAACAGCCTGAGAGCCGAGGACACGGCTGTGTATTAC
TGTGCGAGGGAGTCGTTTACTATGGTTCGGGGACTTATTTTGACTTCTGGGGCCAGG
GAACCCTGGTCACCGTCTCCTCAG Figure 9B-27: SEQ ID #27
GAGCTCGTGCTGACTCAGCCACCCTCGGTGCCAGTGGCCCCAGGACAGACGGCCAAC
ATTAGCTGTGGGGAAACAACATTGGAAGACAGACTGTCCACTGGTACCAGCAGAA
GCCAGGCCAGGCCCCTGTGTTGGTCGTCTTTGATGATAGCGACCGGCCCGCAGGGAT
CCCTGAGCGATTCTCTGGCTCCAACTCTGGGAACACGGCCACCCTGACCATCAGCAG
GGTCGAAGCCGGGGATGAGGCCGACTATTACTGTCAGGTGTGGGATAGTAGTAGTG
ATCATGTGGTCTTCGGCGGAGGCACCCAGCTGACCGTCCTCGGC**GGTGGTTCCTC
TAGATCTTCCTCCTCTGGTGGCGGTGGCTCGGGCGGTGGTGGG**CAG
GTGCAGCTGGTGCAGTCTGGGGGAGGCGTGGTCCAGTCTGGGAGGTCCCTGAGACTC
TCCTGTGCAGCCTCTGGATTCACGTTCAGTGACTATGCCATGCACTGGGTCCGCCAGG
CCCCAGGCAAGGGGCTGGAGTGGGTGGCAGTTATATCACATGGTGGAACCAAAAAA
TACACCGGAGACTCCGTGAAGGGCCGATTTATCATCTCCAGAGACAATTCCAAGAAC
ACAGTGTTTTGCAAATGAACAGCCTGAGAGTTGAGGACACGGCTGTTTATTACTGT
GCGAGAGATCGTGTAGAAGGTTACGTTTGGGGGGGCACGTTTGACCACTGGGGCCA
GGGAACCCCGGTCACCGTCTCCTCAG Figure 9B-28: SEQ ID #28
GAGCTCGTGCTGACTCAGCCACCTTCAGTGGCCGTGTCCCCAGGACAGACAGCCAGC
ATCACCTGCTCTGGAGATAAATTGGGGGATAAATATGTTTCCTGGTATCAGCAGAAG
CCAGGCCAGTCCCCTGTTCTGGTCATGTATCGAGATACCAAGCGGCCCTCAGGGATC
CCTGAGCGATTTTCTGGCTCCAACTCCGGGAACACAGCCACTCTGACCATCAGCGGG
ACCCAGGCTATGGATGAGGCTGACTATTACTGTCAGGCGTGGGACAGCAACACTGGG
GTGTTCGGCGGAGGCACCAAGCTGACCGTCCTAGGCGGTGGTTCCTCTAGATC
TTCCTCCTCTGGTGGCGGTGGCTCGGGCGGTGGTGGGGAGGTGCAGC
TGTTGGAGTCTGGCCCAGGGCTGGAAAAGGTTTCGGAGACCCTGTCCCTCACGTGTA
ATGTCTCTGGTGTCTCCATAAGTAGTCCTGATTATTATTGGGCCTGGATCCGCCAGCC
CCCCGGGAAGGGGCTGGAGTGGATTGGCAGTATCTTTTACAGTGGACCTACCTCCTG
GAATCCGTCCCTCAAGAATCGAGTCACCATCTCAGTAGACACGTCCAAGAATCAATT
CTCCCTGAAAATGAAGTCTGTGACGGCCGCGGACACGGCCGTATATTACTGTGCGAG
GTCCTTCGGTTTCGGGAGATATGAGCCCGCGGATGATGCATTTGATATCTGGGGCCG
AGGGAGACTGGTCATCGTCTCTCCAG Figure 9B-29: SEQ ID #29
GAGCTCGAGCTGACTCAGCCACCCTCAGTGTCAGTGGCCCTGGGACAGACGGCCAGG
ATTACCTGTGGGGGAAACAACATTGGAAGTAAAAATGTGCACTGGTACCAGCAGAA
GCCAGGCCAGGCCCCTGTGCTGGTCATCTATAGGGATAGCAACCGGCCCTCTGGGAT
CCCTGAGCGATTCTCTGGCTCCAACTCGGGGAACACGGCCACCCTGACCATCAGCAG
AGCCCAAGCCGGGGATGAGGCTGACTATTACTGTCAGGCGTGGGACAGAAGCACTG
CTCATGTGGTATTCGGCGGAGGGACCAAGCTGACCGTCCTAGGTGGTGGTTCCT
CTAGATCTTCCTCCTCTGGTGGCGGTGGCTCGGGCGGTGGTGGGCA
GGTGCAGCTGGTGCAGTCTGGGGGAGGCGTGGTCCAGCCTGGGAGGTCCCTGAGACT
CTCCTGTACAGCCTCTAGATTCAATTTCAGGAGTTTTGCCATGCACTGGGTCCGCCAG
GCTCCAGGCAAGGGGCTGGAGTGGGTGGCGATGTTTCCTTATGACGGAAATAATACA
TACTATGGAGACTCCGTGAAGGGCCGATTCACCATCTCCAGAGACAATTCCAAGAAG
ATGCTGTACCTGCAAATGAACGATCTCAGAATTGACGACACGGCACTGTACTACTGT
GCGAGGCAGGGATGGGTAATAGAGACATCTGGTATAAGAGCGAGTGGCTTTGACGT
CTGGGGTCAAGGGACACTGGTCACCGTCTCCTCAG Figure 9B-30: SEQ ID #30
GAGCTCGTGCTGACGCAGCCGCCCTCAGCGTCTGGGACCCCCGGGCAGAGGGTCACC
ATCTCTTGTTCTGGAAGCAGCTCCAACATCGGAAGTAATACTGTAAACTGGTACCAG
CAGCTCCCAGGAACGGCCCCCAAACTCCTCATCTATAGTAATAATCAGCGGCCCTCA
GGGGTCCCTGACCGATTCTCTGGCTCCAAGTCTGGCACCTCAGCCTCCCTGGCCGTCA
GTGGGCTCCAGTCTGAGGATGAGGCTGATTATTACTGTGCAGCATGGGATGACAGCC
TGAATGGTCCGGTATTCGGCGGAGGCACCCAGCTGACCGTCCTCGGTGGTGGTTC
CTCTAGATCTTCCTCCTCTGGTGGCGGTGGCTCGGGCGGTGGTGGG
CAGGTGCAGCTGCAGGAGTCGGGGGGAGGCTTGGTACAGCCTGGCAGGTCCCTGAG
ACTCTCCTGTGCAGCCTCTGGATTCACCTTTGATGATTATGCCATGCACTGGGTCCGG
CAAGCTCCAGGGAAGGGCCTGGAGTGGGTCTCAGGTATTAGTTGGAATAGTGGGAC
CATAGGCTACGCGGACTCTGTGAAGGGCCGATTCACCATCTCCAGAGACAACGCCAA
GAACTCCCTGTATCTGCAAATGAACAGTCTGAGAGCTGAGGACACGGCCGTGTATTA
CTGTGCAAAAGATGGGATTACGGTTTTGGAGTGGGCGATGGTTTGGATATCTGGGG
CCAAGGGACAATGGTCACCGTCTCTTCAG Figure 9B-31: SEQ ID #31
GAGCTCGTGATGACCCAGTCTCCATCTTCCGTGTCTGCATCTGTAGGAGACAGAGTC
ATCATCACTTGTCGGGCGAGTCAGGGTATTAGCAGCAGTTATTTAGCCTGGTATCAG
CAAAAACCAGGGAAAGCCCCTAAGCTCCTGATCTATGCTGCATTCACTTTACAAAGT
GGGGTCCCATCAAGGTTCAGCGGCAGTGGATCTGGGACAGAATTCACTCTCACAATC
AGCAGCCTGCAGCCTGAAGATTTTGCAACTTATTTCTGTCAAGACCTTAGTGGTTATC
CTCGAAACACCTTCGGCCAAGGGACACGACTGGAGATTAAA**GGTGGTTCCTCTA
GATCTTCCTCCTCTGGTGGCGGTGGCTCGGGCGGTGGTGGG**GAGGT
GCAGCTGGTGGAGTCTGGGGGAGGCTTGGTACAGCCTGGCAGGTCCCTGAGACTCTC
CTGTGCAGCCTCTGGATTCACCTTTGATGATTATGCCATGCACTGGGTCCGGCAAGCT
CCAGGGAAGGGCCTGGAGTGGGTCTCAGGTATTAGTTGGAATAGTGGTAGCATAGA
CTATGCGGACTCTGTGAAGGGCCGATTCACCATCTCCAGAGACAACGCCAAGAACTC
CCTGTATCTGCAAATGAACAGTCTGAGAGTTGAGGACACGGCCTTGTATTATTGTGC
AAAAGATGGGAGTAGGGTTTTTGGAGTGGGCGGTGGTTTTGATTTCTGGGGCCAAGG
GACAATGGTCACCGTCTCTTCAG Figure 9B-32: SEQ ID #32
GAGCTCGTGATGACCCAGTCTCCATCCTCCCTGTCTGCATCTGTAGGAGACAGAGTC
ACCATCACTTGCCAGGCGAGTCAGGACATCAGGAAGTATTTAAATTGGTATCAGCAG
AAAGCAGGGAAAGCCCCTAAACTCCTGATCTACGATGCATCTAAGTTGGATATAGGG
CTCCCATCAAGGTTCAGTGGAAGTGGATCTGGGACAGATTTTACTTTCACCATCAGC
AGCCTGCAGCCTGAAGATATTGCAACATATTACTGTCAGCAGTTTGATAATCTCCCCT
TCACTTTCGGCGGAGGGACCAAGGTGGAAATCAAA**GGTGGTTCCTCTAGATC
TTCCTCCTCTGGTGGCGGTGGCTCGGGCGGTGGTGGG**GAGGTGCAGC
TGGTGGAGTCTGGGGGAGGCTTGGTACAGCCTGGCAGGTCCCTGAGACTCTCCTGTG
CAGCCTCTGGATTCACCTTTGATGATTATGCCATGCACTGGGTCCGGCAAGCTCCAG
GGAAGGGCCTGGAGTGGGTCTCAGGTATTAGTTGGAATAGTGGGACCATAGGCTATG
CGGACTCTGTGAAGGGCCGATTCACCATCTCCAGAGACAACGCCAAGAACTCCCTGT
ATCTGCAAATGAACAGTCTGAGAGCTGAGGACACGGCCGTGTATTACTGTGCAAAAG
ATGGGATTACGGTTTTTGGAGTGGGCGATGGTTTGGATATCTGGGGCCAAGGGACAA
TGGTCACCGTCTCTTCAG Figure 9B-33: SEQ ID #33
GAGCTCATGCTGACTCAGCCACCCTCAGCGTCTGGGACCCCCGGGCAGAGGGTCACC
ATCTCTTGTTCTGGAAGCAGCTCCAACATCGGAAGTAATACTGTAAACTGGTACCAG
CAGCTCCCAGGAACGGCCCCCAAACTCCTCATCTATAGGAATAATCAGCGGCCCTCA
GGGGTCCCTGACCGATTCTCTGGCTCCAAGTCTGGCACCTCAGCCTCCCTGGCCATCA
GTGGGCTCCGGTCCGAGGATGAGGCTGATTATTACTGTGCAGCATGGGATGACAGCC
TGAGTGGTTGGGTGTTCGGCGGAGGCACCCAGCTGACCGTCCTCGGC**GGTGGTTC
CTCTAGATCTTCCTCCTCTGGTGGCGGTGGCTCGGGCGGTGGTGGG**
GAGGTGCAGCTGGTGGAGTCTGGAGGAGGCTTGGTCCAGCCTGGGGGTCCGTGAG
ACTCTCCTGTGCAGCCTCTGGATTTCAAGTCAGTAGTGACCACATGAGCTGGGTCCG
CCAGGCTCCAGGGAAGGGACTGCAGTGGGTCTCAGTTATTTATACTGGGGCAACTC
ATACTACGCAGACTCCGTGAAGGGCCGATTCACCGTCTCCAGAGACAACTCCAGGAA
CACACTTTTTCTTCAAATGAACAGCCTGAGAGTCGAGGACACGGCCATTTATTATTGT
GTGAGAGGTCCCGCTTACTATGACATAGACTACTGGGGCCAGGGAGCCCTGGTCACC
GTGTCCTCGG Figure 9B-34: SEQ ID #34
GAGCTCGTGTTGACGCAGCCGCCCTCAGCGTCTGGGACCCCCGGGCAGAGGGTCACC
ATCTCTTGTTCTGGAAGCAGCTCCAACATCGGAAGTAATACTGTAAACTGGTACCAG
CAGCTCCCAGGAACGGCCCCCAAACTCCTCATCTATAGTAATAATCAGCGGCCCTCA
GGGGTCCCTGACCGATTCTCTGGCTCCAAGTCTGGCACCTCAGCCTCCCTGGCCATCA
GTGGGCTCCAGTCTGAGGATGAGGCTGATTATTACTGTGCAGCATGGGATGACAGCC
TGAATGGTGGGGTGTTCGGCGGAGGCACCGAGCTGACCGTCCTCGGC**GGTGGTTC
CTCTAGATCTTCCTCCTCTGGTGGCGGTGGCTCGGGCGGTGGTGGG**
CAGGTGCAGCTGCAGGAGTCGGGGGGAGGCTTGGTACAGCCTGGCAGGTCCCTGAG
ACTCTCCTGTGCAGCCTCTGGATTCACCTTTGATGATTATGCCATGCACTGGGTCCGG
CAAGCTCCAGGGAAGGGCCTGGAGTGGGTCTCAGGTATTAGTTGGAATAGTGGGGC
CATAGGCTATGCGGACTCTGTGAAGGGCCGATTCACCATCTCCAGAGACAACGCCAA
GAACTCCCTGTATCTGCAAATGAACAGTCTGAGAGCTGAGGACACGGCCGTGTATTA
CTGTGCAAAAGATGGGATTACGGTTTTTGGAGTGGGCGATGGTTTGGATATCTGGGG
CCAAGGGACAATGGTCACCGTCTCTTCAG Figure 9B-35: SEQ ID #35
GAGCTCGTGCTGACTCAGCCACCCTCAGCGTCTGGGACCCCCGGGCAGAGGGTCACC
ATCTCTTGTTCTGGAAGCAGCTCCAACATCGGAAGTAATACTGTAAACTGGTACCAG
CAGCTCCCAGGAACGGCCCCCAAACTCCTCATCTATAGTAATAATCAGCGGCCCTCA
GGGGTCCCTGACCGATTCTCTGGCTCCAAGTCTGGCACCTCAGCCTCCCTGGCCATCA
GTGGGCTCCAGTCTGAGGATGAGGCTGATTATTACTGTGCAACATGGGATGACAGCC
TGAATGGTCGGGTGTTCGGCGGAGGCACCAGCTGACCGTCCTCGGC**GGTGGTTC
CTCTAGATCTTCCTCCTCTGGTGGCGGTGGCTCGGGCGGTGGTGGG**
CAGGTGCAGCTGGTGCAGTCTGGGGGAGACTTGGTCCAGCCGGGGGGTCCCTGAG
ACTCTCCTGTGTAGCCTCTGGATTCAACGTCAATGACAACTACATGAGCTGGGTCCG
CCAGGCTCCAGGGAAGGGGCTGGAGTGGGTCTCAACGATTTACAGCGAAACTCTTTC
ATACTACGGAGACTCCGTGAAGGGCAGATTCACCGTCTCCAGAGACGGTTCCAAGAA
CACGGTGTTTCTTCAAATGAGCAGCCTGAAAGGCGAGGACACGGCTGTTTATTATTG
TGCTTCCGAAGGGGGGGGCCTGACAATTGACTATTGGGGCCAGGGAACCCTGGTCGC
CGTCTCCTCAG Figure 9B-36: SEQ ID #36
GAGCTCGTGGTGACGCAGCCGCCCTCTGCATCTGCTGCCCTGGGATCCTCGGCCAAG
CTCACCTGCACCCTGAGCAGTGCCCACAAGACCTACACCATTGACTGGTATCAGCAG
CAGCAAGGGGAGGCCCCTCGGTACCTGATGCAACTTAAGAGTGATGGAAGCTACTCC
AAGGGGACCGGGGTCCCTGATCGCTTCTCGGGCTCCAGCTCTGGGGCTGACCGTTAC
TTGATCATCCCCAGCGTCCAGGCTGATGACGAAGCCGACTACTATTGTGGTGCAGAT
TATAGCGGTGGGTATTATGTGTTCGGCGGAGGCACCAAGCTGACCGTCCTAGGC**GG
TGGTTCCTCTAGATCTTCCCCCTCTGGTGGCGGTGGCTCGGGCGGT
GGTGGG**GAGGTGCAGCTGGTGGAGTCTGGGGCTGAGGTGAAGAAGCCTGGGGCC
TCAGTGAAGGTCTCCTGCAAGGCTTCTACATACATGTTCACCAGTTATGATATCAACT
GGGTGCGACAGGCCGCTGGACAAGGGCTTGAGTGGATGGGATGGATGGACCCGAAT
ACTGGTAACACAGACTATGCACAGAAGTTCCAGGGCAGAGTCACCATGACCAGGAA
CACTTCCATAAATACAGCCTACATGGAGCTGAGAAGCCTGACGTCTGACGACACGGC
CGTATATTACTGTGCGAGAGGCCGGACAGTGCGGTTCGGGGAATTATTTGTTAGTGA
GGGGGGTATGGACGTCTGGGGCCAAGGGACCACGGTCAGCGTCTCCTCAG Figure 9B-37: SEQ ID #37
GAGCTCGTGATGACTCAGTCTCCATCCTCCCTGTCTGCATCTGTAGGAGACAGAGTC
ACCATCACTTGCCGGGCAAGTCAGGGCATTAGAAATGATTTGGGCTGGTATCAGCAG
AAACCAGGGAAAGCCCCTAAACTCCTGATCTATGCTGCATCCAATTTACAAAGTGGG
GTCCCATCAAGGTTCAGCGGCAGTGGATCTGGCACAGATTTCACTCTCACCATCAGC
AGCCTGCAGCCTGAAGATTTTGCAACTTATTACTGTCTACAAGATTACAATTACCCGC
TCACTTTCGGCGGAGGGACCAAGCTGGAGATCAAA**GGTGGTTCCTCTAGATCT
TCCTCCTCTGGTGGCGGTGGCTCGGGCGGTGGTGGG**GAGGTGCAGCT
GGTGGAGTCTGGGGGAGGCTTGGTACAGCCTGGCAGGTCCCTGAGACTCTCCTGTGC
AGCCTCTGGATTCACCTTTGATGATCATGCCATGCACTGGGTCCGGCAAGCTCCAGG
GAAGGGCCTGGAGTGGGTCTCAGGTATTAGTTGGAGTGGTGCTTACATAGCCTATGC
GGACTCTGTGAAGGGCCGATTCACCATCTCCAGAGACAACGCCAGGAACTCCCTGTA
TCTGCAAATGAACAGTCTGAGAGCTGAGGACACGGCCTTGTATTACTGTGCCCGCAG
TAGTGGTTATTATGACCTTCCCTATGCTTTTGATATCTGGGGCCAAGGGACAATGGTC
ACCGTCTCTTCAG Figure 9B-38: SEQ ID #38
GAGCTCGTGCTGACTCAATCGCCCTCAGTGTCTGGGGCCCCAGGGCAGAGGGTCACC
ATCTCCTGCACTGGGAGCAGCTCCAACATCGGGGCAGGTTATGATGTACACTGGTAC
CAGCAGCTTCCAGGAACAGCCCCCAAACTCCTCATCTATGATAACAGCAATCGGCCC
TCAGGGGTCCCTGACCGATTCTCTGGCTCCAAGTCTGGCACCTCAGCCTCCCTGGCCA
TCACTGGGCTCCAGGCTGAGGATGAGGCTGATTATTACTGCCAGTCCTATGACAGCA
GCCTGAGTGCCTGGGTGTTCGGCGGAGGGACCAAGGTGACCGTCCTAGGC**GGTGG
TTCCTCTAGATCTTCCTCCTCTGGTGGCGGTGGCTCGGGCGGTGGT
GGG**GAGGTGCAGCTGGTGGAGTCTGGGGGAGGCTTGGTACAGCCTGGCAGGTCCCT
GAGACTCTCCTGTGCAGCCTCTGGATTCACCTTTGATGATTATGCCATGCACTGGGTC
CGGCAAGCTCCAGGGAAGGGCCTGGAGTGGGTCTCAGGTATTAGTTGGAATAGTGGT
AGCATAGACTATGCGGACTCTGTGAAGGGCCGATTCACCATCTCCAGAGACAACGCC
AAGAACTCCCTGTATCTGCAAATGAACAGTCTGAGAGTTGAGGACACGGCCTTGTAT
TATTGTGCAAAAGATGGGAGTAGGGTTTTTGGAGTGGGCGGTGGTTTTGATTTCTGG
GGCCAAGGGACAATGGTCACCGTCTCTTCAG Figure 9B-39: SEQ ID #39
GAGCTCCAGATGACCCAGTCTCCATCCTCCCTGTCTGCATCTGTAGGAGACAGAGTC
ACCATCACTTGCCGGGCAAGTCAGAGCATTAGCAGCTATTTAAATTGGTATCAGCAG
AAACCAGGGAAAGCCCCTAAGCTCCTGATCTATGCTGCATCCAGTTTGCAAAGTGGG
GTCCCATCAAGGTTCAGTGGCAGTGGATCTGGGACAGATTTCACTCTCACCATCAGC
AGTCTGCAACCTGAAGATTTTGCAACTTACTACTGTCAACAGAGTTACAGTACCCCC
ACCTTCGGCCAAGGGACACGACTGGAGATTAAA**GGTGGTTCCTCTAGATCTT
CCTCCTCTGGTGGCGGTGGCTCGGGCGGTGGTGGG**GAGGTGCAGCTGG
TGGAGTCTGGGGGAGGCTTGGTACAGCCTGGCAGGTCCCTGAGACTCTCCTGTGCAG
CCTCTGGATTCACCTTTGATGATTATGCCATGCACTGGGTCCGGCAAGCTCCAGGGA
AGGGCCTGGAGTGGGTCTCAGGTATTAGTTGGAATAGTGGGACCATAGGCTATGCGG
ACTCTGTGAAGGGCCGATTCACCATCTCCAGAGACAACGCCAAGAACTCCCTGTATC
TGCAAATGAACAGTCTGAGAGCTGAGGACACGGCCGTGTATTACTGTGCAAAAGAT
GGGATTACGGTTTTTGGAGTGGGCGATGGTTTGGATATCTGGGGCCAAGGGACAATG
GTCACCGTCTCTTCAG Figure 9B-40: SEQ ID #40
GAGCTCGAGCTGACTCAGCCACCCTCAGTGTCTGGGACCCCCGGGCAGAGGGTCACC
ATCTCTTGTTCTGGAGGCAGCTCCAACATCGGAAGTAATACTGTAAACTGGTACCAG
CAGCTCCCAGGAACGGCCCCCAAACTCCTCATCTATAGTAATAATCAGCGGCCCTCA
GGGGTCCCTGACCGATTCTCTGGCTCCAAGTCTGGCACCTCAGCCTCCCTGGCCATCA
GTGGGCTCCAGTCTGAGGATGAGGCTGATTATTACTGTGCAGCATGGGATGACAGCC
TGAATGGTGTGGTGTTCGGCGGAGGGACCAAGGTGACCGTCCTAGGC**GGTGGTTC
CTCTAGATCTTCCTCCTCTGGTGGCGGTGGCTCGGGCGGTGGTGGG**
CAGGTGCAGCTGCAGGAGTCGGGGGGAGGCTTGGTACAGCCTGGCAGGTCCCTGAG
ACTCTCCTGTGCAGCCTCTGGATTCACCTTTGATGATTATGCCATGCACTGGGTCCGG
CAAGCTCCAGGGAAGGGCCTGGAGTGGGTCTCAGGTATTAGTTGGAATAGTGGTAGC
ATAGCCTATGCGGACTCTGTGAAGGGCCGATTCACCATCTCCAGAGACAACGCCAAG
AACTCCCTGTATCTGCAAATGAACAGTCTGAGAGCTGAGGACACGGCCTTCTATTAC
TGTGCGAAAGTGGGCGGGGATACCTATGATATTACAAGTGGGGCGGATTACTTCGAT
CTCTGGGGCCGTAGCGCCCTGGTCACTGTCTCCTCAG Figure 9B-41: SEQ ID #41
GAGCTCGAGCTGACTCAGCCACCCTCAGTGTCTGGGACCCCCGGGCAGAGGGTCACC
ATCTCTTGTTCTGGAAGCAGCTCCAACATCGGAAGTAATACTGTAAACTGGTACCAG
CAGCTCCCAGGAACGGCCCCCAAACTCCTCATCTATAGTAATAATCAGCGGCCCTCA
GGGGTCCCTGACCGATTCTCTGGCTCCAAGTCTGGCACCTCAGCCTCCCTGGCCATCA
GTGGGCTCCAGTCTGAGGATGAGGCTGATTATTTCTGTGCAGCATGGGATGACAGCC
TGAATGGCCTCGTTTTCGGCGGAGGGACCAAGCTGACCGTCCTAGGC**GGTGGTTC
CTCTAGATCTTCCTCCTCTGGTGGCGGTGGCTCGGGCGGTGGTGGG**
GAGGTGCAGCTGGTGGAGTCTGGGGGAGGCTTGGTACAGCCTGGCAGGTCCCTGAG
ACTCTCCTGTGCAGCCTCTGGATTCACCTTTGATGATTATGCCATGCACTGGGTCCGG
CAAGGTCCAGGGAAGGGCCTAGAGTGGGTCTCAGGTATTAGTTGGAATAGTGGGAC
CATAGGCTATGCGGACTCTGTGAAGGGCCGATTCACCATCTCCAGAGACAACGCCAA
GAACTCCCTGTATCTGCAAATGAACAGTCTGAGAGCTGAGGACACGGCCGTGTATTA
CTGTGCAAAAGATGGGATTACGGTTTTGGAGTGGGCGATGGTTTGGATATCTGGGG
CCAAGGGACAATGGTCACCGTCTCTTCAG Figure 9B-42: SEQ ID #42
GAGCTCCAGATGACCCAGTCTCCATCCTCCCTGTCTGCATCTGTAGGAGACAGAGTC
ACCATCACTTGCCGGGCAAGTCAGAGCATTAGCACCTATTTAAATTGGTATCAGCAG
AAACCAGGGAAAGCCCCTATGCTCCTGATCTACGCTGCATCCAATTTGCAAAGTGGG
GTCCCATCAAGGTTCAGTGGCAGTGGGTCTGGGACAGATTTCACTCTCACCATCAGC
AGTCTGCAACCTGAAGATTTTGCAACTTACTACTGTCAACAGAGTTACAGTACCCCG
ATCACCTTCGGCCAAGGGACACGACTGGAGATTAAA**GGTGGTTCCTCTAGATC
TTCCTCCTCTGGTGGCGGTGGCTCGGGCGGTGGTGGG**CAGATCACCTT
GAAGGAGTCTGGGGGAGGCGTGGTCCAGCCTGGGAGGTCCCTGCGACTCTCCTGTGC
AGCCTCTGGATTCGACTTCAATATCTATGGCATGCACTGGGTCCGCCAGGCTCCAGA
CAAGGGGCTGGAGTGGGTGGCGGTTATATCAGATGATGGAACTAAAAAATATTATG
CAGACTCTGTGAAGGGCCGAGTCACCATCTCCAGAGACAATTCCAAGAACACGCTGT
ATCTGCAGATGAACAGCCTGAGAGCTGAGGACACGGCTGTGTATTACTGTGCGAAAG
ATCTGGATGTTGTCATGGGACCCGGTGGACTTGATTATTGGGGCCAGGGAACCCTGG
TCACCGTCTCCTCAG Figure 9B-43: SEQ ID #43
GAGCTCGTGCTGACTCAGCCACCCTCAGCGTCTGGGACCCCCGGGCAGAGGGTCACC
ATCTCTTGTTCTGGAAGCAGCTCCAACATCGGAAGTAATACTGTAAACTGGTACCAG
CAGCTCCCAGGAACGGCCCCCAAACTCCTCATCTATAGTAATAATCAGCGGCCCTCA
GGGGTCCCTGACCGATTCTCTGGCTCCAAGTCTGGCACCTCAGCCTCCCTGGCCATCA
GTGGGCTCCAGTCTGAGGATGAGGCTGATTATTACTGTGCAGCATGGGATGACAGCC
TGAATGGTCGGGTGTTCGGCGGAGGCACCAAGCTGACCGTCCTAGGT**GGTGGTTC
CTCTAGATCTTCCTCCTCTGGTGGCGGTGGCTCGGGCGGTGGTGGG**
CAGATCACCTTGAAGGAGTCTGGGGGAGGCTTGGTACAGCCTGGCAGGTCCCTGAGA
CTCTCCTGTGCAGCCTCTGGATTCACCTTTGATGATTATGCCATGCACTGGGTCCGGC
AAGCTCCAGGGAAGGGCCTGGAGTGGGTCTCAGGTATTAGTTGGAATAGTGGGACC
ATAGGCTATGCGGACTCTGTGAAGGGCCGATTCACCATCTCCAGAGACAACGCCAAG
AACTCCCTGTATCTGCAAATGAACAGTCTGAGAGCTGAGGACACGGCCGTGTATTAC
TGTGCAAAAGATGGGATTACGGTTTTTGGAGTGGGCGATGGTTTGGATATCTGGGGC
CAAGGGACAATGGTCACCGTCTCTTCAG Figure 9B-44: SEQ ID #44
ELVLTQSPDSLSVSLGERATINCKSSQTVLYNSDNKNYLSWYQQKPGQPPKLIMNWASIR
ASGVPDRFSGSGSGTDFTLTINSLQAEDVAIYYCQQYYSTPLTFGGGTKVEIK**GGSSRSS
SSGGGGSGGGG**QVQLVQSGAEVKKPGALVKVSCKASGYTFTNYGITWVRQAPGQG
LEWMGWISVYNGDTKYAQKLQGRVTMTTDTPTNTVYMELRSLRSDDTAVYYCARGYG
SGNWDYWGQGTLVTVSS Figure 9B-45: SEQ ID #45
ELTLTQSPSSLSASVGDRVTITCRASQGIASYLAWYQQKPGKAPKLLIYGASTLQSGVPSR
FSGRRSGTDFTLTISSLQPEDAATYYCQQYSNYPLTFGQGTKLEIK**GGSSRSSSSGGG
GSGGGG**QVQLVQSGAEMKKPGASVKVSCKASGYTFTNYGITWVRQAPGQGLEWMG
WISVYNGDTKYAQKLQGRVTMTTDTPTSTVYMELRSLTSDDTAVYYCVRGYGSGNWD
YWGQGTLVTVSS Figure 9B-46: SEQ ID #46
ELQMTQSPSSLSASVGDRVTITCRASQGINNYLAWFQQKPGKAPKLLIYKASSLESGVPS
RFSGSGSGTEFTLTISSLQPDDFATYYCQQYNSYPFTFGPGTKVDIK**GGSSRSSSSGGG
GSGGGG**QVQLVQSGAEVKKPGASVKVSCKASGYTFTNYGITWVRQAPGQGLEWMG
WISVYNGDTKYAQKLQGRVTMTTDTPTNTVYMELRSLRSDDTAVYYCARGYGSGNWD
YWGQGTLVTVSS Figure 9B-47: SEQ ID #47
ELQMTQSPSTLSASVGDRVTITCRASQGISNWLAWYQQKPGKAPKLLIHKASSLESGVPS
RFSGSGSGTEFTLTISSLQPDDFATYYCQQYYTYPLTFGGGTKVEIK**GGSSRSSSSGGG
GSGGGG**QVQLVQSGAEVKKPGASVKVSCKASGYTFTNYGITWVRQAPGQGLEWMG
WISVYNGDTKYAQKLQGRVTMTTDTPTNTVYMELRSLRSDDTAVYYCARGYGSGNWD
YWGQGTLVTVSS Figure 9B-48: SEQ ID #48
ELVLTQSPATLSVSPGERATLSCRASQSVSSNLAWYQQKPGQAPRLLIKGASTRATGIPD
RFSGSGSGTDFTLTISSLQAEDVAVYYCHQYYGPYSFGQGTKVEIK**GGSSRSSSSGGG
GSGGGG**QVQLVQSGAEVKKPGSSVKVSCKASGYTFTNYGITWVRQAPGQGLEWMG
WISVYNGDTKYAQKLQGRVTMTTDTPTNTVYMELRSLRSDDTAVYYCARGYGSGNWD
YWGQGTLVTVSS Figure 9B-49: SEQ ID #49
ELQMTQSPSSLSASVGDRVTITCRATQGISNYLAWFQQKPGKAPKLLIYAASSLQSGVPS
KFSGSGSGTDFTLTISSLQPEDFATYYCQQYNSYPLTFGGGTKVEIK**GGSSRSSSSGGG
GSGGGG**QVQLVQSGAEVKKPGASVKVSCKASGYTFTNYGITWVRQAPGQGLEWMG
WISVYNGDTKYAQKLQGRVTMTTDTLTNTVYMELRSLRSDDTAVYYCARGYGSGNWD
YWGQGTPVTVSS Figure 9B-50: SEQ ID #50
ELQMTQSPSSLSASVGDRVTITCRASQSISSYLNWYQQKPGKAPKLLIYAASSLQSGVPSR
FSGSGSGTDFTLTISSLQPEDFATYYCQQSYSTPRTFGGGTKLEIK**GGSSRSSSSGGGG
SGGGG**QVQLVQSGAEVRKPGASVRVSCKASGYTLTTYDINWVRQATGQGLEWMGW
MNPTSGNTAYAQKFQGRVTMTRNTSISTAYMELSSLRSEDTAVYYCARGLFFGVVTKPN
YYYYAMDVWGQGTTVTVSS Figure 9B-51: SEQ ID #51
ELQMTQSPSSLSVSVGDRVTITCRASQSISGYLNWYQQKPGKAPKLLIYGASSLQSGVPS
RFSGSGSGTDFALTISSVQPEDFASYFCQQSHSVPINFGQGTRLEIK**GGSSRSSSSGGG
GSGGGG**QVQLVQSGGGLAQPGKSLRLSCVASGFTFDDYAMHWVRQAPGKGLEWVS
GINWNSGSIGYADSVKGRFTISRDNAKNSLYLQMNSLRAEDTALYYCAKEQGYCDSTGC
QRGSGMDVWGQGTTVTVSS Figure 9B-52: SEQ ID #52
ELQMTQSPSSLSASVGDRVTITCQASQDISNYLNWYQQKPGKAPKLLIYDASNLETGVPS
RLSGSGSGTDFTFTISSLQPEDIATYYCQQYDDLPLTFGGGTKLEIK**GGSSRSSSSGGG
GSGGGG**QVQLVQSGGGLAQPGKSLRLSCVASGFTFDDYAMHWVRQAPGKGLEWVS
GINWNSGSIGYADSVKGRFTISRDNAKNSLYLQMNSLRAEDTALYYCAKEQGYCDSTGC
QRGSGMDVWGQGTTVTVSS Figure 9B-53: SEQ ID #53
ELQMTQSPSSLAASVGDRVTITCRASHDIKNDLGWYQHQPGKAPKLLIYAASSLQSGVPS
RFSGSGSGTNFTLTINSLQPEDFATYYCLHDYTYPRTFGQGTKVEIK**GGSSRSSSSGG
GGSGGGG**QVQLVQSGGGLAQPGKSLRLSCVASGFTFDDYAMHWVRQAPGKGLEWV
SGINWNSGSIGYADSVKGRFTISRDNAKNSLYLQMNSLRAEDTALYYCAKEQGYCDSTG
CQRGSGMDVWGQGTTVTVSS Figure 9B-54: SEQ ID #54
ELQMTQSPSSLSASVGDRVTITCRASQGIRYDVGWYQQKPGKAPKLLIYAASTLQSGVPS
RFSGSGSETDFTLTINSLQPEDSATYYCQQSYSIPSTFGQGTKVEIK**GGSSRSSSSGGG
GSGGGG**EVQLLESGGGLAQPGKSLRLSCVASGFTFDDYAMHWVRQAPGKGLEWVSG
INWNSGSIGYADSVKGRFTISRDNAKNSLYLQMNSLRAEDTALYYCAKEQGYCDSTGCQ
RGSGMDVWGQGTTVTVSS Figure 9B-55: SEQ ID #55
ELELTQPPSVSGTPGQRVTISCSGSSSNIGSDTVNWYQQLPGTAPKLLIYSNNQRPSGVPD
RFSGSKSGTSASLAISGLQSEDEADYYCATWDDGLRGMVFGEGTKLTVLG**GGSSRSSS
SGGGGSGGGG**QVQLQESGGGLAQPGKSLRLSCVASGFTFDDYAMHWVRQAPGKGL
EWVSGINWNSGSIGYADSVKGRFTISRDNAKNSLYLQMNSLRAEDTALYYCAKEQGYC
DSTGCQRGSGMDVWGQGTTVTVSS Figure 9B-56: SEQ ID #56
ELVLTQPPSVSGAPGRRVTISCTGSSSNIGAAYDVHWYQQLPGTAPKLLIFGNTNRPSGVP
DRFSGSKSGTSASLAITGLQSEDEADYYCATWDDSRDGPEVVFGGGTELTVLG**GGSSR
SSSSGGGGSGGGG**EVQLVESGGGLAQPGKSLRLSCVASGFTFDDYAMHWVRQAPG
KGLEWVSGINWNSGSIGYADSVKGRFTISRDNAKNSLYLQMNSLRAEDTALYYCAKEQ
GYCDSTGCQRGSGMDVWGQGTTVTVSS Figure 9B-57: SEQ ID #57
ELVLTQPPSASGTPGQRVTISCSGSNSNIGSDYVYWYQRFPGTAPKLLIYSNNQRPSGVPD
RFSGSKSGTSASLAISGLQSEDEAEYYCATWDDALRGMVFGEGTKLTVLG**GGSSRSSS
SGGGGSGGGG**EVQLVESGGGLAQPGKSLRLSCVASGFTFDDYAMHWVRQAPGKGL
EWVSGINWNSGSIGYADSVKGRFTISRDNAKNSLYLQMNSLRAEDTALYYCAKEQGYC
DSTGCQRGSGMDVWGQGTTVTVSS Figure 9B-58: SEQ ID #58
ELMLTQPHSVSESPGKTVTISCTRSSGSIASNFVQWYQQRPGKSPTTVIYEDNQRPSGVPD
RFSGSVDRSSNSASLTISGLQTEDEADYYCQSFYDGVPSWVFGGGTELTVLG**GGSSRSS
SSGGGGSGGGG**EVQLVESGGGVVQPGGSLRLSCVASGFTFDDYAMHWVRQAPGKG
LEWVSGINWNSGSIGYADSVKGRFTISRDNAKNSLYLQMNSLRAEDTALYYCAKEQGY
CDSTGCQRGSGMDVWGQGTTVTVSS Figure 9B-59: SEQ ID # 59
ELMLTQPHSVSESPGKTVTISCTRSSGSIASNFVQWYQQRPGKSPTTVIYEDNQRPSGVPD
RFSGSVDRSSNSASLTISGLQTEDEADYYCQSFYDGVPSWVFGGGTELTVLG**GGSSRSS
SSGGGGSGGGG**QVQLVQSGGGVVQPGGSLRLSCVASGFTFDDYAMHWVRQAPGK
GLEWVSGISWNSGAIGYADSVKGRFTISRDNAKNSLYLQMNSLRTEDTAVYYCAKDGIT
IFGVGDGLDVWGQGTMVTVSS Figure 9B-60: SEQ ID #60
ELQMTQSPSSLSASVGDRVTITCQASQDIGNYLNWYQQKPGKAPKLLIYDASYLETGVPS
RFSGSGSGTDFTFTISSLQPEDIATYYCQQYDNLPFTFGPGTKVDIK**GGSSRSSSSGGG
GSGGGG**EVQLVESGGGLVQPGRSLRLSCAASGFTFDDYAMHWVRQAPGKGLEWVSG
ISWNSGSIDYADSVKGRFTISRDNAKNSLYLQMNSLRVEDTALYYCAKDGSRVFGVGGG
FDFWGQGTMVTVSS Figure 9B-61: SEQ ID #61
ELVMTQSPSSLSASVGDRVTITCRASQGITDDLGWYQQKPGKAPKLLIYATSNLESGVPS
RFSGSGSDTEFTLTISSLQPEDLATYYCLQDYSYPYTFGQGTKVEIK**GGSSRSSSSGGG
GSGGGG**EVQLVESGGGLVQPGRSLRLSCAASGFTFDDYAMHWVRQAPGKGLEWVSG
ISWNSGSIDYVDSVKGRFTISRDNAKNYLYLQMNSLRVEDTALYYCAKDGSRVFGVGG
GFDFWGQGTMVTVSS Figure 9B-62: SEQ ID #62
ELQMTQSPSTLSASVGDRVTITCRASQSISSWLAWYQQKPGKAPKLLIYKASSLESGVPS
RFSGSGSGTEFTLTISSLQPDDFATYYCQQYNTYSRTFGQGTKVEIK**GGSSRSSSSGGG
GSGGGG**EVQLVESGGGLVQPGRSLRLSCAASGFTFDDYSMHWVRQAPGKGLEWVSG
ISWNSGGIGYADSVRGRFTISRDNAKNSLYLQMNSLRAEDTALYYCAKDGMRVFGVGG
GFDFWGQGTMVTVSS Figure 9B-63: SEQ ID #63
ELQMTQSPSSLSASVGDRVTITCQASRDISNYLNWYQHIPGKAPKLLIFHASTLEAGIPSRF
SGSGSETSFTFTIRSLQPEDVATYYCQQYDNLPFTFGPGTKVDIK**GGSSRSSSSGGGG
SGGGG**EVQLVESGGGLVQPGRSLRLSCAASGFTFDDYAMYWVRQAPGKGLEWVSGIS
WNSGSIDYADSVKGRFTISRDNAKNSLYLQMNSLRAEDTALYYCAKDGMRVFGVGGGF
DFWGQGTMVTVSS Figure 9B-64: SEQ ID #64
ELMLTQPHSASGTPGQRVTISCSGSSSNIGSNTVNWYQQLPGTAPKLLIYSNNQRPSGVPD
RFSGSKSGTSASLAISGLQSEDEADYYCAAWDDSLNGPVFGGGTKVTVLG**GGSSRSSS
SGGGGSGGGG**EVQLVESGGGLVQPGRSLRLSCAASGFTFDDYAMYWVRQAPGKGL
EWVSGISWNSGSIDYADSVKGRFTISRDNAKNSLYLQMNSLRAEDTALYYCAKDGMRV
FGVGGGFDFWGQGTMVTVSS Figure 9B-65: SEQ ID #65
ELVVTQPPSASGTPGQRVTISCSGSSSNIGSNTVNWYQQLPGTAPKLLIYSNNQRPSGVPD
RFSGSKSGTSASLAISGLQSEDEADYYCATWDDGLNGMVFGGGTKLTVLG**GGSSRSSS
SGGGGSGGGG**EVQLVESGGGLVQPGRSLRLSCAASGFTFDDYAMHWVRQAPGKGL
EWVSGISWNSGTIGYADSVKGRFTISRDNAKNSLYLQMNSLRAEDTAVYYCAKDGITVF
GVGDGLDIWGQGTMVTVSS Figure 9B-66: SEQ ID #66
ELQMTQSPSSLSASVGDRVTITCRASQGIGNDLGWYQQKPGKAPKLLIYAASSLQSGVPS
RFSGSGSGTDFTLTIGSLQPEDFATYYCLQDYNYPFTFGPGTKVDIK**GGSSRSSSSGGG
GSGGGG**EVQLVESGGTLVQPGRSLRLSCAASGFSFDDYAMQWVRQAPGKGLEWVSG
ISWNSGSIAYADSVKGRFTISRDNAKSSLYLLMNSLRAEDTALYYCAKAGTDYYDSSASE
LPDYWGQGTLVTVSS Figure 9B-67: SEQ ID #67
ELQMTQSPSFLSASVGDRVTITCRASQGISSYLAWYQQKPGKAPKLLIYGASTLQSGVPS
RFSGSGSGTEFTLTISSLQPDDFATYYCQQYNSYPWTFGQ
GTKVEIKGGSSRSSSSGGGGSGGGGQVQLQESGGGLVQPGRSLRLSCAASGFTFD
DYAMHWVRQAPGKGLEWVSGISWNSGSIAYADSVKGRFTISRDNAKNSLYLQMNSLRA
EDTAFYYCAKVGGDTYDITSGADYFDLWGRGALVTVSS Figure 9B-68: SEQ ID #68
ELVMTQSPATLSVSPGERATLSCRASQSVSSNLAWYQQKPGQAPRLLIYGASTRATGIPA
RFSGSGSGTEFTLTISSLQSEDFAVYYCQQYNNWPSITFGQGTRLEIK**GGSSRSSSSGG
GGSGGGG**QVQLVQSGGGLVQPGRSLRLSCAASGFTFDDYAMHWVRQAPGKGLEWV
SGISWNSGSIAYADSVKGRFTISRDNAKNSLYLQMNSLRAEDTAFYYCAKVGGDTYDITS
GADYFDLWGRGALVTVSS Figure 9B-69: SEQ ID #69
ELVVTQPPSVSGAPGQRVTISCTGSSSNIGAGYDVHWYQQLPGTAPKLLIYGNKNRPSGV
PDRFSGSKSGTSASLAITGLRAEDEADYYCQSFDSSLGWVFGGGTQLTVLG**GGSSRSSS
SGGGGSGGGG**QVQLVQSGGGLVQPGGSLRVSCAASGFTSNIFWMSWVRQAPGKGL
EWVANIDEDGSEKNYVDSVKGRFTISRDNAKNSLYLQMNSLRAEDTAVYYCARESFYY
GSGTYFDFWGQGTLVTVSS Figure 9B-70: SEQ ID #70
ELVLTQPPSVPVAPGQTANISCGGNNIGRQTVHWYQQKPGQAPVLVVFDDSDRPAGIPE
RFSGSNSGNTATLTISRVEAGDEADYYCQVWDSSSDHVVFGGGTQLTVLG**GGSSRSSS
SGGGGSGGGG**QVQLVQSGGGVVQSGRSLRLSCAASGFTFSDYAMHWVRQAPGKGL
EWVAVISHGGTKKYTGDSVKGRFIISRDNSKNTVFLQMNSLRVEDTAVYYCARDRVEG
YVWGGTFDHWGQGTPVTVSS Figure 9B-71: SEQ ID #71
ELVLTQPPSVAVSPGQTASITCSGDKLGDKYVSWYQQKPGQSPVLVMYRDTKRPSGIPE
RFSGSNSGNTATLTISGTQAMDEADYYCQAWDSNTGVFGGGTKLTVLG**GGSSRSSSS
GGGGSGGGG**EVQLLESGPGLEKVSETLSLTCNVSGVSISSPDYYWAWIRQPPGKGLE
WIGSIFYSGPTSWNPSLKNRVTISVDTSKNQFSLKMKSVTAADTAVYYCARSFGFGRYEP
ADDAFDIWGRGRLVIVSP Figure 9B-72: SEQ ID #72
ELELTQPPSVSVALGQTARITCGGNNIGSKNVHWYQQKPGQAPVLVIYRDSNRPSGIPER
FSGSNSGNTATLTISRAQAGDEADYYCQAWDRSTAHVVFGGGTKLTVLG**GGSSRSSS
SGGGGSGGGG**QVQLVQSGGGVVQPGRSLRLSCTASRFNFRSFAMHWVRQAPGKGL
EWVAMFPYDGNNTYYGDSVKGRFTISRDNSKKMLYLQMNDLRIDDTALYYCARQGWV
IETSGIRASGFDVWGQGTLVTVSS Figure 9B-73: SEQ ID #73
ELVLTQPPSASGTPGQRVTISCSGSSSNIGSNTVNWYQQLPGTAPKLLIYSNNQRPSGVPD
RFSGSKSGTSASLAVSGLQSEDEADYYCAAWDDSLNGPVFGGGTQLTVLG**GGSSRSSS
SGGGGSGGGG**QVQLQESGGGLVQPGRSLRLSCAASGFTFDDYAMHWVRQAPGKGL
EWVSGISWNSGTIGYADSVKGRFTISRDNAKNSLYLQMNSLRAEDTAVYYCAKDGITVF
GVGDGLDIWGQGTMVTVSS Figure 9B-74: SEQ ID #74
ELVMTQSPSSVSASVGDRVIITCRASQGISSSYLAWYQQKPGKAPKLLIYAAFTLQSGVPS
RFSGSGSGTEFTLTISSLQPEDFATYFCQDLSGYPRNTFGQGTRLEIK**GGSSRSSSSGG
GGSGGGG**EVQLVESGGGLVQPGRSLRLSCAASGFTFDDYAMHWVRQAPGKGLEWV
SGISWNSGSIDYADSVKGRFTISRDNAKNSLYLQMNSLRVEDTALYYCAKDGSRVFGVG
GGFDFWGQGTMVTVSS Figure 9B-75: SEQ ID #75
ELVMTQSPSSLSASVGDRVTITCQASQDIRKYLNWYQQKAGKAPKLLIYDASKLDIGLPS
RFSGSGSGTDFTFTISSLQPEDIATYYCQQFDNLPFTFGGGTKVEIK**GGSSRSSSSGGG
GSGGGG**EVQLVESGGGLVQPGRSLRLSCAASGFTFDDYAMHWVRQAPGKGLEWVSG
ISWNSGTIGYADSVKGRFTISRDNAKNSLYLQMNSLRAEDTAVYYCAKDGITVFGVGDG
LDIWGQGTMVTVSS Figure 9B-76: SEQ ID #76
ELMLTQPPSASGTPGQRVTISCSGSSSNIGSNTVNWYQQLPGTAPKLLIYRNNQRPSGVPD
RFSGSKSGTSASLAISGLRSEDEADYYCAAWDDSLSGWVFGGGTQLTVLG**GGSSRSSS
SGGGGSGGGG**EVQLVESGGGLVQPGGSVRLSCAASGFQVSSDHMSWVRQAPGKGL
QWVSVIYTGGNSYYADSVKGRFTVSRDNSRNTLFLQMNSLRVEDTAIYYCVRGPAYYDI
DYWGQGALVTVSS Figure 9B-77: SEQ ID #77
ELVLTQPPSASGTPGQRVTISCSGSSSNIGSNTVNWYQQLPGTAPKLLIYSNNQRPSGVPD
RFSGSKSGTSASLAISGLQSEDEADYYCAAWDDSLNGGVFGGGTELTVLG**GGSSRSSS
SGGGGSGGGG**QVQLQESGGGLVQPGRSLRLSCAASGFTFDDYAMHWVRQAPGKGL
EWVSGISWNSGAIGYADSVKGRFTISRDNAKNSLYLQMNSLRAEDTAVYYCAKDGITVF
GVGDGLDIWGQGTMVTVSS Figure 9B-78: SEQ ID #78
ELVLTQPPSASGTPGQRVTISCSGSSSNIGSNTVNWYQQLPGTAPKLLIYSNNQRPSGVPD
RFSGSKSGTSASLAISGLQSEDEADYYCATWDDSLNGRVFGGGTQLTVLG**GGSSRSSS
SGGGGSGGGG**QVQLVQSGGDLVQPGGSLRLSCVASGFNVNDNYMSWVRQAPGKG
LEWVSTIYSETLSYYGDSVKGRFTVSRDGSKNTVFLQMSSLKGEDTAVYYCASEGGGLT
IDYWGQGTLVAVSS Figure 9B-79: SEQ ID #79
ELVVTQPPSASAALGSSAKLTCTLSSAHKTYTIDWYQQQQGEAPRYLMQLKSDGSYSKG
TGVPDRFSGSSSGADRYLIIPSVQADDEADYYCGADYSGGYYVFGGGTKLTVLG**GGSS
RSSPSGGGGSGGGG**EVQLVESGAEVKKPGASVKVSCKASTYMFTSYDINWVRQAA
GQGLEWMGWMDPNTGNTDYAQKFQGRVTMTRNTSINTAYMELRSLTSDDTAVYYCA
RGRTVRFGELFVSEGGMDVWGQGTTVSVSS Figure 9B-80: SEQ ID #80
ELVMTQSPSSLSASVGDRVTITCRASQGIRNDLGWYQQKPGKAPKLLIYAASNLQSGVPS
RFSGSGSGTDFTLTISSLQPEDFATYYCLQDYNYPLTFGGGTKLEIK**GGSSRSSSSGGG
GSGGGG**EVQLVESGGGLVQPGRSLRLSCAASGFTFDDHAMHWVRQAPGKGLEWVSG
ISWSGAYIAYADSVKGRFTISRDNARNSLYLQMNSLRAEDTALYYCARSSGYYDLPYAF
DIWGQGTMVTVSS Figure 9B-81: SEQ ID #81
ELVLTQSPSVSGAPGQRVTISCTGSSSNIGAGYDVHWYQQLPGTAPKLLIYDNSNRPSGV
PDRFSGSKSGTSASLAITGLQAEDEADYYCQSYDSSLSAWVFGGGTKVTVLG**GGSSRS
SSSGGGGSGGGG**EVQLVESGGGLVQPGRSLRLSCAASGFTFDDYAMHWVRQAPGK
GLEWVSGISWNSGSIDYADSVKGRFTISRDNAKNSLYLQMNSLRVEDTALYYCAKDGSR
VFGVGGGFDFWGQGTMVTVSS Figure 9B-82: SEQ ID #82
ELQMTQSPSSLSASVGDRVTITCRASQSISSYLNWYQQKPGKAPKLLIYAASSLQSGVPSR
FSGSGSGTDFTLTISSLQPEDFATYYCQQSYSTPTFGQGTRLEIK**GGSSRSSSSGGGGS
GGGG**EVQLVESGGGLVQPGRSLRLSCAASGFTFDDYAMHWVRQAPGKGLEWVSGIS
WNSGTIGYADSVKGRFTISRDNAKNSLYLQMNSLRAEDTAVYYCAKDGITVFGVGDGL
DIWGQGTMVTVSS Figure 9B-83: SEQ ID #83
ELELTQPPSVSGTPGQRVTISCSGGSSNIGSNTVNWYQQLPGTAPKLLIYSNNQRPSGVPD
RFSGSKSGTSASLAISGLQSEDEADYYCAAWDDSLNGVVFGGGTKVTVLG**GGSSRSSS
SGGGGSGGGG**QVQLQESGGGLVQPGRSLRLSCAASGFTFDDYAMHWVRQAPGKGL
EWVSGISWNSGSIAYADSVKGRFTISRDNAKNSLYLQMNSLRAEDTAFYYCAKVGGDT
YDITSGADYFDLWGRSALVTVSS Figure 9B-84: SEQ ID #84
ELELTQPPSVSGTPGQRVTISCSGSSSNIGSNTVNWYQQLPGTAPKLLIYSNNQRPSGVPD
RFSGSKSGTSASLAISGLQSEDEADYFCAAWDDSLNGLVFGGGTKLTVLG**GGSSRSSS
SGGGGSGGGG**EVQLVESGGGLVQPGRSLRLSCAASGFTFDDYAMHWVRQGPGKGL
EWVSGISWNSGTIGYADSVKGRFTISRDNAKNSLYLQMNSLRAEDTAVYYCAKDGITVF
GVGDGLDIWGQGTMVTVSS Figure 9B-85: SEQ ID #85
ELQMTQSPSSLSASVGDRVTITCRASQSISTYLNWYQQKPGKAPMLLIYAASNLQSGVPS
RFSGSGSGTDFTLTISSLQPEDFATYYCQQSYSTPITFGQGTRLEIK**GGSSRSSSSGGG
GSGGGG**QITLKESGGGVVQPGRSLRLSCAASGFDFNIYGMHWVRQAPDKGLEWVAVI
SDDGTKKYYADSVKGRVTISRDNSKNTLYLQMNSLRAEDTAVYYCAKDLDVVMGPGG
LDYWGQGTLVTVSS Figure 9B-86: SEQ ID #86
ELVLTQPPSASGTPGQRVTISCSGSSSNIGSNTVNWYQQLPGTAPKLLIYSNNQRPSGVPD
RFSGSKSGTSASLAISGLQSEDEADYYCAAWDDSLNGRVFGGGTKLTVLG**GGSSRSSS
SGGGGSGGGG**QITLKESGGGLVQPGRSLRLSCAASGFTFDDYAMHWVRQAPGKGLE
WVSGISWNSGTIGYADSVKGRFTISRDNAKNSLYLQMNSLRAEDTAVYYCAKDGITVFG
VGDGLDIWGQGTMVTVSS

SEQUENCE LISTING

```
<160> NUMBER OF SEQ ID NOS: 258

<210> SEQ ID NO 1
<211> LENGTH: 748
<212> TYPE: DNA
<213> ORGANISM: Homo sapiens

<400> SEQUENCE: 1
gagctcgtgt tgacacagtc tccagactcc ctgtctgtgt ctctgggcga gagggccacc     60
atcaactgca agtccagcca gactgtttta tacaactccg acaataagaa ctacttaagt    120
tggtaccagc agaaaccagg acagcctcct aagttgatca tgaactgggc atctatccgg    180
gcatccgggg tccctgaccg attcagtggc agcgggtctg ggacagattt cactctcacc    240
atcaacagcc tgcaggctga agatgtggca atttattact gtcagcaata ttatagtact    300
ccgctcacct tcggcggagg gaccaaggtg gaaatcaaag gtggttcctc tagatcttcc    360
```

```
tcctctggtg gcggtggctc gggcggtggt gggcaggtgc agctggtgca gtctggggct   420
gaggtgaaga agcctggggc cttagtgaag gtctcctgca aggcttctgg ttacacgttt   480
accaattatg gtatcacctg ggtgcgacag gcccctggac aagggcttga gtggatggga   540
tggatcagtg tttataatgg tgacacaaag tatgcacaga agctccaggg cagagtcacc   600
atgaccacag acacgcccac gaacacagtg tatatggagt tgaggagcct gagatctgac   660
gacacggccg tgtattattg tgcgagaggt tatggttcgg ggaattggga ctactggggc   720
cagggaaccc tggtcaccgt ctcctcag                                      748
```

<210> SEQ ID NO 2
<211> LENGTH: 730
<212> TYPE: DNA
<213> ORGANISM: Homo sapiens

<400> SEQUENCE: 2

```
gagctcacac tcacgcagtc tccatcctcc ctgtctgcat ctgtaggaga cagagtcacc    60
atcacttgcc gggccagtca gggcattgcc agttatttag cctggtatca gcaaaaacca   120
gggaaagccc ctaagctcct gatctatggt gcatccactt tgcaaagtgg ggtcccatca   180
aggttcagcg gccgtagatc tgggacagat ttcactctca ccatcagcag cctgcagcct   240
gaagatgctg caacttatta ctgccaacaa tatagtaatt accctctgac ttttggccag   300
gggaccaagc tggagatcaa aggtggttcc tctagatctt cctcctctgg tggcggtggc   360
tcgggcggtg gtgggcaggt gcagctggtg cagtctggag ctgagatgaa gaagcctggg   420
gcctcagtga aggtctcctg caaggcttct ggttacacct ttaccaatta tggtatcacc   480
tgggtgcgac aggcccctgg acaagggctt gagtggatgg gatggatcag tgtttataat   540
ggtgacacaa agtatgcaca gaagctccag ggcagagtca ctatgaccac agacacaccc   600
acgagcacag tctacatgga attgaggagc ctgacatctg acgacacggc cgtgtattat   660
tgtgtgagag gttatggttc ggggaattgg gactactggg gccagggaac cctggtcacc   720
gtctcctcag                                                         730
```

<210> SEQ ID NO 3
<211> LENGTH: 730
<212> TYPE: DNA
<213> ORGANISM: Homo sapiens

<400> SEQUENCE: 3

```
gagctccaga tgacccagtc tccatcctca ctgtctgcat ctgtaggaga cagagtcacc    60
atcacttgtc gggcgagtca gggcattaac aattatttag cctggtttca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt acccattcac tttcggccct   300
gggaccaaag tggatatcaa aggtggttcc tctagatctt cctcctctgg tggcggtggc   360
tcgggcggtg gtgggcaggt gcagctggtg cagtctgggg ctgaggtgaa gaagcctggg   420
gcctcagtga aggtctcctg caaggcttct ggttacacgt ttaccaatta tggtatcacc   480
tgggtgcgac aggcccctgg acaagggctt gagtggatgg gatggatcag tgtttataat   540
ggtgacacaa agtatgcaca gaagctccag ggcagagtca ccatgaccac agacacgccc   600
acgaacacag tgtatatgga gttgaggagc ctgagatctg acgacacggc cgtgtattat   660
```

```
tgtgcgagag gttatggttc ggggaattgg gactactggg gccagggaac cctggtcacc      720
gtctcctcag                                                             730

<210> SEQ ID NO 4
<211> LENGTH: 730
<212> TYPE: DNA
<213> ORGANISM: Homo sapiens

<400> SEQUENCE: 4
gagctccaga tgacccagtc tccttccacc ctgtctgcat ctgtaggaga cagagtcacc       60
atcacttgtc gggcgagtca gggtattagc aactggttag cctggtatca gcagaaacca      120
ggaaaagccc ctaagctcct gatccataag gcatctagtt tagaaagtgg ggtcccatca      180
aggttcagcg gcagtggatc tgggacagaa ttcactctca ccatcagcag cctgcagcct      240
gatgattttg caacttatta ctgccaacag tattatactt acccgctcac tttcggcgga      300
gggaccaagg tggaaatcaa aggtggttcc tctagatctt cctcctctgg tggcggtggc      360
tcgggcggtg gtgggcaggt gcagctggtg cagtctgggg ctgaggtgaa gaagcctggg      420
gcctcagtga aggtctcctg caaggcttct ggttacacgt ttaccaatta tggtatcacc      480
tgggtgcgac aggcccctgg acaagggctt gagtggatgg gatggatcag tgtttataat      540
ggtgacacaa agtatgcaca gaagctccag gcagagtca ccatgaccac agacacgccc       600
acgaacacag tgtatatgga gttgaggagc ctgagatctg acgacacggc cgtgtattat      660
tgtgcgagag gttatggttc ggggaattgg gactactggg gccagggaac cctggtcacc      720
gtctcctcag                                                             730

<210> SEQ ID NO 5
<211> LENGTH: 727
<212> TYPE: DNA
<213> ORGANISM: Homo sapiens

<400> SEQUENCE: 5
gagctcgtgt tgacgcagtc tccagccacc ctgtctgtgt ctccagggga aagagccacc       60
ctctcctgca gggccagtca gagtgttagc agcaatttag cctggtacca gcagaaacct      120
ggccaggctc ccaggctcct catcaaagga gcatccacca gggccactgg tatcccagac      180
aggttcagtg gcagcgggtc tgggacagat ttcactctca ccatcagcag cctgcaggct      240
gaagatgtgg cagtttacta ctgtcaccag tattatggtc cttactcttt tggccagggg      300
accaaggtgg aaatcaaagg tggttcctct agatcttcct cctctggtgg cggtggctcg      360
ggcggtggtg ggcaggtgca gctggtgcag tctggggctg aggtgaagaa gcctgggtcc      420
tcggtgaagg tctcctgcaa ggcttctggt tacacgttta ccaattatgg tatcacctgg      480
gtgcgacagg cccctggaca agggcttgag tggatgggat ggatcagtgt ttataatggt      540
gacacaaagt atgcacagaa gctccagggc agagtcacca tgaccacaga cacgcccacg      600
aacacagtgt atatggagtt gaggagcctg agatctgacg acacggccgt gtattattgt      660
gcgagaggtt atggttcggg gaattgggac tactggggcc agggaaccct ggtcaccgtc      720
tcctcag                                                                727

<210> SEQ ID NO 6
<211> LENGTH: 730
<212> TYPE: DNA
<213> ORGANISM: Homo sapiens

<400> SEQUENCE: 6
```

```
gagctccaga tgacccagtc tccatcctca ctgtctgcat ctgttggaga cagagtcacc    60
atcacttgtc gggcgactca gggcattagt aattatttag cctggtttca gcagaaacca   120
gggaaagccc ctaagttgct gatctatgct gcatccagtt tgcaaagtgg ggtcccatca   180
aagttcagcg gcagtggatc tgggacagat ttcactctca ccatcagcag cctgcagcct   240
gaagattttg caacttatta ctgccaacag tataatagtt atcctctcac tttcggcgga   300
gggaccaagg tggaaatcaa aggtggttcc tctagatctt cctcctctgg tggcggtggc   360
tcgggcggtg gtgggcaggt gcagctggtg cagtctgggg ctgaggtgaa gaagcctggg   420
gcctcagtga aggtctcctg caaggcttct ggttacacgt ttaccaatta tggtatcacc   480
tgggtgcgac aggcccctgg acaagggctt gagtggatgg gatggatcag tgtttataat   540
ggtgacacaa agtatgcaca gaagctccag ggcagagtca ccatgaccac agacacgctc   600
acgaacacag tgtatatgga gttgaggagc ctgagatctg acgacacggc cgtgtattat   660
tgtgcgagag gttatggttc ggggaattgg gactactggg gccagggaac cccggtcacc   720
gtctcctcag                                                          730

<210> SEQ ID NO 7
<211> LENGTH: 760
<212> TYPE: DNA
<213> ORGANISM: Homo sapiens

<400> SEQUENCE: 7
gagctccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctcgcac tttcggcgga   300
gggaccaagc tggagatcaa aggtggttcc tctagatctt cctcctctgg tggcggtggc   360
tcgggcggtg gtgggcaggt gcagctggtg cagtctgggg ctgaggtgag gaagcctggg   420
gcctcagtga gggtctcctg caaggcttct ggatacaccc tcaccactta tgatatcaac   480
tgggtgcgac aggctactgg acaagggctt gagtggatgg gatggatgaa ccctaccagt   540
ggtaacacag cctacgcaca gaagttccag ggcagagtca ccatgaccag gaacacctcc   600
ataagcacag cctacatgga gctgagcagc ctgagatctg aggacacggc cgtttactac   660
tgtgcgagag gcctgttttt tggagtggtt acaaaaccca actactacta ctacgctatg   720
gacgtctggg gccaagggac cacggtcacc gtctcctcag                         760

<210> SEQ ID NO 8
<211> LENGTH: 757
<212> TYPE: DNA
<213> ORGANISM: Homo sapiens

<400> SEQUENCE: 8
gagctccaga tgacccagtc tccatcctcc ctgtctgtat cagtaggaga cagagtcacc    60
atcacttgcc gggcaagtca gagcattagc ggctatttaa attggtatca gcagaaacca   120
gggaaagccc ctaaactgct gatctatggt gcatccagtt tgcaaagtgg ggtcccatca   180
aggttcagtg gcagtggatc tgggacagat ttcgctctca ccatcagcag tgtgcaacct   240
gaagattttg caagttactt ctgtcaacag agtcacagcg tcccgatcaa cttcggccaa   300
```

```
gggacacgac tggagattaa aggtggttcc tctagatctt cctcctctgg tggcggtggc    360
tcgggcggtg gtgggcaggt gcagctggtg cagtctgggg gaggcttggc acagcctggc    420
aagtccctga gactctcctg tgtagcctct ggattcacct ttgatgatta tgccatgcac    480
tgggtccggc aagctccagg aagggcctg gagtgggtct caggtattaa ttggaatagt     540
ggtagcattg gttatgcgga ctctgtgaag ggccgattca ccatctccag agacaacgcc    600
aagaactccc tgtatctgca aatgaacagt ctgagagctg aggacacggc cttgtattac    660
tgtgcaaaag agcaaggata ttgtgatagt accggctgcc agagggggatc cggaatggac   720 gtctggggcc aagggaccac ggtcaccgtc tcctcag                             757

<210> SEQ ID NO 9
<211> LENGTH: 757
<212> TYPE: DNA
<213> ORGANISM: Homo sapiens

<400> SEQUENCE: 9
gagctccaga tgacccagtc tccatcctcc ctgtctgcat ctgtaggaga cagagtcacc     60
atcacttgcc aggcgagtca ggacattagc aactatttaa attggtatca gcagaaacca    120
gggaaagccc ctaagctcct gatctacgat gcatccaatt tggaaacagg gtcccatca     180 aggctcagtg aagtggatc tgggacagat tttactttca ccatcagcag cctgcagcct     240
gaagatattg caacatatta ctgtcaacag tatgatgatc tccccctcac tttcggcgga    300
gggaccaagc tggagatcaa aggtggttcc tctagatctt cctcctctgg tggcggtggc    360
tcgggcggtg gtgggcaggt gcagctggtg cagtctgggg gaggcttggc acagcctggc    420
aagtccctga gactctcctg tgtagcctct ggattcacct ttgatgatta tgccatgcac    480
tgggtccggc aagctccagg aagggcctg gagtgggtct caggtattaa ttggaatagt     540
ggtagcattg gttatgcgga ctctgtgaag ggccgattca ccatctccag agacaacgcc    600
aagaactccc tgtatctgca aatgaacagt ctgagagctg aggacacggc cttgtattac    660
tgtgcaaaag agcaaggata ttgtgatagt accggctgcc agagggggatc cggaatggac   720 gtctggggcc aagggaccac ggtcaccgtc tcctcag                             757

<210> SEQ ID NO 10
<211> LENGTH: 757
<212> TYPE: DNA
<213> ORGANISM: Homo sapiens

<400> SEQUENCE: 10
gagctccaga tgacccagtc tccatcgtcc ctggctgcat ctgtgggaga cagagtcacc     60
atcacttgcc gggcaagtca cgacattaaa aatgatttag ctggtatca gcatcaacca     120 gggaaagccc ctaagctcct gatctatgct gcatccagtt tacaaagtgg ggtcccgtca    180
agattcagcg gcagtggatc cggcacaaat ttcacccctca ccatcaatag cctgcagcct    240
gaagattttg caacttatta ctgtctacat gattacactt accctcgcac gttcggccaa    300
gggaccaagg tggaaatcaa aggtggttcc tctagatctt cctcctctgg tggcggtggc    360
tcgggcggtg gtgggcaggt gcagctggtg cagtctgggg gaggcttggc acagcctggc    420
aagtccctga gactctcctg tgtagcctct ggattcacct ttgatgatta tgccatgcac    480
tgggtccggc aagctccagg aagggcctg gagtgggtct caggtattaa ttggaatagt     540
ggtagcattg gttatgcgga ctctgtgaag ggccgattca ccatctccag agacaacgcc    600
aagaactccc tgtatctgca aatgaacagt ctgagagctg aggacacggc cttgtattac    660
```

```
tgtgcaaaag agcaaggata ttgtgatagt accggctgcc agaggggatc cggaatggac    720
gtctggggcc aagggaccac ggtcaccgtc tcctcag                             757

<210> SEQ ID NO 11
<211> LENGTH: 757
<212> TYPE: DNA
<213> ORGANISM: Homo sapiens

<400> SEQUENCE: 11
gagctccaga tgacccagtc tccatcctcc ctgtctgcat ctgtaggaga cagagtcacc     60
atcacttgcc gggcaagtca gggcattaga tatgatgtag ctggtatcag cagaaaccca    120
gggaaagccc ctaagctcct gatctatgct gcatccacct tgcaaagtgg ggtcccatca    180
aggttcagtg gcagcggatc tgagacagat ttcactctca ccatcaacag tctgcagcct    240
gaagattctg caacttacta ctgtcaacag agttacagta tccccttcga cgttcggcca     300
gggaccaagg tggagatcaa aggtggttcc tctagatctt cctcctctgg tggcggtggc    360
tcgggcggtg gtggggaggt gcagctgttg agtctgggg gaggcttggc acagcctggc     420
aagtccctga ctctcctg tgtagcctct ggattcacct ttgatgatta tgccatgcac     480
tgggtccggc aagctccagg aagggcctg gagtgggtct caggtattaa ttggaatagt    540
ggtagcattg gttatgcgga ctctgtgaag ggccgattca ccatctccag agacaacgcc    600
aagaactccc tgtatctgca aatgaacagt ctgagagctg aggacacggc cttgtattac    660
tgtgcaaaag agcaaggata ttgtgatagt accggctgcc agaggggatc cggaatggac    720
gtctggggcc aagggaccac ggtcaccgtc tcctcag                             757

<210> SEQ ID NO 12
<211> LENGTH: 769
<212> TYPE: DNA
<213> ORGANISM: Homo sapiens

<400> SEQUENCE: 12
gagctcgagc tgactcagcc acctcagtg tctgggaccc ccgggcagag ggtcaccatc      60
tcttgttctg gaagcagctc caacatcgga agtgatacta taaactggta ccagcagctc    120
ccaggaacgg ccccccaaact cctcatctat agtaataatc agcggccctc aggggtccct   180
gaccgattct ctggctccaa gtctggcacc tcagcctccc tggccatcag tgggctccag    240
tctgaggatg aggctgacta ttactgtgca acatgggatg acggcctgcg tggcatggtg    300
ttcggcgaag caccaagct gaccgtccta ggcggtggtt cctctagatc ttcctcctct     360
ggtggcggtg gctcgggcgg tggtgggcag gtgcagctgc aggagtcggg gggaggcttg    420
gcacagcctg gcaagtccct gagactctcc tgtgtagcct ctggattcac ctttgatgat    480
tatgccatgc actgggtccg gcaagctcca gggaagggcc tggagtgggt ctcaggtatt    540
aattggaata gtggtagcat tggttatgcg gactctgtga agggccgatt caccatctcc    600
agagacaacg ccaagaactc cctgtatctg caaatgaaca gtctgagagc tgaggacacg    660
gccttgtatt actgtgcaaa agagcaagga tattgtgata gtaccggctg ccagagggga    720
tccggaatgg acgtctgggg ccaagggacc acggtcaccg tctcctcag                769

<210> SEQ ID NO 13
<211> LENGTH: 778
<212> TYPE: DNA
<213> ORGANISM: Homo sapiens
```

<400> SEQUENCE: 13

```
gagctcgtgt tgacgcagcc gccctcagtg tctggggccc cagggcggag ggtcaccatc      60
tcctgcactg ggagcagctc caacatcggg gctgcttatg atgtacactg gtaccagcag     120
cttccaggaa cagcccccaa actcctcatc tttggtaaca ccaatcggcc ctcaggggtc     180
cctgaccgat tctctggctc caagtctggc acctcagcct ccctggccat cactgggctc     240
cagtctgagg atgaggctga ctattactgt gcaacatggg atgacagccg ggatggtccg     300
gaagtggtgt tcggcggagg caccgagctg accgtcctcg gtggtggttc ctctagatct     360
tcctcctctg gtggcggtgg ctcgggcggt ggtggggagg tgcagctggt ggagtctggg     420
ggaggcttgg cacagcctgg caagtccctg agactctcct gtgtagcctc tggattcacc     480
tttgatgatt atgccatgca ctgggtccgg caagctccag ggaagggcct ggagtgggtc     540
tcaggtatta attggaatag tggtagcatt ggttatgcgg actctgtgaa gggccgattc     600
accatctcca gagacaacgc caagaactcc ctgtatctgc aaatgaacag tctgagagct     660
gaggacacgg ccttgtatta ctgtgcaaaa gagcaaggat attgtgatag taccggctgc     720
cagaggggat ccggaatgga cgtctggggc caagggacca cggtcaccgt ctcctcag      778
```

<210> SEQ ID NO 14
<211> LENGTH: 769
<212> TYPE: DNA
<213> ORGANISM: Homo sapiens

<400> SEQUENCE: 14

```
gagctcgtgc tgactcagcc accttcggcg tctgggaccc ccggacagag ggtcaccatc      60
tcttgttctg gaagcaactc caacatcgga agtgattatg tgtactggta tcagcggttc     120
ccaggaacgg cccccaaaact tctcatctat agtaataatc agcggccctc aggggtccct     180
gaccgattct ctggctccaa gtctggcacc tcagcctccc tggccatcag tggactccag     240
tctgaggatg aggctgagta ttactgtgca acatgggatg acgccctgcg tggcatggtg     300
ttcggcgaag gcaccaagct gaccgtccta ggtggtggtt cctctagatc ttcctcctct     360
ggtggcggtg gctcgggcgg tggtggggag gtgcagctgg tggagtctgg gggaggcttg     420
gcacagcctg gcaagtccct gagactctcc tgtgtagcct ctggattcac ctttgatgat     480
tatgccatgc actgggtccg gcaagctcca gggaagggcc tggagtgggt ctcaggtatt     540
aattggaata gtggtagcat tggttatgcg gactctgtga agggccgatt caccatctcc     600
agagacaacg ccaagaactc cctgtatctg caaatgaaca gtctgagagc tgaggacacg     660
gccttgtatt actgtgcaaa agagcaagga tattgtgata gtaccggctg ccagagggga     720
tccggaatgg acgtctgggg ccaagggacc acggtcaccg tctcctcag                769
```

<210> SEQ ID NO 15
<211> LENGTH: 775
<212> TYPE: DNA
<213> ORGANISM: Homo sapiens

<400> SEQUENCE: 15

```
gagctcatgc tgactcagcc ccactctgtg tcggagtctc cggggaagac ggtaaccatc      60
tcctgcaccc gcagcagtgg cagcattgcc agcaactttg tccagtggta ccagcagcgc     120
ccgggcaagt cccccaccac tgtaatttat gaggacaacc aaagaccgtc tggggtacct     180
gatcggttct ctggctccgt cgacaggtcc tccaactctg cctccctcac catctctgga     240
ctgcagactg aggacgaggc tgactattac tgtcagtctt tttatgacgg cgtcccttct     300
```

```
tgggtgttcg gcggaggcac cgagctgacc gtcctcggcg gtggttcctc tagatcttcc    360
tcctctggtg gcggtggctc gggcggtggt ggggaggtgc agctggtgga gtctggggga    420
ggcgtggtcc aacctggggg gtccctaaga ctctcctgtg tagcctctgg attcaccttt    480
gatgattatg ccatgcactg ggtccggcaa gctccaggga agggcctgga gtgggtctca    540
ggtattaatt ggaatagtgg tagcattggt tatgcggact ctgtgaaggg ccgattcacc    600
atctccagag acaacgccaa gaactccctg tatctgcaaa tgaacagtct gagagctgag    660
gacacggcct tgtattactg tgcaaaagag caaggatatt gtgatagtac cggctgccag    720
aggggatccg gaatggacgt ctggggccaa gggaccacgg tcaccgtctc ctcag        775
```

<210> SEQ ID NO 16
<211> LENGTH: 763
<212> TYPE: DNA
<213> ORGANISM: Homo sapiens

<400> SEQUENCE: 16

```
gagctcatgc tgactcagcc ccactctgtg tcggagtctc cggggaagac ggtaaccatc    60
tcctgcaccc gcagcagtgg cagcattgcc agcaactttg tccagtggta ccagcagcgc   120
ccgggcaagt cccccaccac tgtaatttat gaggacaacc aaagaccgtc tggggtacct   180
gatcggttct ctggctccgt cgacaggtcc tccaactctg cctccctcac catctctgga   240
ctgcagactg aggacgaggc tgactattac tgtcagtctt tttatgacgg cgtcccttct   300
tgggtgttcg gcggaggcac cgagctgacc gtcctcggcg gtggttcctc tagatcttcc   360
tcctctggtg gcggtggctc gggcggtggt ggcaggtgc agctggtgca gtctggggga   420
ggcgtggtcc agcctggggg gtccctgaga ctctcctgtg tagcctctgg attcaccttt   480
gatgattatg ccatgcactg ggtccggcaa gctccaggga agggcctgga gtgggtctca   540
ggtattagtt ggaatagtgg tgccataggc tatgcagact ctgtgaaggg ccgattcacc   600
atctccagag acaacgccaa gaactccctg tatctgcaaa tgaacagtct gagaactgag   660
gacacggccg tgtattactg tgcaaaagat gggattacaa ttttggagt gggcgacggt   720 ctggatgtct ggggccaagg gacaatggtc accgtctctt cag                    763
```

<210> SEQ ID NO 17
<211> LENGTH: 745
<212> TYPE: DNA
<213> ORGANISM: Homo sapiens

<400> SEQUENCE: 17

```
gagctccaga tgacccagtc tccatcctcc ctgtctgcat ctgtaggaga cagagtcacc    60
atcacttgcc aggcgagtca ggacattggc aactatttaa attggtatca gcagaaacca   120
gggaaagccc ctaaactcct gatctacgat gcatcctatt ggaaacaggg gtcccatca   180 aggttcagtg aagtggatc tgggacagat tttactttca ccatcagcag cctacagcct   240
gaagatattg caacatatta ctgtcaacag tatgataatc tcccgttcac tttcggccct   300
gggaccaaag tggatatcaa aggtggttcc tctagatctt cctcctctgg tggcggtggc   360
tcgggcggtg gtgggaggt gcagctggtg agtctgggg gaggcttggt acagcctggc   420
aggtccctga gactctcctg tgcagcctct ggattcacct ttgatgatta tgccatgcac   480
tgggtccggc aagctccagg gaagggcctg agtgggtct caggtattag ttggaatagt   540
ggtagcatag actatgcgga ctctgtgaag ggccgattca ccatctccag agacaacgcc   600
```

```
aagaactccc tgtatctgca aatgaacagt ctgagagttg aggacacggc cttgtattat    660
tgtgcaaaag atgggagtag ggttttttgga gtgggcggtg ttttgatttt ctggggccaa    720
gggacaatgg tcaccgtctc ttcag                                           745
```

<210> SEQ ID NO 18
<211> LENGTH: 745
<212> TYPE: DNA
<213> ORGANISM: Homo sapiens

<400> SEQUENCE: 18

```
gagctcgtga tgactcagtc tccatcctcc ctgtctgcat ctgtaggaga cagagtcacc     60
atcacttgcc gggcaagtca gggcattacc gatgacttag ggtggtatca gcagaagcca    120
ggaaaagccc ctaagctcct gatctatgcc acatccaatt tagaaagtgg ggtcccatca    180
aggttcagcg gcagtggatc tgacacagaa ttcactctca ccatcagtag cctgcagcct    240
gaagatcttg caacttatta ctgtctacaa gattacagtt acccgtacac ttttggccag    300
gggaccaagg tggagatcaa aggtggttcc tctagatctt cctcctctgg tggcggtggc    360
tcgggcggtg gtggggaggt gcagctagtg gagtctgggg gaggcttggt acagcctggc    420
aggtccctga gactctcctg tgcagcctct ggattcacct ttgatgatta cgccatgcac    480
tgggtccggc aagctccagg aagggcctg gagtgggtct caggtattag ttggaatagt    540
ggtagcatag actatgtgga ctctgtgaag ggccgattca ccatctccag agacaacgcc    600
aagaactacc tgtatctgca aatgaacagt ctgagagttg aggacacggc cttatattat    660
tgtgcaaaag atggcagtag ggttttttgga gtgggcggtg ttttgatttt ctggggccaa    720
gggacaatgg tcaccgtctc ttcag                                           745
```

<210> SEQ ID NO 19
<211> LENGTH: 745
<212> TYPE: DNA
<213> ORGANISM: Homo sapiens

<400> SEQUENCE: 19

```
gagctccaga tgacccagtc tccttccacc ctgtctgcat ctgtaggaga cagagtcacc     60
atcacttgcc gggccagtca gagtattagt agttggttgg cctggtatca gcagaaacca    120
ggaaaagccc ctaagctcct gatctataag cgtctagtt tagaaagtgg ggtcccatca    180
aggttcagcg gcagtggatc tgggacagaa ttcactctca ccatcagcag cctgcagcct    240
gatgattttg caacttatta ctgccaacag tataatactt attcgaggac gttcggccaa    300
gggaccaagg tggaaatcaa aggtggttcc tctagatctt cctcctctgg tggcggtggc    360
tcgggcggtg gtggggaggt gcagctggtg gagtctgggg gaggcttggt acagcctggc    420
aggtccctga gactctcctg tgcagcctct ggattcacct ttgatgatta ttccatgcac    480
tgggtccggc aagctccagg aagggcctg gagtgggtct caggtatcag ttggaacagt    540
ggtggcatag ctatgcgga ctctgtgagg ggccgattca ccatctccag agacaacgcc    600
aagaactccc tgtatctgca aatgaacagt ctgagagctg aggacacggc cttgtattat    660
tgtgcaaaag atgggatgag ggttttttgga gtgggcggtg ttttgatttt ctggggccaa    720
gggacaatgg tcaccgtctc ttcag                                           745
```

<210> SEQ ID NO 20
<211> LENGTH: 745
<212> TYPE: DNA
<213> ORGANISM: Homo sapiens

<400> SEQUENCE: 20

```
gagctccaga tgacccagtc tccatcctcc ctgtctgcat ctgttggaga cagagtcacc        60
atcacttgcc aggcgagtcg tgacattagc aactatttaa attggtatca acacattcca       120
ggaaaggccc ctaagctcct catattccat gcatccactt tggaagcagg gatcccatca       180
aggttcagtg gaagtggatc agagacatct tttactttca ccataagaag cctacagcct       240
gaagatgttg caacatatta ctgtcaacaa tatgataatc tccccttcac tttcggccct       300
gggaccaaag tggatatcaa aggtggttcc tctagatctt cctcctctgg tggcggtggc       360
tcgggcggtg tggggaggt gcagctggtg agtctgggg gaggcttggt acagcctggc        420
aggtccctga ctctcctg tgcagcctct ggattcacct ttgatgatta tgccatgtac        480
tgggtccggc aagctccagg aagggcctg agtgggtct caggtattag ttggaatagt        540
ggtagcatag actatgcgga ctctgtgaag gccgattca ccatctccag agacaacgcc        600
aagaactccc tgtatctgca aatgaacagt ctgagagctg aggacacggc cttgtattat       660
tgtgcaaaag atgggatgag ggttttttgga gtgggcggtg gttttgattt ctggggccaa       720
gggacaatgg tcaccgtctc ttcag                                              745
```

<210> SEQ ID NO 21
<211> LENGTH: 757
<212> TYPE: DNA
<213> ORGANISM: Homo sapiens

<400> SEQUENCE: 21

```
gagctcatgc tgactcagcc ccactcagcg tctgggaccc ccgggcagag ggtcaccatc        60
tcttgttctg gaagcagctc caacatcgga agtaatactg taaactggta ccagcagctc       120
ccaggaacgg cccccaaact cctcatctat agtaataatc agcggccctc aggggtccct       180
gaccgattct ctggctccaa gtctggcacc tcagcctccc tggccatcag tgggctccag       240
tctgaggatg aggctgatta ttactgtgca gcatgggatg acagcctgaa tggtccggta       300
ttcggcggag gcaccaaggt gaccgtccta ggcggtggtt cctctagatc ttcctcctct       360
ggtggcggtg gctcgggcgg tggtggggag gtgcagctgg tggagtctgg gggaggcttg       420
gtacagcctg gcaggtccct gagactctct gtgcagcct ctggattcac ctttgatgat       480
tatgccatgt actgggtccg gcaagctcca gggaagggcc tggagtgggt ctcaggtatt       540
agttggaata gtggtagcat agactatgcg gactctgtga agggccgatt caccatctcc       600
agagacaacg ccaagaactc cctgtatctg caaatgaaca gtctgagagc tgaggacacg       660
gccttgtatt attgtgcaaa agatgggatg agggttttg gagtgggcgg tggttttgat       720
ttctggggcc aagggacaat ggtcaccgtc tcttcag                                757
```

<210> SEQ ID NO 22
<211> LENGTH: 757
<212> TYPE: DNA
<213> ORGANISM: Homo sapiens

<400> SEQUENCE: 22

```
gagctcgtgg tgacgcagcc gccctcagcg tctgggaccc ccgggcagag ggtcaccatc        60
tcttgttctg gaagcagctc caacatcgga agtaatactg taaactggta ccagcagctc       120
ccaggaacgg cccccaaact cctcatctat agtaataatc agcggccctc aggggtccct       180
gaccgattct ctggctccaa gtctggcacc tcagcctccc tggccatcag tgggctccag       240
```

```
tctgaggatg aggctgatta ttactgtgca acgtgggatg acggcctgaa tggcatggtg      300
ttcggcggag ggaccaagct gaccgtccta ggcggtggtt cctctagatc ttcctcctct      360
ggtggcggtg gctcgggcgg tggtggggag gtgcagctgg tggagtctgg gggaggcttg      420
gtacagcctg gcaggtccct gagactctcc tgtgcagcct ctggattcac ctttgatgat      480
tatgccatgc actgggtccg gcaagctcca gggaagggcc tggagtgggt ctcaggtatt      540
agttggaata gtgggaccat aggctatgcg actctgtga agggccgatt caccatctcc      600
agagacaacg ccaagaactc cctgtatctg caaatgaaca gtctgagagc tgaggacacg      660
gccgtgtatt actgtgcaaa agatgggatt acggttttttg gagtgggcga tggtttggat      720
atctggggcc aagggacaat ggtcaccgtc tcttcag                               757
```

<210> SEQ ID NO 23
<211> LENGTH: 751
<212> TYPE: DNA
<213> ORGANISM: Homo sapiens

<400> SEQUENCE: 23

```
gagctccaga tgacccagtc tccttcctcc ctgtctgcat ctgtaggaga cagagtcacc       60
atcacttgcc gggcaagtca gggcattgga aatgatttag ctggtatca gcagaaacca      120 gggaaagccc ctaagctcct gatctatgct gcatccagtt tacaaagtgg ggtcccatca      180
aggttcagcg gcagtggatc tggcacagat ttcactctca ccatcggcag cctgcagcct      240
gaagattttg caacttatta ctgtctacaa gattacaatt acccattcac tttcggccct      300
gggaccaaag tggatatcaa aagtggttcc tctagatctt cctcctctgg tggcggtggc      360
tcgggcggtg gtggggaggt gcagctggtg gagtctgggg gaaccttggt acagcctggc      420
aggtccctga gactcctctg tgcagcctct ggattcagct ttgatgatta tgccatgcag      480
tgggtccggc aagctccagg aagggcctg gagtgggtct caggtattag ctggaatagt      540
ggtagcatag cctatgcgga ctctgtgaag ggccgattca ccatctccag agacaacgcc      600
aagagctccc tgtatctgct aatgaacagt ctgagagctg aggacacggc cttgtattac      660
tgtgcaaaag cgggcacaga ttattatgat agtagtgctt ccgaacttcc tgactactgg      720
ggccagggaa ccctggtcac cgtctcctca g                                     751
```

<210> SEQ ID NO 24
<211> LENGTH: 754
<212> TYPE: DNA
<213> ORGANISM: Homo sapiens

<400> SEQUENCE: 24

```
gagctccaga tgacccagtc tccatccttc ctgtctgcat ctgtaggaga cagagtcacc       60
atcacttgcc gggccagtca gggcattagc agttatttag cctggtatca gcaaaaaccg      120
gggaaagccc ctaaactcct gatctatggt gcatctactt tgcaaagtgg ggtcccatca      180
aggttcagcg gcagtggatc tgggacagaa ttcactctca ccatcagcag cctgcagcct      240
gatgattttg caacttatta ctgccaacag tataatagtt atccgtggac gttcggccaa      300
gggaccaagg tggaaatcaa aagtggttcc tctagatctt cctcctctgg tggcggtggc      360
tcgggcggtg gtgggcaggt gcagctgcag gagtcggggg gaggcttggt acagcctggc      420
aggtccctga gactcctctg tgcagcctct ggattcacct ttgatgatta tgccatgcac      480
tgggtccggc aagctccagg aagggcctg gagtgggtct caggtattag ttggaatagt      540
ggtagcatag cctatgcgga ctctgtgaag ggccgattca ccatctccag agacaacgcc      600
```

```
aagaactccc tgtatctgca aatgaacagt ctgagagctg aggacacggc cttctattac    660
tgtgcgaaag tgggcgggga tacctatgat attacaagtg gggcggatta cttcgatctc    720
tggggccgtg gcgccctggt cactgtctcc tcag                                754
```

<210> SEQ ID NO 25
<211> LENGTH: 757
<212> TYPE: DNA
<213> ORGANISM: Homo sapiens

<400> SEQUENCE: 25

```
gagctcgtga tgacccagtc tccagccacc ctgtctgtgt ctccagggga aagagccacc     60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataataact ggccctcgat caccttcggc    300
caagggacac gactggagat taaggtggt tcctctagat cttcctcctc tggtggcggt    360
ggctcgggcg gtggtgggca ggtgcagctg gtgcagtctg ggggaggctt ggtacagcct    420
ggcaggtccc tgagactctc ctgtgcagcc tctggattca cctttgatga ttatgccatg    480
cactgggtcc ggcaagctcc agggaagggc ctggagtggg tctcaggtat tagttggaat    540
agtggtagca tagcctatgc ggactctgtg aagggccgat tcaccatctc cagagacaac    600
gccaagaact ccctgtatct gcaaatgaac agtctgagag ctgaggacac ggccttctat    660
tactgtgcga aagtgggcgg ggatacctat gatattacaa gtgggcgga ttacttcgat    720 ctctggggcc gtggcgccct ggtcactgtc cctcag                              757
```

<210> SEQ ID NO 26
<211> LENGTH: 754
<212> TYPE: DNA
<213> ORGANISM: Homo sapiens

<400> SEQUENCE: 26

```
gagctcgtgg tgacgcagcc gccctcagtg tctggggccc cagggcagag ggtcaccatc     60
tcctgcactg ggagcagctc caacatcggg gcaggttatg atgtacactg gtaccagcag    120
cttccaggaa cagccccca actcctcatt tatggtaaca aaaatcggcc ctcagggtc    180 cctgaccggt tctctggctc caagtctggc acctcagcct ccctggccat cactgggctc    240
cgggctgagg atgaggctga ttactactgc agtccttcg acagcagcct ggggtgggtg    300
ttcggcggag ggacccagct gaccgtcctc ggcggtggtt cctctagatc ttcctcctct    360
ggtggcggtg gctcggcgg tggtgggcag gtgcagctgg tgcagtctgg gggaggcttg    420
gtccagcctg gggggtccct gagagtctcc tgcgcagcct ctggattcac ctctaatatc    480
ttttggatga gttgggtccg ccaggctcca ggtaaggggc tggagtgggt ggccaacata    540
gacgaagatg gaagtgagaa aaactatgtg gactctgtga agggccgatt caccatctcc    600
agagacaacg ccaagaactc actgtatctg caaatgaaca gcctgagagc cgaggacacg    660
gctgtgtatt actgtgcgag ggagtcgttt tactatggtt cggggactta ttttgacttc    720
tggggccagg gaaccctggt caccgtctcc tcag                                754
```

<210> SEQ ID NO 27
<211> LENGTH: 751
<212> TYPE: DNA

<213> ORGANISM: Homo sapiens

<400> SEQUENCE: 27

| gagctcgtgc tgactcagcc accctcggtg ccagtggccc caggacagac ggccaacatt | 60 |
| agctgtgggg gaaacaacat tggaagacag actgtccact ggtaccagca gaagccaggc | 120 |
| caggcccctg tgttggtcgt ctttgatgat agcgaccggc ccgcagggat ccctgagcga | 180 |
| ttctctggct ccaactctgg gaacacggcc accctgacca tcagcagggt cgaagccggg | 240 |
| gatgaggccg actattactg tcaggtgtgg atagtagta gtgatcatgt ggtcttcggc | 300 |
| ggaggcaccc agctgaccgt cctcggcggt ggttcctcta gatcttcctc ctctggtggc | 360 |
| ggtggctcgg gcggtggtgg gcaggtgcag ctggtgcagt ctggggagg cgtggtccag | 420 |
| tctggaggt ccctgagact ctcctgtgca gcctctggat tcacgttcag tgactatgcc | 480 |
| atgcactggg tccgccaggc cccagcaag gggctggagt gggtggcagt tatatcacat | 540 |
| ggtgaaccaa aaaatacac cggagactcc gtgaagggcc gatttatcat ctccagagac | 600 |
| aattccaaga cacagtgtt tttgcaaatg aacagcctga gagttgagga cacggctgtt | 660 |
| tattactgtg cgagagatcg tgtagaaggt tacgtttggg ggcacgtt tgaccactgg | 720 |
| ggccagggaa ccccggtcac cgtctcctca g | 751 |

<210> SEQ ID NO 28
<211> LENGTH: 754
<212> TYPE: DNA
<213> ORGANISM: Homo sapiens

<400> SEQUENCE: 28

| gagctcgtgc tgactcagcc accttcagtg gccgtgtccc caggacagac agccagcatc | 60 |
| acctgctctg gagataaatt gggggataaa tatgtttcct ggtatcagca gaagccaggc | 120 |
| cagtcccctg ttctggtcat gtatcgagat accaagcggc cctcagggat ccctgagcga | 180 |
| ttttctggct ccaactccgg gaacacagcc actctgacca tcagcgggac ccaggctatg | 240 |
| gatgaggctg actattactg tcaggcgtgg acagcaaca ctggggtgtt cggcggaggc | 300 |
| accaagctga ccgtcctagg cggtggttcc tctagatctt cctcctctgg tggcggtggc | 360 |
| tcgggcggtg gtgggaggt gcagctgttg gagtctggcc cagggctgga aaaggtttcg | 420 |
| gagaccctgt ccctcacgtg taatgtctct ggtgtctcca taagtagtcc tgattattat | 480 |
| tgggcctgga tccgccagcc ccccgggaag gggctggagt ggattggcag tatctttttac | 540 |
| agtggaccta cctcctggaa tccgtccctc aagaatcgag tcaccatctc agtagacacg | 600 |
| tccaagaatc aattctccct gaaaatgaag tctgtgacgg ccgcggacac ggccgtatat | 660 |
| tactgtgcga ggtccttcgg tttcgggaga tatgagcccg cggatgatgc atttgatatc | 720 |
| tggggccgag ggagactggt catcgtctct ccag | 754 |

<210> SEQ ID NO 29
<211> LENGTH: 760
<212> TYPE: DNA
<213> ORGANISM: Homo sapiens

<400> SEQUENCE: 29

| gagctcgagc tgactcagcc accctcagtg tcagtggccc tgggacagac ggccaggatt | 60 |
| acctgtgggg gaaacaacat tggaagtaaa aatgtgcact ggtaccagca gaagccaggc | 120 |
| caggcccctg tgctggtcat ctatagggat agcaaccggc cctctgggat ccctgagcga | 180 |
| ttctctggct ccaactcggg gaacacggcc accctgacca tcagcagagc caagccggg | 240 |

```
gatgaggctg actattactg tcaggcgtgg gacagaagca ctgctcatgt ggtattcggc    300
ggagggacca agctgaccgt cctaggtggt ggttcctcta gatcttcctc ctctggtggc    360
ggtggctcgg gcggtggtgg gcaggtgcag ctggtgcagt ctgggggagg cgtggtccag    420
cctgggaggt ccctgagact ctcctgtaca gcctctagat tcaatttcag gagttttgcc    480
atgcactggg tccgccaggc tccaggcaag ggctggagt gggtggcgat gtttccttat    540
gacgaaaata atacatacta tggagactcc gtgaagggcc gattcaccat ctccagagac    600
aattccaaga gatgctgta cctgcaaatg aacgatctca gaattgacga cacggcactg    660
tactactgtg cgaggcaggg atgggtaata gagacatctg gtataagagc gagtggcttt    720
gacgtctggg gtcaagggac actggtcacc gtctcctcag                         760

<210> SEQ ID NO 30
<211> LENGTH: 757
<212> TYPE: DNA
<213> ORGANISM: Homo sapiens

<400> SEQUENCE: 30
gagctcgtgc tgacgcagcc gccctcagcg tctgggaccc ccgggcagag ggtcaccatc     60
tcttgttctg gaagcagctc caacatcgga agtaatactg taaactggta ccagcagctc    120
ccaggaacgg cccccaaact cctcatctat agtaataatc agcggccctc aggggtccct    180
gaccgattct ctggctccaa gtctggcacc tcagcctccc tggccgtcag tgggctccag    240
tctgaggatg aggctgatta ttactgtgca gcatgggatg acagcctgaa tggtccggta    300
ttcggcggag gcacccagct gaccgtcctc ggtggtggtt cctctagatc ttcctcctct    360
ggtggcggtg gctcgggcgg tggtgggcag gtgcagctgc aggagtcggg gggaggcttg    420
gtacagcctg gcaggtccct gagactctcc tgtgcagcct ctggattcac ctttgatgat    480
tatgccatgc actgggtccg gcaagctcca gggaagggcc tggagtgggt ctcaggtatt    540
agttggaata gtgggaccat aggctacgcg gactctgtga agggccgatt caccatctcc    600
agagacaacg ccaagaactc cctgtatctg caaatgaaca gtctgagagc tgaggacacg    660
gccgtgtatt actgtgcaaa gatgggatt acggttttg gagtgggcga tggtttggat    720
atctggggcc aagggacaat ggtcaccgtc tcttcag                            757

<210> SEQ ID NO 31
<211> LENGTH: 751
<212> TYPE: DNA
<213> ORGANISM: Homo sapiens

<400> SEQUENCE: 31
gagctcgtga tgacccagtc tccatcttcc gtgtctgcat ctgtaggaga cagagtcatc     60
atcacttgtc gggcgagtca gggtattagc agcagttatt tagcctggta tcagcaaaaa    120
ccagggaaag cccctaagct cctgatctat gctgcattca ctttacaaag tggggtccca    180
tcaaggttca gcggcagtgg atctgggaca gaattcactc tcacaatcag cagcctgcag    240
cctgaagatt ttgcaactta tttctgtcaa gaccttagtg ttatcctcg aaacaccttc    300 ggccaaggga cacgactgga gattaaaggt ggttcctcta gatcttcctc ctctggtggc    360
ggtggctcgg gcggtggtgg ggaggtgcag ctggtggagt ctgggggagg cttggtacag    420
cctggcaggt ccctgagact ctcctgtgca gcctctggat tcacctttga tgattatgcc    480
atgcactggg tccggcaagc tccagggaag ggcctggagt gggtctcagg tattagttgg    540
```

```
aatagtggta gcatagacta tgcggactct gtgaagggcc gattcaccat ctccagagac    600
aacgccaaga actccctgta tctgcaaatg aacagtctga gagttgagga cacggccttg    660
tattattgtg caaaagatgg gagtagggtt tttggagtgg gcggtggttt tgatttctgg    720
ggccaaggga caatggtcac cgtctcttca g                                   751
```

<210> SEQ ID NO 32
<211> LENGTH: 745
<212> TYPE: DNA
<213> ORGANISM: Homo sapiens

<400> SEQUENCE: 32

```
gagctcgtga tgacccagtc tccatcctcc ctgtctgcat ctgtaggaga cagagtcacc     60
atcacttgcc aggcgagtca ggacatcagg aagtatttaa attggtatca gcagaaagca    120
gggaaagccc ctaaactcct gatctacgat gcatctaagt tggatatagg gctcccatca    180
aggttcagtg aagtggatc tgggacagat tttactttca ccatcagcag cctgcagcct    240
gaagatattg caacatatta ctgtcagcag tttgataatc tccccttcac tttcggcgga    300
gggaccaagg tggaaatcaa aggtggttcc tctagatctt cctcctctgg tggcggtggc    360
tcgggcggtg gtggggaggt gcagctggtg gagtctgggg gaggcttggt acagcctggc    420
aggtccctga gactctcctg tgcagcctct ggattcacct tgatgattta tgccatgcac    480
tgggtccggc aagctccagg aagggcctg gagtgggtct caggtattag ttggaatagt    540
gggaccatag gctatgcgga ctctgtgaag ggccgattca ccatctccag agacaacgcc    600
aagaactccc tgtatctgca aatgaacagt ctgagagctg aggacacggc cgtgtattac    660
tgtgcaaaag atgggattac ggttttgga gtgggcgatg gtttggatat ctggggccaa    720
gggacaatgg tcaccgtctc ttcag                                         745
```

<210> SEQ ID NO 33
<211> LENGTH: 739
<212> TYPE: DNA
<213> ORGANISM: Homo sapiens

<400> SEQUENCE: 33

```
gagctcatgc tgactcagcc accctcagcg tctgggaccc ccgggcagag ggtcaccatc     60
tcttgttctg gaagcagctc caacatcgga agtaatactg taaactggta ccagcagctc    120
ccaggaacgg cccccaaact cctcatctat aggaataatc agcggccctc aggggtccct    180
gaccgattct ctggctccaa gtctggcacc tcagcctccc tggccatcag tgggctccgg    240
tccgaggatg aggctgatta ttactgtgca gcatgggatg acagcctgag tggttgggtg    300
ttcggcggag gcacccagct gaccgtcctc ggcggtggtt cctctagatc ttcctcctct    360
ggtggcggtg gctcgggcgg tggtggggag gtgcagctgg tggagtctgg aggaggcttg    420
gtccagcctg gggggtccgt gagactctcc tgtgcagcct ctggatttca agtcagtagt    480
gaccacatga gctgggtccg ccaggctcca gggaagggac tgcagtgggt ctcagttatt    540
tatactgggg gcaactcata ctacgcagac tccgtgaagg gccgattcac cgtctccaga    600
gacaactcca ggaacacact ttttcttcaa atgaacagcc tgagtcgga ggacacggcc    660 atttattatt gtgtgagagg tccgcttac tatgacatag actactgggg ccagggagcc    720
ctggtcaccg tgtcctcgg                                                739
```

<210> SEQ ID NO 34
<211> LENGTH: 757

<212> TYPE: DNA
<213> ORGANISM: Homo sapiens

<400> SEQUENCE: 34

```
gagctcgtgt tgacgcagcc gccctcagcg tctgggaccc ccgggcagag ggtcaccatc    60
tcttgttctg gaagcagctc caacatcgga agtaatactg taaactggta ccagcagctc   120
ccaggaacgg cccccaaact cctcatctat agtaataatc agcggccctc agggtccct    180
gaccgattct ctggctccaa gtctggcacc tcagcctccc tggccatcag tgggctccag   240
tctgaggatg aggctgatta ttactgtgca gcatgggatg acagcctgaa tggtggggtg   300
ttcggcggag gcaccgagct gaccgtcctc ggcggtggtt cctctagatc ttcctcctct   360
ggtggcggtg gctcgggcgg tggtgggcag gtgcagctgc aggagtcggg gggaggcttg   420
gtacagcctg gcaggtccct gagactctcc tgtgcagcct ctggattcac ctttgatgat   480
tatgccatgc actgggtccg gcaagctcca gggaagggcc tggagtgggt ctcaggtatt   540
agttggaata gtggggccat aggctatgcg gactctgtga aggccgatt caccatctcc    600
agagacaacg ccaagaactc cctgtatctg caaatgaaca gtctgagagc tgaggacacg   660
gccgtgtatt actgtgcaaa agatgggatt acggttttg gagtgggcga tggtttggat   720
atctggggcc aagggacaat ggtcaccgtc tcttcag                            757
```

<210> SEQ ID NO 35
<211> LENGTH: 739
<212> TYPE: DNA
<213> ORGANISM: Homo sapiens

<400> SEQUENCE: 35

```
gagctcgtgc tgactcagcc accctcagcg tctgggaccc ccgggcagag ggtcaccatc    60
tcttgttctg gaagcagctc caacatcgga agtaatactg taaactggta ccagcagctc   120
ccaggaacgg cccccaaact cctcatctat agtaataatc agcggccctc agggtccct    180
gaccgattct ctggctccaa gtctggcacc tcagcctccc tggccatcag tgggctccag   240
tctgaggatg aggctgatta ttactgtgca acatgggatg acagcctgaa tggtcgggtg   300
ttcggcggag gcacccagct gaccgtcctc ggcggtggtt cctctagatc ttcctcctct   360
ggtggcggtg gctcgggcgg tggtgggcag gtgcagctgg tgcagtctgg gggagacttg   420
gtccagccgg ggggtccct gagactctcc tgtgtagcct ctggattcaa cgtcaatgac   480
aactacatga gctgggtccg ccaggctcca gggaaggggc tggagtgggt ctcaacgatt   540
tacagcgaaa ctctttcata ctacggagac tccgtgaagg gcagattcac cgtctccaga   600
gacggttcca agaacacggt gtttcttcaa atgagcagcc tgaaaggcga ggacacggct   660
gtttattatt gtgcttccga ggggggggc ctgacaattg actattgggg ccagggaacc   720
ctggtcgccg tctcctcag                                                 739
```

<210> SEQ ID NO 36
<211> LENGTH: 775
<212> TYPE: DNA
<213> ORGANISM: Homo sapiens

<400> SEQUENCE: 36

```
gagctcgtgg tgacgcagcc gccctctgca tctgctgccc tgggatcctc ggccaagctc    60
acctgcaccc tgagcagtgc ccacaagacc tacaccattg actggtatca gcagcagcaa   120
ggggaggccc ctcggtacct gatgcaactt aagagtgatg gaagctactc caaggggacc   180
```

```
ggggtccctg atcgcttctc gggctccagc tctggggctg accgttactt gatcatcccc    240
agcgtccagg ctgatgacga agccgactac tattgtggtg cagattatag cggtgggtat    300
tatgtgttcg gcggaggcac caagctgacc gtcctaggcg gtggttcctc tagatcttcc    360
ccctctggtg gcggtggctc gggcggtggt ggggaggtgc agctggtgga gtctgggget    420 gaggtgaaga agcctggggc ctcagtgaag gtctcctgca aggcttctac atacatgttc    480
accagttatg atatcaactg ggtgcgacag gccgctggac aagggcttga gtggatggga    540
tggatggacc cgaatactgg taacacagac tatgcacaga agttccaggg cagagtcacc    600
atgaccagga acacttccat aaatacagcc tacatggagc tgagaagcct gacgtctgac    660
gacacggccg tatattactg tgcgagaggc cggacagtgc ggttcgggga attatttgtt    720
agtgaggggg gtatggacgt ctggggccaa gggaccacgg tcagcgtctc ctcag          775

<210> SEQ ID NO 37
<211> LENGTH: 742
<212> TYPE: DNA
<213> ORGANISM: Homo sapiens

<400> SEQUENCE: 37
gagctcgtga tgactcagtc tccatcctcc ctgtctgcat ctgtaggaga cagagtcacc     60
atcacttgcc gggcaagtca gggcattaga aatgatttgg gctggtatca gcagaaacca    120
gggaaagccc ctaaactcct gatctatgct gcatccaatt tacaaagtgg ggtcccatca    180
aggttcagcg gcagtggatc tggcacagat ttcactctca ccatcagcag cctgcagcct    240
gaagattttg caacttatta ctgtctacaa gattacaatt acccgctcac tttcggcgga    300
gggaccaagc tggagatcaa aggtggttcc tctagatctt cctcctctgg tggcggtggc    360
tcgggcggtg gtgggaggt gcagctggtg gagtctgggg gaggcttggt acagcctggc    420
aggtccctga gactctcctg tgcagcctct ggattcacct ttgatgatca tgccatgcac    480
tgggtccggc aagctccagg aagggcctg gagtgggtct caggtattag ttggagtggt    540
gcttacatag cctatgcgga ctctgtgaag ggccgattca ccatctccag agacaacgcc    600
aggaactccc tgtatctgca aatgaacagt ctgagagctg aggacacggc cttgtattac    660
tgtgcccgca gtagtggtta ttatgacctt ccctatgctt ttgatatctg ggggccaaggg    720 acaatggtca ccgtctcttc ag                                             742

<210> SEQ ID NO 38
<211> LENGTH: 760
<212> TYPE: DNA
<213> ORGANISM: Homo sapiens

<400> SEQUENCE: 38
gagctcgtgc tgactcaatc gccctcagtg tctggggccc cagggcagag ggtcaccatc      60
tcctgcactg ggagcagctc caacatcggg gcaggttatg atgtacactg gtaccagcag    120
cttccaggaa cagccccccaa actcctcatc tatgataaca gcaatcggcc ctcagggggtc    180 cctgaccgat tctctggctc caagtctggc acctcagcct cctggccat cactgggctc    240 caggctgagg atgaggctga ttattactgc cagtcctatg acagcagcct gagtgcctgg    300
gtgttcggcg gagggaccaa ggtgaccgtc ctaggcggtg gttcctctag atcttcctcc    360
tctggtggcg gtggctcggg cggtggtggg gaggtgcagc tggtggagtc tgggggaggc    420
ttggtacagc ctggcaggtc cctgagactc tcctgtgcag cctctggatt cacctttgat    480
gattatgcca tgcactgggt ccggcaagct ccagggaagg gcctggagtg ggtctcaggt    540
```

```
attagttgga atagtggtag catagactat gcggactctg tgaagggccg attcaccatc    600
tccagagaca acgccaagaa ctccctgtat ctgcaaatga acagtctgag agttgaggac    660
acggccttgt attattgtgc aaaagatggg agtagggttt ttggagtggg cggtggtttt    720
gatttctggg gccaagggac aatggtcacc gtctcttcag                          760

<210> SEQ ID NO 39
<211> LENGTH: 742
<212> TYPE: DNA
<213> ORGANISM: Homo sapiens

<400> SEQUENCE: 39
gagctccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccccacctt cggccaaggg    300 acacgactgg agattaaagg tggttcctct agatcttcct cctctggtgg cggtggctcg    360
ggcggtggtg gggaggtgca gctggtggag tctgggggag gcttggtaca gcctggcagg    420
tccctgagac tctcctgtgc agcctctgga ttcacctttg atgattatgc catgcactgg    480
gtccggcaag ctccagggaa gggcctggag tgggtctcag gtattagttg gaatagtggg    540
accataggct atgcggactc tgtgaagggc cgattcacca tctccagaga caacgccaag    600
aactccctgt atctgcaaat gaacagtctg agagctgagg acacggccgt gtattactgt    660
gcaaaagatg ggattacggt ttttggagtg ggcgatggtt tggatatctg ggggccaaggg   720 acaatggtca ccgtctcttc ag                                             742

<210> SEQ ID NO 40
<211> LENGTH: 766
<212> TYPE: DNA
<213> ORGANISM: Homo sapiens

<400> SEQUENCE: 40
gagctcgagc tgactcagcc accctcagtg tctgggaccc ccgggcagag ggtcaccatc     60
tcttgttctg gaggcagctc caacatcgga agtaatactg taaactggta ccagcagctc    120
ccaggaacgg cccccaaact cctcatctat agtaataatc agcggccctc agggtccct    180 gaccgattct ctggctccaa gtctggcacc tcagcctccc tggccatcag tgggctccag    240
tctgaggatg aggctgatta ttactgtgca gcatgggatg acagcctgaa tggtgtggtg    300
ttcggcggag ggaccaaggt gaccgtccta ggcggtggtt cctctagatc ttcctcctct    360
ggtggcggtg gctcgggcgg tggtgggcag gtgcagctgc aggagtcggg gggaggcttg    420
gtacagcctg gcaggtccct gagactctcc tgtgcagcct ctggattcac ctttgatgat    480
tatgccatgc actgggtccg gcaagctcca gggaagggcc tggagtgggt ctcaggtatt    540
agttggaata gtggtagcat agcctatgcg gactctgtga agggccgatt caccatctcc    600
agagacaacg ccaagaactc cctgtatctg caaatgaaca gtctgagagc tgaggacacg    660
gccttctatt actgtgcgaa agtgggcggg gatacctatg atattacaag tggggcggat    720
tacttcgatc tctggggccg tagcgccctg gtcactgtct cctcag                    766

<210> SEQ ID NO 41
```

-continued

<211> LENGTH: 757
<212> TYPE: DNA
<213> ORGANISM: Homo sapiens

<400> SEQUENCE: 41

| | | | | | |
|---|---|---|---|---|---|
| gagctcgagc | tgactcagcc | accctcagtg | tctgggaccc | ccgggcagag | ggtcaccatc | 60 |
| tcttgttctg | gaagcagctc | caacatcgga | agtaatactg | taaactggta | ccagcagctc | 120 |
| ccaggaacgg | cccccaaact | cctcatctat | agtaataatc | agcggccctc | agggtccct | 180 |
| gaccgattct | ctggctccaa | gtctggcacc | tcagcctccc | tggccatcag | tgggctccag | 240 |
| tctgaggatg | aggctgatta | tttctgtgca | gcatgggatg | acagcctgaa | tggcctcgtt | 300 |
| ttcggcggag | ggaccaagct | gaccgtccta | ggcggtggtt | cctctagatc | ttcctcctct | 360 |
| ggtggcggtg | gctcgggcgg | tggtggggag | gtgcagctgg | tggagtctgg | gggaggcttg | 420 |
| gtacagcctg | gcaggtccct | gagactctcc | tgtgcagcct | ctggattcac | ctttgatgat | 480 |
| tatgccatgc | actgggtccg | gcaaggtcca | gggaagggcc | tagagtgggt | ctcaggtatt | 540 |
| agttggaata | gtgggaccat | aggctatgcg | gactctgtga | agggccgatt | caccatctcc | 600 |
| agagacaacg | ccaagaactc | cctgtatctg | caaatgaaca | gtctgagagc | tgaggacacg | 660 |
| gccgtgtatt | actgtgcaaa | agatgggatt | acgttttttg | gagtgggcga | tggtttggat | 720 |
| atctggggcc | aagggacaat | ggtcaccgtc | tcttcag | | | 757 |

<210> SEQ ID NO 42
<211> LENGTH: 742
<212> TYPE: DNA
<213> ORGANISM: Homo sapiens

<400> SEQUENCE: 42

| | | | | | |
|---|---|---|---|---|---|
| gagctccaga | tgacccagtc | tccatcctcc | ctgtctgcat | ctgtaggaga | cagagtcacc | 60 |
| atcacttgcc | gggcaagtca | gagcattagc | acctatttaa | attggtatca | gcagaaacca | 120 |
| gggaaagccc | ctatgctcct | gatctacgct | gcatccaatt | tgcaaagtgg | ggtcccatca | 180 |
| aggttcagtg | gcagtgggtc | tgggacagat | ttcactctca | ccatcagcag | tctgcaacct | 240 |
| gaagattttg | caacttacta | ctgtcaacag | agttacagta | ccccgatcac | cttcggccaa | 300 |
| gggacacgac | tggagattaa | aggtggttcc | tctagatctt | cctcctctgg | tggcggtggc | 360 |
| tcgggcggtg | gtgggcagat | caccttgaag | gagtctgggg | gaggcgtggt | ccagcctggg | 420 |
| aggtccctgc | gactctcctg | tgcagcctct | ggattcgact | tcaatatcta | tggcatgcac | 480 |
| tgggtccgcc | aggctccaga | caaggggctg | gagtgggtgg | cggttatatc | agatgatgga | 540 |
| actaaaaaat | attatgcaga | ctctgtgaag | ggccgagtca | ccatctccag | agacaattcc | 600 |
| aagaacacgc | tgtatctgca | gatgaacagc | ctgagagctg | aggacacggc | tgtgtattac | 660 |
| tgtgcgaaag | atctggatgt | tgtcatggga | cccggtggac | ttgattattg | gggccaggga | 720 |
| accctggtca | ccgtctcctc | ag | | | | 742 |

<210> SEQ ID NO 43
<211> LENGTH: 757
<212> TYPE: DNA
<213> ORGANISM: Homo sapiens

<400> SEQUENCE: 43

| | | | | | |
|---|---|---|---|---|---|
| gagctcgtgc | tgactcagcc | accctcagcg | tctgggaccc | ccgggcagag | ggtcaccatc | 60 |
| tcttgttctg | gaagcagctc | caacatcgga | agtaatactg | taaactggta | ccagcagctc | 120 |
| ccaggaacgg | cccccaaact | cctcatctat | agtaataatc | agcggccctc | agggtccct | 180 |

```
gaccgattct ctggctccaa gtctggcacc tcagcctccc tggccatcag tgggctccag      240
tctgaggatg aggctgatta ttactgtgca gcatgggatg acagcctgaa tggtcgggtg      300
ttcggcggag gcaccaagct gaccgtccta ggtggtggtt cctctagatc ttcctcctct      360
ggtggcggtg gctcgggcgg tgtgggcag atcaccttga aggagtctgg gggaggcttg       420
gtacagcctg gcaggtccct gagactctcc tgtgcagcct ctggattcac ctttgatgat      480
tatgccatgc actgggtccg gcaagctcca gggaagggcc tggagtgggt ctcaggtatt      540
agttggaata gtgggaccat aggctatgcg gactctgtga agggccgatt caccatctcc      600
agagacaacg ccaagaactc cctgtatctg caaatgaaca gtctgagagc tgaggacacg      660
gccgtgtatt actgtgcaaa gatgggatt acggtttttg gagtgggcga tggtttggat       720
atctggggcc aagggacaat ggtcaccgtc tcttcag                               757
```

```
<210> SEQ ID NO 44
<211> LENGTH: 249
<212> TYPE: PRT
<213> ORGANISM: Homo sapiens

<400> SEQUENCE: 44

Glu Leu Val Leu Thr Gln Ser Pro Asp Ser Leu Ser Val Ser Leu Gly
1               5                   10                  15

Glu Arg Ala Thr Ile Asn Cys Lys Ser Ser Gln Thr Val Leu Tyr Asn
            20                  25                  30

Ser Asp Asn Lys Asn Tyr Leu Ser Trp Tyr Gln Gln Lys Pro Gly Gln
        35                  40                  45

Pro Pro Lys Leu Ile Met Asn Trp Ala Ser Ile Arg Ala Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Ile Tyr Tyr Cys Gln Gln
                85                  90                  95

Tyr Tyr Ser Thr Pro Leu Thr Phe Gly Gly Gly Thr Lys Val Glu Ile
            100                 105                 110

Lys Gly Gly Ser Ser Arg Ser Ser Ser Gly Gly Gly Gly Ser Gly
        115                 120                 125

Gly Gly Gly Gln Val Gln Leu Val Gln Ser Gly Ala Glu Val Lys Lys
    130                 135                 140

Pro Gly Ala Leu Val Lys Val Ser Cys Lys Ala Ser Gly Tyr Thr Phe
145                 150                 155                 160

Thr Asn Tyr Gly Ile Thr Trp Val Arg Gln Ala Pro Gly Gln Gly Leu
                165                 170                 175

Glu Trp Met Gly Trp Ile Ser Val Tyr Asn Gly Asp Thr Lys Tyr Ala
            180                 185                 190

Gln Lys Leu Gln Gly Arg Val Thr Met Thr Thr Asp Thr Pro Thr Asn
        195                 200                 205

Thr Val Tyr Met Glu Leu Arg Ser Leu Arg Ser Asp Asp Thr Ala Val
    210                 215                 220

Tyr Tyr Cys Ala Arg Gly Tyr Gly Ser Gly Asn Trp Asp Tyr Trp Gly
225                 230                 235                 240

Gln Gly Thr Leu Val Thr Val Ser Ser
                245

<210> SEQ ID NO 45
```

<211> LENGTH: 243
<212> TYPE: PRT
<213> ORGANISM: Homo sapiens

<400> SEQUENCE: 45

Glu Leu Thr Leu Thr Gln Ser Pro Ser Ser Leu Ser Ala Ser Val Gly
1               5                   10                  15

Asp Arg Val Thr Ile Thr Cys Arg Ala Ser Gln Gly Ile Ala Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
50                  55                  60

Arg Arg Ser Gly Thr Asp Phe Thr Leu Thr Ile Ser Ser Leu Gln Pro
65                  70                  75                  80

Glu Asp Ala Ala Thr Tyr Tyr Cys Gln Gln Tyr Ser Asn Tyr Pro Leu
                85                  90                  95

Thr Phe Gly Gln Gly Thr Lys Leu Glu Ile Lys Gly Gly Ser Ser Arg
            100                 105                 110

Ser Ser Ser Ser Gly Gly Gly Ser Gly Gly Gly Gly Gln Val Gln
        115                 120                 125

Leu Val Gln Ser Gly Ala Glu Met Lys Lys Pro Gly Ala Ser Val Lys
130                 135                 140

Val Ser Cys Lys Ala Ser Gly Tyr Thr Phe Thr Asn Tyr Gly Ile Thr
145                 150                 155                 160

Trp Val Arg Gln Ala Pro Gly Gln Gly Leu Glu Trp Met Gly Trp Ile
                165                 170                 175

Ser Val Tyr Asn Gly Asp Thr Lys Tyr Ala Gln Lys Leu Gln Gly Arg
            180                 185                 190

Val Thr Met Thr Thr Asp Thr Pro Thr Ser Thr Val Tyr Met Glu Leu
        195                 200                 205

Arg Ser Leu Thr Ser Asp Asp Thr Ala Val Tyr Tyr Cys Val Arg Gly
210                 215                 220

Tyr Gly Ser Gly Asn Trp Asp Tyr Trp Gly Gln Gly Thr Leu Val Thr
225                 230                 235                 240

Val Ser Ser

<210> SEQ ID NO 46
<211> LENGTH: 243
<212> TYPE: PRT
<213> ORGANISM: Homo sapiens

<400> SEQUENCE: 46

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Phe
                85                  90                  95

Thr Phe Gly Pro Gly Thr Lys Val Asp Ile Lys Gly Ser Ser Arg
            100                 105                 110

Ser Ser Ser Ser Gly Gly Gly Ser Gly Gly Gly Gln Val Gln
        115                 120                 125

Leu Val Gln Ser Gly Ala Glu Val Lys Lys Pro Gly Ala Ser Val Lys
        130                 135                 140

Val Ser Cys Lys Ala Ser Gly Tyr Thr Phe Thr Asn Tyr Gly Ile Thr
145                 150                 155                 160

Trp Val Arg Gln Ala Pro Gly Gln Gly Leu Glu Trp Met Gly Trp Ile
                165                 170                 175

Ser Val Tyr Asn Gly Asp Thr Lys Tyr Ala Gln Lys Leu Gln Gly Arg
                180                 185                 190

Val Thr Met Thr Thr Asp Thr Pro Thr Asn Thr Val Tyr Met Glu Leu
            195                 200                 205

Arg Ser Leu Arg Ser Asp Asp Thr Ala Val Tyr Tyr Cys Ala Arg Gly
210                 215                 220

Tyr Gly Ser Gly Asn Trp Asp Tyr Trp Gly Gln Gly Thr Leu Val Thr
225                 230                 235                 240

Val Ser Ser

<210> SEQ ID NO 47
<211> LENGTH: 243
<212> TYPE: PRT
<213> ORGANISM: Homo sapiens

<400> SEQUENCE: 47

Glu Leu Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

His Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Thr Tyr Pro Leu
                85                  90                  95

Thr Phe Gly Gly Gly Thr Lys Val Glu Ile Lys Gly Ser Ser Arg
            100                 105                 110

Ser Ser Ser Ser Gly Gly Gly Ser Gly Gly Gly Gln Val Gln
        115                 120                 125

Leu Val Gln Ser Gly Ala Glu Val Lys Lys Pro Gly Ala Ser Val Lys
        130                 135                 140

Val Ser Cys Lys Ala Ser Gly Tyr Thr Phe Thr Asn Tyr Gly Ile Thr
145                 150                 155                 160

Trp Val Arg Gln Ala Pro Gly Gln Gly Leu Glu Trp Met Gly Trp Ile
                165                 170                 175

Ser Val Tyr Asn Gly Asp Thr Lys Tyr Ala Gln Lys Leu Gln Gly Arg
                180                 185                 190

Val Thr Met Thr Thr Asp Thr Pro Thr Asn Thr Val Tyr Met Glu Leu
            195                 200                 205

Arg Ser Leu Arg Ser Asp Asp Thr Ala Val Tyr Tyr Cys Ala Arg Gly
210                 215                 220

```
Tyr Gly Ser Gly Asn Trp Asp Tyr Trp Gly Gln Gly Thr Leu Val Thr
225                 230                 235                 240

Val Ser Ser

<210> SEQ ID NO 48
<211> LENGTH: 242
<212> TYPE: PRT
<213> ORGANISM: Homo sapiens

<400> SEQUENCE: 48

Glu Leu Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Lys Gly Ala Ser Thr Arg Ala Thr Gly Ile Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln Tyr Tyr Gly Pro Tyr Ser
                85                  90                  95

Phe Gly Gln Gly Thr Lys Val Glu Ile Lys Gly Gly Ser Ser Arg Ser
            100                 105                 110

Ser Ser Ser Gly Gly Gly Gly Ser Gly Gly Gly Gly Gln Val Gln Leu
        115                 120                 125

Val Gln Ser Gly Ala Glu Val Lys Lys Pro Gly Ser Ser Val Lys Val
130                 135                 140

Ser Cys Lys Ala Ser Gly Tyr Thr Phe Thr Asn Tyr Gly Ile Thr Trp
145                 150                 155                 160

Val Arg Gln Ala Pro Gly Gln Gly Leu Glu Trp Met Gly Trp Ile Ser
                165                 170                 175

Val Tyr Asn Gly Asp Thr Lys Tyr Ala Gln Lys Leu Gln Gly Arg Val
            180                 185                 190

Thr Met Thr Thr Asp Thr Pro Thr Asn Thr Val Tyr Met Glu Leu Arg
        195                 200                 205

Ser Leu Arg Ser Asp Asp Thr Ala Val Tyr Tyr Cys Ala Arg Gly Tyr
210                 215                 220

Gly Ser Gly Asn Trp Asp Tyr Trp Gly Gln Gly Thr Leu Val Thr Val
225                 230                 235                 240

Ser Ser

<210> SEQ ID NO 49
<211> LENGTH: 243
<212> TYPE: PRT
<213> ORGANISM: Homo sapiens

<400> SEQUENCE: 49

Glu Leu Gln Met Thr Gln Ser Pro Ser Ser Leu Ser Ala Ser Val Gly
1               5                   10                  15

Asp Arg Val Thr Ile Thr Cys Arg Ala Thr Gln Gly Ile Ser Asn Tyr
                20                  25                  30

Leu Ala Trp Phe Gln Gln Lys Pro Gly Lys Ala Pro Lys Leu Leu Ile
            35                  40                  45

Tyr Ala Ala Ser Ser Leu Gln Ser Gly Val Pro Ser Lys Phe Ser Gly
50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Gly Ser Ser Arg
                100                 105                 110

Ser Ser Ser Ser Gly Gly Gly Ser Gly Gly Gly Gln Val Gln
        115                 120                 125

Leu Val Gln Ser Gly Ala Glu Val Lys Lys Pro Gly Ala Ser Val Lys
        130                 135                 140

Val Ser Cys Lys Ala Ser Gly Tyr Thr Phe Thr Asn Tyr Gly Ile Thr
145                 150                 155                 160

Trp Val Arg Gln Ala Pro Gly Gln Gly Leu Glu Trp Met Gly Trp Ile
                165                 170                 175

Ser Val Tyr Asn Gly Asp Thr Lys Tyr Ala Gln Lys Leu Gln Gly Arg
                180                 185                 190

Val Thr Met Thr Thr Asp Thr Leu Thr Asn Thr Val Tyr Met Glu Leu
                195                 200                 205

Arg Ser Leu Arg Ser Asp Asp Thr Ala Val Tyr Tyr Cys Ala Arg Gly
210                 215                 220

Tyr Gly Ser Gly Asn Trp Asp Tyr Trp Gly Gln Gly Thr Pro Val Thr
225                 230                 235                 240

Val Ser Ser

<210> SEQ ID NO 50
<211> LENGTH: 253
<212> TYPE: PRT
<213> ORGANISM: Homo sapiens

<400> SEQUENCE: 50

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gly Gly Thr Lys Leu Glu Ile Lys Gly Ser Ser Arg
                100                 105                 110

Ser Ser Ser Ser Gly Gly Gly Gly Ser Gly Gly Gly Gly Gln Val Gln
        115                 120                 125

Leu Val Gln Ser Gly Ala Glu Val Arg Lys Pro Gly Ala Ser Val Arg
        130                 135                 140

Val Ser Cys Lys Ala Ser Gly Tyr Thr Leu Thr Thr Tyr Asp Ile Asn
145                 150                 155                 160

Trp Val Arg Gln Ala Thr Gly Gln Gly Leu Glu Trp Met Gly Trp Met
                165                 170                 175

Asn Pro Thr Ser Gly Asn Thr Ala Tyr Ala Gln Lys Phe Gln Gly Arg
                180                 185                 190

```
Val Thr Met Thr Arg Asn Thr Ser Ile Ser Thr Ala Tyr Met Glu Leu
            195                 200                 205

Ser Ser Leu Arg Ser Glu Asp Thr Ala Val Tyr Tyr Cys Ala Arg Gly
    210                 215                 220

Leu Phe Phe Gly Val Val Thr Lys Pro Asn Tyr Tyr Tyr Tyr Ala Met
225                 230                 235                 240

Asp Val Trp Gly Gln Gly Thr Thr Val Thr Val Ser Ser
                245                 250

<210> SEQ ID NO 51
<211> LENGTH: 252
<212> TYPE: PRT
<213> ORGANISM: Homo sapiens

<400> SEQUENCE: 51

Glu Leu Gln Met Thr Gln Ser Pro Ser Ser Leu Ser Val Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Ala Leu Thr Ile Ser Ser Val Gln Pro
65                  70                  75                  80

Glu Asp Phe Ala Ser Tyr Phe Cys Gln Gln Ser His Ser Val Pro Ile
                85                  90                  95

Asn Phe Gly Gln Gly Thr Arg Leu Glu Ile Lys Gly Gly Ser Ser Arg
            100                 105                 110

Ser Ser Ser Ser Gly Gly Gly Ser Gly Gly Gly Gln Val Gln
        115                 120                 125

Leu Val Gln Ser Gly Gly Gly Leu Ala Gln Pro Gly Lys Ser Leu Arg
    130                 135                 140

Leu Ser Cys Val Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Asn Trp Asn Ser Gly Ser Ile Gly Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Leu Tyr Tyr Cys Ala Lys Glu
    210                 215                 220

Gln Gly Tyr Cys Asp Ser Thr Gly Cys Gln Arg Gly Ser Gly Met Asp
225                 230                 235                 240

Val Trp Gly Gln Gly Thr Thr Val Thr Val Ser Ser
                245                 250

<210> SEQ ID NO 52
<211> LENGTH: 252
<212> TYPE: PRT
<213> ORGANISM: Homo sapiens

<400> SEQUENCE: 52

Glu Leu Gln Met Thr Gln Ser Pro Ser Ser Leu Ser Ala Ser Val Gly
1               5                   10                  15
```

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
                35                  40                  45

Tyr Asp Ala Ser Asn Leu Glu Thr Gly Val Pro Ser Arg Leu Ser Gly
     50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asp Leu Pro Leu
                85                  90                  95

Thr Phe Gly Gly Gly Thr Lys Leu Glu Ile Lys Gly Ser Ser Arg
            100                 105                 110

Ser Ser Ser Ser Gly Gly Gly Ser Gly Gly Gly Gln Val Gln
        115                 120                 125

Leu Val Gln Ser Gly Gly Gly Leu Ala Gln Pro Gly Lys Ser Leu Arg
130                 135                 140

Leu Ser Cys Val Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Asn Trp Asn Ser Gly Ser Ile Gly Tyr Ala Asp Ser Val Lys Gly Arg
            180                 185                 190

Phe Thr Ile Ser Arg Asp Asn Ala Lys Asn Ser Leu Tyr Leu Gln Met
            195                 200                 205

Asn Ser Leu Arg Ala Glu Asp Thr Ala Leu Tyr Tyr Cys Ala Lys Glu
        210                 215                 220

Gln Gly Tyr Cys Asp Ser Thr Gly Cys Gln Arg Gly Ser Gly Met Asp
225                 230                 235                 240

Val Trp Gly Gln Gly Thr Thr Val Thr Val Ser Ser
                245                 250

<210> SEQ ID NO 53
<211> LENGTH: 252
<212> TYPE: PRT
<213> ORGANISM: Homo sapiens

<400> SEQUENCE: 53

Glu Leu Gln Met Thr Gln Ser Pro Ser Ser Leu Ala Ala Ser Val Gly
1               5                   10                  15

Asp Arg Val Thr Ile Thr Cys Arg Ala Ser His Asp Ile Lys Asn Asp
            20                  25                  30

Leu Gly Trp Tyr Gln His Gln Pro Gly Lys Ala Pro Lys Leu Leu Ile
                35                  40                  45

Tyr Ala Ala Ser Ser Leu Gln Ser Gly Val Pro Ser Arg Phe Ser Gly
     50                  55                  60

Ser Gly Ser Gly Thr Asn Phe Leu Thr Ile Asn Ser Leu Gln Pro
65                  70                  75                  80

Glu Asp Phe Ala Thr Tyr Tyr Cys Leu His Asp Tyr Thr Tyr Pro Arg
                85                  90                  95

Thr Phe Gly Gln Gly Thr Lys Val Glu Ile Lys Gly Ser Ser Arg
            100                 105                 110

Ser Ser Ser Ser Gly Gly Gly Gly Ser Gly Gly Gly Gln Val Gln
        115                 120                 125

Leu Val Gln Ser Gly Gly Gly Leu Ala Gln Pro Gly Lys Ser Leu Arg

Leu Ser Cys Val Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Asn Trp Asn Ser Gly Ser Ile Gly Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Leu Tyr Tyr Cys Ala Lys Glu
    210                 215                 220

Gln Gly Tyr Cys Asp Ser Thr Gly Cys Gln Arg Gly Ser Gly Met Asp
225                 230                 235                 240

Val Trp Gly Gln Gly Thr Thr Val Thr Val Ser Ser
                245                 250

<210> SEQ ID NO 54
<211> LENGTH: 252
<212> TYPE: PRT
<213> ORGANISM: Homo sapiens

<400> SEQUENCE: 54

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Tyr Asp
            20                  25                  30

Val Gly Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Glu Thr Asp Phe Thr Leu Thr Ile Asn Ser Leu Gln Pro
65                  70                  75                  80

Glu Asp Ser Ala Thr Tyr Tyr Cys Gln Gln Ser Tyr Ser Ile Pro Ser
                85                  90                  95

Thr Phe Gly Gln Gly Thr Lys Val Glu Ile Lys Gly Gly Ser Ser Arg
            100                 105                 110

Ser Ser Ser Ser Gly Gly Gly Gly Ser Gly Gly Gly Gly Glu Val Gln
        115                 120                 125

Leu Leu Glu Ser Gly Gly Gly Leu Ala Gln Pro Gly Lys Ser Leu Arg
    130                 135                 140

Leu Ser Cys Val Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Asn Trp Asn Ser Gly Ser Ile Gly Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Leu Tyr Tyr Cys Ala Lys Glu
    210                 215                 220

Gln Gly Tyr Cys Asp Ser Thr Gly Cys Gln Arg Gly Ser Gly Met Asp
225                 230                 235                 240

Val Trp Gly Gln Gly Thr Thr Val Thr Val Ser Ser
                245                 250

```
<210> SEQ ID NO 55
<211> LENGTH: 256
<212> TYPE: PRT
<213> ORGANISM: Homo sapiens

<400> SEQUENCE: 55

Glu Leu Glu Leu Thr Gln Pro Pro Ser Val Ser Gly Thr Pro Gly Gln
1               5                   10                  15

Arg Val Thr Ile Ser Cys Ser Gly Ser Ser Asn Ile Gly Ser Asp
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Gly Leu
                85                  90                  95

Arg Gly Met Val Phe Gly Glu Gly Thr Lys Leu Thr Val Leu Gly Gly
            100                 105                 110

Gly Ser Ser Arg Ser Ser Ser Gly Gly Gly Ser Gly Gly Gly
            115                 120                 125

Gly Gln Val Gln Leu Gln Glu Ser Gly Gly Leu Ala Gln Pro Gly
            130                 135                 140

Lys Ser Leu Arg Leu Ser Cys Val Ala Ser Gly Phe Thr Phe Asp Asp
145                 150                 155                 160

Tyr Ala Met His Trp Val Arg Gln Ala Pro Gly Lys Gly Leu Glu Trp
                165                 170                 175

Val Ser Gly Ile Asn Trp Asn Ser Gly Ser Ile Gly Tyr Ala Asp Ser
            180                 185                 190

Val Lys Gly Arg Phe Thr Ile Ser Arg Asp Asn Ala Lys Asn Ser Leu
        195                 200                 205

Tyr Leu Gln Met Asn Ser Leu Arg Ala Glu Asp Thr Ala Leu Tyr Tyr
    210                 215                 220

Cys Ala Lys Glu Gln Gly Tyr Cys Asp Ser Thr Gly Cys Gln Arg Gly
225                 230                 235                 240

Ser Gly Met Asp Val Trp Gly Gln Gly Thr Thr Val Thr Val Ser Ser
                245                 250                 255

<210> SEQ ID NO 56
<211> LENGTH: 259
<212> TYPE: PRT
<213> ORGANISM: Homo sapiens

<400> SEQUENCE: 56

Glu Leu Val Leu Thr Gln Pro Pro Ser Val Ser Gly Ala Pro Gly Arg
1               5                   10                  15

Arg Val Thr Ile Ser Cys Thr Gly Ser Ser Asn Ile Gly Ala Ala
            20                  25                  30

Tyr Asp Val His Trp Tyr Gln Gln Leu Pro Gly Thr Ala Pro Lys Leu
        35                  40                  45

Leu Ile Phe Gly Asn Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80
```

```
Gln Ser Glu Asp Glu Ala Asp Tyr Tyr Cys Ala Thr Trp Asp Asp Ser
            85                  90                  95
Arg Asp Gly Pro Glu Val Val Phe Gly Gly Gly Thr Glu Leu Thr Val
            100                 105                 110
Leu Gly Gly Gly Ser Ser Arg Ser Ser Ser Gly Gly Gly Gly Ser
        115                 120                 125
Gly Gly Gly Gly Glu Val Gln Leu Val Glu Ser Gly Gly Gly Leu Ala
        130                 135                 140
Gln Pro Gly Lys Ser Leu Arg Leu Ser Cys Val Ala Ser Gly Phe Thr
145                 150                 155                 160
Phe Asp Asp Tyr Ala Met His Trp Val Arg Gln Ala Pro Gly Lys Gly
            165                 170                 175
Leu Glu Trp Val Ser Gly Ile Asn Trp Asn Ser Gly Ser Ile Gly Tyr
        180                 185                 190
Ala Asp Ser Val Lys Gly Arg Phe Thr Ile Ser Arg Asp Asn Ala Lys
        195                 200                 205
Asn Ser Leu Tyr Leu Gln Met Asn Ser Leu Arg Ala Glu Asp Thr Ala
    210                 215                 220
Leu Tyr Tyr Cys Ala Lys Glu Gln Gly Tyr Cys Asp Ser Thr Gly Cys
225                 230                 235                 240
Gln Arg Gly Ser Gly Met Asp Val Trp Gly Gln Gly Thr Thr Val Thr
            245                 250                 255
Val Ser Ser

<210> SEQ ID NO 57
<211> LENGTH: 256
<212> TYPE: PRT
<213> ORGANISM: Homo sapiens

<400> SEQUENCE: 57

Glu Leu Val Leu Thr Gln Pro Pro Ser Ala Ser Gly Thr Pro Gly Gln
1               5                   10                  15
Arg Val Thr Ile Ser Cys Ser Gly Ser Asn Ser Asn Ile Gly Ser Asp
            20                  25                  30
Tyr Val Tyr Trp Tyr Gln Arg Phe Pro Gly Thr Ala Pro Lys Leu Leu
        35                  40                  45
Ile Tyr Ser Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Glu Tyr Tyr Cys Ala Thr Trp Asp Asp Ala Leu
            85                  90                  95
Arg Gly Met Val Phe Gly Glu Thr Lys Leu Thr Val Leu Gly Gly
            100                 105                 110
Gly Ser Ser Arg Ser Ser Ser Gly Gly Gly Gly Ser Gly Gly Gly
        115                 120                 125
Gly Glu Val Gln Leu Val Glu Ser Gly Gly Gly Leu Ala Gln Pro Gly
        130                 135                 140
Lys Ser Leu Arg Leu Ser Cys Val Ala Ser Gly Phe Thr Phe Asp Asp
145                 150                 155                 160
Tyr Ala Met His Trp Val Arg Gln Ala Pro Gly Lys Gly Leu Glu Trp
            165                 170                 175
Val Ser Gly Ile Asn Trp Asn Ser Gly Ser Ile Gly Tyr Ala Asp Ser
        180                 185                 190
```

```
Val Lys Gly Arg Phe Thr Ile Ser Arg Asp Asn Ala Lys Asn Ser Leu
            195                 200                 205

Tyr Leu Gln Met Asn Ser Leu Arg Ala Glu Asp Thr Ala Leu Tyr Tyr
210                 215                 220

Cys Ala Lys Glu Gln Gly Tyr Cys Asp Ser Thr Gly Cys Gln Arg Gly
225                 230                 235                 240

Ser Gly Met Asp Val Trp Gly Gln Gly Thr Thr Val Thr Val Ser Ser
                245                 250                 255
```

<210> SEQ ID NO 58
<211> LENGTH: 258
<212> TYPE: PRT
<213> ORGANISM: Homo sapiens

<400> SEQUENCE: 58

```
Glu Leu Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Phe Val Gln Trp Tyr Gln Gln Arg Pro Gly Lys Ser Pro Thr Thr Val
        35                  40                  45

Ile Tyr Glu Asp Asn Gln Arg Pro Ser Gly Val Pro Asp Arg Phe Ser
50                  55                  60

Gly Ser Val Asp Arg Ser Ser Asn Ser Ala Ser Leu Thr Ile Ser Gly
65                  70                  75                  80

Leu Gln Thr Glu Asp Glu Ala Asp Tyr Tyr Cys Gln Ser Phe Tyr Asp
                85                  90                  95

Gly Val Pro Ser Trp Val Phe Gly Gly Gly Thr Glu Leu Thr Val Leu
            100                 105                 110

Gly Gly Gly Ser Ser Arg Ser Ser Ser Gly Gly Gly Gly Ser Gly
        115                 120                 125

Gly Gly Gly Glu Val Gln Leu Val Glu Ser Gly Gly Gly Val Val Gln
130                 135                 140

Pro Gly Gly Ser Leu Arg Leu Ser Cys Val Ala Ser Gly Phe Thr Phe
145                 150                 155                 160

Asp Asp Tyr Ala Met His Trp Val Arg Gln Ala Pro Gly Lys Gly Leu
                165                 170                 175

Glu Trp Val Ser Gly Ile Asn Trp Asn Ser Gly Ser Ile Gly Tyr Ala
            180                 185                 190

Asp Ser Val Lys Gly Arg Phe Thr Ile Ser Arg Asp Asn Ala Lys Asn
        195                 200                 205

Ser Leu Tyr Leu Gln Met Asn Ser Leu Arg Ala Glu Asp Thr Ala Leu
210                 215                 220

Tyr Tyr Cys Ala Lys Glu Gln Gly Tyr Cys Asp Ser Thr Gly Cys Gln
225                 230                 235                 240

Arg Gly Ser Gly Met Asp Val Trp Gly Gln Gly Thr Thr Val Thr Val
                245                 250                 255

Ser Ser
```

<210> SEQ ID NO 59
<211> LENGTH: 254
<212> TYPE: PRT
<213> ORGANISM: Homo sapiens

<400> SEQUENCE: 59

```
Glu Leu Met Leu Thr Gln Pro His Ser Val Ser Glu Ser Pro Gly Lys
```

```
  1               5                  10                 15
Thr Val Thr Ile Ser Cys Thr Arg Ser Ser Gly Ser Ile Ala Ser Asn
                20                 25                 30

Phe Val Gln Trp Tyr Gln Gln Arg Pro Gly Lys Ser Pro Thr Thr Val
            35                 40                 45

Ile Tyr Glu Asp Asn Gln Arg Pro Ser Gly Val Pro Asp Arg Phe Ser
        50                 55                 60

Gly Ser Val Asp Arg Ser Ser Asn Ser Ala Ser Leu Thr Ile Ser Gly
 65                 70                 75                 80

Leu Gln Thr Glu Asp Glu Ala Asp Tyr Tyr Cys Gln Ser Phe Tyr Asp
                85                 90                 95

Gly Val Pro Ser Trp Val Phe Gly Gly Thr Glu Leu Thr Val Leu
            100                105                110

Gly Gly Gly Ser Ser Arg Ser Ser Ser Gly Gly Gly Ser Gly
        115                120                125

Gly Gly Gly Gln Val Gln Leu Val Gln Ser Gly Gly Val Val Gln
    130                135                140

Pro Gly Gly Ser Leu Arg Leu Ser Cys Val Ala Ser Gly Phe Thr Phe
145                150                155                160

Asp Asp Tyr Ala Met His Trp Val Arg Gln Ala Pro Gly Lys Gly Leu
                165                170                175

Glu Trp Val Ser Gly Ile Ser Trp Asn Ser Gly Ala Ile Gly Tyr Ala
            180                185                190

Asp Ser Val Lys Gly Arg Phe Thr Ile Ser Arg Asp Asn Ala Lys Asn
        195                200                205

Ser Leu Tyr Leu Gln Met Asn Ser Leu Arg Thr Glu Asp Thr Ala Val
210                215                220

Tyr Tyr Cys Ala Lys Asp Gly Ile Thr Ile Phe Gly Val Gly Asp Gly
225                230                235                240

Leu Asp Val Trp Gly Gln Gly Thr Met Val Thr Val Ser Ser
                245                250
```

<210> SEQ ID NO 60
<211> LENGTH: 248
<212> TYPE: PRT
<213> ORGANISM: Homo sapiens

<400> SEQUENCE: 60

```
Glu Leu Gln Met Thr Gln Ser Pro Ser Ser Leu Ser Ala Ser Val Gly
 1               5                  10                 15

Asp Arg Val Thr Ile Thr Cys Gln Ala Ser Gln Asp Ile Gly Asn Tyr
                20                 25                 30

Leu Asn Trp Tyr Gln Gln Lys Pro Gly Lys Ala Pro Lys Leu Leu Ile
            35                 40                 45

Tyr Asp Ala Ser Tyr Leu Glu Thr Gly Val Pro Ser Arg Phe Ser Gly
        50                 55                 60

Ser Gly Ser Gly Thr Asp Phe Thr Phe Thr Ile Ser Ser Leu Gln Pro
 65                 70                 75                 80

Glu Asp Ile Ala Thr Tyr Tyr Cys Gln Gln Tyr Asp Asn Leu Pro Phe
                85                 90                 95

Thr Phe Gly Pro Gly Thr Lys Val Asp Ile Lys Gly Ser Ser Arg
            100                105                110

Ser Ser Ser Gly Gly Gly Gly Ser Gly Gly Gly Glu Val Gln
        115                120                125
```

```
Leu Val Glu Ser Gly Gly Gly Leu Val Gln Pro Gly Arg Ser Leu Arg
        130                 135                 140

Leu Ser Cys Ala Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Ser Trp Asn Ser Gly Ser Ile Asp Tyr Ala Asp Ser Val Lys Gly Arg
                180                 185                 190

Phe Thr Ile Ser Arg Asp Asn Ala Lys Asn Ser Leu Tyr Leu Gln Met
                195                 200                 205

Asn Ser Leu Arg Val Glu Asp Thr Ala Leu Tyr Tyr Cys Ala Lys Asp
210                 215                 220

Gly Ser Arg Val Phe Gly Val Gly Gly Gly Phe Asp Phe Trp Gly Gln
225                 230                 235                 240

Gly Thr Met Val Thr Val Ser Ser
                245

<210> SEQ ID NO 61
<211> LENGTH: 248
<212> TYPE: PRT
<213> ORGANISM: Homo sapiens

<400> SEQUENCE: 61

Glu Leu Val Met Thr Gln Ser Pro Ser Ser Leu Ser Ala Ser Val Gly
1               5                   10                  15

Asp Arg Val Thr Ile Thr Cys Arg Ala Ser Gln Gly Ile Thr Asp Asp
                20                  25                  30

Leu Gly Trp Tyr Gln Gln Lys Pro Gly Lys Ala Pro Lys Leu Leu Ile
            35                  40                  45

Tyr Ala Thr Ser Asn Leu Glu Ser Gly Val Pro Ser Arg Phe Ser Gly
50                  55                  60

Ser Gly Ser Asp Thr Glu Phe Thr Leu Thr Ile Ser Ser Leu Gln Pro
65                  70                  75                  80

Glu Asp Leu Ala Thr Tyr Tyr Cys Leu Gln Asp Tyr Ser Tyr Pro Tyr
                85                  90                  95

Thr Phe Gly Gln Gly Thr Lys Val Glu Ile Lys Gly Gly Ser Ser Arg
                100                 105                 110

Ser Ser Ser Ser Gly Gly Gly Ser Gly Gly Gly Gly Glu Val Gln
            115                 120                 125

Leu Val Glu Ser Gly Gly Gly Leu Val Gln Pro Gly Arg Ser Leu Arg
        130                 135                 140

Leu Ser Cys Ala Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Ser Trp Asn Ser Gly Ser Ile Asp Tyr Val Asp Ser Val Lys Gly Arg
                180                 185                 190

Phe Thr Ile Ser Arg Asp Asn Ala Lys Asn Tyr Leu Tyr Leu Gln Met
                195                 200                 205

Asn Ser Leu Arg Val Glu Asp Thr Ala Leu Tyr Tyr Cys Ala Lys Asp
210                 215                 220

Gly Ser Arg Val Phe Gly Val Gly Gly Gly Phe Asp Phe Trp Gly Gln
225                 230                 235                 240

Gly Thr Met Val Thr Val Ser Ser
                245
```

<210> SEQ ID NO 62
<211> LENGTH: 248
<212> TYPE: PRT
<213> ORGANISM: Homo sapiens

<400> SEQUENCE: 62

```
Glu Leu Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Ser Arg
                85                  90                  95

Thr Phe Gly Gln Gly Thr Lys Val Glu Ile Lys Gly Gly Ser Ser Arg
            100                 105                 110

Ser Ser Ser Ser Gly Gly Gly Ser Gly Gly Gly Gly Glu Val Gln
            115                 120                 125

Leu Val Glu Ser Gly Gly Gly Leu Val Gln Pro Gly Arg Ser Leu Arg
    130                 135                 140

Leu Ser Cys Ala Ala Ser Gly Phe Thr Phe Asp Asp Tyr Ser Met His
145                 150                 155                 160

Trp Val Arg Gln Ala Pro Gly Lys Gly Leu Glu Trp Val Ser Gly Ile
                165                 170                 175

Ser Trp Asn Ser Gly Gly Ile Gly Tyr Ala Asp Ser Val Arg Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Leu Tyr Tyr Cys Ala Lys Asp
210                 215                 220

Gly Met Arg Val Phe Gly Val Gly Gly Phe Asp Phe Trp Gly Gln
225                 230                 235                 240

Gly Thr Met Val Thr Val Ser Ser
                245
```

<210> SEQ ID NO 63
<211> LENGTH: 248
<212> TYPE: PRT
<213> ORGANISM: Homo sapiens

<400> SEQUENCE: 63

```
Glu Leu Gln Met Thr Gln Ser Pro Ser Ser Leu Ser Ala Ser Val Gly
1               5                   10                  15

Asp Arg Val Thr Ile Thr Cys Gln Ala Ser Arg Asp Ile Ser Asn Tyr
            20                  25                  30

Leu Asn Trp Tyr Gln His Ile Pro Gly Lys Ala Pro Lys Leu Leu Ile
        35                  40                  45

Phe His Ala Ser Thr Leu Glu Ala Gly Ile Pro Ser Arg Phe Ser Gly
50                  55                  60

Ser Gly Ser Glu Thr Ser Phe Thr Phe Thr Ile Arg Ser Leu Gln Pro
65                  70                  75                  80
```

```
Glu Asp Val Ala Thr Tyr Tyr Cys Gln Gln Tyr Asp Asn Leu Pro Phe
                85                  90                  95
Thr Phe Gly Pro Gly Thr Lys Val Asp Ile Lys Gly Gly Ser Ser Arg
            100                 105                 110
Ser Ser Ser Ser Gly Gly Gly Ser Gly Gly Gly Glu Val Gln
        115                 120                 125
Leu Val Glu Ser Gly Gly Gly Leu Val Gln Pro Gly Arg Ser Leu Arg
145                 135                 140
Leu Ser Cys Ala Ala Ser Gly Phe Thr Phe Asp Asp Tyr Ala Met Tyr
145                 150                 155                 160
Trp Val Arg Gln Ala Pro Gly Lys Gly Leu Glu Trp Val Ser Gly Ile
                165                 170                 175
Ser Trp Asn Ser Gly Ser Ile Asp Tyr Ala Asp Ser Val Lys Gly Arg
            180                 185                 190
Phe Thr Ile Ser Arg Asp Asn Ala Lys Asn Ser Leu Tyr Leu Gln Met
        195                 200                 205
Asn Ser Leu Arg Ala Glu Asp Thr Ala Leu Tyr Tyr Cys Ala Lys Asp
    210                 215                 220
Gly Met Arg Val Phe Gly Val Gly Gly Phe Asp Phe Trp Gly Gln
225                 230                 235                 240
Gly Thr Met Val Thr Val Ser Ser
                245

<210> SEQ ID NO 64
<211> LENGTH: 252
<212> TYPE: PRT
<213> ORGANISM: Homo sapiens

<400> SEQUENCE: 64

Glu Leu Met Leu Thr Gln Pro His Ser Ala Ser Gly Thr Pro Gly Gln
1               5                   10                  15
Arg Val Thr Ile Ser Cys Ser Gly Ser Ser Ser Asn Ile Gly Ser Asn
                20                  25                  30
Thr Val Asn Trp Tyr Gln Gln Leu Pro Gly Thr Ala Pro Lys Leu Leu
            35                  40                  45
Ile Tyr Ser Asn Asn Gln Arg Pro Ser Gly Val Pro Asp Arg Phe Ser
        50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
Asn Gly Pro Val Phe Gly Gly Gly Thr Lys Val Thr Val Leu Gly Gly
            100                 105                 110
Gly Ser Ser Arg Ser Ser Ser Gly Gly Gly Ser Gly Gly Gly
        115                 120                 125
Gly Glu Val Gln Leu Val Glu Ser Gly Gly Gly Leu Val Gln Pro Gly
    130                 135                 140
Arg Ser Leu Arg Leu Ser Cys Ala Ala Ser Gly Phe Thr Phe Asp Asp
145                 150                 155                 160
Tyr Ala Met Tyr Trp Val Arg Gln Ala Pro Gly Lys Gly Leu Glu Trp
                165                 170                 175
Val Ser Gly Ile Ser Trp Asn Ser Gly Ser Ile Asp Tyr Ala Asp Ser
            180                 185                 190
Val Lys Gly Arg Phe Thr Ile Ser Arg Asp Asn Ala Lys Asn Ser Leu
```

```
                195                 200                 205
Tyr Leu Gln Met Asn Ser Leu Arg Ala Glu Asp Thr Ala Leu Tyr Tyr
    210                 215                 220

Cys Ala Lys Asp Gly Met Arg Val Phe Gly Val Gly Gly Phe Asp
225                 230                 235                 240

Phe Trp Gly Gln Gly Thr Met Val Thr Val Ser Ser
                245                 250

<210> SEQ ID NO 65
<211> LENGTH: 252
<212> TYPE: PRT
<213> ORGANISM: Homo sapiens

<400> SEQUENCE: 65

Glu Leu Val Val Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Gly Leu
                85                  90                  95

Asn Gly Met Val Phe Gly Gly Gly Thr Lys Leu Thr Val Leu Gly Gly
            100                 105                 110

Gly Ser Ser Arg Ser Ser Ser Gly Gly Gly Ser Gly Gly Gly
        115                 120                 125

Gly Glu Val Gln Leu Val Glu Ser Gly Gly Leu Val Gln Pro Gly
130                 135                 140

Arg Ser Leu Arg Leu Ser Cys Ala Ala Ser Gly Phe Thr Phe Asp Asp
145                 150                 155                 160

Tyr Ala Met His Trp Val Arg Gln Ala Pro Gly Lys Gly Leu Glu Trp
                165                 170                 175

Val Ser Gly Ile Ser Trp Asn Ser Gly Thr Ile Gly Tyr Ala Asp Ser
            180                 185                 190

Val Lys Gly Arg Phe Thr Ile Ser Arg Asp Asn Ala Lys Asn Ser Leu
        195                 200                 205

Tyr Leu Gln Met Asn Ser Leu Arg Ala Glu Asp Thr Ala Val Tyr Tyr
    210                 215                 220

Cys Ala Lys Asp Gly Ile Thr Val Phe Gly Val Gly Asp Gly Leu Asp
225                 230                 235                 240

Ile Trp Gly Gln Gly Thr Met Val Thr Val Ser Ser
                245                 250

<210> SEQ ID NO 66
<211> LENGTH: 250
<212> TYPE: PRT
<213> ORGANISM: Homo sapiens

<400> SEQUENCE: 66

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asn Asp
```

```
                        20                  25                  30
Leu Gly Trp Tyr Gln Gln Lys Pro Gly Lys Ala Pro Lys Leu Leu Ile
                35                  40                  45
Tyr Ala Ala Ser Ser Leu Gln Ser Gly Val Pro Ser Arg Phe Ser Gly
            50                  55                  60
Ser Gly Ser Gly Thr Asp Phe Thr Leu Thr Ile Gly Ser Leu Gln Pro
65                  70                  75                  80
Glu Asp Phe Ala Thr Tyr Tyr Cys Leu Gln Asp Tyr Asn Tyr Pro Phe
                85                  90                  95
Thr Phe Gly Pro Gly Thr Lys Val Asp Ile Lys Gly Gly Ser Ser Arg
            100                 105                 110
Ser Ser Ser Ser Gly Gly Gly Ser Gly Gly Gly Glu Val Gln
        115                 120                 125
Leu Val Glu Ser Gly Gly Thr Leu Val Gln Pro Gly Arg Ser Leu Arg
130                 135                 140
Leu Ser Cys Ala Ala Ser Gly Phe Ser Phe Asp Asp Tyr Ala Met Gln
145                 150                 155                 160
Trp Val Arg Gln Ala Pro Gly Lys Gly Leu Glu Trp Val Ser Gly Ile
                165                 170                 175
Ser Trp Asn Ser Gly Ser Ile Ala Tyr Ala Asp Ser Val Lys Gly Arg
            180                 185                 190
Phe Thr Ile Ser Arg Asp Asn Ala Lys Ser Ser Leu Tyr Leu Leu Met
        195                 200                 205
Asn Ser Leu Arg Ala Glu Asp Thr Ala Leu Tyr Tyr Cys Ala Lys Ala
210                 215                 220
Gly Thr Asp Tyr Tyr Asp Ser Ser Ala Ser Glu Leu Pro Asp Tyr Trp
225                 230                 235                 240
Gly Gln Gly Thr Leu Val Thr Val Ser Ser
                245                 250

<210> SEQ ID NO 67
<211> LENGTH: 251
<212> TYPE: PRT
<213> ORGANISM: Homo sapiens

<400> SEQUENCE: 67

Glu Leu Gln Met Thr Gln Ser Pro Ser Phe Leu Ser Ala Ser Val Gly
1               5                   10                  15
Asp Arg Val Thr Ile Thr Cys Arg Ala Ser Gln Gly Ile Ser Ser Tyr
            20                  25                  30
Leu Ala Trp Tyr Gln Gln Lys Pro Gly Lys Ala Pro Lys Leu Leu Ile
        35                  40                  45
Tyr Gly Ala Ser Thr Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Asn Ser Tyr Pro Trp
                85                  90                  95
Thr Phe Gly Gln Gly Thr Lys Val Glu Ile Lys Gly Gly Ser Ser Arg
            100                 105                 110
Ser Ser Ser Ser Gly Gly Gly Ser Gly Gly Gly Gln Val Gln
        115                 120                 125
Leu Gln Glu Ser Gly Gly Gly Leu Val Gln Pro Gly Arg Ser Leu Arg
130                 135                 140
```

```
Leu Ser Cys Ala Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Ser Trp Asn Ser Gly Ser Ile Ala Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Phe Tyr Tyr Cys Ala Lys Val
    210                 215                 220

Gly Gly Asp Thr Tyr Asp Ile Thr Ser Gly Ala Asp Tyr Phe Asp Leu
225                 230                 235                 240

Trp Gly Arg Gly Ala Leu Val Thr Val Ser Ser
                245                 250
```

<210> SEQ ID NO 68
<211> LENGTH: 252
<212> TYPE: PRT
<213> ORGANISM: Homo sapiens

<400> SEQUENCE: 68

```
Glu Leu Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ser
                85                  90                  95

Ile Thr Phe Gly Gln Gly Thr Arg Leu Glu Ile Lys Gly Gly Ser Ser
            100                 105                 110

Arg Ser Ser Ser Ser Gly Gly Gly Gly Ser Gly Gly Gly Gly Gln Val
        115                 120                 125

Gln Leu Val Gln Ser Gly Gly Gly Leu Val Gln Pro Gly Arg Ser Leu
    130                 135                 140

Arg Leu Ser Cys Ala Ala Ser Gly Phe Thr Phe Asp Asp Tyr Ala Met
145                 150                 155                 160

His Trp Val Arg Gln Ala Pro Gly Lys Gly Leu Glu Trp Val Ser Gly
                165                 170                 175

Ile Ser Trp Asn Ser Gly Ser Ile Ala Tyr Ala Asp Ser Val Lys Gly
            180                 185                 190

Arg Phe Thr Ile Ser Arg Asp Asn Ala Lys Asn Ser Leu Tyr Leu Gln
        195                 200                 205

Met Asn Ser Leu Arg Ala Glu Asp Thr Ala Phe Tyr Tyr Cys Ala Lys
    210                 215                 220

Val Gly Gly Asp Thr Tyr Asp Ile Thr Ser Gly Ala Asp Tyr Phe Asp
225                 230                 235                 240

Leu Trp Gly Arg Gly Ala Leu Val Thr Val Ser Ser
                245                 250
```

<210> SEQ ID NO 69

```
<211> LENGTH: 251
<212> TYPE: PRT
<213> ORGANISM: Homo sapiens

<400> SEQUENCE: 69

Glu Leu Val Val Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Lys Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Arg Ala Glu Asp Glu Ala Asp Tyr Tyr Cys Gln Ser Phe Asp Ser Ser
                85                  90                  95

Leu Gly Trp Val Phe Gly Gly Gly Thr Gln Leu Thr Val Leu Gly Gly
            100                 105                 110

Gly Ser Ser Arg Ser Ser Ser Gly Gly Gly Ser Gly Gly Gly
            115                 120                 125

Gly Gln Val Gln Leu Val Gln Ser Gly Gly Leu Val Gln Pro Gly
130                 135                 140

Gly Ser Leu Arg Val Ser Cys Ala Ala Ser Gly Phe Thr Ser Asn Ile
145                 150                 155                 160

Phe Trp Met Ser Trp Val Arg Gln Ala Pro Gly Lys Gly Leu Glu Trp
                165                 170                 175

Val Ala Asn Ile Asp Glu Asp Gly Ser Glu Lys Asn Tyr Val Asp Ser
            180                 185                 190

Val Lys Gly Arg Phe Thr Ile Ser Arg Asp Asn Ala Lys Asn Ser Leu
        195                 200                 205

Tyr Leu Gln Met Asn Ser Leu Arg Ala Glu Asp Thr Ala Val Tyr Tyr
    210                 215                 220

Cys Ala Arg Glu Ser Phe Tyr Tyr Gly Ser Gly Thr Tyr Phe Asp Phe
225                 230                 235                 240

Trp Gly Gln Gly Thr Leu Val Thr Val Ser Ser
                245                 250

<210> SEQ ID NO 70
<211> LENGTH: 250
<212> TYPE: PRT
<213> ORGANISM: Homo sapiens

<400> SEQUENCE: 70

Glu Leu Val Leu Thr Gln Pro Pro Ser Val Pro Val Ala Pro Gly Gln
1               5                   10                  15

Thr Ala Asn Ile Ser Cys Gly Gly Asn Asn Ile Gly Arg Gln Thr Val
            20                  25                  30

His Trp Tyr Gln Gln Lys Pro Gly Gln Ala Pro Val Leu Val Val Phe
        35                  40                  45

Asp Asp Ser Asp Arg Pro Ala Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95
```

```
Val Val Phe Gly Gly Gly Thr Gln Leu Thr Val Leu Gly Gly Gly Ser
            100                 105                 110

Ser Arg Ser Ser Ser Gly Gly Gly Ser Gly Gly Gly Gly Gln
        115                 120                 125

Val Gln Leu Val Gln Ser Gly Gly Val Val Gln Ser Gly Arg Ser
    130                 135                 140

Leu Arg Leu Ser Cys Ala Ala Ser Gly Phe Thr Phe Ser Asp Tyr Ala
145                 150                 155                 160

Met His Trp Val Arg Gln Ala Pro Gly Lys Gly Leu Glu Trp Val Ala
                165                 170                 175

Val Ile Ser His Gly Gly Thr Lys Lys Tyr Thr Gly Asp Ser Val Lys
            180                 185                 190

Gly Arg Phe Ile Ile Ser Arg Asp Asn Ser Lys Asn Thr Val Phe Leu
            195                 200                 205

Gln Met Asn Ser Leu Arg Val Glu Asp Thr Ala Val Tyr Tyr Cys Ala
    210                 215                 220

Arg Asp Arg Val Glu Gly Tyr Val Trp Gly Gly Thr Phe Asp His Trp
225                 230                 235                 240

Gly Gln Gly Thr Pro Val Thr Val Ser Ser
                245                 250

<210> SEQ ID NO 71
<211> LENGTH: 251
<212> TYPE: PRT
<213> ORGANISM: Homo sapiens

<400> SEQUENCE: 71

Glu Leu Val Leu Thr Gln Pro Pro Ser Val Ala Val Ser Pro Gly Gln
1               5                   10                  15

Thr Ala Ser Ile Thr Cys Ser Gly Asp Lys Leu Gly Asp Lys Tyr Val
            20                  25                  30

Ser Trp Tyr Gln Gln Lys Pro Gly Gln Ser Pro Val Leu Val Met Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Asn Thr Gly Val
                85                  90                  95

Phe Gly Gly Gly Thr Lys Leu Thr Val Leu Gly Gly Gly Ser Ser Arg
            100                 105                 110

Ser Ser Ser Ser Gly Gly Gly Ser Gly Gly Gly Gly Glu Val Gln
        115                 120                 125

Leu Leu Glu Ser Gly Pro Gly Leu Glu Lys Val Ser Glu Thr Leu Ser
    130                 135                 140

Leu Thr Cys Asn Val Ser Gly Val Ser Ile Ser Ser Pro Asp Tyr Tyr
145                 150                 155                 160

Trp Ala Trp Ile Arg Gln Pro Pro Gly Lys Gly Leu Glu Trp Ile Gly
                165                 170                 175

Ser Ile Phe Tyr Ser Gly Pro Thr Ser Trp Asn Pro Ser Leu Lys Asn
            180                 185                 190

Arg Val Thr Ile Ser Val Asp Thr Ser Lys Asn Gln Phe Ser Leu Lys
            195                 200                 205

Met Lys Ser Val Thr Ala Ala Asp Thr Ala Val Tyr Tyr Cys Ala Arg
```

```
                210               215                220
Ser Phe Gly Phe Gly Arg Tyr Glu Pro Ala Asp Asp Ala Phe Asp Ile
225                 230                 235                 240

Trp Gly Arg Gly Arg Leu Val Ile Val Ser Pro
                245                 250

<210> SEQ ID NO 72
<211> LENGTH: 253
<212> TYPE: PRT
<213> ORGANISM: Homo sapiens

<400> SEQUENCE: 72

Glu Leu Glu Leu Thr Gln Pro Pro Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ala Trp Asp Arg Ser Thr Ala His
                85                  90                  95

Val Val Phe Gly Gly Gly Thr Lys Leu Thr Val Leu Gly Gly Gly Ser
            100                 105                 110

Ser Arg Ser Ser Ser Gly Gly Gly Ser Gly Gly Gly Gly Gln
            115                 120                 125

Val Gln Leu Val Gln Ser Gly Gly Gly Val Val Gln Pro Gly Arg Ser
        130                 135                 140

Leu Arg Leu Ser Cys Thr Ala Ser Arg Phe Asn Phe Arg Ser Phe Ala
145                 150                 155                 160

Met His Trp Val Arg Gln Ala Pro Gly Lys Gly Leu Glu Trp Val Ala
                165                 170                 175

Met Phe Pro Tyr Asp Gly Asn Asn Thr Tyr Tyr Gly Asp Ser Val Lys
            180                 185                 190

Gly Arg Phe Thr Ile Ser Arg Asp Asn Ser Lys Lys Met Leu Tyr Leu
        195                 200                 205

Gln Met Asn Asp Leu Arg Ile Asp Asp Thr Ala Leu Tyr Tyr Cys Ala
    210                 215                 220

Arg Gln Gly Trp Val Ile Glu Thr Ser Gly Ile Arg Ala Ser Gly Phe
225                 230                 235                 240

Asp Val Trp Gly Gln Gly Thr Leu Val Thr Val Ser Ser
                245                 250

<210> SEQ ID NO 73
<211> LENGTH: 252
<212> TYPE: PRT
<213> ORGANISM: Homo sapiens

<400> SEQUENCE: 73

Glu Leu Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
```

-continued

```
                35                  40                  45
Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Val Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Gly Gly Thr Gln Leu Thr Val Leu Gly Gly
                100                 105                 110

Gly Ser Ser Arg Ser Ser Ser Gly Gly Gly Gly Ser Gly Gly Gly
                115                 120                 125

Gly Gln Val Gln Leu Gln Glu Ser Gly Gly Gly Leu Val Gln Pro Gly
130                 135                 140

Arg Ser Leu Arg Leu Ser Cys Ala Ala Ser Gly Phe Thr Phe Asp Asp
145                 150                 155                 160

Tyr Ala Met His Trp Val Arg Gln Ala Pro Gly Lys Gly Leu Glu Trp
                165                 170                 175

Val Ser Gly Ile Ser Trp Asn Ser Gly Thr Ile Gly Tyr Ala Asp Ser
                180                 185                 190

Val Lys Gly Arg Phe Thr Ile Ser Arg Asp Asn Ala Lys Asn Ser Leu
                195                 200                 205

Tyr Leu Gln Met Asn Ser Leu Arg Ala Glu Asp Thr Ala Val Tyr Tyr
            210                 215                 220

Cys Ala Lys Asp Gly Ile Thr Val Phe Gly Val Gly Asp Gly Leu Asp
225                 230                 235                 240

Ile Trp Gly Gln Gly Thr Met Val Thr Val Ser Ser
                245                 250
```

```
<210> SEQ ID NO 74
<211> LENGTH: 250
<212> TYPE: PRT
<213> ORGANISM: Homo sapiens

<400> SEQUENCE: 74

Glu Leu Val Met Thr Gln Ser Pro Ser Ser Val Ser Ala Ser Val Gly
 1               5                  10                  15

Asp Arg Val Ile Ile Thr Cys Arg Ala Ser Gln Gly Ile Ser Ser Ser
                 20                  25                  30

Tyr Leu Ala Trp Tyr Gln Gln Lys Pro Gly Lys Ala Pro Lys Leu Leu
             35                  40                  45

Ile Tyr Ala Ala Phe Thr Leu Gln Ser Gly Val Pro Ser Arg Phe Ser
 50                  55                  60

Gly Ser Gly Ser Gly Thr Glu Phe Thr Leu Thr Ile Ser Ser Leu Gln
 65                  70                  75                  80

Pro Glu Asp Phe Ala Thr Tyr Phe Cys Gln Asp Leu Ser Gly Tyr Pro
                 85                  90                  95

Arg Asn Thr Phe Gly Gln Gly Thr Arg Leu Glu Ile Lys Gly Gly Ser
                100                 105                 110

Ser Arg Ser Ser Ser Ser Gly Gly Gly Ser Gly Gly Gly Gly Glu
                115                 120                 125

Val Gln Leu Val Glu Ser Gly Gly Gly Leu Val Gln Pro Gly Arg Ser
            130                 135                 140

Leu Arg Leu Ser Cys Ala Ala Ser Gly Phe Thr Phe Asp Asp Tyr Ala
145                 150                 155                 160
```

Met His Trp Val Arg Gln Ala Pro Gly Lys Gly Leu Glu Trp Val Ser
                165                 170                 175

Gly Ile Ser Trp Asn Ser Gly Ser Ile Asp Tyr Ala Asp Ser Val Lys
            180                 185                 190

Gly Arg Phe Thr Ile Ser Arg Asp Asn Ala Lys Asn Ser Leu Tyr Leu
        195                 200                 205

Gln Met Asn Ser Leu Arg Val Glu Asp Thr Ala Leu Tyr Tyr Cys Ala
    210                 215                 220

Lys Asp Gly Ser Arg Val Phe Gly Val Gly Gly Phe Asp Phe Trp
225                 230                 235                 240

Gly Gln Gly Thr Met Val Thr Val Ser Ser
            245                 250

<210> SEQ ID NO 75
<211> LENGTH: 248
<212> TYPE: PRT
<213> ORGANISM: Homo sapiens

<400> SEQUENCE: 75

Glu Leu Val Met Thr Gln Ser Pro Ser Ser Leu Ser Ala Ser Val Gly
1               5                   10                  15

Asp Arg Val Thr Ile Thr Cys Gln Ala Ser Gln Asp Ile Arg Lys Tyr
            20                  25                  30

Leu Asn Trp Tyr Gln Lys Ala Gly Lys Ala Pro Lys Leu Leu Ile
        35                  40                  45

Tyr Asp Ala Ser Lys Leu Asp Ile Gly Leu Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asp Asn Leu Pro Phe
                85                  90                  95

Thr Phe Gly Gly Gly Thr Lys Val Glu Ile Lys Gly Gly Ser Ser Arg
            100                 105                 110

Ser Ser Ser Ser Gly Gly Gly Ser Gly Gly Gly Gly Glu Val Gln
        115                 120                 125

Leu Val Glu Ser Gly Gly Gly Leu Val Gln Pro Gly Arg Ser Leu Arg
    130                 135                 140

Leu Ser Cys Ala Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Ser Trp Asn Ser Gly Thr Ile Gly Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Lys Asp
    210                 215                 220

Gly Ile Thr Val Phe Gly Val Gly Asp Gly Leu Asp Ile Trp Gly Gln
225                 230                 235                 240

Gly Thr Met Val Thr Val Ser Ser
            245

<210> SEQ ID NO 76
<211> LENGTH: 246
<212> TYPE: PRT
<213> ORGANISM: Homo sapiens

<400> SEQUENCE: 76

Glu Leu Met Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Gln Leu Thr Val Leu Gly Gly
            100                 105                 110

Gly Ser Ser Arg Ser Ser Ser Gly Gly Gly Ser Gly Gly Gly
        115                 120                 125

Gly Glu Val Gln Leu Val Glu Ser Gly Gly Leu Val Gln Pro Gly
130                 135                 140

Gly Ser Val Arg Leu Ser Cys Ala Ala Ser Gly Phe Gln Val Ser Ser
145                 150                 155                 160

Asp His Met Ser Trp Val Arg Gln Ala Pro Gly Lys Gly Leu Gln Trp
            165                 170                 175

Val Ser Val Ile Tyr Thr Gly Gly Asn Ser Tyr Tyr Ala Asp Ser Val
            180                 185                 190

Lys Gly Arg Phe Thr Val Ser Arg Asp Asn Ser Arg Asn Thr Leu Phe
        195                 200                 205

Leu Gln Met Asn Ser Leu Arg Val Glu Asp Thr Ala Ile Tyr Tyr Cys
    210                 215                 220

Val Arg Gly Pro Ala Tyr Tyr Asp Ile Asp Tyr Trp Gly Gln Gly Ala
225                 230                 235                 240

Leu Val Thr Val Ser Ser
                245

<210> SEQ ID NO 77
<211> LENGTH: 252
<212> TYPE: PRT
<213> ORGANISM: Homo sapiens

<400> SEQUENCE: 77

Glu Leu Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Gly Val Phe Gly Gly Gly Thr Glu Leu Thr Val Leu Gly Gly
            100                 105                 110

Gly Ser Ser Arg Ser Ser Ser Gly Gly Gly Ser Gly Gly Gly
            115                 120                 125

Gly Gln Val Gln Leu Gln Glu Ser Gly Gly Leu Val Gln Pro Gly
        130                 135                 140

Arg Ser Leu Arg Leu Ser Cys Ala Ala Ser Gly Phe Thr Phe Asp Asp
145                 150                 155                 160

Tyr Ala Met His Trp Val Arg Gln Ala Pro Gly Lys Gly Leu Glu Trp
                165                 170                 175

Val Ser Gly Ile Ser Trp Asn Ser Gly Ala Ile Gly Tyr Ala Asp Ser
            180                 185                 190

Val Lys Gly Arg Phe Thr Ile Ser Arg Asp Asn Ala Lys Asn Ser Leu
        195                 200                 205

Tyr Leu Gln Met Asn Ser Leu Arg Ala Glu Asp Thr Ala Val Tyr Tyr
    210                 215                 220

Cys Ala Lys Asp Gly Ile Thr Val Phe Gly Val Gly Asp Gly Leu Asp
225                 230                 235                 240

Ile Trp Gly Gln Gly Thr Met Val Thr Val Ser Ser
                245                 250

<210> SEQ ID NO 78
<211> LENGTH: 246
<212> TYPE: PRT
<213> ORGANISM: Homo sapiens

<400> SEQUENCE: 78

Glu Leu Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Arg Val Phe Gly Gly Gly Thr Gln Leu Thr Val Leu Gly Gly
            100                 105                 110

Gly Ser Ser Arg Ser Ser Ser Gly Gly Gly Ser Gly Gly Gly
        115                 120                 125

Gly Gln Val Gln Leu Val Gln Ser Gly Gly Asp Leu Val Gln Pro Gly
        130                 135                 140

Gly Ser Leu Arg Leu Ser Cys Val Ala Ser Gly Phe Asn Val Asn Asp
145                 150                 155                 160

Asn Tyr Met Ser Trp Val Arg Gln Ala Pro Gly Lys Gly Leu Glu Trp
                165                 170                 175

Val Ser Thr Ile Tyr Ser Glu Thr Leu Ser Tyr Tyr Gly Asp Ser Val
            180                 185                 190

Lys Gly Arg Phe Thr Val Ser Arg Asp Gly Ser Lys Asn Thr Val Phe
        195                 200                 205

Leu Gln Met Ser Ser Leu Lys Gly Glu Asp Thr Ala Val Tyr Tyr Cys
    210                 215                 220

Ala Ser Glu Gly Gly Gly Leu Thr Ile Asp Tyr Trp Gly Gln Gly Thr

Leu Val Ala Val Ser Ser
                245

<210> SEQ ID NO 79
<211> LENGTH: 258
<212> TYPE: PRT
<213> ORGANISM: Homo sapiens

<400> SEQUENCE: 79

Glu Leu Val Val Thr Gln Pro Ser Ala Ser Ala Leu Gly Ser
1               5                   10                  15

Ser Ala Lys Leu Thr Cys Thr Leu Ser Ser Ala His Lys Thr Tyr Thr
            20                  25                  30

Ile Asp Trp Tyr Gln Gln Gln Gly Glu Ala Pro Arg Tyr Leu Met
            35                  40                  45

Gln Leu Lys Ser Asp Gly Ser Tyr Ser Lys Gly Thr Gly Val Pro Asp
        50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ser Gly Gly Tyr Tyr Val Phe Gly Gly Gly Thr Lys Leu Thr Val Leu
            100                 105                 110

Gly Gly Gly Ser Ser Arg Ser Ser Pro Ser Gly Gly Gly Ser Gly
            115                 120                 125

Gly Gly Gly Glu Val Gln Leu Val Glu Ser Gly Ala Glu Val Lys Lys
        130                 135                 140

Pro Gly Ala Ser Val Lys Val Ser Cys Lys Ala Ser Thr Tyr Met Phe
145                 150                 155                 160

Thr Ser Tyr Asp Ile Asn Trp Val Arg Gln Ala Ala Gly Gln Gly Leu
                165                 170                 175

Glu Trp Met Gly Trp Met Asp Pro Asn Thr Gly Asn Thr Asp Tyr Ala
            180                 185                 190

Gln Lys Phe Gln Gly Arg Val Thr Met Thr Arg Asn Thr Ser Ile Asn
            195                 200                 205

Thr Ala Tyr Met Glu Leu Arg Ser Leu Thr Ser Asp Asp Thr Ala Val
        210                 215                 220

Tyr Tyr Cys Ala Arg Gly Arg Thr Val Arg Phe Gly Glu Leu Phe Val
225                 230                 235                 240

Ser Glu Gly Gly Met Asp Val Trp Gly Gln Gly Thr Thr Val Ser Val
                245                 250                 255

Ser Ser

<210> SEQ ID NO 80
<211> LENGTH: 247
<212> TYPE: PRT
<213> ORGANISM: Homo sapiens

<400> SEQUENCE: 80

Glu Leu Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

```
Tyr Ala Ala Ser Asn Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Leu
                    85                  90                  95

Thr Phe Gly Gly Gly Thr Lys Leu Glu Ile Lys Gly Gly Ser Ser Arg
                100                 105                 110

Ser Ser Ser Ser Gly Gly Gly Ser Gly Gly Gly Gly Glu Val Gln
            115                 120                 125

Leu Val Glu Ser Gly Gly Gly Leu Val Gln Pro Gly Arg Ser Leu Arg
        130                 135                 140

Leu Ser Cys Ala Ala Ser Gly Phe Thr Phe Asp Asp His Ala Met His
145                 150                 155                 160

Trp Val Arg Gln Ala Pro Gly Lys Gly Leu Glu Trp Val Ser Gly Ile
                    165                 170                 175

Ser Trp Ser Gly Ala Tyr Ile Ala Tyr Ala Asp Ser Val Lys Gly Arg
                180                 185                 190

Phe Thr Ile Ser Arg Asp Asn Ala Arg Asn Ser Leu Tyr Leu Gln Met
            195                 200                 205

Asn Ser Leu Arg Ala Glu Asp Thr Ala Leu Tyr Tyr Cys Ala Arg Ser
210                 215                 220

Ser Gly Tyr Tyr Asp Leu Pro Tyr Ala Phe Asp Ile Trp Gly Gln Gly
225                 230                 235                 240

Thr Met Val Thr Val Ser Ser
                245

<210> SEQ ID NO 81
<211> LENGTH: 253
<212> TYPE: PRT
<213> ORGANISM: Homo sapiens

<400> SEQUENCE: 81

Glu Leu Val Leu Thr Gln Ser Pro Ser Val Ser Gly Ala Pro Gly Gln
 1               5                  10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
                35                  40                  45

Leu Ile Tyr Asp Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                    85                  90                  95

Leu Ser Ala Trp Val Phe Gly Gly Gly Thr Lys Val Thr Val Leu Gly
                100                 105                 110

Gly Gly Ser Ser Arg Ser Ser Ser Gly Gly Gly Ser Gly Gly Gly
            115                 120                 125

Gly Gly Glu Val Gln Leu Val Glu Ser Gly Gly Gly Leu Val Gln Pro
        130                 135                 140

Gly Arg Ser Leu Arg Leu Ser Cys Ala Ala Ser Gly Phe Thr Phe Asp
145                 150                 155                 160

Asp Tyr Ala Met His Trp Val Arg Gln Ala Pro Gly Lys Gly Leu Glu
```

165                 170                 175

Trp Val Ser Gly Ile Ser Trp Asn Ser Gly Ser Ile Asp Tyr Ala Asp
            180                 185                 190

Ser Val Lys Gly Arg Phe Thr Ile Ser Arg Asp Asn Ala Lys Asn Ser
        195                 200                 205

Leu Tyr Leu Gln Met Asn Ser Leu Arg Val Glu Asp Thr Ala Leu Tyr
    210                 215                 220

Tyr Cys Ala Lys Asp Gly Ser Arg Val Phe Gly Val Gly Gly Phe
225                 230                 235                 240

Asp Phe Trp Gly Gln Gly Thr Met Val Thr Val Ser Ser
                245                 250

<210> SEQ ID NO 82
<211> LENGTH: 247
<212> TYPE: PRT
<213> ORGANISM: Homo sapiens

<400> SEQUENCE: 82

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Arg Leu Glu Ile Lys Gly Gly Ser Ser Arg Ser
            100                 105                 110

Ser Ser Ser Gly Gly Gly Gly Ser Gly Gly Gly Glu Val Gln Leu
        115                 120                 125

Val Glu Ser Gly Gly Gly Leu Val Gln Pro Gly Arg Ser Leu Arg Leu
    130                 135                 140

Ser Cys Ala Ala Ser Gly Phe Thr Phe Asp Asp Tyr Ala Met His Trp
145                 150                 155                 160

Val Arg Gln Ala Pro Gly Lys Gly Leu Glu Trp Val Ser Gly Ile Ser
                165                 170                 175

Trp Asn Ser Gly Thr Ile Gly Tyr Ala Asp Ser Val Lys Gly Arg Phe
            180                 185                 190

Thr Ile Ser Arg Asp Asn Ala Lys Asn Ser Leu Tyr Leu Gln Met Asn
        195                 200                 205

Ser Leu Arg Ala Glu Asp Thr Ala Val Tyr Tyr Cys Ala Lys Asp Gly
    210                 215                 220

Ile Thr Val Phe Gly Val Gly Asp Gly Leu Asp Ile Trp Gly Gln Gly
225                 230                 235                 240

Thr Met Val Thr Val Ser Ser
                245

<210> SEQ ID NO 83
<211> LENGTH: 255
<212> TYPE: PRT
<213> ORGANISM: Homo sapiens -continued

<400> SEQUENCE: 83

```
Glu Leu Glu Leu Thr Gln Pro Pro Ser Val Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Val Thr Val Leu Gly Gly
            100                 105                 110

Gly Ser Ser Arg Ser Ser Ser Gly Gly Gly Ser Gly Gly Gly
            115                 120                 125

Gly Gln Val Gln Leu Gln Glu Ser Gly Gly Gly Leu Val Gln Pro Gly
130                 135                 140

Arg Ser Leu Arg Leu Ser Cys Ala Ala Ser Gly Phe Thr Phe Asp Asp
145                 150                 155                 160

Tyr Ala Met His Trp Val Arg Gln Ala Pro Gly Lys Gly Leu Glu Trp
                165                 170                 175

Val Ser Gly Ile Ser Trp Asn Ser Gly Ser Ile Ala Tyr Ala Asp Ser
            180                 185                 190

Val Lys Gly Arg Phe Thr Ile Ser Arg Asp Asn Ala Lys Asn Ser Leu
        195                 200                 205

Tyr Leu Gln Met Asn Ser Leu Arg Ala Glu Asp Thr Ala Phe Tyr Tyr
    210                 215                 220

Cys Ala Lys Val Gly Gly Asp Thr Tyr Asp Ile Thr Ser Gly Ala Asp
225                 230                 235                 240

Tyr Phe Asp Leu Trp Gly Arg Ser Ala Leu Val Thr Val Ser Ser
                245                 250                 255
```

<210> SEQ ID NO 84
<211> LENGTH: 252
<212> TYPE: PRT
<213> ORGANISM: Homo sapiens

<400> SEQUENCE: 84

```
Glu Leu Glu Leu Thr Gln Pro Pro Ser Val Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ala Trp Asp Asp Ser Leu
                85                  90                  95

Asn Gly Leu Val Phe Gly Gly Gly Thr Lys Leu Thr Val Leu Gly Gly
            100                 105                 110
```

```
Gly Ser Ser Arg Ser Ser Ser Gly Gly Gly Ser Gly Gly
            115                 120                 125

Gly Glu Val Gln Leu Val Glu Ser Gly Gly Leu Val Gln Pro Gly
130                 135                 140

Arg Ser Leu Arg Leu Ser Cys Ala Ala Ser Gly Phe Thr Phe Asp Asp
145                 150                 155                 160

Tyr Ala Met His Trp Val Arg Gln Pro Gly Lys Gly Leu Glu Trp
                165                 170                 175

Val Ser Gly Ile Ser Trp Asn Ser Thr Ile Gly Tyr Ala Asp Ser
                180                 185                 190

Val Lys Gly Arg Phe Thr Ile Ser Arg Asp Asn Ala Lys Asn Ser Leu
                195                 200                 205

Tyr Leu Gln Met Asn Ser Leu Arg Ala Glu Asp Thr Ala Val Tyr Tyr
    210                 215                 220

Cys Ala Lys Asp Gly Ile Thr Val Phe Gly Val Gly Asp Gly Leu Asp
225                 230                 235                 240

Ile Trp Gly Gln Gly Thr Met Val Thr Val Ser Ser
                245                 250
```

<210> SEQ ID NO 85
<211> LENGTH: 247
<212> TYPE: PRT
<213> ORGANISM: Homo sapiens

<400> SEQUENCE: 85

```
Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
                20                  25                  30

Leu Asn Trp Tyr Gln Gln Lys Pro Gly Lys Ala Pro Met Leu Leu Ile
            35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Gly Gly Ser Ser Arg
            100                 105                 110

Ser Ser Ser Ser Gly Gly Gly Ser Gly Gly Gly Gln Ile Thr
            115                 120                 125

Leu Lys Glu Ser Gly Gly Gly Val Val Gln Pro Gly Arg Ser Leu Arg
130                 135                 140

Leu Ser Cys Ala Ala Ser Gly Phe Asp Phe Asn Ile Tyr Gly Met His
145                 150                 155                 160

Trp Val Arg Gln Ala Pro Asp Lys Gly Leu Glu Trp Val Ala Val Ile
                165                 170                 175

Ser Asp Asp Gly Thr Lys Lys Tyr Tyr Ala Asp Ser Val Lys Gly Arg
            180                 185                 190

Val Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Lys Asp
    210                 215                 220

Leu Asp Val Val Met Gly Pro Gly Gly Leu Asp Tyr Trp Gly Gln Gly
225                 230                 235                 240
```

```
Thr Leu Val Thr Val Ser Ser
            245

<210> SEQ ID NO 86
<211> LENGTH: 252
<212> TYPE: PRT
<213> ORGANISM: Homo sapiens

<400> SEQUENCE: 86

Glu Leu Val Leu Thr Gln Pro Pro Ser Ala Ser Gly Thr Pro Gly Gln
1               5                  10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Arg Val Phe Gly Gly Gly Thr Lys Leu Thr Val Leu Gly Gly
            100                 105                 110

Gly Ser Ser Arg Ser Ser Ser Gly Gly Gly Ser Gly Gly Gly
            115                 120                 125

Gly Gln Ile Thr Leu Lys Glu Ser Gly Gly Leu Val Gln Pro Gly
        130                 135                 140

Arg Ser Leu Arg Leu Ser Cys Ala Ala Ser Gly Phe Thr Phe Asp Asp
145                 150                 155                 160

Tyr Ala Met His Trp Val Arg Gln Ala Pro Gly Lys Gly Leu Glu Trp
                165                 170                 175

Val Ser Gly Ile Ser Trp Asn Ser Gly Thr Ile Gly Tyr Ala Asp Ser
            180                 185                 190

Val Lys Gly Arg Phe Thr Ile Ser Arg Asp Asn Ala Lys Asn Ser Leu
        195                 200                 205

Tyr Leu Gln Met Asn Ser Leu Arg Ala Glu Asp Thr Ala Val Tyr Tyr
    210                 215                 220

Cys Ala Lys Asp Gly Ile Thr Val Phe Gly Val Gly Asp Gly Leu Asp
225                 230                 235                 240

Ile Trp Gly Gln Gly Thr Met Val Thr Val Ser Ser
                245                 250

<210> SEQ ID NO 87
<211> LENGTH: 339
<212> TYPE: DNA
<213> ORGANISM: Homo sapiens

<400> SEQUENCE: 87
gagctcgtgt tgacacagtc tccagactcc ctgtctgtgt ctctgggcga gagggccacc     60
atcaactgca agtccagcca gactgtttta tacaactccg acaataagaa ctacttaagt    120
tggtaccagc agaaaccagg acagcctcct aagttgatca tgaactgggc atctatccgg    180
gcatccgggg tccctgaccg attcagtggc agcgggtctg ggacagattt cactctcacc    240
atcaacagcc tgcaggctga agatgtggca atttattact gtcagcaata ttatagtact    300
ccgctcacct tcggcggagg gaccaaggtg gaaatcaaa                           339
```

<210> SEQ ID NO 88
<211> LENGTH: 321
<212> TYPE: DNA
<213> ORGANISM: Homo sapiens

<400> SEQUENCE: 88

```
gagctcacac tcacgcagtc tccatcctcc ctgtctgcat ctgtaggaga cagagtcacc      60
atcacttgcc gggccagtca gggcattgcc agttatttag cctggtatca gcaaaaacca     120
gggaaagccc ctaagctcct gatctatggt gcatccactt tgcaaagtgg ggtcccatca     180
aggttcagcg gccgtagatc tgggacagat ttcactctca ccatcagcag cctgcagcct     240
gaagatgctg caacttatta ctgccaacaa tatagtaatt accctctgac ttttggccag     300
gggaccaagc tggagatcaa a                                                321
```

<210> SEQ ID NO 89
<211> LENGTH: 321
<212> TYPE: DNA
<213> ORGANISM: Homo sapiens

<400> SEQUENCE: 89

```
gagctccaga tgacccagtc tccatcctca ctgtctgcat ctgtaggaga cagagtcacc      60
atcacttgtc gggcgagtca gggcattaac aattatttag cctggtttca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt acccattcac tttcggccct     300
gggaccaaag tggatatcaa a                                                321
```

<210> SEQ ID NO 90
<211> LENGTH: 321
<212> TYPE: DNA
<213> ORGANISM: Homo sapiens

<400> SEQUENCE: 90

```
gagctccaga tgacccagtc tccttccacc ctgtctgcat ctgtaggaga cagagtcacc      60
atcacttgtc gggcgagtca gggtattagc aactggttag cctggtatca gcagaaacca     120
ggaaaagccc ctaagctcct gatccataag gcatctagtt tagaaagtgg ggtcccatca     180
aggttcagcg gcagtggatc tgggacagaa ttcactctca ccatcagcag cctgcagcct     240
gatgattttg caacttatta ctgccaacag tattatactt acccgctcac tttcggcgga     300
gggaccaagg tggaaatcaa a                                                321
```

<210> SEQ ID NO 91
<211> LENGTH: 318
<212> TYPE: DNA
<213> ORGANISM: Homo sapiens

<400> SEQUENCE: 91

```
gagctcgtgt tgacgcagtc tccagccacc ctgtctgtgt ctccagggga aagagccacc      60
ctctcctgca gggccagtca gagtgttagc agcaatttag cctggtacca gcagaaacct     120
ggccaggctc ccaggctcct catcaaagga gcatccacca gggccactgg tatcccagac     180
aggttcagtg gcagcgggtc tgggacagat ttcactctca ccatcagcag cctgcaggct     240
gaagatgtgg cagtttacta ctgtcaccag tattatggtc cttactcttt tggccagggg     300
```

```
accaaggtgg aaatcaaa                                                 318

<210> SEQ ID NO 92
<211> LENGTH: 321
<212> TYPE: DNA
<213> ORGANISM: Homo sapiens

<400> SEQUENCE: 92
gagctccaga tgacccagtc tccatcctca ctgtctgcat ctgttggaga cagagtcacc    60
atcacttgtc gggcgactca gggcattagt aattatttag cctggtttca gcagaaacca   120
gggaaagccc ctaagttgct gatctatgct gcatccagtt tgcaaagtgg ggtcccatca   180
aagttcagcg gcagtggatc tgggacagat ttcactctca ccatcagcag cctgcagcct   240
gaagattttg caacttatta ctgccaacag tataatagtt atcctctcac tttcggcgga   300
gggaccaagg tggaaatcaa a                                             321

<210> SEQ ID NO 93
<211> LENGTH: 321
<212> TYPE: DNA
<213> ORGANISM: Homo sapiens

<400> SEQUENCE: 93
gagctccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctcgcac tttcggcgga   300
gggaccaagc tggagatcaa a                                             321

<210> SEQ ID NO 94
<211> LENGTH: 321
<212> TYPE: DNA
<213> ORGANISM: Homo sapiens

<400> SEQUENCE: 94
gagctccaga tgacccagtc tccatcctcc ctgtctgtat cagtaggaga cagagtcacc    60
atcacttgcc gggcaagtca gagcattagc ggctatttaa attggtatca gcagaaacca   120
gggaaagccc ctaaactgct gatctatggt gcatccagtt tgcaaagtgg ggtcccatca   180
aggttcagtg gcagtggatc tgggacagat ttcgctctca ccatcagcag tgtgcaacct   240
gaagattttg caagttactt ctgtcaacag agtcacagcg tcccgatcaa cttcggccaa   300
gggacacgac tggagattaa a                                             321

<210> SEQ ID NO 95
<211> LENGTH: 321
<212> TYPE: DNA
<213> ORGANISM: Homo sapiens

<400> SEQUENCE: 95
gagctccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaagctcct gatctacgat gcatccaatt tggaaacagg ggtcccatca   180
aggctcagtg gaagtggatc tgggacagat tttactttca ccatcagcag cctgcagcct   240
gaagatattg caacatatta ctgtcaacag tatgatgatc tccccctcac tttcggcgga   300
```

```
gggaccaagc tggagatcaa a                                           321

<210> SEQ ID NO 96
<211> LENGTH: 321
<212> TYPE: DNA
<213> ORGANISM: Homo sapiens

<400> SEQUENCE: 96
gagctccaga tgacccagtc tccatcgtcc ctggctgcat ctgtgggaga cagagtcacc    60
atcacttgcc gggcaagtca cgacattaaa aatgatttag ctggtatca gcatcaacca   120 gggaaagccc ctaagctcct gatctatgct gcatccagtt tacaaagtgg ggtcccgtca   180
agattcagcg gcagtggatc cggcacaaat ttcaccctca ccatcaatag cctgcagcct   240
gaagattttg caacttatta ctgtctacat gattacactt accctcgcac gttcggccaa   300
gggaccaagg tggaaatcaa a                                           321

<210> SEQ ID NO 97
<211> LENGTH: 321
<212> TYPE: DNA
<213> ORGANISM: Homo sapiens

<400> SEQUENCE: 97
gagctccaga tgacccagtc tccatcctcc ctgtctgcat ctgtaggaga cagagtcacc    60
atcacttgcc gggcaagtca gggcattaga tatgatgtag ctggtatca gcagaaacca   120 gggaaagccc ctaagctcct gatctatgct gcatccacct tgcaaagtgg ggtcccatca   180
aggttcagtg gcagcggatc tgagacagat ttcactctca ccatcaacag tctgcagcct   240
gaagattctg caacttacta ctgtcaacag agttacagta cccttcgac gttcggccag   300 gggaccaagg tggagatcaa a                                           321

<210> SEQ ID NO 98
<211> LENGTH: 333
<212> TYPE: DNA
<213> ORGANISM: Homo sapiens

<400> SEQUENCE: 98
gagctcgagc tgactcagcc accctcagtg tctgggaccc ccgggcagag ggtcaccatc    60
tcttgttctg gaagcagctc caacatcgga agtgatacta taaactggta ccagcagctc   120
ccaggaacgg cccccaaaac cctcatctat agtaataatc agcggccctc aggggtccct   180
gaccgattct ctggctccaa gtctggcacc tcagcctccc tggccatcag tgggctccag   240
tctgaggatg aggctgacta ttactgtgca acatgggatg acggcctgcg tggcatggtg   300
ttcggcgaag caccaagct gaccgtccta ggc                                333

<210> SEQ ID NO 99
<211> LENGTH: 342
<212> TYPE: DNA
<213> ORGANISM: Homo sapiens

<400> SEQUENCE: 99
gagctcgtgt tgacgcagcc gccctcagtg tctggggccc cagggcggag ggtcaccatc    60
tcctgcactg ggagcagctc caacatcggg gctgcttatg atgtacactg gtaccagcag   120
cttccaggaa cagccccaa actcctcatc tttggtaaca ccaatcggcc ctcagggtc    180 cctgaccgat tctctggctc caagtctggc acctcagcct ccctggccat cactgggctc   240
```

| | |
|---|---|
| cagtctgagg atgaggctga ctattactgt gcaacatggg atgacagccg ggatggtccg | 300 |
| gaagtggtgt tcggcggagg caccgagctg accgtcctcg gt | 342 |

<210> SEQ ID NO 100
<211> LENGTH: 333
<212> TYPE: DNA
<213> ORGANISM: Homo sapiens

<400> SEQUENCE: 100

| | |
|---|---|
| gagctcgtgc tgactcagcc accttcggcg tctgggaccc ccggacagag ggtcaccatc | 60 |
| tcttgttctg gaagcaactc caacatcgga agtgattatg tgtactggta tcagcggttc | 120 |
| ccaggaacgg cccccaaact tctcatctat agtaataatc agcggccctc aggggtccct | 180 |
| gaccgattct ctggctccaa gtctggcacc tcagcctccc tggccatcag tggactccag | 240 |
| tctgaggatg aggctgagta ttactgtgca acatgggatg acgccctgcg tggcatggtg | 300 |
| ttcggcgaag caccaagct gaccgtccta ggt | 333 |

<210> SEQ ID NO 101
<211> LENGTH: 339
<212> TYPE: DNA
<213> ORGANISM: Homo sapiens

<400> SEQUENCE: 101

| | |
|---|---|
| gagctcatgc tgactcagcc ccactctgtg tcggagtctc cggggaagac ggtaaccatc | 60 |
| tcctgcaccc gcagcagtgg cagcattgcc agcaactttg tccagtggta ccagcagcgc | 120 |
| ccgggcaagt cccccaccac tgtaatttat gaggacaacc aaagaccgtc tggggtacct | 180 |
| gatcggttct ctggctccgt cgacaggtcc tccaactctg cctccctcac catctctgga | 240 |
| ctgcagactg aggacgaggc tgactattac tgtcagtctt tttatgacgg cgtcccttct | 300 |
| tgggtgttcg gcggaggcac cgagctgacc gtcctcggc | 339 |

<210> SEQ ID NO 102
<211> LENGTH: 339
<212> TYPE: DNA
<213> ORGANISM: Homo sapiens

<400> SEQUENCE: 102

| | |
|---|---|
| gagctcatgc tgactcagcc ccactctgtg tcggagtctc cggggaagac ggtaaccatc | 60 |
| tcctgcaccc gcagcagtgg cagcattgcc agcaactttg tccagtggta ccagcagcgc | 120 |
| ccgggcaagt cccccaccac tgtaatttat gaggacaacc aaagaccgtc tggggtacct | 180 |
| gatcggttct ctggctccgt cgacaggtcc tccaactctg cctccctcac catctctgga | 240 |
| ctgcagactg aggacgaggc tgactattac tgtcagtctt tttatgacgg cgtcccttct | 300 |
| tgggtgttcg gcggaggcac cgagctgacc gtcctcggc | 339 |

<210> SEQ ID NO 103
<211> LENGTH: 321
<212> TYPE: DNA
<213> ORGANISM: Homo sapiens

<400> SEQUENCE: 103

| | |
|---|---|
| gagctccaga tgacccagtc tccatcctcc ctgtctgcat ctgtaggaga cagagtcacc | 60 |
| atcacttgcc aggcgagtca ggacattggc aactatttaa attggtatca gcagaaacca | 120 |
| gggaaagccc ctaaactcct gatctacgat gcatcctatt tggaaacagg ggtcccatca | 180 |
| aggttcagtg gaagtggatc tgggacagat tttactttca ccatcagcag cctacagcct | 240 |

```
gaagatattg caacatatta ctgtcaacag tatgataatc tcccgttcac tttcggccct    300
gggaccaaag tggatatcaa a                                              321
```

<210> SEQ ID NO 104
<211> LENGTH: 321
<212> TYPE: DNA
<213> ORGANISM: Homo sapiens

<400> SEQUENCE: 104

```
gagctcgtga tgactcagtc tccatcctcc ctgtctgcat ctgtaggaga cagagtcacc    60
atcacttgcc gggcaagtca gggcattacc gatgacttag gtggtatca  gcagaagcca    120 gggaaagccc ctaagctcct gatctatgcc acatccaatt tagaaagtgg ggtcccatca    180
aggttcagcg gcagtggatc tgacacagaa ttcactctca ccatcagtag cctgcagcct    240
gaagatcttg caacttatta ctgtctacaa gattacagtt acccgtacac ttttggccag    300
gggaccaagg tggagatcaa a                                              321
```

<210> SEQ ID NO 105
<211> LENGTH: 321
<212> TYPE: DNA
<213> ORGANISM: Homo sapiens

<400> SEQUENCE: 105

```
gagctccaga tgacccagtc tccttccacc ctgtctgcat ctgtaggaga cagagtcacc    60
atcacttgcc gggccagtca gagtattagt agttggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatactt attcgaggac gttcggccaa    300
gggaccaagg tggaaatcaa a                                              321
```

<210> SEQ ID NO 106
<211> LENGTH: 321
<212> TYPE: DNA
<213> ORGANISM: Homo sapiens

<400> SEQUENCE: 106

```
gagctccaga tgacccagtc tccatcctcc ctgtctgcat ctgttggaga cagagtcacc    60
atcacttgcc aggcgagtcg tgacattagc aactatttaa attggtatca acacattcca    120
ggaaaggccc ctaagctcct catattccat gcatccactt tggaagcagg gatcccatca    180
aggttcagtg gaagtggatc agagacatct tttactttca ccataagaag cctacagcct    240
gaagatgttg caacatatta ctgtcaacaa tatgataatc tccccttcac tttcggccct    300
gggaccaaag tggatatcaa a                                              321
```

<210> SEQ ID NO 107
<211> LENGTH: 333
<212> TYPE: DNA
<213> ORGANISM: Homo sapiens

<400> SEQUENCE: 107

```
gagctcatgc tgactcagcc ccactcagcg tctgggaccc ccgggcagag ggtcaccatc    60
tcttgttctg gaagcagctc caacatcgga agtaatactg taaactggta ccagcagctc    120
ccaggaacgg cccccaaact cctcatctat agtaataatc agcggccctc agggggtccct  180
```

```
gaccgattct ctggctccaa gtctggcacc tcagcctccc tggccatcag tgggctccag    240
tctgaggatg aggctgatta ttactgtgca gcatgggatg acagcctgaa tggtccggta    300
ttcggcggag gcaccaaggt gaccgtccta ggc                                 333
```

<210> SEQ ID NO 108
<211> LENGTH: 333
<212> TYPE: DNA
<213> ORGANISM: Homo sapiens

<400> SEQUENCE: 108

```
gagctcgtgg tgacgcagcc gccctcagcg tctgggaccc ccgggcagag ggtcaccatc     60
tcttgttctg gaagcagctc caacatcgga agtaatactg taaactggta ccagcagctc    120
ccaggaacgg cccccaaact cctcatctat agtaataatc agcggccctc agggtccct    180 gaccgattct ctggctccaa gtctggcacc tcagcctccc tggccatcag tgggctccag    240
tctgaggatg aggctgatta ttactgtgca acgtgggatg acggcctgaa tggcatggtg    300
ttcggcggag gaccaagct gaccgtccta ggc                                  333
```

<210> SEQ ID NO 109
<211> LENGTH: 321
<212> TYPE: DNA
<213> ORGANISM: Homo sapiens

<400> SEQUENCE: 109

```
gagctccaga tgacccagtc tccttcctcc ctgtctgcat ctgtaggaga cagagtcacc     60
atcacttgcc gggcaagtca gggcattgga aatgatttag ctggtatca gcagaaacca    120 gggaaagccc ctaagctcct gatctatgct gcatccagtt tacaaagtgg ggtcccatca    180
aggttcagcg gcagtggatc tggcacagat ttcactctca ccatcggcag cctgcagcct    240
gaagattttg caacttatta ctgtctacaa gattacaatt acccattcac tttcggccct    300
gggaccaaag tggatatcaa a                                              321
```

<210> SEQ ID NO 110
<211> LENGTH: 321
<212> TYPE: DNA
<213> ORGANISM: Homo sapiens

<400> SEQUENCE: 110

```
gagctccaga tgacccagtc tccatccttc ctgtctgcat ctgtaggaga cagagtcacc     60
atcacttgcc gggccagtca gggcattagc agttatttag cctggtatca gcaaaaaccg    120
gggaaagccc ctaaactcct gatctatggt gcatctactt tgcaaagtgg ggtcccatca    180
aggttcagcg gcagtggatc tgggacagaa ttcactctca ccatcagcag cctgcagcct    240
gatgattttg caacttatta ctgccaacag tataatagtt atccgtggac gttcggccaa    300
gggaccaagg tggaaatcaa a                                              321
```

<210> SEQ ID NO 111
<211> LENGTH: 324
<212> TYPE: DNA
<213> ORGANISM: Homo sapiens

<400> SEQUENCE: 111

```
gagctcgtga tgacccagtc tccagccacc ctgtctgtgt ctccagggga aagagccacc     60
ctctcctgca gggccagtca gagtgttagc agcaacttag cctggtacca gcagaaacct    120
ggccaggctc ccaggctcct catctatggt gcatccacca gggccactgg tatcccagcc    180
```

```
aggttcagtg gcagtgggtc tgggacagag ttcactctca ccatcagcag cctgcagtct    240
gaagattttg cagtttatta ctgtcagcag tataataact ggccctcgat caccttcggc    300
caagggacac gactggagat taaa                                           324

<210> SEQ ID NO 112
<211> LENGTH: 333
<212> TYPE: DNA
<213> ORGANISM: Homo sapiens

<400> SEQUENCE: 112
gagctcgtgg tgacgcagcc gccctcagtg tctggggccc cagggcagag ggtcaccatc    60
tcctgcactg ggagcagctc caacatcggg gcaggttatg atgtacactg gtaccagcag   120
cttccaggaa cagcccccaa actcctcatt tatggtaaca aaaatcggcc ctcaggggtc   180
cctgaccggt tctctggctc caagtctggc acctcagcct ccctggccat cactgggctc   240
cgggctgagg atgaggctga ttactactgc cagtccttcg acagcagcct ggggtgggtg   300
ttcggcggag ggaccagct gaccgtcctc ggc                                  333

<210> SEQ ID NO 113
<211> LENGTH: 327
<212> TYPE: DNA
<213> ORGANISM: Homo sapiens

<400> SEQUENCE: 113
gagctcgtgc tgactcagcc accctcggtg ccagtggccc caggacagac ggccaacatt    60
agctgtgggg gaaacaacat tggaagacag actgtccact ggtaccagca gaagccaggc   120
caggcccctg tgttggtcgt ctttgatgat agcgaccggc cgcaggatc cctgagcga    180 ttctctggct ccaactctgg gaacacggcc accctgacca tcagcagggt cgaagccggg   240
gatgaggccg actattactg tcaggtgtgg gatagtagta gtgatcatgt ggtcttcggc   300
ggaggcaccc agctgaccgt cctcggc                                       327

<210> SEQ ID NO 114
<211> LENGTH: 321
<212> TYPE: DNA
<213> ORGANISM: Homo sapiens

<400> SEQUENCE: 114
gagctcgtgc tgactcagcc accttcagtg gccgtgtccc caggacagac agccagcatc    60
acctgctctg gagataaatt gggggataaa tatgtttcct ggtatcagca gaagccaggc   120
cagtcccctg ttctggtcat gtatcgagat accaagcggc cctcagggat ccctgagcga   180
ttttctggct ccaactccgg gaacacagcc actctgacca tcagcgggac ccaggctatg   240
gatgaggctg actattactg tcaggcgtgg gacagcaaca ctggggtgtt cggcggaggc   300
accaagctga ccgtcctagg c                                             321

<210> SEQ ID NO 115
<211> LENGTH: 327
<212> TYPE: DNA
<213> ORGANISM: Homo sapiens

<400> SEQUENCE: 115
gagctcgagc tgactcagcc accctcagtg tcagtggccc tgggacagac ggccaggatt    60
acctgtgggg gaaacaacat tggaagtaaa aatgtgcact ggtaccagca gaagccaggc   120
```

| | |
|---|---|
| caggcccctg tgctggtcat ctatagggat agcaaccggc cctctgggat ccctgagcga | 180 |
| ttctctggct ccaactcggg gaacacggcc accctgacca tcagcagagc ccaagccggg | 240 |
| gatgaggctg actattactg tcaggcgtgg acagaagca ctgctcatgt ggtattcggc | 300 |
| ggagggacca agctgaccgt cctaggt | 327 |

```
<210> SEQ ID NO 116
<211> LENGTH: 333
<212> TYPE: DNA
<213> ORGANISM: Homo sapiens

<400> SEQUENCE: 116
```

| | |
|---|---|
| gagctcgtgc tgacgcagcc gccctcagcg tctgggaccc ccgggcagag ggtcaccatc | 60 |
| tcttgttctg gaagcagctc caacatcgga agtaatactg taaactggta ccagcagctc | 120 |
| ccaggaacgg ccccccaaact cctcatctat agtaataatc agcggccctc aggggtccct | 180 |
| gaccgattct ctggctccaa gtctggcacc tcagcctccc tggccgtcag tgggctccag | 240 |
| tctgaggatg aggctgatta ttactgtgca gcatgggatg acagcctgaa tggtccggta | 300 |
| ttcggcggag gcacccagct gaccgtcctc ggt | 333 |

```
<210> SEQ ID NO 117
<211> LENGTH: 327
<212> TYPE: DNA
<213> ORGANISM: Homo sapiens

<400> SEQUENCE: 117
```

| | |
|---|---|
| gagctcgtga tgacccagtc tccatcttcc gtgtctgcat ctgtaggaga cagagtcatc | 60 |
| atcacttgtc gggcgagtca gggtattagc agcagttatt tagcctggta tcagcaaaaa | 120 |
| ccagggaaag cccctaagct cctgatctat gctgcattca ctttacaaag tggggtccca | 180 |
| tcaaggttca gcggcagtgg atctgggaca gaattcactc tcacaatcag cagcctgcag | 240 |
| cctgaagatt ttgcaactta tttctgtcaa gaccttagtg ttatcctcg aaacaccttc | 300 |
| ggccaaggga cacgactgga gattaaa | 327 |

```
<210> SEQ ID NO 118
<211> LENGTH: 321
<212> TYPE: DNA
<213> ORGANISM: Homo sapiens

<400> SEQUENCE: 118
```

| | |
|---|---|
| gagctcgtga tgacccagtc tccatcctcc ctgtctgcat ctgtaggaga cagagtcacc | 60 |
| atcacttgcc aggcgagtca ggacatcagg aagtatttaa attggtatca gcagaaagca | 120 |
| gggaaagccc ctaaactcct gatctacgat gcatctaagt tggatatagg gctcccatca | 180 |
| aggttcagtg gaagtggatc tgggacagat tttactttca ccatcagcag cctgcagcct | 240 |
| gaagatattg caacatatta ctgtcagcag tttgataatc tccccttcac tttcggcgga | 300 |
| gggaccaagg tggaaatcaa a | 321 |

```
<210> SEQ ID NO 119
<211> LENGTH: 333
<212> TYPE: DNA
<213> ORGANISM: Homo sapiens

<400> SEQUENCE: 119
```

| | |
|---|---|
| gagctcatgc tgactcagcc accctcagcg tctgggaccc ccgggcagag ggtcaccatc | 60 |
| tcttgttctg gaagcagctc caacatcgga agtaatactg taaactggta ccagcagctc | 120 |

```
ccaggaacgg cccccaaact cctcatctat aggaataatc agcggccctc agggtccct      180 gaccgattct ctggctccaa gtctggcacc tcagcctccc tggccatcag tgggctccgg      240
tccgaggatg aggctgatta ttactgtgca gcatgggatg acagcctgag tggttgggtg      300
ttcggcggag gcacccagct gaccgtcctc ggc                                  333

<210> SEQ ID NO 120
<211> LENGTH: 333
<212> TYPE: DNA
<213> ORGANISM: Homo sapiens

<400> SEQUENCE: 120
gagctcgtgt tgacgcagcc gccctcagcg tctgggaccc ccgggcagag ggtcaccatc       60
tcttgttctg gaagcagctc caacatcgga agtaatactg taaactggta ccagcagctc      120
ccaggaacgg cccccaaact cctcatctat agtaataatc agcggccctc aggggtccct      180
gaccgattct ctggctccaa gtctggcacc tcagcctccc tggccatcag tgggctccag      240
tctgaggatg aggctgatta ttactgtgca gcatgggatg acagcctgaa tggtggggtg      300
ttcggcggag gcaccgagct gaccgtcctc ggc                                  333

<210> SEQ ID NO 121
<211> LENGTH: 333
<212> TYPE: DNA
<213> ORGANISM: Homo sapiens

<400> SEQUENCE: 121
gagctcgtgc tgactcagcc accctcagcg tctgggaccc ccgggcagag ggtcaccatc       60
tcttgttctg gaagcagctc caacatcgga agtaatactg taaactggta ccagcagctc      120
ccaggaacgg cccccaaact cctcatctat agtaataatc agcggccctc aggggtccct      180
gaccgattct ctggctccaa gtctggcacc tcagcctccc tggccatcag tgggctccag      240
tctgaggatg aggctgatta ttactgtgca acatgggatg acagcctgaa tggtcgggtg      300
ttcggcggag gcacccagct gaccgtcctc ggc                                  333

<210> SEQ ID NO 122
<211> LENGTH: 339
<212> TYPE: DNA
<213> ORGANISM: Homo sapiens

<400> SEQUENCE: 122
gagctcgtgg tgacgcagcc gccctctgca tctgctgccc tgggatcctc ggccaagctc       60
acctgcaccc tgagcagtgc ccacaagacc tacaccattg actggtatca gcagcagcaa      120
ggggaggccc ctcggtacct gatgcaactt aagagtgatg gaagctactc caaggggacc      180
ggggtccctg atcgcttctc gggctccagc tctgggggctg accgttactt gatcatcccc      240
agcgtccagg ctgatgacga agccgactac tattgtggtg cagattatag cggtgggtat      300
tatgtgttcg gcggaggcac caagctgacc gtcctaggc                            339

<210> SEQ ID NO 123
<211> LENGTH: 321
<212> TYPE: DNA
<213> ORGANISM: Homo sapiens

<400> SEQUENCE: 123
gagctcgtga tgactcagtc tccatcctcc ctgtctgcat ctgtaggaga cagagtcacc       60
```

| | |
|---|---|
| atcacttgcc gggcaagtca gggcattaga aatgatttgg gctggtatca gcagaaacca | 120 |
| gggaaagccc ctaaactcct gatctatgct gcatccaatt tacaaagtgg ggtcccatca | 180 |
| aggttcagcg gcagtggatc tggcacagat ttcactctca ccatcagcag cctgcagcct | 240 |
| gaagattttg caacttatta ctgtctacaa gattacaatt acccgctcac tttcggcgga | 300 |
| gggaccaagc tggagatcaa a | 321 |

<210> SEQ ID NO 124
<211> LENGTH: 336
<212> TYPE: DNA
<213> ORGANISM: Homo sapiens

<400> SEQUENCE: 124

| | |
|---|---|
| gagctcgtgc tgactcaatc gccctcagtg tctggggccc cagggcagag ggtcaccatc | 60 |
| tcctgcactg ggagcagctc caacatcggg gcaggttatg atgtacactg gtaccagcag | 120 |
| cttccaggaa cagcccccaa actcctcatc tatgataaca gcaatcggcc ctcaggggtc | 180 |
| cctgaccgat tctctggctc caagtctggc acctcagcct ccctggccat cactgggctc | 240 |
| caggctgagg atgaggctga ttattactgc cagtcctatg acagcagcct gagtgcctgg | 300 |
| gtgttcggcg gagggaccaa ggtgaccgtc ctaggc | 336 |

<210> SEQ ID NO 125
<211> LENGTH: 318
<212> TYPE: DNA
<213> ORGANISM: Homo sapiens

<400> SEQUENCE: 125

| | |
|---|---|
| gagctccaga tgacccagtc tccatcctcc ctgtctgcat ctgtaggaga cagagtcacc | 60 |
| atcacttgcc gggcaagtca gagcattagc agctatttaa attggtatca gcagaaacca | 120 |
| gggaaagccc ctaagctcct gatctatgct gcatccagtt tgcaaagtgg ggtcccatca | 180 |
| aggttcagtg gcagtggatc tgggacagat ttcactctca ccatcagcag tctgcaacct | 240 |
| gaagattttg caacttacta ctgtcaacag agttacagta cccccacctt cggccaaggg | 300 |
| acacgactgg agattaaa | 318 |

<210> SEQ ID NO 126
<211> LENGTH: 333
<212> TYPE: DNA
<213> ORGANISM: Homo sapiens

<400> SEQUENCE: 126

| | |
|---|---|
| gagctcgagc tgactcagcc accctcagtg tctgggaccc ccgggcagag ggtcaccatc | 60 |
| tcttgttctg gaggcagctc caacatcgga agtaatactg taaactggta ccagcagctc | 120 |
| ccaggaacgg cccccaaact cctcatctat agtaataatc agcggccctc aggggtccct | 180 |
| gaccgattct ctggctccaa gtctggcacc tcagcctccc tggccatcag tgggctccag | 240 |
| tctgaggatg aggctgatta ttactgtgca gcatgggatg acagcctgaa tggtgtggtg | 300 |
| ttcggcggag ggaccaaggt gaccgtccta ggc | 333 |

<210> SEQ ID NO 127
<211> LENGTH: 333
<212> TYPE: DNA
<213> ORGANISM: Homo sapiens

<400> SEQUENCE: 127

| | |
|---|---|
| gagctcgagc tgactcagcc accctcagtg tctgggaccc ccgggcagag ggtcaccatc | 60 |

```
tcttgttctg gaagcagctc aacatcgga agtaatactg taaactggta ccagcagctc      120
ccaggaacgg ccccaaaact cctcatctat agtaataatc agcggccctc agggggtccct   180 gaccgattct ctggctccaa gtctggcacc tcagcctccc tggccatcag tgggctccag    240
tctgaggatg aggctgatta tttctgtgca gcatgggatg acagcctgaa tggcctcgtt    300
ttcggcggag ggaccaagct gaccgtccta ggc                                 333
```

<210> SEQ ID NO 128
<211> LENGTH: 321
<212> TYPE: DNA
<213> ORGANISM: Homo sapiens

<400> SEQUENCE: 128

```
gagctccaga tgacccagtc tccatcctcc ctgtctgcat ctgtaggaga cagagtcacc     60
atcacttgcc gggcaagtca gagcattagc acctatttaa attggtatca gcagaaacca   120
gggaaagccc ctatgctcct gatctacgct gcatccaatt tgcaaagtgg ggtcccatca    180
aggttcagtg gcagtgggtc tgggacagat ttcactctca ccatcagcag tctgcaacct   240
gaagattttg caacttacta ctgtcaacag agttacagta ccccgatcac cttcggccaa   300
gggacacgac tggagattaa a                                              321
```

<210> SEQ ID NO 129
<211> LENGTH: 333
<212> TYPE: DNA
<213> ORGANISM: Homo sapiens

<400> SEQUENCE: 129

```
gagctcgtgc tgactcagcc accctcagcg tctgggaccc ccgggcagag ggtcaccatc     60
tcttgttctg gaagcagctc caacatcgga agtaatactg taaactggta ccagcagctc   120
ccaggaacgg ccccaaaact cctcatctat agtaataatc agcggccctc agggggtccct   180 gaccgattct ctggctccaa gtctggcacc tcagcctccc tggccatcag tgggctccag    240
tctgaggatg aggctgatta ttactgtgca gcatgggatg acagcctgaa tggtcgggtg    300
ttcggcggag gcaccaagct gaccgtccta ggt                                 333
```

<210> SEQ ID NO 130
<211> LENGTH: 355
<212> TYPE: DNA
<213> ORGANISM: Homo sapiens

<400> SEQUENCE: 130

```
caggtgcagc tggtgcagtc tggggctgag gtgaagaagc ctggggcctt agtgaaggtc     60
tcctgcaagg cttctggtta cacgtttacc aattatggta tcacctgggt gcgacaggcc   120
cctggacaag gcttgagtg gatgggatgg atcagtgttt ataatggtga cacaaagtat    180
gcacagaagc tccagggcag agtcaccatg accacagaca cgcccacgaa cacagtgtat    240
atggagttga ggagcctgag atctgacgac acggccgtgt attattgtgc gagaggttat    300
ggttcgggga attgggacta ctggggccag ggaaccctgg tcaccgtctc ctcag         355
```

<210> SEQ ID NO 131
<211> LENGTH: 355
<212> TYPE: DNA
<213> ORGANISM: Homo sapiens

<400> SEQUENCE: 131

| | | |
|---|---|---|
| caggtgcagc tggtgcagtc tggagctgag atgaagaagc ctggggcctc agtgaaggtc | 60 | |
| tcctgcaagg cttctggtta cacctttacc aattatggta tcacctgggt gcgacaggcc | 120 | |
| cctggacaag ggcttgagtg gatgggatgg atcagtgttt ataatggtga cacaaagtat | 180 | |
| gcacagaagc tccagggcag agtcactatg accacagaca cacccacgag cacagtctac | 240 | |
| atggaattga ggagcctgac atctgacgac acggccgtgt attattgtgt gagaggttat | 300 | |
| ggttcgggga attgggacta ctggggccag ggaaccctgg tcaccgtctc ctcag | 355 | |

<210> SEQ ID NO 132
<211> LENGTH: 355
<212> TYPE: DNA
<213> ORGANISM: Homo sapiens

<400> SEQUENCE: 132

| | | |
|---|---|---|
| caggtgcagc tggtgcagtc tggggctgag gtgaagaagc ctggggcctc agtgaaggtc | 60 | |
| tcctgcaagg cttctggtta cacgtttacc aattatggta tcacctgggt gcgacaggcc | 120 | |
| cctggacaag ggcttgagtg gatgggatgg atcagtgttt ataatggtga cacaaagtat | 180 | |
| gcacagaagc tccagggcag agtcaccatg accacagaca cgcccacgaa cacagtgtat | 240 | |
| atggagttga ggagcctgag atctgacgac acggccgtgt attattgtgc gagaggttat | 300 | |
| ggttcgggga attgggacta ctggggccag ggaaccctgg tcaccgtctc ctcag | 355 | |

<210> SEQ ID NO 133
<211> LENGTH: 355
<212> TYPE: DNA
<213> ORGANISM: Homo sapiens

<400> SEQUENCE: 133

| | | |
|---|---|---|
| caggtgcagc tggtgcagtc tggggctgag gtgaagaagc ctggggcctc agtgaaggtc | 60 | |
| tcctgcaagg cttctggtta cacgtttacc aattatggta tcacctgggt gcgacaggcc | 120 | |
| cctggacaag ggcttgagtg gatgggatgg atcagtgttt ataatggtga cacaaagtat | 180 | |
| gcacagaagc tccagggcag agtcaccatg accacagaca cgcccacgaa cacagtgtat | 240 | |
| atggagttga ggagcctgag atctgacgac acggccgtgt attattgtgc gagaggttat | 300 | |
| ggttcgggga attgggacta ctggggccag ggaaccctgg tcaccgtctc ctcag | 355 | |

<210> SEQ ID NO 134
<211> LENGTH: 355
<212> TYPE: DNA
<213> ORGANISM: Homo sapiens

<400> SEQUENCE: 134

| | | |
|---|---|---|
| caggtgcagc tggtgcagtc tggggctgag gtgaagaagc ctgggtcctc ggtgaaggtc | 60 | |
| tcctgcaagg cttctggtta cacgtttacc aattatggta tcacctgggt gcgacaggcc | 120 | |
| cctggacaag ggcttgagtg gatgggatgg atcagtgttt ataatggtga cacaaagtat | 180 | |
| gcacagaagc tccagggcag agtcaccatg accacagaca cgcccacgaa cacagtgtat | 240 | |
| atggagttga ggagcctgag atctgacgac acggccgtgt attattgtgc gagaggttat | 300 | |
| ggttcgggga attgggacta ctggggccag ggaaccctgg tcaccgtctc ctcag | 355 | |

<210> SEQ ID NO 135
<211> LENGTH: 355
<212> TYPE: DNA
<213> ORGANISM: Homo sapiens

<400> SEQUENCE: 135

```
caggtgcagc tggtgcagtc tggggctgag gtgaagaagc ctggggcctc agtgaaggtc        60
tcctgcaagg cttctggtta cacgtttacc aattatggta tcacctgggt gcgacaggcc       120
cctggacaag ggcttgagtg gatgggatgg atcagtgttt ataatggtga cacaaagtat       180
gcacagaagc tccagggcag agtcaccatg accacagaca cgctcacgaa cacagtgtat       240
atggagttga ggagcctgag atctgacgac acggccgtgt attattgtgc gagaggttat       300
ggttcgggga attgggacta ctggggccag ggaaccccgg tcaccgtctc ctcag            355
```

<210> SEQ ID NO 136
<211> LENGTH: 385
<212> TYPE: DNA
<213> ORGANISM: Homo sapiens

<400> SEQUENCE: 136

```
caggtgcagc tggtgcagtc tggggctgag gtgaggaagc ctggggcctc agtgagggtc        60
tcctgcaagg cttctggata caccctcacc acttatgata tcaactgggt gcgacaggct       120
actggacaag ggcttgagtg gatgggatgg atgaacccta ccagtggtaa cacagcctac       180
gcacagaagt tccagggcag agtcaccatg accaggaaca cctccataag cacagcctac       240
atggagctga gcagcctgag atctgaggac acggccgttt actactgtgc gagaggcctg       300
ttttttggag tggttacaaa acccaactac tactactacg ctatggacgt ctggggccaa       360
gggaccacgg tcaccgtctc ctcag                                              385
```

<210> SEQ ID NO 137
<211> LENGTH: 382
<212> TYPE: DNA
<213> ORGANISM: Homo sapiens

<400> SEQUENCE: 137

```
caggtgcagc tggtgcagtc tgggggaggc ttggcacagc ctggcaagtc cctgagactc        60
tcctgtgtag cctctggatt caccttt gat gattatgcca tgcactgggt ccggcaagct       120
ccagggaagg gcctggagtg ggtctcaggt attaattgga atagtggtag cattggttat       180
gcggactctg tgaagggccg attcaccatc tccagagaca cgccaagaa ctccctgtat        240 ctgcaaatga acagtctgag agctgaggac acggccttgt attactgtgc aaaagagcaa       300
ggatattgtg atagtaccgg ctgccagagg ggatccggaa tggacgtctg gggccaaggg       360
accacggtca ccgtctcctc ag                                                 382
```

<210> SEQ ID NO 138
<211> LENGTH: 382
<212> TYPE: DNA
<213> ORGANISM: Homo sapiens

<400> SEQUENCE: 138

```
caggtgcagc tggtgcagtc tgggggaggc ttggcacagc ctggcaagtc cctgagactc        60
tcctgtgtag cctctggatt caccttt gat gattatgcca tgcactgggt ccggcaagct       120
ccagggaagg gcctggagtg ggtctcaggt attaattgga atagtggtag cattggttat       180
gcggactctg tgaagggccg attcaccatc tccagagaca cgccaagaa ctccctgtat        240 ctgcaaatga acagtctgag agctgaggac acggccttgt attactgtgc aaaagagcaa       300
ggatattgtg atagtaccgg ctgccagagg ggatccggaa tggacgtctg gggccaaggg       360
accacggtca ccgtctcctc ag                                                 382
```

<210> SEQ ID NO 139
<211> LENGTH: 382
<212> TYPE: DNA
<213> ORGANISM: Homo sapiens

<400> SEQUENCE: 139

```
caggtgcagc tggtgcagtc tgggggaggc ttggcacagc ctggcaagtc cctgagactc      60
tcctgtgtag cctctggatt cacctttgat gattatgcca tgcactgggt ccggcaagct     120
ccagggaagg gcctggagtg ggtctcaggt attaattgga atagtggtag cattggttat     180
gcggactctg tgaagggccg attcaccatc tccagagaca cgccaagaa ctccctgtat      240
ctgcaaatga acagtctgag agctgaggac acggccttgt attactgtgc aaaagagcaa     300
ggatattgtg atagtaccgg ctgccagagg ggatccggaa tggacgtctg gggccaaggg     360
accacggtca ccgtctcctc ag                                              382
```

<210> SEQ ID NO 140
<211> LENGTH: 382
<212> TYPE: DNA
<213> ORGANISM: Homo sapiens

<400> SEQUENCE: 140

```
gaggtgcagc tgttggagtc tgggggaggc ttggcacagc ctggcaagtc cctgagactc      60
tcctgtgtag cctctggatt cacctttgat gattatgcca tgcactgggt ccggcaagct     120
ccagggaagg gcctggagtg ggtctcaggt attaattgga atagtggtag cattggttat     180
gcggactctg tgaagggccg attcaccatc tccagagaca cgccaagaa ctccctgtat      240
ctgcaaatga acagtctgag agctgaggac acggccttgt attactgtgc aaaagagcaa     300
ggatattgtg atagtaccgg ctgccagagg ggatccggaa tggacgtctg gggccaaggg     360
accacggtca ccgtctcctc ag                                              382
```

<210> SEQ ID NO 141
<211> LENGTH: 382
<212> TYPE: DNA
<213> ORGANISM: Homo sapiens

<400> SEQUENCE: 141

```
caggtgcagc tgcaggagtc gggggaggc ttggcacagc ctggcaagtc cctgagactc       60
tcctgtgtag cctctggatt cacctttgat gattatgcca tgcactgggt ccggcaagct     120
ccagggaagg gcctggagtg ggtctcaggt attaattgga atagtggtag cattggttat     180
gcggactctg tgaagggccg attcaccatc tccagagaca cgccaagaa ctccctgtat      240
ctgcaaatga acagtctgag agctgaggac acggccttgt attactgtgc aaaagagcaa     300
ggatattgtg atagtaccgg ctgccagagg ggatccggaa tggacgtctg gggccaaggg     360
accacggtca ccgtctcctc ag                                              382
```

<210> SEQ ID NO 142
<211> LENGTH: 382
<212> TYPE: DNA
<213> ORGANISM: Homo sapiens

<400> SEQUENCE: 142

```
gaggtgcagc tggtggagtc tgggggaggc ttggcacagc ctggcaagtc cctgagactc      60
tcctgtgtag cctctggatt cacctttgat gattatgcca tgcactgggt ccggcaagct     120
ccagggaagg gcctggagtg ggtctcaggt attaattgga atagtggtag cattggttat     180
```

```
gcggactctg tgaagggccg attcaccatc tccagagaca acgccaagaa ctccctgtat      240
ctgcaaatga acagtctgag agctgaggac acggccttgt attactgtgc aaaagagcaa      300
ggatattgtg atagtaccgg ctgccagagg ggatccggaa tggacgtctg gggccaaggg      360
accacggtca ccgtctcctc ag                                               382
```

<210> SEQ ID NO 143
<211> LENGTH: 382
<212> TYPE: DNA
<213> ORGANISM: Homo sapiens

<400> SEQUENCE: 143

```
gaggtgcagc tggtggagtc tgggggaggc ttggcacagc ctggcaagtc cctgagactc      60
tcctgtgtag cctctggatt cacctttgat gattatgcca tgcactgggt ccggcaagct      120
ccagggaagg gcctggagtg ggtctcaggt attaattgga atagtggtag cattggttat      180
gcggactctg tgaagggccg attcaccatc tccagagaca acgccaagaa ctccctgtat      240
ctgcaaatga acagtctgag agctgaggac acggccttgt attactgtgc aaaagagcaa      300
ggatattgtg atagtaccgg ctgccagagg ggatccggaa tggacgtctg gggccaaggg      360
accacggtca ccgtctcctc ag                                               382
```

<210> SEQ ID NO 144
<211> LENGTH: 382
<212> TYPE: DNA
<213> ORGANISM: Homo sapiens

<400> SEQUENCE: 144

```
gaggtgcagc tggtggagtc tgggggaggc gtggtccaac ctggggggtc cctaagactc      60
tcctgtgtag cctctggatt cacctttgat gattatgcca tgcactgggt ccggcaagct      120
ccagggaagg gcctggagtg ggtctcaggt attaattgga atagtggtag cattggttat      180
gcggactctg tgaagggccg attcaccatc tccagagaca acgccaagaa ctccctgtat      240
ctgcaaatga acagtctgag agctgaggac acggccttgt attactgtgc aaaagagcaa      300
ggatattgtg atagtaccgg ctgccagagg ggatccggaa tggacgtctg gggccaaggg      360
accacggtca ccgtctcctc ag                                               382
```

<210> SEQ ID NO 145
<211> LENGTH: 370
<212> TYPE: DNA
<213> ORGANISM: Homo sapiens

<400> SEQUENCE: 145

```
caggtgcagc tggtgcagtc tgggggaggc gtggtccagc ctggggggtc cctgagactc      60
tcctgtgtag cctctggatt cacctttgat gattatgcca tgcactgggt ccggcaagct      120
ccagggaagg gcctggagtg ggtctcaggt attagttgga atagtggtgc cataggctat      180
gcagactctg tgaagggccg attcaccatc tccagagaca acgccaagaa ctccctgtat      240
ctgcaaatga acagtctgag aactgaggac acggccgtgt attactgtgc aaaagatggg      300
attacaattt ttggagtggg cgacggtctg gatgtctggg gccaagggac aatggtcacc      360
gtctcttcag                                                             370
```

<210> SEQ ID NO 146
<211> LENGTH: 370
<212> TYPE: DNA

<213> ORGANISM: Homo sapiens

<400> SEQUENCE: 146

| | |
|---|---|
| gaggtgcagc tggtggagtc tgggggaggc ttggtacagc ctggcaggtc cctgagactc | 60 |
| tcctgtgcag cctctggatt cacctttgat gattatgcca tgcactgggt ccggcaagct | 120 |
| ccagggaagg gcctggagtg ggtctcaggt attagttgga atagtggtag catagactat | 180 |
| gcggactctg tgaagggccg attcaccatc tccagagaca cgccaagaa ctccctgtat | 240 |
| ctgcaaatga acagtctgag agttgaggac acggccttgt attattgtgc aaaagatggg | 300 |
| agtagggttt ttggagtggg cggtggtttt gatttctggg gccaagggac aatggtcacc | 360 |
| gtctcttcag | 370 |

<210> SEQ ID NO 147
<211> LENGTH: 370
<212> TYPE: DNA
<213> ORGANISM: Homo sapiens

<400> SEQUENCE: 147

| | |
|---|---|
| gaggtgcagc tagtggagtc tgggggaggc ttggtacagc ctggcaggtc cctgagactc | 60 |
| tcctgtgcag cctctggatt cacctttgat gattacgcca tgcactgggt ccggcaagct | 120 |
| ccagggaagg gcctggagtg ggtctcaggt attagttgga atagtggtag catagactat | 180 |
| gtggactctg tgaagggccg attcaccatc tccagagaca cgccaagaa ctacctgtat | 240 |
| ctgcaaatga acagtctgag agttgaggac acggccttat attattgtgc aaaagatggc | 300 |
| agtagggttt ttggagtggg cggtggtttt gatttctggg gccaagggac aatggtcacc | 360 |
| gtctcttcag | 370 |

<210> SEQ ID NO 148
<211> LENGTH: 370
<212> TYPE: DNA
<213> ORGANISM: Homo sapiens

<400> SEQUENCE: 148

| | |
|---|---|
| gaggtgcagc tggtggagtc tgggggaggc ttggtacagc ctggcaggtc cctgagactc | 60 |
| tcctgtgcag cctctggatt cacctttgat gattattcca tgcactgggt ccggcaagct | 120 |
| ccagggaagg gcctggagtg ggtctcaggt atcagttgga acagtggtgg cataggctat | 180 |
| gcggactctg tgaggggccg attcaccatc tccagagaca cgccaagaa ctccctgtat | 240 |
| ctgcaaatga acagtctgag agctgaggac acggccttgt attattgtgc aaaagatggg | 300 |
| atgagggttt ttggagtggg cggtggtttt gatttctggg gccaagggac aatggtcacc | 360 |
| gtctcttcag | 370 |

<210> SEQ ID NO 149
<211> LENGTH: 370
<212> TYPE: DNA
<213> ORGANISM: Homo sapiens

<400> SEQUENCE: 149

| | |
|---|---|
| gaggtgcagc tggtggagtc tgggggaggc ttggtacagc ctggcaggtc cctgagactc | 60 |
| tcctgtgcag cctctggatt cacctttgat gattatgcca tgtactgggt ccggcaagct | 120 |
| ccagggaagg gcctggagtg ggtctcaggt attagttgga atagtggtag catagactat | 180 |
| gcggactctg tgaagggccg attcaccatc tccagagaca cgccaagaa ctccctgtat | 240 |
| ctgcaaatga acagtctgag agctgaggac acggccttgt attattgtgc aaaagatggg | 300 |

```
atgagggttt ttggagtggg cggtggtttt gatttctggg gccaagggac aatggtcacc    360
gtctcttcag                                                           370

<210> SEQ ID NO 150
<211> LENGTH: 370
<212> TYPE: DNA
<213> ORGANISM: Homo sapiens

<400> SEQUENCE: 150
gaggtgcagc tggtggagtc tgggggaggc ttggtacagc ctggcaggtc cctgagactc     60
tcctgtgcag cctctggatt cacctttgat gattatgcca tgtactgggt ccggcaagct    120
ccagggaagg gcctggagtg ggtctcaggt attagttgga atagtggtag catagactat    180
gcggactctg tgaagggccg attcaccatc tccagagaca cgccaagaa ctccctgtat     240 ctgcaaatga acagtctgag agctgaggac acggccttgt attattgtgc aaaagatggg    300
atgagggttt ttggagtggg cggtggtttt gatttctggg gccaagggac aatggtcacc    360
gtctcttcag                                                           370

<210> SEQ ID NO 151
<211> LENGTH: 370
<212> TYPE: DNA
<213> ORGANISM: Homo sapiens

<400> SEQUENCE: 151
gaggtgcagc tggtggagtc tgggggaggc ttggtacagc ctggcaggtc cctgagactc     60
tcctgtgcag cctctggatt cacctttgat gattatgcca tgcactgggt ccggcaagct    120
ccagggaagg gcctggagtg ggtctcaggt attagttgga atagtgggac cataggctat    180
gcggactctg tgaagggccg attcaccatc tccagagaca cgccaagaa ctccctgtat     240 ctgcaaatga acagtctgag agctgaggac acggccgtgt attactgtgc aaaagatggg    300
attacggttt ttggagtggg cgatggtttg gatatctggg gccaagggac aatggtcacc    360
gtctcttcag                                                           370

<210> SEQ ID NO 152
<211> LENGTH: 376
<212> TYPE: DNA
<213> ORGANISM: Homo sapiens

<400> SEQUENCE: 152
gaggtgcagc tggtggagtc tgggggaacc ttggtacagc ctggcaggtc cctgagactc     60
tcctgtgcag cctctggatt cagctttgat gattatgcca tgcagtgggt ccggcaagct    120
ccagggaagg gcctggagtg ggtctcaggt attagctgga atagtggtag catagcctat    180
gcggactctg tgaagggccg attcaccatc tccagagaca cgccaagag ctccctgtat     240 ctgctaatga acagtctgag agctgaggac acggccttgt attactgtgc aaaagcgggc    300
acagattatt atgatagtag tgcttccgaa cttcctgact actggggcca gggaaccctg    360
gtcaccgtct cctcag                                                    376

<210> SEQ ID NO 153
<211> LENGTH: 379
<212> TYPE: DNA
<213> ORGANISM: Homo sapiens

<400> SEQUENCE: 153
```

| | |
|---|---|
| caggtgcagc tgcaggagtc gggggaggc ttggtacagc ctggcaggtc cctgagactc | 60 |
| tcctgtgcag cctctggatt cacctttgat gattatgcca tgcactgggt ccggcaagct | 120 |
| ccagggaagg gcctggagtg ggtctcaggt attagttgga atagtggtag catagcctat | 180 |
| gcggactctg tgaagggccg attcaccatc tccagagaca cgccaagaa ctccctgtat | 240 |
| ctgcaaatga acagtctgag agctgaggac acggccttct attactgtgc gaaagtgggc | 300 |
| ggggatacct atgatattac aagtggggcg gattacttcg atctctgggg ccgtggcgcc | 360 |
| ctggtcactg tctcctcag | 379 |

<210> SEQ ID NO 154
<211> LENGTH: 379
<212> TYPE: DNA
<213> ORGANISM: Homo sapiens

<400> SEQUENCE: 154

| | |
|---|---|
| caggtgcagc tggtgcagtc tgggggaggc ttggtacagc ctggcaggtc cctgagactc | 60 |
| tcctgtgcag cctctggatt cacctttgat gattatgcca tgcactgggt ccggcaagct | 120 |
| ccagggaagg gcctggagtg ggtctcaggt attagttgga atagtggtag catagcctat | 180 |
| gcggactctg tgaagggccg attcaccatc tccagagaca cgccaagaa ctccctgtat | 240 |
| ctgcaaatga acagtctgag agctgaggac acggccttct attactgtgc gaaagtgggc | 300 |
| ggggatacct atgatattac aagtggggcg gattacttcg atctctgggg ccgtggcgcc | 360 |
| ctggtcactg tctcctcag | 379 |

<210> SEQ ID NO 155
<211> LENGTH: 367
<212> TYPE: DNA
<213> ORGANISM: Homo sapiens

<400> SEQUENCE: 155

| | |
|---|---|
| caggtgcagc tggtgcagtc tgggggaggc ttggtccagc ctgggggtc cctgagagtc | 60 |
| tcctgcgcag cctctggatt cacctctaat atcttttgga tgagttgggt ccgccaggct | 120 |
| ccaggtaagg ggctggagtg ggtggccaac atagacgaag atggaagtga aaaaactat | 180 |
| gtggactctg tgaagggccg attcaccatc tccagagaca cgccaagaa ctcactgtat | 240 |
| ctgcaaatga acagcctgag agccgaggac acggctgtgt attactgtgc gagggagtcg | 300 |
| ttttactatg gttcggggac ttattttgac ttctgggggcc agggaaccct ggtcaccgtc | 360 |
| tcctcag | 367 |

<210> SEQ ID NO 156
<211> LENGTH: 370
<212> TYPE: DNA
<213> ORGANISM: Homo sapiens

<400> SEQUENCE: 156

| | |
|---|---|
| caggtgcagc tggtgcagtc tgggggaggc gtggtccagt ctggggaggtc cctgagactc | 60 |
| tcctgtgcag cctctggatt cacgttcagt gactatgcca tgcactgggt ccgccaggcc | 120 |
| ccaggcaagg ggctggagtg ggtggcagtt atatcacatg gtggaaccaa aaatacacc | 180 |
| ggagactccg tgaagggccg atttatcatc tccagagaca attccaagaa cacagtgttt | 240 |
| ttgcaaatga acagcctgag agttgaggac acggctgttt attactgtgc gagagatcgt | 300 |
| gtagaaggtt acgtttgggg gggcacgttt gaccactggg gccagggaac cccggtcacc | 360 |
| gtctcctcag | 370 |

<210> SEQ ID NO 157
<211> LENGTH: 379
<212> TYPE: DNA
<213> ORGANISM: Homo sapiens

<400> SEQUENCE: 157

```
gaggtgcagc tgttggagtc tggcccaggg ctggaaaagg tttcggagac cctgtccctc      60
acgtgtaatg tctctggtgt ctccataagt agtcctgatt attattgggc ctggatccgc     120
cagccccccg ggaaggggct ggagtggatt ggcagtatct tttacagtgg acctacctcc     180
tggaatccgt ccctcaagaa tcgagtcacc atctcagtag acacgtccaa gaatcaattc     240
tccctgaaaa tgaagtctgt gacggccgcg gacacggccg tatattactg tgcgaggtcc     300
ttcggtttcg ggagatatga gcccgcggat gatgcatttg atatctgggg ccagggagac     360
ctggtcatcg tctctccag                                                  379
```

<210> SEQ ID NO 158
<211> LENGTH: 379
<212> TYPE: DNA
<213> ORGANISM: Homo sapiens

<400> SEQUENCE: 158

```
caggtgcagc tggtgcagtc tggggggaggc gtggtccagc ctgggaggtc cctgagactc      60
tcctgtacag cctctagatt caatttcagg agttttgcca tgcactgggt ccgccaggct     120
ccaggcaagg ggctggagtg gtggcgatg tttccttatg acggaaataa tacatactat     180
ggagactccg tgaagggccg attcaccatc tccagagaca attccaagaa gatgctgtac     240
ctgcaaatga acgatctcag aattgacgac acggcactgt actactgtgc gaggcaggga     300
tgggtaatag agacatctgg tataagagcg agtggctttg acgtctgggg tcaagggaca     360
ctggtcaccg tctcctcag                                                  379
```

<210> SEQ ID NO 159
<211> LENGTH: 370
<212> TYPE: DNA
<213> ORGANISM: Homo sapiens

<400> SEQUENCE: 159

```
caggtgcagc tgcaggagtc gggggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtgggac cataggctac     180
gcggactctg tgaagggccg attcaccatc tccagagaca acgccaagaa ctccctgtat     240
ctgcaaatga acagtctgag agctgaggac acggccgtgt attactgtgc aaaagatggg     300
attacggttt ttggagtggg cgatggtttg atatctgggg ccaagggac aatggtcacc     360
gtctcttcag                                                            370
```

<210> SEQ ID NO 160
<211> LENGTH: 370
<212> TYPE: DNA
<213> ORGANISM: Homo sapiens

<400> SEQUENCE: 160

```
gaggtgcagc tggtgagtc tggggggaggc ttggtacagc ctggcaggtc cctgagactc      60
tcctgtgcag cctctggatt cacctttgat gattatgcca tgcactgggt ccggcaagct     120
```

```
ccagggaagg gcctggagtg ggtctcaggt attagttgga atagtggtag catagactat      180
gcggactctg tgaagggccg attcaccatc tccagagaca acgccaagaa ctccctgtat      240
ctgcaaatga acagtctgag agttgaggac acggccttgt attattgtgc aaaagatggg      300
agtaggtttt ttggagtggg cggtggtttt gatttctggg gccaagggac aatggtcacc      360
gtctcttcag                                                             370

<210> SEQ ID NO 161
<211> LENGTH: 370
<212> TYPE: DNA
<213> ORGANISM: Homo sapiens

<400> SEQUENCE: 161
gaggtgcagc tggtggagtc tggggggaggc ttggtacagc ctggcaggtc cctgagactc     60
tcctgtgcag cctctggatt cacctttgat gattatgcca tgcactgggt ccggcaagct     120
ccagggaagg gcctggagtg ggtctcaggt attagttgga atagtgggac cataggctat     180
gcggactctg tgaagggccg attcaccatc tccagagaca acgccaagaa ctccctgtat     240
ctgcaaatga acagtctgag agctgaggac acggccgtgt attactgtgc aaaagatggg    300
attacggttt ttggagtggg cgatggtttg atatctggg gccaagggac aatggtcacc     360
gtctcttcag                                                             370

<210> SEQ ID NO 162
<211> LENGTH: 352
<212> TYPE: DNA
<213> ORGANISM: Homo sapiens

<400> SEQUENCE: 162
gaggtgcagc tggtggagtc tgaggaggc ttggtccagc ctgggggtc cgtgagactc        60 tcctgtgcag cctctggatt tcaagtcagt agtgaccaca tgagctgggt ccgccaggct    120
ccagggaagg gactgcagtg ggtctcagtt atttatactg ggggcaactc atactacgca    180
gactccgtga agggccgatt caccgtctcc agagacaact ccaggaacac acttttctct   240
caaatgaaca gcctgagagt cgaggacacg gccatttatt attgtgtgag aggtcccgct    300
tactatgaca tagactactg gggccaggga gccctggtca ccgtgtcctc gg            352

<210> SEQ ID NO 163
<211> LENGTH: 370
<212> TYPE: DNA
<213> ORGANISM: Homo sapiens

<400> SEQUENCE: 163
caggtgcagc tgcaggagtc gggggagggc ttggtacagc ctggcaggtc cctgagactc     60
tcctgtgcag cctctggatt cacctttgat gattatgcca tgcactgggt ccggcaagct   120
ccagggaagg gcctggagtg ggtctcaggt attagttgga atagtggggc cataggctat    180
gcggactctg tgaagggccg attcaccatc tccagagaca acgccaagaa ctccctgtat    240
ctgcaaatga acagtctgag agctgaggac acggccgtgt attactgtgc aaaagatggg    300
attacggttt ttggagtggg cgatggtttg atatctggg gccaagggac aatggtcacc    360
gtctcttcag                                                             370

<210> SEQ ID NO 164
<211> LENGTH: 352
<212> TYPE: DNA
<213> ORGANISM: Homo sapiens
```

<400> SEQUENCE: 164

```
caggtgcagc tggtgcagtc tgggggagac ttggtccagc cggggggtc cctgagactc      60
tcctgtgtag cctctggatt caacgtcaat gacaactaca tgagctgggt ccgccaggct    120
ccagggaagg ggctggagtg ggtctcaacg atttacagcg aaactctttc atactacgga    180
gactccgtga agggcagatt caccgtctcc agagacggtt ccaagaacac ggtgtttctt    240
caaatgagca gcctgaaagg cgaggacacg gctgtttatt attgtgcttc cgaagggggg    300
ggcctgacaa ttgactattg gggccaggga accctggtcg ccgtctcctc ag            352
```

<210> SEQ ID NO 165
<211> LENGTH: 382
<212> TYPE: DNA
<213> ORGANISM: Homo sapiens

<400> SEQUENCE: 165

```
gaggtgcagc tggtggagtc tgggctgag gtgaagaagc ctggggcctc agtgaaggtc      60
tcctgcaagg cttctacata catgttcacc agttatgata tcaactgggt gcgacaggcc    120
gctggacaag gcttgagtg gatgggatgg atggacccga atactggtaa cacagactat    180
gcacagaagt tccagggcag agtcaccatg accaggaaca cttccataaa tacagcctac    240
atggagctga aagcctgac gtctgacgac acggccgtat attactgtgc gagaggccgg    300
acagtgcggt tcggggaatt atttgttagt gagggggta tggacgtctg gggccaaggg    360
accacggtca gcgtctcctc ag                                              382
```

<210> SEQ ID NO 166
<211> LENGTH: 367
<212> TYPE: DNA
<213> ORGANISM: Homo sapiens

<400> SEQUENCE: 166

```
gaggtgcagc tggtggagtc tgggggaggc ttggtacagc ctggcaggtc cctgagactc      60
tcctgtgcag cctctggatt cacctttgat gatcatgcca tgcactgggt ccggcaagct    120
ccagggaagg gcctggagtg ggtctcaggt attagttgga gtggtgctta catagcctat    180
gcggactctg tgaagggccg attcaccatc tccagagaca acgccaggaa ctccctgtat    240
ctgcaaatga acagtctgag agctgaggac acggccttgt attactgtgc ccgcagtagt    300
ggttattatg accttcccta tgcttttgat atctggggcc aagggacaat ggtcaccgtc    360
tcttcag                                                               367
```

<210> SEQ ID NO 167
<211> LENGTH: 370
<212> TYPE: DNA
<213> ORGANISM: Homo sapiens

<400> SEQUENCE: 167

```
gaggtgcagc tggtggagtc tgggggaggc ttggtacagc ctggcaggtc cctgagactc      60
tcctgtgcag cctctggatt cacctttgat gattatgcca tgcactgggt ccggcaagct    120
ccagggaagg gcctggagtg ggtctcaggt attagttgga atagtggtag catagactat    180
gcggactctg tgaagggccg attcaccatc tccagagaca acgccaagaa ctccctgtat    240
ctgcaaatga acagtctgag agttgaggac acggccttgt attattgtgc aaaagatggg    300
agtagggttt ttggagtggg cggtggtttt gatttctggg gccaagggac aatggtcacc    360
```

```
gtctcttcag                                                                  370
```

<210> SEQ ID NO 168
<211> LENGTH: 370
<212> TYPE: DNA
<213> ORGANISM: Homo sapiens

<400> SEQUENCE: 168

```
gaggtgcagc tggtggagtc tggggaggc ttggtacagc ctggcaggtc cctgagactc    60
tcctgtgcag cctctggatt cacctttgat gattatgcca tgcactgggt ccggcaagct   120
ccagggaagg gcctggagtg gtctcaggt attagttgga atagtgggac cataggctat   180
gcggactctg tgaagggccg attcaccatc tccagagaca acgccaagaa ctccctgtat   240
ctgcaaatga acagtctgag agctgaggac acggccgtgt attactgtgc aaaagatggg   300
attacggttt ttggagtggg cgatggtttg gatatctggg gccaagggac aatggtcacc   360
gtctcttcag                                                          370
```

<210> SEQ ID NO 169
<211> LENGTH: 379
<212> TYPE: DNA
<213> ORGANISM: Homo sapiens

<400> SEQUENCE: 169

```
caggtgcagc tgcaggagtc gggggaggc ttggtacagc ctggcaggtc cctgagactc    60
tcctgtgcag cctctggatt cacctttgat gattatgcca tgcactgggt ccggcaagct   120
ccagggaagg gcctggagtg gtctcaggt attagttgga atagtggtag catagcctat   180
gcggactctg tgaagggccg attcaccatc tccagagaca acgccaagaa ctccctgtat   240
ctgcaaatga acagtctgag agctgaggac acggccttct attactgtgc gaaagtgggc   300
ggggatacct atgatattac aagtggggcg gattacttcg atctctgggg ccgtagcgcc   360
ctggtcactg tctcctcag                                                379
```

<210> SEQ ID NO 170
<211> LENGTH: 370
<212> TYPE: DNA
<213> ORGANISM: Homo sapiens

<400> SEQUENCE: 170

```
gaggtgcagc tggtggagtc tggggaggc ttggtacagc ctggcaggtc cctgagactc    60
tcctgtgcag cctctggatt cacctttgat gattatgcca tgcactgggt ccggcaaggt   120
ccagggaagg gcctagagtg gtctcaggt attagttgga atagtgggac cataggctat   180
gcggactctg tgaagggccg attcaccatc tccagagaca acgccaagaa ctccctgtat   240
ctgcaaatga acagtctgag agctgaggac acggccgtgt attactgtgc aaaagatggg   300
attacggttt ttggagtggg cgatggtttg gatatctggg gccaagggac aatggtcacc   360
gtctcttcag                                                          370
```

<210> SEQ ID NO 171
<211> LENGTH: 367
<212> TYPE: DNA
<213> ORGANISM: Homo sapiens

<400> SEQUENCE: 171

```
cagatcacct tgaaggagtc tgggggaggc gtggtccagc ctgggaggtc cctgcgactc    60
tcctgtgcag cctctggatt cgacttcaat atctatggca tgcactgggt ccgccaggct   120
```

-continued

```
ccagacaagg ggctggagtg ggtggcggtt atatcagatg atggaactaa aaaatattat    180
gcagactctg tgaagggccg agtcaccatc tccagagaca attccaagaa cacgctgtat    240
ctgcagatga acagcctgag agctgaggac acggctgtgt attactgtgc gaaagatctg    300
gatgttgtca tgggacccgg tggacttgat tattggggcc agggaaccct ggtcaccgtc    360
tcctcag                                                              367
```

<210> SEQ ID NO 172
<211> LENGTH: 370
<212> TYPE: DNA
<213> ORGANISM: Homo sapiens
<400> SEQUENCE: 172

```
cagatcacct tgaaggagtc tggggaggc ttggtacagc ctggcaggtc cctgagactc     60
tcctgtgcag cctctggatt cacctttgat gattatgcca tgcactgggt ccggcaagct    120
ccagggaagg gcctggagtg gtctcaggt attagttgga atagtgggac cataggctat     180
gcggactctg tgaagggccg attcaccatc tccagagaca cgccaagaa ctccctgtat     240 ctgcaaatga acagtctgag agctgaggac acggccgtgt attactgtgc aaaagatggg    300
attacggttt ttggagtggg cgatggtttg gatatctggg gccaagggac aatggtcacc    360
gtctcttcag                                                           370
```

<210> SEQ ID NO 173
<211> LENGTH: 113
<212> TYPE: PRT
<213> ORGANISM: Homo sapiens
<400> SEQUENCE: 173

```
Glu Leu Val Leu Thr Gln Ser Pro Asp Ser Leu Ser Val Ser Leu Gly
1               5                   10                  15

Glu Arg Ala Thr Ile Asn Cys Lys Ser Ser Gln Thr Val Leu Tyr Asn
            20                  25                  30

Ser Asp Asn Lys Asn Tyr Leu Ser Trp Tyr Gln Gln Lys Pro Gly Gln
        35                  40                  45

Pro Pro Lys Leu Ile Met Asn Trp Ala Ser Ile Arg Ala Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Ile Tyr Tyr Cys Gln Gln
                85                  90                  95

Tyr Tyr Ser Thr Pro Leu Thr Phe Gly Gly Gly Thr Lys Val Glu Ile
            100                 105                 110

Lys
```

<210> SEQ ID NO 174
<211> LENGTH: 107
<212> TYPE: PRT
<213> ORGANISM: Homo sapiens
<400> SEQUENCE: 174

```
Glu Leu Thr Leu Thr Gln Ser Pro Ser Ser Leu Ser Ala Ser Val Gly
1               5                   10                  15

Asp Arg Val Thr Ile Thr Cys Arg Ala Ser Gln Gly Ile Ala Ser Tyr
            20                  25                  30

Leu Ala Trp Tyr Gln Gln Lys Pro Gly Lys Ala Pro Lys Leu Leu Ile
```

```
                35                  40                  45
Tyr Gly Ala Ser Thr Leu Gln Ser Gly Val Pro Ser Arg Phe Ser Gly
 50                  55                  60

Arg Arg Ser Gly Thr Asp Phe Thr Leu Thr Ile Ser Ser Leu Gln Pro
 65                  70                  75                  80

Glu Asp Ala Ala Thr Tyr Tyr Cys Gln Gln Tyr Ser Asn Tyr Pro Leu
                 85                  90                  95

Thr Phe Gly Gln Gly Thr Lys Leu Glu Ile Lys
                100                 105

<210> SEQ ID NO 175
<211> LENGTH: 107
<212> TYPE: PRT
<213> ORGANISM: Homo sapiens

<400> SEQUENCE: 175

Glu Leu Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Asn Asn Tyr
                20                  25                  30

Leu Ala Trp Phe Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Pro Phe
                 85                  90                  95

Thr Phe Gly Pro Gly Thr Lys Val Asp Ile Lys
                100                 105

<210> SEQ ID NO 176
<211> LENGTH: 107
<212> TYPE: PRT
<213> ORGANISM: Homo sapiens

<400> SEQUENCE: 176

Glu Leu Gln Met Thr Gln Ser Pro Ser Thr Leu Ser Ala Ser Val Gly
 1               5                  10                  15

Asp Arg Val Thr Ile Thr Cys Arg Ala Ser Gln Gly Ile Ser Asn Trp
                20                  25                  30

Leu Ala Trp Tyr Gln Gln Lys Pro Gly Lys Ala Pro Lys Leu Leu Ile
             35                  40                  45

His Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Tyr Thr Tyr Pro Leu
                 85                  90                  95

Thr Phe Gly Gly Gly Thr Lys Val Glu Ile Lys
                100                 105

<210> SEQ ID NO 177
<211> LENGTH: 106
<212> TYPE: PRT
<213> ORGANISM: Homo sapiens

<400> SEQUENCE: 177
```

```
Glu Leu Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Lys Gly Ala Ser Thr Arg Ala Thr Gly Ile Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln Tyr Tyr Gly Pro Tyr Ser
                85                  90                  95

Phe Gly Gln Gly Thr Lys Val Glu Ile Lys
            100                 105

<210> SEQ ID NO 178
<211> LENGTH: 107
<212> TYPE: PRT
<213> ORGANISM: Homo sapiens

<400> SEQUENCE: 178

Glu Leu Gln Met Thr Gln Ser Pro Ser Ser Leu Ser Ala Ser Val Gly
1               5                   10                  15

Asp Arg Val Thr Ile Thr Cys Arg Ala Thr Gln Gly Ile Ser Asn Tyr
            20                  25                  30

Leu Ala Trp Phe Gln Gln Lys Pro Gly Lys Ala Pro Lys Leu Leu Ile
        35                  40                  45

Tyr Ala Ala Ser Ser Leu Gln Ser Gly Val Pro Ser Lys Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 179
<211> LENGTH: 107
<212> TYPE: PRT
<213> ORGANISM: Homo sapiens

<400> SEQUENCE: 179

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gly Gly Thr Lys Leu Glu Ile Lys
            100                 105
```

<210> SEQ ID NO 180
<211> LENGTH: 107
<212> TYPE: PRT
<213> ORGANISM: Homo sapiens

<400> SEQUENCE: 180

Glu Leu Gln Met Thr Gln Ser Pro Ser Ser Leu Ser Val Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Ala Leu Thr Ile Ser Ser Val Gln Pro
65                  70                  75                  80

Glu Asp Phe Ala Ser Tyr Phe Cys Gln Gln Ser His Ser Val Pro Ile
                85                  90                  95

Asn Phe Gly Gln Gly Thr Arg Leu Glu Ile Lys
            100                 105

<210> SEQ ID NO 181
<211> LENGTH: 107
<212> TYPE: PRT
<213> ORGANISM: Homo sapiens

<400> SEQUENCE: 181

Glu Leu Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Leu Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asp Leu Pro Leu
                85                  90                  95

Thr Phe Gly Gly Gly Thr Lys Leu Glu Ile Lys
            100                 105

<210> SEQ ID NO 182
<211> LENGTH: 107
<212> TYPE: PRT
<213> ORGANISM: Homo sapiens

<400> SEQUENCE: 182

Glu Leu Gln Met Thr Gln Ser Pro Ser Ser Leu Ala Ala Ser Val Gly
1               5                   10                  15

Asp Arg Val Thr Ile Thr Cys Arg Ala Ser His Asp Ile Lys Asn Asp
            20                  25                  30

Leu Gly Trp Tyr Gln His Gln Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asn Phe Thr Leu Thr Ile Asn Ser Leu Gln Pro
65                  70                  75                  80

Glu Asp Phe Ala Thr Tyr Tyr Cys Leu His Asp Tyr Thr Tyr Pro Arg
                85                  90                  95

Thr Phe Gly Gln Gly Thr Lys Val Glu Ile Lys
            100                 105

<210> SEQ ID NO 183
<211> LENGTH: 107
<212> TYPE: PRT
<213> ORGANISM: Homo sapiens

<400> SEQUENCE: 183

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Tyr Asp
            20                  25                  30

Val Gly Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Glu Thr Asp Phe Thr Leu Thr Ile Asn Ser Leu Gln Pro
65                  70                  75                  80

Glu Asp Ser Ala Thr Tyr Tyr Cys Gln Gln Ser Tyr Ser Ile Pro Ser
                85                  90                  95

Thr Phe Gly Gln Gly Thr Lys Val Glu Ile Lys
            100                 105

<210> SEQ ID NO 184
<211> LENGTH: 111
<212> TYPE: PRT
<213> ORGANISM: Homo sapiens

<400> SEQUENCE: 184

Glu Leu Glu Leu Thr Gln Pro Pro Ser Val Ser Gly Thr Pro Gly Gln
1               5                   10                  15

Arg Val Thr Ile Ser Cys Ser Gly Ser Ser Ser Asn Ile Gly Ser Asp
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Gly Leu
                85                  90                  95

Arg Gly Met Val Phe Gly Glu Gly Thr Lys Leu Thr Val Leu Gly
            100                 105                 110

<210> SEQ ID NO 185
<211> LENGTH: 114
<212> TYPE: PRT
<213> ORGANISM: Homo sapiens

<400> SEQUENCE: 185

Glu Leu Val Leu Thr Gln Pro Pro Ser Val Ser Gly Ala Pro Gly Arg
1               5                   10                  15

Arg Val Thr Ile Ser Cys Thr Gly Ser Ser Ser Asn Ile Gly Ala Ala

```
                    20                  25                  30

Tyr Asp Val His Trp Tyr Gln Gln Leu Pro Gly Thr Ala Pro Lys Leu
                35                  40                  45

Leu Ile Phe Gly Asn Thr Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ser Glu Asp Glu Ala Asp Tyr Tyr Cys Ala Thr Trp Asp Asp Ser
                85                  90                  95

Arg Asp Gly Pro Glu Val Val Phe Gly Gly Gly Thr Glu Leu Thr Val
                100                 105                 110

Leu Gly

<210> SEQ ID NO 186
<211> LENGTH: 111
<212> TYPE: PRT
<213> ORGANISM: Homo sapiens

<400> SEQUENCE: 186

Glu Leu Val Leu Thr Gln Pro Pro Ser Ala Ser Gly Thr Pro Gly Gln
 1               5                  10                  15

Arg Val Thr Ile Ser Cys Ser Gly Ser Asn Ser Asn Ile Gly Ser Asp
                20                  25                  30

Tyr Val Tyr Trp Tyr Gln Arg Phe Pro Gly Thr Ala Pro Lys Leu Leu
                35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Glu Tyr Tyr Cys Ala Thr Trp Asp Asp Ala Leu
                85                  90                  95

Arg Gly Met Val Phe Gly Glu Gly Thr Lys Leu Thr Val Leu Gly
                100                 105                 110

<210> SEQ ID NO 187
<211> LENGTH: 113
<212> TYPE: PRT
<213> ORGANISM: Homo sapiens

<400> SEQUENCE: 187

Glu Leu Met Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
                20                  25                  30

Phe Val Gln Trp Tyr Gln Gln Arg Pro Gly Lys Ser Pro Thr Thr Val
                35                  40                  45

Ile Tyr Glu Asp Asn Gln Arg Pro Ser Gly Val Pro Asp Arg Phe Ser
 50                  55                  60

Gly Ser Val Asp Arg Ser Ser Asn Ser Ala Ser Leu Thr Ile Ser Gly
 65                  70                  75                  80

Leu Gln Thr Glu Asp Glu Ala Asp Tyr Tyr Cys Gln Ser Phe Tyr Asp
                85                  90                  95

Gly Val Pro Ser Trp Val Phe Gly Gly Gly Thr Glu Leu Thr Val Leu
                100                 105                 110

Gly
```

<210> SEQ ID NO 188
<211> LENGTH: 113
<212> TYPE: PRT
<213> ORGANISM: Homo sapiens

<400> SEQUENCE: 188

```
Glu Leu Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Phe Val Gln Trp Tyr Gln Gln Arg Pro Gly Lys Ser Pro Thr Thr Val
        35                  40                  45

Ile Tyr Glu Asp Asn Gln Arg Pro Ser Gly Val Pro Asp Arg Phe Ser
    50                  55                  60

Gly Ser Val Asp Arg Ser Ser Asn Ser Ala Ser Leu Thr Ile Ser Gly
65                  70                  75                  80

Leu Gln Thr Glu Asp Glu Ala Asp Tyr Tyr Cys Gln Ser Phe Tyr Asp
                85                  90                  95

Gly Val Pro Ser Trp Val Phe Gly Gly Gly Thr Glu Leu Thr Val Leu
            100                 105                 110

Gly
```

<210> SEQ ID NO 189
<211> LENGTH: 107
<212> TYPE: PRT
<213> ORGANISM: Homo sapiens

<400> SEQUENCE: 189

```
Glu Leu Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Gly Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Tyr Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Phe
                85                  90                  95

Thr Phe Gly Pro Gly Thr Lys Val Asp Ile Lys
            100                 105
```

<210> SEQ ID NO 190
<211> LENGTH: 107
<212> TYPE: PRT
<213> ORGANISM: Homo sapiens

<400> SEQUENCE: 190

```
Glu Leu Val Met Thr Gln Ser Pro Ser Ser Leu Ser Ala Ser Val Gly
1               5                   10                  15

Asp Arg Val Thr Ile Thr Cys Arg Ala Ser Gln Gly Ile Thr Asp Asp
            20                  25                  30

Leu Gly Trp Tyr Gln Gln Lys Pro Gly Lys Ala Pro Lys Leu Leu Ile
        35                  40                  45

Tyr Ala Thr Ser Asn Leu Glu Ser Gly Val Pro Ser Arg Phe Ser Gly
    50                  55                  60
```

```
Ser Gly Ser Asp Thr Glu Phe Thr Leu Thr Ile Ser Ser Leu Gln Pro
 65                  70                  75                  80

Glu Asp Leu Ala Thr Tyr Tyr Cys Leu Gln Asp Tyr Ser Tyr Pro Tyr
                 85                  90                  95

Thr Phe Gly Gln Gly Thr Lys Val Glu Ile Lys
            100                 105

<210> SEQ ID NO 191
<211> LENGTH: 107
<212> TYPE: PRT
<213> ORGANISM: Homo sapiens

<400> SEQUENCE: 191

Glu Leu Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Ser Trp
                 20                  25                  30

Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Thr Tyr Ser Arg
                 85                  90                  95

Thr Phe Gly Gln Gly Thr Lys Val Glu Ile Lys
            100                 105

<210> SEQ ID NO 192
<211> LENGTH: 107
<212> TYPE: PRT
<213> ORGANISM: Homo sapiens

<400> SEQUENCE: 192

Glu Leu Gln Met Thr Gln Ser Pro Ser Ser Leu Ser Ala Ser Val Gly
  1               5                  10                  15

Asp Arg Val Thr Ile Thr Cys Gln Ala Ser Arg Asp Ile Ser Asn Tyr
                 20                  25                  30

Leu Asn Trp Tyr Gln His Ile Pro Gly Lys Ala Pro Lys Leu Leu Ile
             35                  40                  45

Phe His Ala Ser Thr Leu Glu Ala Gly Ile Pro Ser Arg Phe Ser Gly
 50                  55                  60

Ser Gly Ser Glu Thr Ser Phe Thr Phe Thr Ile Arg Ser Leu Gln Pro
 65                  70                  75                  80

Glu Asp Val Ala Thr Tyr Tyr Cys Gln Gln Tyr Asp Asn Leu Pro Phe
                 85                  90                  95

Thr Phe Gly Pro Gly Thr Lys Val Asp Ile Lys
            100                 105

<210> SEQ ID NO 193
<211> LENGTH: 111
<212> TYPE: PRT
<213> ORGANISM: Homo sapiens

<400> SEQUENCE: 193

Glu Leu Met Leu Thr Gln Pro His Ser Ala Ser Gly Thr Pro Gly Gln
  1               5                  10                  15
```

```
Arg Val Thr Ile Ser Cys Ser Gly Ser Ser Asn Ile Gly Ser Asn
             20                  25                  30

Thr Val Asn Trp Tyr Gln Gln Leu Pro Gly Thr Ala Pro Lys Leu Leu
         35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
             85                  90                  95

Asn Gly Pro Val Phe Gly Gly Gly Thr Lys Val Thr Val Leu Gly
            100                 105                 110
```

<210> SEQ ID NO 194
<211> LENGTH: 111
<212> TYPE: PRT
<213> ORGANISM: Homo sapiens

<400> SEQUENCE: 194

```
Glu Leu Val Val Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
             20                  25                  30

Thr Val Asn Trp Tyr Gln Gln Leu Pro Gly Thr Ala Pro Lys Leu Leu
         35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Thr Trp Asp Asp Gly Leu
             85                  90                  95

Asn Gly Met Val Phe Gly Gly Gly Thr Lys Leu Thr Val Leu Gly
            100                 105                 110
```

<210> SEQ ID NO 195
<211> LENGTH: 107
<212> TYPE: PRT
<213> ORGANISM: Homo sapiens

<400> SEQUENCE: 195

```
Glu Leu Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Gly Asn Asp
             20                  25                  30

Leu Gly Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Gly Ser Leu Gln Pro
 65                  70                  75                  80

Glu Asp Phe Ala Thr Tyr Tyr Cys Leu Gln Asp Tyr Asn Tyr Pro Phe
             85                  90                  95

Thr Phe Gly Pro Gly Thr Lys Val Asp Ile Lys
            100                 105
```

<210> SEQ ID NO 196
<211> LENGTH: 107

```
<212> TYPE: PRT
<213> ORGANISM: Homo sapiens

<400> SEQUENCE: 196

Glu Leu Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
            100                 105

<210> SEQ ID NO 197
<211> LENGTH: 108
<212> TYPE: PRT
<213> ORGANISM: Homo sapiens

<400> SEQUENCE: 197

Glu Leu Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ser
                85                  90                  95

Ile Thr Phe Gly Gln Gly Thr Arg Leu Glu Ile Lys
            100                 105

<210> SEQ ID NO 198
<211> LENGTH: 111
<212> TYPE: PRT
<213> ORGANISM: Homo sapiens

<400> SEQUENCE: 198

Glu Leu Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Lys Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Arg Ala Glu Asp Glu Ala Asp Tyr Tyr Cys Gln Ser Phe Asp Ser Ser
```

```
                85                  90                  95

Leu Gly Trp Val Phe Gly Gly Gly Thr Gln Leu Thr Val Leu Gly
            100                 105                 110

<210> SEQ ID NO 199
<211> LENGTH: 109
<212> TYPE: PRT
<213> ORGANISM: Homo sapiens

<400> SEQUENCE: 199

Glu Leu Val Leu Thr Gln Pro Pro Ser Val Pro Val Ala Pro Gly Gln
1               5                   10                  15

Thr Ala Asn Ile Ser Cys Gly Gly Asn Asn Ile Gly Arg Gln Thr Val
            20                  25                  30

His Trp Tyr Gln Gln Lys Pro Gly Gln Ala Pro Val Leu Val Val Phe
        35                  40                  45

Asp Asp Ser Asp Arg Pro Ala Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Gln Leu Thr Val Leu Gly
            100                 105

<210> SEQ ID NO 200
<211> LENGTH: 107
<212> TYPE: PRT
<213> ORGANISM: Homo sapiens

<400> SEQUENCE: 200

Glu Leu Val Leu Thr Gln Pro Pro Ser Val Ala Val Ser Pro Gly Gln
1               5                   10                  15

Thr Ala Ser Ile Thr Cys Ser Gly Asp Lys Leu Gly Asp Lys Tyr Val
            20                  25                  30

Ser Trp Tyr Gln Gln Lys Pro Gly Gln Ser Pro Val Leu Val Met Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Asn Thr Gly Val
                85                  90                  95

Phe Gly Gly Gly Thr Lys Leu Thr Val Leu Gly
            100                 105

<210> SEQ ID NO 201
<211> LENGTH: 109
<212> TYPE: PRT
<213> ORGANISM: Homo sapiens

<400> SEQUENCE: 201

Glu Leu Glu Leu Thr Gln Pro Pro Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45
```

-continued

```
Arg Asp Ser Asn Arg Pro Ser Gly Ile Pro Glu Arg Phe Ser Gly Ser
 50                  55                  60
Asn Ser Gly Asn Thr Ala Thr Leu Thr Ile Ser Arg Ala Gln Ala Gly
 65                  70                  75                  80
Asp Glu Ala Asp Tyr Tyr Cys Gln Ala Trp Asp Arg Ser Thr Ala His
                 85                  90                  95
Val Val Phe Gly Gly Gly Thr Lys Leu Thr Val Leu Gly
            100                 105

<210> SEQ ID NO 202
<211> LENGTH: 111
<212> TYPE: PRT
<213> ORGANISM: Homo sapiens

<400> SEQUENCE: 202

Glu Leu Val Leu Thr Gln Pro Pro Ser Ala Ser Gly Thr Pro Gly Gln
 1               5                  10                  15
Arg Val Thr Ile Ser Cys Ser Gly Ser Ser Ser Asn Ile Gly Ser Asn
                20                  25                  30
Thr Val Asn Trp Tyr Gln Gln Leu Pro Gly Thr Ala Pro Lys Leu Leu
            35                  40                  45
Ile Tyr Ser Asn Asn Gln Arg Pro Ser Gly Val Pro Asp Arg Phe Ser
 50                  55                  60
Gly Ser Lys Ser Gly Thr Ser Ala Ser Leu Ala Val Ser Gly Leu Gln
 65                  70                  75                  80
Ser Glu Asp Glu Ala Asp Tyr Tyr Cys Ala Ala Trp Asp Asp Ser Leu
                 85                  90                  95
Asn Gly Pro Val Phe Gly Gly Gly Thr Gln Leu Thr Val Leu Gly
            100                 105                 110

<210> SEQ ID NO 203
<211> LENGTH: 109
<212> TYPE: PRT
<213> ORGANISM: Homo sapiens

<400> SEQUENCE: 203

Glu Leu Val Met Thr Gln Ser Pro Ser Ser Val Ser Ala Ser Val Gly
 1               5                  10                  15
Asp Arg Val Ile Ile Thr Cys Arg Ala Ser Gln Gly Ile Ser Ser Ser
                20                  25                  30
Tyr Leu Ala Trp Tyr Gln Gln Lys Pro Gly Lys Ala Pro Lys Leu Leu
            35                  40                  45
Ile Tyr Ala Ala Phe Thr Leu Gln Ser Gly Val Pro Ser Arg Phe Ser
 50                  55                  60
Gly Ser Gly Ser Gly Thr Glu Phe Thr Leu Thr Ile Ser Ser Leu Gln
 65                  70                  75                  80
Pro Glu Asp Phe Ala Thr Tyr Phe Cys Gln Asp Leu Ser Gly Tyr Pro
                 85                  90                  95
Arg Asn Thr Phe Gly Gln Gly Thr Arg Leu Glu Ile Lys
            100                 105

<210> SEQ ID NO 204
<211> LENGTH: 107
<212> TYPE: PRT
<213> ORGANISM: Homo sapiens

<400> SEQUENCE: 204
```

-continued

Glu Leu Val Met Thr Gln Ser Pro Ser Leu Ser Ala Ser Val Gly
1               5                   10                  15

Asp Arg Val Thr Ile Thr Cys Gln Ala Ser Gln Asp Ile Arg Lys Tyr
            20                  25                  30

Leu Asn Trp Tyr Gln Gln Lys Ala Gly Lys Ala Pro Lys Leu Leu Ile
            35                  40                  45

Tyr Asp Ala Ser Lys Leu Asp Ile Gly Leu Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asp Asn Leu Pro Phe
            85                  90                  95

Thr Phe Gly Gly Gly Thr Lys Val Glu Ile Lys
            100                 105

<210> SEQ ID NO 205
<211> LENGTH: 111
<212> TYPE: PRT
<213> ORGANISM: Homo sapiens

<400> SEQUENCE: 205

Glu Leu Met Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
            85                  90                  95

Ser Gly Trp Val Phe Gly Gly Gly Thr Gln Leu Thr Val Leu Gly
            100                 105                 110

<210> SEQ ID NO 206
<211> LENGTH: 111
<212> TYPE: PRT
<213> ORGANISM: Homo sapiens

<400> SEQUENCE: 206

Glu Leu Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
            85                  90                  95

Asn Gly Gly Val Phe Gly Gly Gly Thr Glu Leu Thr Val Leu Gly
            100                 105                 110

<210> SEQ ID NO 207
<211> LENGTH: 111
<212> TYPE: PRT
<213> ORGANISM: Homo sapiens

<400> SEQUENCE: 207

Glu Leu Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Arg Val Phe Gly Gly Gly Thr Gln Leu Thr Val Leu Gly
            100                 105                 110

<210> SEQ ID NO 208
<211> LENGTH: 113
<212> TYPE: PRT
<213> ORGANISM: Homo sapiens

<400> SEQUENCE: 208

Glu Leu Val Val Thr Gln Pro Pro Ser Ala Ser Ala Ala Leu Gly Ser
1               5                   10                  15

Ser Ala Lys Leu Thr Cys Thr Leu Ser Ser Ala His Lys Thr Tyr Thr
            20                  25                  30

Ile Asp Trp Tyr Gln Gln Gln Gly Glu Ala Pro Arg Tyr Leu Met
        35                  40                  45

Gln Leu Lys Ser Asp Gly Ser Tyr Ser Lys Gly Thr Gly Val Pro Asp
    50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ser Gly Gly Tyr Tyr Val Phe Gly Gly Gly Thr Lys Leu Thr Val Leu
            100                 105                 110

Gly

<210> SEQ ID NO 209
<211> LENGTH: 107
<212> TYPE: PRT
<213> ORGANISM: Homo sapiens

<400> SEQUENCE: 209

Glu Leu Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Leu
                85                  90                  95

Thr Phe Gly Gly Gly Thr Lys Leu Glu Ile Lys
            100                 105

<210> SEQ ID NO 210
<211> LENGTH: 112
<212> TYPE: PRT
<213> ORGANISM: Homo sapiens

<400> SEQUENCE: 210

Glu Leu Val Leu Thr Gln Ser Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Asp Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Trp Val Phe Gly Gly Gly Thr Lys Val Thr Val Leu Gly
            100                 105                 110

<210> SEQ ID NO 211
<211> LENGTH: 106
<212> TYPE: PRT
<213> ORGANISM: Homo sapiens

<400> SEQUENCE: 211

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Arg Leu Glu Ile Lys
            100                 105

<210> SEQ ID NO 212
<211> LENGTH: 111
<212> TYPE: PRT
<213> ORGANISM: Homo sapiens

<400> SEQUENCE: 212

Glu Leu Glu Leu Thr Gln Pro Pro Ser Val Ser Gly Thr Pro Gly Gln
1               5                   10                  15
```

-continued

Arg Val Thr Ile Ser Cys Ser Gly Gly Ser Ser Asn Ile Gly Ser Asn
        20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Val Thr Val Leu Gly
            100                 105                 110

<210> SEQ ID NO 213
<211> LENGTH: 111
<212> TYPE: PRT
<213> ORGANISM: Homo sapiens

<400> SEQUENCE: 213

Glu Leu Glu Leu Thr Gln Pro Pro Ser Val Ser Gly Thr Pro Gly Gln
1               5                   10                  15

Arg Val Thr Ile Ser Cys Ser Gly Ser Ser Asn Ile Gly Ser Asn
        20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ala Trp Asp Asp Ser Leu
                85                  90                  95

Asn Gly Leu Val Phe Gly Gly Gly Thr Lys Leu Thr Val Leu Gly
            100                 105                 110

<210> SEQ ID NO 214
<211> LENGTH: 107
<212> TYPE: PRT
<213> ORGANISM: Homo sapiens

<400> SEQUENCE: 214

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
        20                  25                  30

Leu Asn Trp Tyr Gln Gln Lys Pro Gly Lys Ala Pro Met Leu Leu Ile
        35                  40                  45

Tyr Ala Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 215
<211> LENGTH: 111

-continued

<212> TYPE: PRT
<213> ORGANISM: Homo sapiens

<400> SEQUENCE: 215

Glu Leu Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Arg Val Phe Gly Gly Gly Thr Lys Leu Thr Val Leu Gly
            100                 105                 110

<210> SEQ ID NO 216
<211> LENGTH: 118
<212> TYPE: PRT
<213> ORGANISM: Homo sapiens

<400> SEQUENCE: 216

Gln Val Gln Leu Val Gln Ser Gly Ala Glu Val Lys Lys Pro Gly Ala
1               5                   10                  15

Leu Val Lys Val Ser Cys Lys Ala Ser Gly Tyr Thr Phe Thr Asn Tyr
            20                  25                  30

Gly Ile Thr Trp Val Arg Gln Ala Pro Gly Gln Gly Leu Glu Trp Met
        35                  40                  45

Gly Trp Ile Ser Val Tyr Asn Gly Asp Thr Lys Tyr Ala Gln Lys Leu
    50                  55                  60

Gln Gly Arg Val Thr Met Thr Thr Asp Thr Pro Thr Asn Thr Val Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Ser Gly Asn Trp Asp Tyr Trp Gly Gln Gly Thr
            100                 105                 110

Leu Val Thr Val Ser Ser
        115

<210> SEQ ID NO 217
<211> LENGTH: 118
<212> TYPE: PRT
<213> ORGANISM: Homo sapiens

<400> SEQUENCE: 217

Gln Val Gln Leu Val Gln Ser Gly Ala Glu Met Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Thr Trp Val Arg Gln Ala Pro Gly Gln Gly Leu Glu Trp Met
        35                  40                  45

Gly Trp Ile Ser Val Tyr Asn Gly Asp Thr Lys Tyr Ala Gln Lys Leu
    50                  55                  60

Gln Gly Arg Val Thr Met Thr Thr Asp Thr Pro Thr Ser Thr Val Tyr

```
                65                  70                  75                  80
Met Glu Leu Arg Ser Leu Thr Ser Asp Asp Thr Ala Val Tyr Tyr Cys
                85                  90                  95

Val Arg Gly Tyr Gly Ser Gly Asn Trp Asp Tyr Trp Gly Gln Gly Thr
                100                 105                 110

Leu Val Thr Val Ser Ser
        115

<210> SEQ ID NO 218
<211> LENGTH: 118
<212> TYPE: PRT
<213> ORGANISM: Homo sapiens

<400> SEQUENCE: 218

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Ile Thr Trp Val Arg Gln Ala Pro Gly Gln Gly Leu Glu Trp Met
                35                  40                  45

Gly Trp Ile Ser Val Tyr Asn Gly Asp Thr Lys Tyr Ala Gln Lys Leu
        50                  55                  60

Gln Gly Arg Val Thr Met Thr Thr Asp Thr Pro Thr Asn Thr Val Tyr
65              70                  75                  80

Met Glu Leu Arg Ser Leu Arg Ser Asp Asp Thr Ala Val Tyr Tyr Cys
                85                  90                  95

Ala Arg Gly Tyr Gly Ser Gly Asn Trp Asp Tyr Trp Gly Gln Gly Thr
                100                 105                 110

Leu Val Thr Val Ser Ser
        115

<210> SEQ ID NO 219
<211> LENGTH: 118
<212> TYPE: PRT
<213> ORGANISM: Homo sapiens

<400> SEQUENCE: 219

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Ile Thr Trp Val Arg Gln Ala Pro Gly Gln Gly Leu Glu Trp Met
                35                  40                  45

Gly Trp Ile Ser Val Tyr Asn Gly Asp Thr Lys Tyr Ala Gln Lys Leu
        50                  55                  60

Gln Gly Arg Val Thr Met Thr Thr Asp Thr Pro Thr Asn Thr Val Tyr
65              70                  75                  80

Met Glu Leu Arg Ser Leu Arg Ser Asp Asp Thr Ala Val Tyr Tyr Cys
                85                  90                  95

Ala Arg Gly Tyr Gly Ser Gly Asn Trp Asp Tyr Trp Gly Gln Gly Thr
                100                 105                 110

Leu Val Thr Val Ser Ser
        115

<210> SEQ ID NO 220
<211> LENGTH: 118
<212> TYPE: PRT
```

<213> ORGANISM: Homo sapiens

<400> SEQUENCE: 220

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Gly Ile Thr Trp Val Arg Gln Ala Pro Gly Gln Gly Leu Glu Trp Met
        35                  40                  45

Gly Trp Ile Ser Val Tyr Asn Gly Asp Thr Lys Tyr Ala Gln Lys Leu
    50                  55                  60

Gln Gly Arg Val Thr Met Thr Thr Asp Thr Pro Thr Asn Thr Val Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Ser Gly Asn Trp Asp Tyr Trp Gly Gln Gly Thr
            100                 105                 110

Leu Val Thr Val Ser Ser
        115

<210> SEQ ID NO 221
<211> LENGTH: 118
<212> TYPE: PRT
<213> ORGANISM: Homo sapiens

<400> SEQUENCE: 221

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Thr Trp Val Arg Gln Ala Pro Gly Gln Gly Leu Glu Trp Met
        35                  40                  45

Gly Trp Ile Ser Val Tyr Asn Gly Asp Thr Lys Tyr Ala Gln Lys Leu
    50                  55                  60

Gln Gly Arg Val Thr Met Thr Thr Asp Thr Leu Thr Asn Thr Val Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Ser Gly Asn Trp Asp Tyr Trp Gly Gln Gly Thr
            100                 105                 110

Pro Val Thr Val Ser Ser
        115

<210> SEQ ID NO 222
<211> LENGTH: 128
<212> TYPE: PRT
<213> ORGANISM: Homo sapiens

<400> SEQUENCE: 222

Gln Val Gln Leu Val Gln Ser Gly Ala Glu Val Arg Lys Pro Gly Ala
1               5                   10                  15

Ser Val Arg Val Ser Cys Lys Ala Ser Gly Tyr Thr Leu Thr Thr Tyr
            20                  25                  30

Asp Ile Asn Trp Val Arg Gln Ala Thr Gly Gln Gly Leu Glu Trp Met
        35                  40                  45

Gly Trp Met Asn Pro Thr Ser Gly Asn Thr Ala Tyr Ala Gln Lys Phe
    50                  55                  60

```
Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Leu Phe Phe Gly Val Val Thr Lys Pro Asn Tyr Tyr Tyr
            100                 105                 110

Tyr Ala Met Asp Val Trp Gly Gln Gly Thr Thr Val Thr Val Ser Ser
        115                 120                 125
```

<210> SEQ ID NO 223
<211> LENGTH: 127
<212> TYPE: PRT
<213> ORGANISM: Homo sapiens

<400> SEQUENCE: 223

```
Gln Val Gln Leu Val Gln Ser Gly Gly Gly Leu Ala Gln Pro Gly Lys
  1               5                  10                  15

Ser Leu Arg Leu Ser Cys Val Ala Ser Gly Phe Thr Phe Asp Asp Tyr
                 20                  25                  30

Ala Met His Trp Val Arg Gln Ala Pro Gly Lys Gly Leu Glu Trp Val
             35                  40                  45

Ser Gly Ile Asn Trp Asn Ser Gly Ser Ile Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Glu Gln Gly Tyr Cys Asp Ser Thr Gly Cys Gln Arg Gly Ser
            100                 105                 110

Gly Met Asp Val Trp Gly Gln Gly Thr Thr Val Thr Val Ser Ser
        115                 120                 125
```

<210> SEQ ID NO 224
<211> LENGTH: 127
<212> TYPE: PRT
<213> ORGANISM: Homo sapiens

<400> SEQUENCE: 224

```
Gln Val Gln Leu Val Gln Ser Gly Gly Gly Leu Ala Gln Pro Gly Lys
  1               5                  10                  15

Ser Leu Arg Leu Ser Cys Val Ala Ser Gly Phe Thr Phe Asp Asp Tyr
                 20                  25                  30

Ala Met His Trp Val Arg Gln Ala Pro Gly Lys Gly Leu Glu Trp Val
             35                  40                  45

Ser Gly Ile Asn Trp Asn Ser Gly Ser Ile Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Glu Gln Gly Tyr Cys Asp Ser Thr Gly Cys Gln Arg Gly Ser
            100                 105                 110

Gly Met Asp Val Trp Gly Gln Gly Thr Thr Val Thr Val Ser Ser
        115                 120                 125
```

<210> SEQ ID NO 225

```
<211> LENGTH: 127
<212> TYPE: PRT
<213> ORGANISM: Homo sapiens

<400> SEQUENCE: 225

Gln Val Gln Leu Val Gln Ser Gly Gly Gly Leu Ala Gln Pro Gly Lys
1               5                   10                  15

Ser Leu Arg Leu Ser Cys Val Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gln Gly Tyr Cys Asp Ser Thr Gly Cys Gln Arg Gly Ser
            100                 105                 110

Gly Met Asp Val Trp Gly Gln Gly Thr Thr Val Thr Val Ser Ser
        115                 120                 125

<210> SEQ ID NO 226
<211> LENGTH: 127
<212> TYPE: PRT
<213> ORGANISM: Homo sapiens

<400> SEQUENCE: 226

Glu Val Gln Leu Leu Glu Ser Gly Gly Gly Leu Ala Gln Pro Gly Lys
1               5                   10                  15

Ser Leu Arg Leu Ser Cys Val Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gln Gly Tyr Cys Asp Ser Thr Gly Cys Gln Arg Gly Ser
            100                 105                 110

Gly Met Asp Val Trp Gly Gln Gly Thr Thr Val Thr Val Ser Ser
        115                 120                 125

<210> SEQ ID NO 227
<211> LENGTH: 127
<212> TYPE: PRT
<213> ORGANISM: Homo sapiens

<400> SEQUENCE: 227

Gln Val Gln Leu Gln Glu Ser Gly Gly Gly Leu Ala Gln Pro Gly Lys
1               5                   10                  15

Ser Leu Arg Leu Ser Cys Val Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45
```

```
Ser Gly Ile Asn Trp Asn Ser Gly Ser Ile Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Glu Gln Gly Tyr Cys Asp Ser Thr Gly Cys Gln Arg Gly Ser
            100                 105                 110

Gly Met Asp Val Trp Gly Gln Gly Thr Thr Val Thr Val Ser Ser
            115                 120                 125

<210> SEQ ID NO 228
<211> LENGTH: 127
<212> TYPE: PRT
<213> ORGANISM: Homo sapiens

<400> SEQUENCE: 228

Glu Val Gln Leu Val Glu Ser Gly Gly Gly Leu Ala Gln Pro Gly Lys
 1               5                  10                  15

Ser Leu Arg Leu Ser Cys Val Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Asn Trp Asn Ser Gly Ser Ile Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Glu Gln Gly Tyr Cys Asp Ser Thr Gly Cys Gln Arg Gly Ser
            100                 105                 110

Gly Met Asp Val Trp Gly Gln Gly Thr Thr Val Thr Val Ser Ser
            115                 120                 125

<210> SEQ ID NO 229
<211> LENGTH: 127
<212> TYPE: PRT
<213> ORGANISM: Homo sapiens

<400> SEQUENCE: 229

Glu Val Gln Leu Val Glu Ser Gly Gly Gly Leu Ala Gln Pro Gly Lys
 1               5                  10                  15

Ser Leu Arg Leu Ser Cys Val Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Asn Trp Asn Ser Gly Ser Ile Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Glu Gln Gly Tyr Cys Asp Ser Thr Gly Cys Gln Arg Gly Ser
            100                 105                 110

Gly Met Asp Val Trp Gly Gln Gly Thr Thr Val Thr Val Ser Ser
            115                 120                 125
```

<210> SEQ ID NO 230
<211> LENGTH: 127
<212> TYPE: PRT
<213> ORGANISM: Homo sapiens

<400> SEQUENCE: 230

Glu Val Gln Leu Val Glu Ser Gly Gly Gly Val Val Gln Pro Gly Gly
1               5                   10                  15

Ser Leu Arg Leu Ser Cys Val Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gln Gly Tyr Cys Asp Ser Thr Gly Cys Gln Arg Gly Ser
            100                 105                 110

Gly Met Asp Val Trp Gly Gln Gly Thr Thr Val Thr Val Ser Ser
        115                 120                 125

<210> SEQ ID NO 231
<211> LENGTH: 123
<212> TYPE: PRT
<213> ORGANISM: Homo sapiens

<400> SEQUENCE: 231

Gln Val Gln Leu Val Gln Ser Gly Gly Gly Val Val Gln Pro Gly Gly
1               5                   10                  15

Ser Leu Arg Leu Ser Cys Val Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ala Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Val Tyr Tyr Cys
                85                  90                  95

Ala Lys Asp Gly Ile Thr Ile Phe Gly Val Gly Asp Gly Leu Asp Val
            100                 105                 110

Trp Gly Gln Gly Thr Met Val Thr Val Ser Ser
        115                 120

<210> SEQ ID NO 232
<211> LENGTH: 123
<212> TYPE: PRT
<213> ORGANISM: Homo sapiens

<400> SEQUENCE: 232

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val

```
            35                  40                  45

Ser Gly Ile Ser Trp Asn Ser Gly Ser Ile Asp Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Leu Tyr Tyr Cys
                 85                  90                  95

Ala Lys Asp Gly Ser Arg Val Phe Gly Val Gly Gly Phe Asp Phe
                100                 105                 110

Trp Gly Gln Gly Thr Met Val Thr Val Ser Ser
            115                 120
```

<210> SEQ ID NO 233
<211> LENGTH: 123
<212> TYPE: PRT
<213> ORGANISM: Homo sapiens

<400> SEQUENCE: 233

```
Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Glu Trp Val
             35                  40                  45

Ser Gly Ile Ser Trp Asn Ser Gly Ser Ile Asp Tyr Val Asp Ser Val
 50                  55                  60

Lys Gly Arg Phe Thr Ile Ser Arg Asp Asn Ala Lys Asn Tyr Leu Tyr
 65                  70                  75                  80

Leu Gln Met Asn Ser Leu Arg Val Glu Asp Thr Ala Leu Tyr Tyr Cys
                 85                  90                  95

Ala Lys Asp Gly Ser Arg Val Phe Gly Val Gly Gly Phe Asp Phe
                100                 105                 110

Trp Gly Gln Gly Thr Met Val Thr Val Ser Ser
            115                 120
```

<210> SEQ ID NO 234
<211> LENGTH: 123
<212> TYPE: PRT
<213> ORGANISM: Homo sapiens

<400> SEQUENCE: 234

```
Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
                 20                  25                  30

Ser Met His Trp Val Arg Gln Ala Pro Gly Lys Gly Leu Glu Trp Val
             35                  40                  45

Ser Gly Ile Ser Trp Asn Ser Gly Gly Ile Gly Tyr Ala Asp Ser Val
 50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Gly Met Arg Val Phe Gly Val Gly Gly Phe Asp Phe
                100                 105                 110

Trp Gly Gln Gly Thr Met Val Thr Val Ser Ser
```

```
                115                 120

<210> SEQ ID NO 235
<211> LENGTH: 123
<212> TYPE: PRT
<213> ORGANISM: Homo sapiens

<400> SEQUENCE: 235

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met Tyr Trp Val Arg Gln Ala Pro Gly Lys Gly Leu Glu Trp Val
        35                  40                  45

Ser Gly Ile Ser Trp Asn Ser Gly Ser Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Met Arg Val Phe Gly Val Gly Gly Phe Asp Phe
            100                 105                 110

Trp Gly Gln Gly Thr Met Val Thr Val Ser Ser
        115                 120

<210> SEQ ID NO 236
<211> LENGTH: 123
<212> TYPE: PRT
<213> ORGANISM: Homo sapiens

<400> SEQUENCE: 236

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met Tyr Trp Val Arg Gln Ala Pro Gly Lys Gly Leu Glu Trp Val
        35                  40                  45

Ser Gly Ile Ser Trp Asn Ser Gly Ser Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Met Arg Val Phe Gly Val Gly Gly Phe Asp Phe
            100                 105                 110

Trp Gly Gln Gly Thr Met Val Thr Val Ser Ser
        115                 120

<210> SEQ ID NO 237
<211> LENGTH: 123
<212> TYPE: PRT
<213> ORGANISM: Homo sapiens

<400> SEQUENCE: 237

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30
```

```
Ala Met His Trp Val Arg Gln Ala Pro Gly Lys Gly Leu Glu Trp Val
        35                  40                  45

Ser Gly Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ile Thr Val Phe Gly Val Gly Asp Gly Leu Asp Ile
                100                 105                 110

Trp Gly Gln Gly Thr Met Val Thr Val Ser Ser
            115                 120
```

<210> SEQ ID NO 238
<211> LENGTH: 125
<212> TYPE: PRT
<213> ORGANISM: Homo sapiens

<400> SEQUENCE: 238

```
Glu Val Gln Leu Val Glu Ser Gly Gly Thr Leu Val Gln Pro Gly Arg
1               5                   10                  15

Ser Leu Arg Leu Ser Cys Ala Ala Ser Gly Phe Ser Phe Asp Asp Tyr
            20                  25                  30

Ala Met Gln Trp Val Arg Gln Ala Pro Gly Lys Gly Leu Glu Trp Val
        35                  40                  45

Ser Gly Ile Ser Trp Asn Ser Gly Ser Ile Ala Tyr Ala Asp Ser Val
    50                  55                  60

Lys Gly Arg Phe Thr Ile Ser Arg Asp Asn Ala Lys Ser Ser Leu Tyr
65                  70                  75                  80

Leu Leu Met Asn Ser Leu Arg Ala Glu Asp Thr Ala Leu Tyr Tyr Cys
                85                  90                  95

Ala Lys Ala Gly Thr Asp Tyr Tyr Asp Ser Ser Ala Ser Glu Leu Pro
                100                 105                 110

Asp Tyr Trp Gly Gln Gly Thr Leu Val Thr Val Ser Ser
            115                 120                 125
```

<210> SEQ ID NO 239
<211> LENGTH: 126
<212> TYPE: PRT
<213> ORGANISM: Homo sapiens

<400> SEQUENCE: 239

```
Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr Tyr Cys
                85                  90                  95

Ala Lys Val Gly Gly Asp Thr Tyr Asp Ile Thr Ser Gly Ala Asp Tyr
                100                 105                 110
```

Phe Asp Leu Trp Gly Arg Gly Ala Leu Val Thr Val Ser Ser
            115                 120                 125

<210> SEQ ID NO 240
<211> LENGTH: 126
<212> TYPE: PRT
<213> ORGANISM: Homo sapiens

<400> SEQUENCE: 240

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr Tyr Cys
                85                  90                  95

Ala Lys Val Gly Gly Asp Thr Tyr Asp Ile Thr Ser Gly Ala Asp Tyr
            100                 105                 110

Phe Asp Leu Trp Gly Arg Gly Ala Leu Val Thr Val Ser Ser
            115                 120                 125

<210> SEQ ID NO 241
<211> LENGTH: 122
<212> TYPE: PRT
<213> ORGANISM: Homo sapiens

<400> SEQUENCE: 241

Gln Val Gln Leu Val Gln Ser Gly Gly Gly Leu Val Gln Pro Gly Gly
1               5                   10                  15

Ser Leu Arg Val Ser Cys Ala Ala Ser Gly Phe Thr Ser Asn Ile Phe
            20                  25                  30

Trp Met Ser Trp Val Arg Gln Ala Pro Gly Lys Gly Leu Glu Trp Val
        35                  40                  45

Ala Asn Ile Asp Glu Asp Gly Ser Glu Lys Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Phe Tyr Tyr Gly Ser Gly Thr Tyr Phe Asp Phe Trp
            100                 105                 110

Gly Gln Gly Thr Leu Val Thr Val Ser Ser
            115                 120

<210> SEQ ID NO 242
<211> LENGTH: 123
<212> TYPE: PRT
<213> ORGANISM: Homo sapiens

<400> SEQUENCE: 242

Gln Val Gln Leu Val Gln Ser Gly Gly Gly Val Val Gln Ser Gly Arg
1               5                   10                  15

-continued

Ser Leu Arg Leu Ser Cys Ala Ala Ser Gly Phe Thr Phe Ser Asp Tyr
            20                  25                  30

Ala Met His Trp Val Arg Gln Ala Pro Gly Lys Gly Leu Glu Trp Val
            35                  40                  45

Ala Val Ile Ser His Gly Gly Thr Lys Lys Tyr Thr Gly Asp Ser Val
50                  55                  60

Lys Gly Arg Phe Ile Ile Ser Arg Asp Asn Ser Lys Asn Thr Val Phe
65                  70                  75                  80

Leu Gln Met Asn Ser Leu Arg Val Glu Asp Thr Ala Val Tyr Tyr Cys
            85                  90                  95

Ala Arg Asp Arg Val Glu Gly Tyr Val Trp Gly Gly Thr Phe Asp His
            100                 105                 110

Trp Gly Gln Gly Thr Pro Val Thr Val Ser Ser
            115                 120

<210> SEQ ID NO 243
<211> LENGTH: 126
<212> TYPE: PRT
<213> ORGANISM: Homo sapiens

<400> SEQUENCE: 243

Glu Val Gln Leu Leu Glu Ser Gly Pro Gly Leu Glu Lys Val Ser Glu
1               5                   10                  15

Thr Leu Ser Leu Thr Cys Asn Val Ser Gly Val Ser Ile Ser Ser Pro
            20                  25                  30

Asp Tyr Tyr Trp Ala Trp Ile Arg Gln Pro Pro Gly Lys Gly Leu Glu
            35                  40                  45

Trp Ile Gly Ser Ile Phe Tyr Ser Gly Pro Thr Ser Trp Asn Pro Ser
50                  55                  60

Leu Lys Asn Arg Val Thr Ile Ser Val Asp Thr Ser Lys Asn Gln Phe
65                  70                  75                  80

Ser Leu Lys Met Lys Ser Val Thr Ala Ala Asp Thr Ala Val Tyr Tyr
            85                  90                  95

Cys Ala Arg Ser Phe Gly Phe Gly Arg Tyr Glu Pro Ala Asp Asp Ala
            100                 105                 110

Phe Asp Ile Trp Gly Arg Gly Arg Leu Val Ile Val Ser Pro
            115                 120                 125

<210> SEQ ID NO 244
<211> LENGTH: 126
<212> TYPE: PRT
<213> ORGANISM: Homo sapiens

<400> SEQUENCE: 244

Gln Val Gln Leu Val Gln Ser Gly Gly Gly Val Val Gln Pro Gly Arg
1               5                   10                  15

Ser Leu Arg Leu Ser Cys Thr Ala Ser Arg Phe Asn Phe Arg Ser Phe
            20                  25                  30

Ala Met His Trp Val Arg Gln Ala Pro Gly Lys Gly Leu Glu Trp Val
            35                  40                  45

Ala Met Phe Pro Tyr Asp Gly Asn Asn Thr Tyr Tyr Gly Asp Ser Val
50                  55                  60

Lys Gly Arg Phe Thr Ile Ser Arg Asp Asn Ser Lys Lys Met Leu Tyr
65                  70                  75                  80

Leu Gln Met Asn Asp Leu Arg Ile Asp Asp Thr Ala Leu Tyr Tyr Cys
            85                  90                  95

Ala Arg Gln Gly Trp Val Ile Glu Thr Ser Gly Ile Arg Ala Ser Gly
            100                 105                 110

Phe Asp Val Trp Gly Gln Gly Thr Leu Val Thr Val Ser Ser
            115                 120                 125

<210> SEQ ID NO 245
<211> LENGTH: 123
<212> TYPE: PRT
<213> ORGANISM: Homo sapiens

<400> SEQUENCE: 245

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ile Thr Val Phe Gly Val Gly Asp Gly Leu Asp Ile
            100                 105                 110

Trp Gly Gln Gly Thr Met Val Thr Val Ser Ser
            115                 120

<210> SEQ ID NO 246
<211> LENGTH: 123
<212> TYPE: PRT
<213> ORGANISM: Homo sapiens

<400> SEQUENCE: 246

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Ala Lys Asp Gly Ser Arg Val Phe Gly Val Gly Gly Phe Asp Phe
            100                 105                 110

Trp Gly Gln Gly Thr Met Val Thr Val Ser Ser
            115                 120

<210> SEQ ID NO 247
<211> LENGTH: 123
<212> TYPE: PRT
<213> ORGANISM: Homo sapiens

<400> SEQUENCE: 247

Glu Val Gln Leu Val Glu Ser Gly Gly Gly Leu Val Gln Pro Gly Arg

```
            1               5                  10                 15
          Ser Leu Arg Leu Ser Cys Ala Ala Ser Gly Phe Thr Phe Asp Asp Tyr
                        20                  25                  30

Ala Met His Trp Val Arg Gln Ala Pro Gly Lys Gly Leu Glu Trp Val
                        35                  40                  45

Ser Gly Ile Ser Trp Asn Ser Gly Thr Ile Gly Tyr Ala Asp Ser Val
                        50                  55                  60

Lys Gly Arg Phe Thr Ile Ser Arg Asp Asn Ala Lys Asn Ser Leu Tyr
          65                  70                  75                  80

Leu Gln Met Asn Ser Leu Arg Ala Glu Asp Thr Ala Val Tyr Tyr Cys
                        85                  90                  95

Ala Lys Asp Gly Ile Thr Val Phe Gly Val Gly Asp Gly Leu Asp Ile
                        100                 105                 110

Trp Gly Gln Gly Thr Met Val Thr Val Ser Ser
                        115                 120

<210> SEQ ID NO 248
<211> LENGTH: 117
<212> TYPE: PRT
<213> ORGANISM: Homo sapiens

<400> SEQUENCE: 248

Glu Val Gln Leu Val Glu Ser Gly Gly Gly Leu Val Gln Pro Gly Gly
          1               5                  10                 15

Ser Val Arg Leu Ser Cys Ala Ala Ser Gly Phe Gln Val Ser Ser Asp
                        20                  25                  30

His Met Ser Trp Val Arg Gln Ala Pro Gly Lys Gly Leu Gln Trp Val
                        35                  40                  45

Ser Val Ile Tyr Thr Gly Gly Asn Ser Tyr Tyr Ala Asp Ser Val Lys
                        50                  55                  60

Gly Arg Phe Thr Val Ser Arg Asp Asn Ser Arg Asn Thr Leu Phe Leu
          65                  70                  75                  80

Gln Met Asn Ser Leu Arg Val Glu Asp Thr Ala Ile Tyr Tyr Cys Val
                        85                  90                  95

Arg Gly Pro Ala Tyr Tyr Asp Ile Asp Tyr Trp Gly Gln Gly Ala Leu
                        100                 105                 110

Val Thr Val Ser Ser
                        115

<210> SEQ ID NO 249
<211> LENGTH: 123
<212> TYPE: PRT
<213> ORGANISM: Homo sapiens

<400> SEQUENCE: 249

Gln Val Gln Leu Gln Glu Ser Gly Gly Gly Leu Val Gln Pro Gly Arg
          1               5                  10                 15

Ser Leu Arg Leu Ser Cys Ala Ala Ser Gly Phe Thr Phe Asp Asp Tyr
                        20                  25                  30

Ala Met His Trp Val Arg Gln Ala Pro Gly Lys Gly Leu Glu Trp Val
                        35                  40                  45

Ser Gly Ile Ser Trp Asn Ser Gly Ala Ile Gly Tyr Ala Asp Ser Val
                        50                  55                  60

Lys Gly Arg Phe Thr Ile Ser Arg Asp Asn Ala Lys Asn Ser Leu Tyr
          65                  70                  75                  80

Leu Gln Met Asn Ser Leu Arg Ala Glu Asp Thr Ala Val Tyr Tyr Cys
```

```
                85                  90                  95
Ala Lys Asp Gly Ile Thr Val Phe Gly Val Gly Asp Gly Leu Asp Ile
            100                 105                 110

Trp Gly Gln Gly Thr Met Val Thr Val Ser Ser
            115                 120
```

<210> SEQ ID NO 250
<211> LENGTH: 117
<212> TYPE: PRT
<213> ORGANISM: Homo sapiens

<400> SEQUENCE: 250

```
Gln Val Gln Leu Val Gln Ser Gly Gly Asp Leu Val Gln Pro Gly Gly
1               5                   10                  15

Ser Leu Arg Leu Ser Cys Val Ala Ser Gly Phe Asn Val Asn Asp Asn
            20                  25                  30

Tyr Met Ser Trp Val Arg Gln Ala Pro Gly Lys Gly Leu Glu Trp Val
        35                  40                  45

Ser Thr Ile Tyr Ser Glu Thr Leu Ser Tyr Tyr Gly Asp Ser Val Lys
    50                  55                  60

Gly Arg Phe Thr Val Ser Arg Asp Gly Ser Lys Asn Thr Val Phe Leu
65                  70                  75                  80

Gln Met Ser Ser Leu Lys Gly Glu Asp Thr Ala Val Tyr Tyr Cys Ala
                85                  90                  95

Ser Glu Gly Gly Gly Leu Thr Ile Asp Tyr Trp Gly Gln Gly Thr Leu
            100                 105                 110

Val Ala Val Ser Ser
            115
```

<210> SEQ ID NO 251
<211> LENGTH: 127
<212> TYPE: PRT
<213> ORGANISM: Homo sapiens

<400> SEQUENCE: 251

```
Glu Val Gln Leu Val Glu Ser Gly Ala Glu Val Lys Lys Pro Gly Ala
1               5                   10                  15

Ser Val Lys Val Ser Cys Lys Ala Ser Thr Tyr Met Phe Thr Ser Tyr
            20                  25                  30

Asp Ile Asn Trp Val Arg Gln Ala Ala Gly Gln Gly Leu Glu Trp Met
        35                  40                  45

Gly Trp Met Asp Pro Asn Thr Gly Asn Thr Asp Tyr Ala Gln Lys Phe
    50                  55                  60

Gln Gly Arg Val Thr Met Thr Arg Asn Thr Ser Ile Asn Thr Ala Tyr
65                  70                  75                  80

Met Glu Leu Arg Ser Leu Thr Ser Asp Asp Thr Ala Val Tyr Tyr Cys
                85                  90                  95

Ala Arg Gly Arg Thr Val Arg Phe Gly Glu Leu Phe Val Ser Glu Gly
            100                 105                 110

Gly Met Asp Val Trp Gly Gln Gly Thr Thr Val Ser Val Ser Ser
            115                 120                 125
```

<210> SEQ ID NO 252
<211> LENGTH: 122
<212> TYPE: PRT
<213> ORGANISM: Homo sapiens

<400> SEQUENCE: 252

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp His
            20                  25                  30

Ala Met His Trp Val Arg Gln Ala Pro Gly Lys Gly Leu Glu Trp Val
        35                  40                  45

Ser Gly Ile Ser Trp Ser Gly Ala Tyr Ile Tyr Ala Asp Ser Val
50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Leu Tyr Tyr Cys
            85                  90                  95

Ala Arg Ser Ser Gly Tyr Tyr Asp Leu Pro Tyr Ala Phe Asp Ile Trp
            100                 105                 110

Gly Gln Gly Thr Met Val Thr Val Ser Ser
            115                 120

<210> SEQ ID NO 253
<211> LENGTH: 123
<212> TYPE: PRT
<213> ORGANISM: Homo sapiens

<400> SEQUENCE: 253

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Asp Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
            85                  90                  95

Ala Lys Asp Gly Ser Arg Val Phe Gly Val Gly Gly Phe Asp Phe
            100                 105                 110

Trp Gly Gln Gly Thr Met Val Thr Val Ser Ser
            115                 120

<210> SEQ ID NO 254
<211> LENGTH: 123
<212> TYPE: PRT
<213> ORGANISM: Homo sapiens

<400> SEQUENCE: 254

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Thr Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Val Tyr Tyr Cys
                85                  90                  95

Ala Lys Asp Gly Ile Thr Val Phe Gly Val Gly Asp Gly Leu Asp Ile
            100                 105                 110

Trp Gly Gln Gly Thr Met Val Thr Val Ser Ser
        115                 120

<210> SEQ ID NO 255
<211> LENGTH: 126
<212> TYPE: PRT
<213> ORGANISM: Homo sapiens

<400> SEQUENCE: 255

Gln Val Gln Leu Gln Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Ala Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr Tyr Cys
                85                  90                  95

Ala Lys Val Gly Gly Asp Thr Tyr Asp Ile Thr Ser Gly Ala Asp Tyr
            100                 105                 110

Phe Asp Leu Trp Gly Arg Ser Ala Leu Val Thr Val Ser Ser
            115                 120                 125

<210> SEQ ID NO 256
<211> LENGTH: 123
<212> TYPE: PRT
<213> ORGANISM: Homo sapiens

<400> SEQUENCE: 256

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Gly Pro Gly Lys Gly Leu Glu Trp Val
            35                  40                  45

Ser Gly Ile Ser Trp Asn Ser Gly Thr Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ile Thr Val Phe Gly Val Gly Asp Gly Leu Asp Ile
            100                 105                 110

Trp Gly Gln Gly Thr Met Val Thr Val Ser Ser
        115                 120

<210> SEQ ID NO 257
<211> LENGTH: 122
<212> TYPE: PRT
<213> ORGANISM: Homo sapiens
```

```
<400> SEQUENCE: 257

Gln Ile Thr Leu Lys Glu Ser Gly Gly Val Val Gln Pro Gly Arg
1               5                   10                  15

Ser Leu Arg Leu Ser Cys Ala Ala Ser Gly Phe Asp Phe Asn Ile Tyr
            20                  25                  30

Gly Met His Trp Val Arg Gln Ala Pro Asp Lys Gly Leu Glu Trp Val
            35                  40                  45

Ala Val Ile Ser Asp Asp Gly Thr Lys Lys Tyr Tyr Ala Asp Ser Val
        50                  55                  60

Lys Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Asp Val Val Met Gly Pro Gly Gly Leu Asp Tyr Trp
                100                 105                 110

Gly Gln Gly Thr Leu Val Thr Val Ser Ser
            115                 120

<210> SEQ ID NO 258
<211> LENGTH: 123
<212> TYPE: PRT
<213> ORGANISM: Homo sapiens

<400> SEQUENCE: 258

Gln Ile Thr Leu Lys Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Thr Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ile Thr Val Phe Gly Val Gly Asp Gly Leu Asp Ile
                100                 105                 110

Trp Gly Gln Gly Thr Met Val Thr Val Ser Ser
            115                 120
```

ISOLATION OF ANTI-DESMOGLEIN 1 ANTIBODIES BY PHAGE DISPLAY OF PEMPHIGUS FOLIACEUS AUTOANTIBODIES

CROSS-REFERENCE TO RELATED APPLICATIONS

This is a National Stage application of PCT International Application No. PCT/US2008/005924, filed May 9, 2008, which in turn claims the benefit pursuant to 35U.S.C. §119(e) of U.S. Provisional Application No. 60/929,405, filed on Jun. 26, 2007 which is hereby incorporated by reference in its entirety herein.

STATEMENT REGARDING FEDERALLY SPONSORED RESEARCH OR DEVELOPMENT

This research was supported, in part, by U.S. Government funds (National Institutes of Health Grant No. RO1AR048223 and RO1AR1052672), and therefore the U.S. Government has certain rights in the invention.

BACKGROUND OF THE INVENTION

Pemphigus foliaceus (PF) is a tissue-specific autoimmune disease in which antibodies against the keratinocyte cell surface cause skin blisters. These blisters are due to loss of cell adhesion in the superficial living epidermis (i.e. the granular layer) as shown by the diagnostic histology from biopsies of the skin lesions of these patients. The autoantibodies bind desmoglein 1 (Dsg1), a desmosomal cadherin found predominantly in the superficial layers of stratified squamous epithelia. Desmogleins are thought to function as cell-cell adhesion molecules which, in epidermis, maintain its integrity. Polyclonal anti-Dsg1 antibodies from PF patients are pathogenic in organ culture of normal human skin and by passive transfer to neonatal mice, which result in blisters with the typical histology of PF from loss of cell-cell adhesion.

In most PF patients the predominant antibody response is directed against the amino terminal 161 amino acids of the 496 amino acids in the extracellular domain of Dsg1. These antibodies directed against the amino terminus, where the trans-adhesion binding site is located, are necessary for pathogenicity. Furthermore, in the preclinical phase of fogo selvagem, a form of endemic PF in Brazil, patients develop IgG1 antibodies against the carboxy-terminus of the extracellular domain of Dsg1. In clinically affected patients, the antibody response migrates to an IgG4 antibody against the amino-terminus of Dsg1. The switch from an IgG1 to an IgG4 response is believed to indicate a maturation of the immune response. This switch does not implicate the Fc region of IgG as necessary for disease because neither the effector region of IgG nor crosslinking by IgG is necessary for these PF antibodies to cause blisters.

Study of PF serum-derived polyclonal antibodies has limitations for addressing many of the remaining questions regarding the pathophysiology of the autoantibodies in this disease. For example, it has yet to be determined whether antibodies directed against the amino-terminus of Dsg1 are both necessary and sufficient for disease. In order to consider the feasibility of developing specific therapy targeted to pathogenic autoantibodies, it is necessary to determine the genetic diversity of PF antibodies and whether specific antibody genes are preferentially used to produce them. Therefore, there has been a long felt need in the field for more specific antibody-targeted therapies for pemphigus that would suppress or eliminate only the anti-Dsg autoantibodies. The present invention satisfies this need.

SUMMARY OF THE INVENTION

The present invention includes an isolated anti-desmoglein 1 (Dsg1) antibody or fragment thereof comprising a heavy chain ($V_H$) encoded by the gene selected from the group consisting of VH1-18,VH1-08,VH3-09,VH3-07,VH3-30, VH4-b, VH3-53, VH3-66, and any combination thereof.

In one embodiment, the antibody or fragment thereof of is pathogenic and comprises a consensus sequence represented by Asp-X-X-X-Trp (SEQ ID NO: 259) or Glu-X-X-X-Trp (SEQ ID NO: 260).

In another embodiment, the antibody or fragment thereof of comprises a heavy chain variable domain comprising the amino acid sequence selected from the group is consisting of SEQ ID NOs: 216-258,and any combination thereof. In another embodiment, the antibody or fragment thereof of comprises a light chain variable domain comprising the amino acid sequence selected from the group consisting of SEQ ID NOs: 173-215,and any combination thereof In yet another embodiment, the antibody or fragment thereof of comprises the amino acid sequence selected from the group consisting of SEQ ID NOs: 44-86,and any combination thereof.

In one embodiment, antibody or fragment thereof is a single chain Fv (scFv), a Fab, a $(Fab')_2$ or a $(scFv')_2$.

The present invention also includes a composition comprising an anti-autoimmune reagent, wherein the anti-autoimmune reagent specifically binds to an anti-desmoglein 1 (Dsg1) antibody or fragment thereof comprising a heavy chain ($V_H$) encoded by the gene selected from the group consisting of VH1-18,VH1-08,VH3-09,VH3-07,VH3-30, VH4-b, VH3-53,VH3-66,and any combination thereof.

In one embodiment, the anti-autoimmune reagent is selected from the group consisting of a peptide, a small molecule, an antibody, a humanized antibody, a recombinant antibody, and any combination thereof.

In another embodiment, the anti autoimmune reagent specifically binds to antibody or fragment thereof of comprising a heavy chain variable domain comprising the amino acid sequence selected from the group consisting of SEQ ID NOs: 216-258,and any combination thereof.

In another embodiment, the anti autoimmune reagent specifically binds to antibody or fragment thereof of comprising the amino acid sequence selected from the group consisting of SEQ ID NOs: 173-215,and any combination thereof.

In another embodiment, the anti autoimmune reagent specifically binds to antibody or fragment thereof comprising the amino acid sequence selected from the group consisting of SEQ ID NOs: 44-86,and any combination thereof.

The invention also includes an isolated nucleic acid sequence having at least 85% complementarity to a nucleic acid sequence selected from the group consisting of SEQ ID NOs: 1-43, 87-129, 130-172,and any combination thereof.

The invention also includes an inhibitor of an anti-desmoglein autoantibody or fragment thereof, wherein the inhibitor inhibits the expression of a nucleic acid sequence selected from the group consisting of SEQ ID NOs: 1-43, 87-129, 130-172,and any combination thereof.

In one embodiment, the inhibitor is selected from the group consisting of a is small interfering RNA (siRNA), a microRNA, an antisense nucleic acid, a ribozyme, a polyamide, a triple-helix-forming agent, a synthetic peptide nucleic acids (PNAs), an agRNA, a LNA/DNA copolymer, and any combination thereof.

The invention also provides a method of inhibiting the binding of an anti-desmoglein 1 autoantibody or fragment thereof to desmoglein. The method comprises contacting the anti-desmoglein 1 autoantibody or fragment thereof with a composition comprising an anti-autoimmune reagent that specifically binds to an anti-desmoglein 1 autoantibody or fragment thereof. Preferably, the antibody or fragment thereof is associated with the pathology of pemphigus foliaceus (PF)

In one embodiment, the anti-desmoglein 1 antibody or fragment thereof comprises a heavy chain ($V_H$) encoded by the gene selected from the group consisting of VH1-18,VH1-08,VH3-09,VH3-07,VH3-30,VH4-b, VH3-53,VH3-66, and any combination thereof.

In another embodiment, the antibody or fragment thereof of comprises a heavy chain variable domain comprising the amino acid sequence selected from the group consisting of SEQ ID NOs: 216-258,and any combination thereof.

In yet another embodiment, the antibody or fragment thereof of comprises a light chain variable domain comprising the amino acid sequence selected from the group consisting of SEQ ID NOs: 173-215,and any combination thereof.

In another embodiment, the antibody or fragment thereof of comprises the amino acid sequence selected from the group consisting of SEQ ID NOs: 44-86,and any combination thereof.

The invention provides a method of modulating the expression of an anti-desmoglein autoantibody or fragment thereof comprising a heavy chain ($V_H$) encoded by the gene selected from the group consisting of VH1-18,VH1-08,VH3-09,VH3-07,VH3-30, VH4-b, VH3-53,VH3-66,and any combination thereof. The method comprises contacting a nucleotide sequence encoding an anti-desmoglein autoantibody or fragment thereof with an inhibitor of an anti-desmoglein autoantibody or fragment thereof, wherein the inhibitor is inhibits the expression of said anti-desmoglein autoantibody or fragment thereof.

In one embodiment, the nucleotide sequence encoding an anti-desmoglein autoantibody or fragment thereof is a sequence selected from the group consisting of SEQ ID NOs: 1-43, 87-129, 130-172,and any combination thereof.

In another embodiment, the nucleotide sequence encoding an anti-desmoglein autoantibody or fragment thereof is at least 85% homology to a nucleic acid sequence selected from the group consisting of SEQ ID NOs: 1-43, 87-129, 130-172, and any combination thereof.

The invention provides a method of treating an autoimmune pathology associated with pemphigus foliaceus (PF). The method comprises administering to a subject in need thereof a composition comprising an anti-autoimmune reagent that specifically binds to an anti-desmoglein 1 autoantibody or fragment thereof, thereby inhibiting the binding of the anti-desmoglein 1 autoantibody or fragment thereof to desmoglein.

In one embodiment, the anti-desmoglein 1 antibody or fragment thereof comprises a heavy chain ($V_H$) encoded by the gene selected from the group consisting of VH1-18,VH1-08,VH3-09,VH3-07,VH3-30,VH4-b, VH3-53,VH3-66, and any combination thereof.

In another embodiment, the anti-autoimmune reagent is selected from the group consisting of a peptide, a small molecule, an antibody, a humanized antibody, a recombinant antibody, and any combination thereof.

In another embodiment, the antibody or fragment thereof of comprises a heavy chain variable domain comprising the amino acid sequence selected from the group consisting of SEQ ID NOs: 216-258,and any combination thereof.

In yet another embodiment, the antibody or fragment thereof of comprises a light chain variable domain comprising the amino acid sequence selected from the group consisting of SEQ ID NOs: 173-215,and any combination thereof.

In still yet another embodiment, the antibody or fragment thereof of comprises s the amino acid sequence selected from the group consisting of SEQ ID NOs: 1-43,and any combination thereof.

The invention includes a method of treating an autoimmune pathology associated with pemphigus foliaceus (PF). The method comprising contacting a nucleotide sequence of the subject encoding an anti-desmoglein 1 antibody or fragment thereof with an inhibitor capable of inhibiting the expression of the nucleotide sequence encoding the anti-desmoglein autoantibody or fragment thereof, thereby inhibiting the expression of the anti-desmoglein autoantibody or fragment thereof.

In one embodiment, the anti-desmoglein I antibody or fragment thereof comprising a heavy chain ($V_H$) encoded by the gene selected from the group consisting of VH1-18,VH1-08,VH3-09,VH3-07,VH3-30,VH4-b, VH3-53,VH3-66, and any combination thereof.

In another embodiment, the nucleotide sequence encoding an anti-desmoglein 1 autoantibody or fragment thereof is a sequence selected from the group consisting of SEQ ID NOs: 1-43, 87-129, 130-172,and any combination thereof.

In another embodiment, the nucleotide sequence encoding an anti-desmoglein autoantibody or fragment thereof is at least 85% homology to a sequence selected from the group consisting of SEQ ID NOs: 1-43, 87-129, 130-172,and any combination thereof.

In yet another embodiment, the inhibitor is selected from the group consisting of a small interfering RNA (siRNA), a microRNA, an antisense nucleic acid, a ribozyme, a polyamide, a triple-helix-forming agent, a synthetic peptide nucleic acids (PNAs), an agRNA, a LNA/DNA copolymer, and any combination thereof.

The invention includes a method of depleting a biological sample from an anti-desmoglein 1 antibody or fragment thereof. The method comprises contacting the sample with an immobile composition comprising an anti-autoimmune reagent capable of specifically binding to an anti-desmoglein 1 autoantibody or fragment thereof; and removing the biological sample without the bound anti-desmoglein 1 autoantibody or fragment thereof, thereby depleting the biological sample of anti-desmoglein 1 autoantibody or fragment thereof.

In one embodiment, the anti-desmoglein 1 antibody or fragment thereof comprises a heavy chain ($V_H$) encoded by the gene selected from the group consisting of VH1-18,VH1-08,VH3-09,VH3-07,VH3-30,VH4-b, VH3-53,VH3-66, and any combination thereof.

In another embodiment, the anti-desmoglein autoantibody or fragment thereof is associated with the pathology of pemphigus foliaceus (PF).

In another embodiment, the anti-desmoglein 1 autoantibody or fragment thereof comprises a heavy chain variable domain comprising the amino acid sequence selected from the group consisting of SEQ ID NOs: 216-258,and any combination thereof.

In another embodiment, the anti-desmoglein 1 autoantibody or fragment thereof comprises a light chain variable domain comprising the amino acid sequence selected from the group consisting of SEQ ID NOs: 173-215,and any combination thereof.

In yet another embodiment, the anti-desmoglein 1 autoantibody or fragment thereof comprises the amino acid sequence selected from the group consisting of SEQ ID NOS: 1-43, and any combination thereof.

In another embodiment, the step of contacting the sample with an immobile composition is carried out during a plasmapheresis procedure performed on a subject.

The invention provides a method of diagnosing pemphigus foliaceus (PF) in a subject. The method comprising contacting a biological sample of a subject with a composition comprising an anti-autoimmune reagent that specifically binds to an anti-desmoglein 1 autoantibody or fragment thereof; and analyzing the biological sample for the presence of antibody-antigen complex, whereby the presence of antibody-antigen complex indicates the subject has or is predisposed to pemphigus foliaceus (PF).

In one embodiment, the anti-autoimmune reagent specifically binds to an anti-desmoglein 1 (Dsg1) antibody or fragment thereof comprising a heavy chain ($V_H$) encoded by the gene selected from the group consisting of VH1-18, VH1-08, VH3-09, VH3-07, VH3-30, VH4-b, VH3-53, VH3-66, and any combination thereof.

In another embodiment, the anti-autoimmune reagent is selected from the group consisting of a peptide, a small molecule, an antibody, a humanized antibody, a recombinant antibody, and any combination thereof.

In another embodiment, the antibody or fragment thereof of comprises a heavy chain variable domain comprising the amino acid sequence selected from the group consisting of SEQ ID NOs: 216-258, and any combination thereof.

In yet another embodiment, the antibody or fragment thereof of comprises a light chain variable domain comprising the amino acid sequence selected from the group consisting of SEQ ID NOs: 173-215, and any combination thereof.

In another embodiment, the antibody or fragment thereof of comprises the amino acid sequence selected from the group consisting of SEQ ID NOs: 1-43, and any combination thereof.

In one embodiment, contacting the biological sample with the composition comprising an anti-autoimmune reagent is evaluated using a radio-immunoassay (RIA), an enzyme linked immunosorbent assay (ELISA), a western blot, an immunohistochemical to analysis, or a combination thereof.

Other features and advantages of the present invention will become apparent from the following detailed description examples and figures. It should be understood, however, that the detailed description and the specific examples while indicating preferred embodiments of the invention are given by way of illustration only, since various changes is and modifications within the spirit and scope of the invention will become apparent to those skilled in the art from this detailed description.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 2A-2C, is a series of impages depicting an indirect immunofluorescence micrograph of anti-Dsg1 scFvs on human skin. Clone 3-30/3h scFv antibodies stained the cell surface of keratinocytes throughout human epidermis (FIG. 2A). Pretreatment of human skin with EDTA prevented cell surface staining by 3-30/3h (FIG. 2B). Clone 3-094/O18O8 showed cytoplasmic staining in the superficial layers of the epidermis (FIG. 2C).

FIG. 3, comprising FIG. 3B represents binding to Dsg1 (FIGS. 7A and 7B). Phage or scFv derived from Dsg3/Dsg1 alternating panning scheme showed binding to both desmogleins by ELISA (FIG. 7C).

FIGS. 8A and 8B, shows inhibition of H44L4 (an anti-α2bβ3 platelet monoclonal autoantibody) to α2bβ3 by the respective peptides. FIG. 8A depicts a bar graph showing that peptides P4-12 and P4-7 (from a linear 12-mer library) and P4-2a and P3-4 (from a constrained 7-mer "C7C" library) inhibit the binding of H44L4 immobilized purified α2bβ3. FIG. 8B is a flow cytogram of platelets incubated with H44L4 in the presence of no peptide (curve 2), irrelevant peptide (curve 3), or inhibitory peptide "P4-12" (curve 4) followed by detection of H44L4 with phycoerythrin-labeled anti-human IgG. Platelets incubated with EIM2 (an irrelevant human monoclonal anti-Rh(D) antibody) is shown in curve 1.

FIG. 9A is a chart showing representative scFvs, including the desmoglein specificity, heavy chain identifier, and light chain identifier. FIG. 9B depicts the identification of each clone listed as a complete single chain variable fragment molecule (light chain of antibody followed by a glycine-rich linker indicated in boldface, followed by the heavy chain of the antibody).

DETAILED DESCRIPTION OF THE INVENTION

Figure 1:
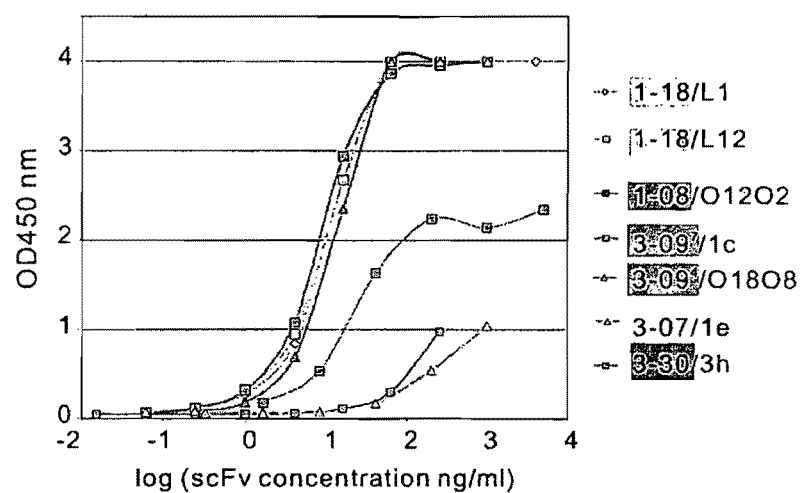
FIG. 1 is a graph depicting serial dilutions of representative scFvs that were measured by Dsg1 ELISA. Clones 1-18/L1 and 1-18/L12 (light green lines) and 3-094/O18O8 and 3-097/1c (dark green lines) are depicted. Clones 1-08/O12O2 and 3-07/1e showed weak binding to Dsg1 as measured by ELISA. Clone 3-30/3h exhibited intermediate binding capacity.

The present invention provides a method of producing anti-desmoglein (Dsg) antibodies. The invention also includes anti-desmoglein antibodies (e.g., pathogenic or non pathogenic) as well as compositions and methods of identifying an anti-autoimmune reagent capable of binding to the anti-desmoglein antibody.

In another embodiment, the anti-desmoglien antibody targets Dsg1. Preferably, the anti-desmoglein antibody targets a calcium-binding transmembrane glycoprotein component of desmosomes. In some instances, Dsg1 comprises three desmoglein subfamily members that are members of the cadherin cell adhesion molecule superfamily. In another aspect, Dsg1 is located in a cluster on chromosome 18. In yet another aspect, Dsg1 is an autoantigen of the autoimmune skin blistering disease pemphigus foliaceus (PF).

The invention also provides methods and compositions for targeting anti-desmoglien antibodies. In one embodiment, the invention includes methods and compositions for targeting pathogenic antibodies associated with PF. Accordingly, the invention includes compositions and methods for modulating anti-desmoglein pathogenic antibodies using an inhibitor of anti-desmoglein pathogenic PF antibodies. The inhibitor of anti-desmoglein pathogenic PF antibodies is able to alleviate the pathology associated with the anti-desmoglein pathogenic PF antibody. In one aspect, the inhibitor is able to specifically bind to an anti-desmoglein pathogenic PF antibody and inhibit the biological activity of the anti-desmoglein pathogenic PF antibody. Inhibition of anti-desmoglein to pathogenic PF antibodies can be achieved on the protein level, for example by contacting the pathogenic PF antibody with a binding partner. The binding partner can sequester, inhibit activity, or prevent the pathogenic PF antibody from otherwise binding to its cognate binding partner. For example, the pathogenic PF antibody can be inhibited with an anti-idiotypic antibody or a peptide (or other small molecule) that is capable of binding to the pathogenic PF antibody and inhibiting the biological activity of the pathogenic PF antibody.

In another aspect, the inhibition of the pathogenic PF antibody can be achieved at the genetic level. For example, inhibition of the pathogenic PF antibody can be achieved by inhibiting gene expression using for example small interfering RNA (siRNA), a microRNA, an antisense nucleic acid, a ribozyme, a polyamide, a triple-helix-forming agent, a synthetic peptide nucleic acids (PNAs), an agRNA, a LNA/DNA copolymer, and any combination thereof.

The invention includes any method capable of inhibiting the biological activity of pathogenic PF antibodies. For example, any method of negatively regulating the expression or activity of the pathogenic PF antibody, including but not limited to transcription of the pathogenic antibody mRNA, stability of the pathogenic PF antibody mRNA, translation of the pathogenic PF antibody mRNA, stability of the pathogenic PF antibody, post-translational modifications of the pathogenic PF antibody, or any combination thereof, is encompassed in the invention.

This invention relates in one embodiment to compositions and methods for the use of an anti-autoimmune antibody, peptide, or small molecule that is specific against a pathogenic PF antibody whereby the pathogenic PF antibody is responsible for pemphigus foliaceus conditions. Accordingly, the invention includes anti-autoimmune reagents that target at least antibodies associated with PF.

The anti-autoimmune reagents of the invention are at least useful for targeting a B cell by way of contacting the anti-autoimmune reagent with the corresponding autoantibody expressed on the B cell.

The invention also includes the use of the anti-autoimmune reagents for diagnosing the pathology of pemphigus. In one aspect, the ant-autoimmune reagents are able to specifically bind to pathogenic PF antibodies and therefore reduce the number of false positive identification of pemphigus patients. This is because in some instances, the anti-autoimmune reagents of the present invention are more specific to pathogenic PF antibodies than the prior art reagents.

The invention also relates to the discovery that a number of non-pathogenic antibodies were identified from a PF patient. The non-pathogenic can be used to target therapeutic molecules to a specific site of interest in a mammal. Preferably, the mammal is a human. In an aspect of the invention, such antibodies are non-pathogenic to their target, e.g., target tissue.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001,Molecular Cloning, A Laboratory Approach, Cold Spring Harbor Press, Cold Spring Harbor, N.Y., and Ausubel et al., 2002,Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

The articles "a" and "an" are used herein to refer to one or to more than one (i.e., to at least one) of the grammatical object of the article. By way of example, "an element" means one element or more than one element.

The term "about" as used herein means in quantitative terms plus or minus 5%, or in another embodiment plus or minus 10%, or in another embodiment plus or minus 15%, or in another embodiment plus or minus 20%.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Some antibodies are typically tetramers of immunoglobulin molecules. The antibodies in the present invention may exist in a variety of forms including, for example, polyclonal antibodies, monoclonal antibodies, chimeric, hybrid, Fv, Fab and F(ab)$_2$, as well as single chain antibodies, primatized, and humanized antibodies. Antibody fragments refer to antigen-binding immunoglobulin peptides which are at least about 5 to about 15 amino acids or more in length, and which retain the capacity to bind to the antigen. (Harlow et al., 1999,Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883;Bird et al., 1988,Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, an "autoantibody" or an "autoimmune antibody" is an antibody produced by the immune system that is directed against one or more of the host's own proteins. Autoantibodies may be produced by a host's immune system when it fails to distinguish between "self" and "non-self" proteins. Usually the immune system is able to discriminate by recognizing foreign substances ("non-self") and ignoring the host's own cells ("self"). When the immune system ceases to recognize one or more of the host's normal constituents as "self", it may produce autoantibodies that attack its own cells, tissues, and/or organs.

As used herein, an "anti-autoimmune reagent" refers to an agent that is capable of binding to an autoimmune antibody. An example of an autoimmune antibody is an anti-desmoglein antibody. Therefore, an anti-autoimmune reagent can be any agent that can bind to an anti-desmoglein antibody. In some instances, the anti-autoimmune reagent is an antibody that can bind to an anti-desmoglein antibody. In another aspect, the anti-autoimmune reagent is a peptide, polypeptide or other small molecule that can bind to an anti-desmoglein antibody.

By the term "Fab/phage" as used herein, is meant a phage particle which expresses the Fab portion of an antibody.

By the term "scFv/phage" as used herein, is meant a phage particle which is expresses the Fv portion of an antibody as a single chain.

"Phage," or "phage particle," as these terms are used herein, include bacteriophage that contain phage nucleic acid encoding, inter alia, an antibody. This is because, as would be appreciated by the skilled artisan, unlike peptide phage display (where the peptide DNA insert is small and it is actually cloned into the phage DNA), the larger scFv or Fab DNA inserts are actually cloned into, among other things, a plasmid. Thus, the nucleic acid encoding the antibody, e.g., a plasmid such as, but not limited to, pComb3X, not only comprises a plasmid origin of replication, but also a phage (e.g., M13) origin of replication sequence and an M13 packaging sequence, so that when the nucleic acid is produced, a helper phage can be used to provide the required phage (e.g., M13) proteins in trans to make "phage-like" particles. That is, these particles resemble phage on the outside, but on the inside they contain plasmid (also referred to as a "phagemid") DNA. In other words, the phagemid DNA need not encode any M13 phage proteins, except a piece of M13 gene III fused to the DNA for antibody or peptide. Thus, it should be understood that the terms "phage," "phage particle," "phage-like particle" and "phagemid" are used interchangeably herein.

As used herein, to "alleviate" a disease, disorder or condition means reducing the severity of one or more symptoms of the disease, disorder or condition.

"Derivative" in the context of proteins and peptides includes any purposefully generated amino acid sequence that in its entirety, or in part, comprises a substantially similar amino acid sequence to a desired protein. The term derivative can also be applied to the antibodies described herein such that "derivative" includes any purposefully generated peptide, which in its entirety, or in part, comprises a substantially similar amino acid sequence to an anti-desmoglein antibody or an anti-idiotypic antibody that is capable of specifically binding to an anti-desmoglein antibody. Derivatives of the antibodies may be characterized by single or multiple amino acid substitutions, deletions, additions, or replacements. Derivatives may include: (a) derivatives in which one or more amino acid residues are substituted with conservative or non-conservative amino acids; (b) derivatives in which one or more amino acids are added; (c) derivatives in which one or more of the amino acids of the amino acid sequence includes a substituent group; (d) derivatives in which amino acid sequences or a portion thereof is fused to another peptide (e.g., serum albumin or protein transduction domain); (e) derivatives in which one or more nonstandard amino acid residues (e.g., those other than the 20 standard L-amino acids found in naturally occurring proteins) are incorporated or substituted into the amino acid sequences; (f) derivatives in which one or more non-amino acid linking groups are incorporated into or replace a portion of the amino acids; and (g) derivatives in which one or more amino acid is modified by glycosylation, acetylation, myristoylation, and the like.

"Immunization" is the process of administering an immunogenic composition and stimulating an immune response to an antigen in a host (i.e., rodents and rabbits). Preferred hosts are mammals, such as primates (e.g., humans) as well as veterinary animals and agricultural animals. An "immunogen" is an immunogenic composition used to immunized the host. "Immunogen" also refers to a substance that is able to stimulate or induce a humoral antibody and/or cell-mediated immune response in a mammal. In some instances, the immunogen comprises an anti-desmoglein pathogenic antibody or any fragment thereof.

An "immune response" refers to the activities of the immune system, including activation and proliferation of specific cytotoxic T-cells and B-cells resulting in antigen-specific antibody production, after contact with an antigen.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between).

As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

As used herein, the terms "gene" and "recombinant gene" refer to nucleic acid molecules comprising an open reading frame encoding a polypeptide. Such natural allelic variations can typically result in 1-5% variance in the nucleotide sequence of a given gene.

Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins from other species (homologs), which have a nucleotide sequence which differs from that of the human proteins described herein are within the scope of the invention. Nucleic acid molecules corresponding to natural allelic variants and homologs of a cDNA of the invention can be isolated based on their identity to human nucleic acid molecules using the human cDNAs, or a portion thereof, as a hybridization probe according to standard hybridization techniques under stringent hybridization conditions.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

As used herein, the term "modulate" is meant to refer to any change in biological state, i.e. increasing, decreasing, and the like. For example, the term "modulate" refers to the ability to regulate positively or negatively the expression or activity of, for example, an anti-desmoglein pathogenic antibody, including but not limited to transcription of the desired anti-desmoglein pathogenic antibody mRNA, stability of the desired anti-desmoglein pathogenic antibody mRNA, translation of the desired anti-desmoglein pathogenic antibody mRNA, stability of the desired anti-desmoglein pathogenic antibody polypeptide, post-translational modifications of the desired anti-desmoglein pathogenic antibody, or any combinations thereof Further, the term modulate can be used to refer to an increase, decrease, masking, altering, overriding or restoring of activity of an anti-desmoglein pathogenic antibody.

A "portion" of a polynucleotide means at least about twenty sequential nucleotide residues of the polynucleotide. It is understood that a portion of a polynucleotide may include every nucleotide residue of the polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides. Conventional notation is used herein to portray polypeptide sequences: the left-hand end of a polypeptide sequence is the amino-terminus; the right-hand end of a polypeptide sequence is the carboxyl-terminus. As used herein the term polypeptide is mutually inclusive of the terms "peptides" and "proteins".

A "recombinant polypeptide" is one which is produced upon expression of a recombinant nucleic acid.

By the term "specifically binds," as used herein, is meant a compound, e.g., a protein, a nucleic acid, an antibody, and the like, which recognizes and binds a specific molecule, but does not substantially recognize or bind other molecules in a sample.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

As used herein, to "treat" means reducing the frequency with which symptoms of a disease, disorder, or adverse condition, and the like, are experienced by a patient. Such non-limiting conditions include bona tide illness as well as cosmetic or other conditions for example removal of unwanted hair or treating baldness where hair growth is desired.

A molecule (e.g., a ligand, a receptor, an antibody, and the like) "specifically binds with" or "is specifically immunoreactive with" another molecule where it binds preferentially with the compound and does not bind in a significant amount to other compounds present in the sample.

As used herein, a "therapeutic agent" is a molecule or atom, which is conjugated to an anti-autoimmune reagent to produce a conjugate which is useful for therapy. Examples of therapeutic agents include drugs, toxins, enzymes, hormones, cytokines, immunomodulators, anti-tumor agents, chemotherapeutic agents, anti-cell proliferation agents, boron compounds, and therapeutic radioisotopes.

"Therapeutic plasmapheresis" is herein meant as a method for removing toxic or unwanted elements, for example, plasma constituents implicated in disease, such as complement or autoantibodies, from the blood of a patient. In one embodiment, the invention provides a method for removing blood from a patient, separating the plasma, filtering the unwanted elements from the plasma, such as plasma constituents implicated in disease, such as complement or autoantibodies, and reinfusing the plasma replacement back to the patient, wherein the filtering step utilizes an anti-autoimmune reagent of the invention to remove pathogenic autoantibodies from the blood sample.

Description of the Invention

Pemphigus is an autoimmune blistering disease of the skin. Pemphigus foliaceus (PF) is characterized in some aspects by the presence of autoantibodies against Dsg1, which cause blistering of the skin, but not mucous membranes, due to loss of cell adhesion in the superficial epidermis. The present invention relates to the isolation of both pathogenic and non-pathogenic using phage display technology from a PF patient.

In one embodiment, the provides a non-pathogenic antibody comprising a heavy chain encoded by VH1-18 gene, VH1-08 gene, VH3-09 gene, VH4-b gene, or VH3-66 gene. In another embodiment, the present invention provides a pathogenic antibody comprising a heavy chain encoded by VH3-07 gene, VH3-30 gene, or VH3-53 gene. The pathogenic PF antibodies share a conserved sequence at the amino acid level. The consensus sequence shared among the pathogenic PF antibodies resides in the CDR3 region of the antibody. The consensus sequence shared among the pathogenic PF antibodies is D/E-X-X-X-W, wherein X can represent any amino acid. D-X-X-X-W is set forth in SEQ ID NO: 259. E-X-X-X-W is set forth in SEQ ID NO: 260).

The invention also provides a method of targeting pathogenic PF antibodies. For example, the pathogenic PF antibodies can be used to screen peptides or other small molecules for specific binding to the pathogenic PF antibody. Preferably, the pathogenic PF antibody is an anti-desmoglein antibody. Accordingly, the invention also provides an anti-autoimmune reagent capable of binding to a pathogenic PF antibody. In some instances, the anti-autoimmune reagent is an antibody that can bind to a desired pathogenic PF antibody.

In another embodiment, the present invention provides a method of analyzing to PF in a model animal, comprising the steps of: administering a pathogenic human anti-Dsg1 antibody, comprising a heavy chain encoded by a VH3-07 gene, VH3-30 gene, and/or VH3-53 gene to a model animal; and analyzing PF progression and/or pathogenesis in a model animal, thereby analyzing PF in a model animal.

Anti-desmoglein Pathogenic Antibodies:

The present invention relates, in part, to the isolation of an anti-desmoglein pathogenic antibody from a PF patient. In one aspect, an anti-desmoglein pathogenic antibody can bind to Dsg1, but not to Dsg3. In yet another aspect, an anti-desmoglein pathogenic binds to both Dsg1 and Dsg3.

In another embodiment, the anti-Dsg pathogenic autoantibody used in the methods and compositions provided herein, is an anti-Dsg1 autoantibody. In another embodiment the anti-Dsg pathogenic autoantibody is an anti-$Dsg_1$ and anti-$Dsg_3$ autoantibody (Anti-$Dsg_{1,3}$ autoantibody). In one embodiment, the anti-Dsg pathogenic autoantibody is pathognomonic of pemphigus foliaceus (PF).

In one embodiment, the genetic analysis of cloned antibodies from the PF library show a restriction of autoantibody variable heavy ($V_H$) gene usage, with different $V_H$ gene usage by pathogenic and non-pathogenic antibodies. In another embodiment, PF mAb $V_H$ gene usage correlates with antibody function, with respect to Dsg antigen binding in one embodiment, or its pathogenicity in another embodiment. In one embodiment, genetic restriction in the light chain repertoire indicates functional importance. In one embodiment, limited genetic diversity in PF mAbs indicates it is feasible to improve the specificity and safety of pemphigus therapies by targeting the anti-Dsg antibodies, as opposed to generally suppressing the immune system.

In one embodiment, the $V_H$ of the anti-desmoglein pathogenic autoantibody, against which the anti-autoimmune antibodies described in the methods and compositions provided herein are used, is encoded by VH3-07,VH3-30,VH3-53 or any combination thereof.

In another embodiment, a pathogenic antibody of the invention blocks at least about 30% of PF patient serum binding to Dsg1. In another embodiment, a pathogenic antibody of the invention blocks at least about 40% of PF patient serum binding to Dsg1. In another embodiment, a pathogenic antibody of the invention blocks at least about 50% of PF patient serum binding to Dsg1. In another embodiment, a pathogenic antibody of the invention blocks at least about 55% of PF patient serum binding to Dsg1. In another embodiment, a pathogenic antibody of the invention blocks at least about 60% of PF patient serum binding to Dsg1. In another embodiment, a pathogenic antibody of the invention blocks at least about 65% of PF patient serum binding to Dsg1. In another embodiment, a pathogenic antibody of the invention blocks at least about 70% of PF patient serum binding is to Dsg1. In another embodiment, a pathogenic antibody of the invention blocks at least about 75% of PF patient serum binding to Dsg1. In another embodiment, a pathogenic antibody of the invention blocks at least about 80% of PF patient serum binding to Dsg1. In another embodiment, a pathogenic antibody of the invention blocks at least about 85% of PF patient serum binding to Dsg1. In another embodiment, a pathogenic antibody of the invention blocks at least about 90% of PF patient serum binding to Dsg1.

In another embodiment, pathogenic antibody response among patients with PF is limited and directed at similar or identical epitopes on Dsg1. In another embodiment, a pathogenic antibody of the present invention binds to epitopes that are located in the amino-terminus of Dsg1. In another embodiment, a pathogenic antibody of the present invention binds to epitopes in an area that includes the trans-adhesive interface. In another embodiment, a pathogenic antibody of the present invention binds to conformational epitopes. In another embodiment, a pathogenic antibody of the present invention binds to calcium-stabilized epitopes.

In another embodiment, the non-pathogenic and pathogenic anti-Dsg1 correlated with their heavy chain gene usage. Very restricted heavy chain gene usage, limited to only five genes, characterized the anti-Dsg1 antibodies. In another embodiment, only certain light chains are permissive for Dsg1 binding.

In another embodiment, the present invention provides antibodies that bind the precursor protein of Dsg1. In another embodiment, the present invention provides that antibodies that bind the precursor protein of Dsg1 do not bind the mature protein.

In one embodiment, the pathogenic antibodies share a conserved sequence at the amino acid level. The consensus sequence shared among the pathogenic antibodies resides in the CDR3 region of the antibody. The consensus sequence shared among the pathogenic antibodies is D/E-X-X-X-W, wherein X can represent any amino acid.

The consensus sequence of D/E-X-X-X-W identified with the pathogenic cloned antibodies represents a structural binding motif that is believed to be a candidate for targeted therapy. Without wishing to be bound by any particular theory, it is believed that the consensus sequence of D/E-X-X-X-W may mimic the desmosomal cadherin tertiary structure, thereby directly (sterically) interfering with desmosomal trans-adhesion between cells.

Thus, the invention encompasses small molecules or peptidomimetic compounds that are able to inhibit the binding of an antibody comprising the D/E-X-X-X-W consensus sequence to its target sequence. Accordingly, the invention includes inhibitors based on the peptide sequences of D/E-X-X-X-W, as well as to methods of making them.

A preferred peptide interferes with at least the activity of a pathogenic anti-desmoglein antibody mediated by the D/E-X-X-X-W consensus sequence. The skilled person is aware that a peptidomimetic compound can be made in which one or more amino acid residues is replaced by its corresponding D-amino acid, substitutions or modifications are made to one or more amino acids in the sequence, peptide bonds can be replaced by a structure more resistant to metabolic degradation and different cyclizing constraints and dimerization groups can be incorporated.

With respect to compounds in which one or more ammo acids is replaced by its corresponding D-amino acid, the skilled person is aware that retro-inverso amino acid sequences can be synthesized by standard methods; see, for example, Chorev and Goodman, 1993 Acc. Chem. Res. 26: 266. Olson et al., 1993 J. Med. Chem. 36: 3039 provides an example of replacing a peptide bond with a structure more resistant to metabolic degradation.

Peptidomimetic compounds can also be made where individual amino acids are replaced by analogous structures, for example gem-diaminoalkyl groups or alkylmalonyl groups, with or without modified termini or alkyl, acyl or amine substitutions to modify their charge. The use of such alternative structures can provide significantly longer half-life in the body, since they are more resistant to breakdown under physiological conditions.

Methods for combinatorial synthesis of peptide analogs and for screening of peptides and peptide analogs are well known in the art (see, for example, Gallop et al., 1994 J. Med. Chem. 37: 1233). It is particularly contemplated that the compounds of the invention are useful as templates for design and synthesis of compounds of improved activity, stability and bioavailability. Preferably where amino acid substitution is used, the substitution is conservative, i.e. an amino acid is replaced by one of similar size and with similar charge properties. As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted amino acid in place of an unsubstituted parent amino acid.

Phage Display

The antibodies of the present invention include those cloned from a phage antibody library, as described in detail elsewhere herein. For example, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab or scFv fragments on their surface. Phage which display the antibody of interest are selected by antigen binding and are propagated in bacteria to produce soluble human Fab or scFv immunoglobulin. Thus, in contrast to conventional monoclonal antibody synthesis, this procedure immortalizes DNA encoding human immunoglobulin rather than cells which express human immunoglobulin.

In one embodiment, the methods of the present invention provide utilizing antibody phage display on a Dsg1 thus isolating anti-Dsg1 antibodies. In another embodiment, using the phage display technique results in the isolation of anti-Dsg1 scFv mAbs.

Phage display libraries allow for the in vitro identification of human antibody products directed against molecular targets. In one embodiment, the methods of the present invention provide that phage display libraries enable the in vitro identification of human antibody products directed against an isolated Dsg1 protein or fragment thereof.

Antibody phage display of the present invention provides the linkage between genotype and phenotype. In another embodiment, selection of phage clones of the present invention is based on binding affinity. In another embodiment, selection of phage clones of the present invention is based on binding specificity. In another embodiment, selection of phage clones of the present invention is based on functional activity of the displayed antibody (phenotype). In another embodiment, selection of phage clones of the present invention is based on binding affinity, specificity, and functional activity of the displayed antibody (phenotype). Each phage carries the DNA for the antibody it displays on its surface, the phenotype is directly linked to the antibody genotype (cDNA sequence). This enables rapid selection of clones displaying antibody chains with desirable characteristics with desirable affinity to a target antigen.

In another embodiment, the present invention provides a high affinity human antibody which is specific for Dsg1. In another embodiment, the present invention provides that light chain shuffling while retaining the heavy chain variable region using phage display technology is able to modify the ultrafine specificity of the antigen-binding construct. In another embodiment, the present invention provides that heavy chain shuffling while retaining the light chain variable region using phage display technology is able to modify the ultrafine specificity of the antigen-binding construct. In another embodiment, the present invention provides that heavy chain promiscuity is limited in in vivo developed antibodies. In another embodiment, the present invention provides that light chain promiscuity is limited in in vivo developed antibodies. In another embodiment, the present invention allows such to form antigen-binding structures following random assortment of heavy and light chain variable regions. In another embodiment, the present invention provides that phage display technology selects against clones which are restricted with respect to light chain usage. In another embodiment, the present invention provides that phage display technology selects against clones which are restricted with respect to heavy chain usage. In another embodiment, the present invention provides that phage display technology represents a population which is restricted in this respect.

In another embodiment, the present invention provides isolation of non-pathogenic anti-Dsg1 scFvs from a PF patient. Peripheral blood lymphocytes from a patient with active PF are used to construct a library in which each phage particle displays a scFv antibody fragment on its surface and contains the cDNA encoding the heavy and light chain variable regions for that particular scFv within. In another embodiment, the library is screened by multiple rounds of panning as described hereinabove on immobilized, baculovirus-produced Dsg1. In another embodiment, the library is screened by multiple rounds of panning as described hereinabove on immobilized, baculovirus-produced Dsg1 using standard ELISA plate panning methods known to one skilled in the art.

In another embodiment, selection of clones is based upon methods which provide that after an initial screening, unique clones are isolated based on their heavy and light chain nucleotide sequences. For example, some of the clones are derived from heavy chain genes VH1-18 and VH3-09. In some instances, the clones derived from heavy chain genes VH1-18 and VH3-09 used multiple light chain genes. In some instances, clones comprising heavy chain genes VH1-18 and VH3-09 produce antibodies that are non-pathogenic (see table 1).

In another embodiment, the methods of the present invention provide that the diversity of the selected clones is increased in order to find pathogenic antibodies. The methods provide that an antibody phage library is tested again by a second panning procedure on baculovirus-produced Dsg1 ELISA plates. The methods of the present invention provide that in the second round of panning additional non-pathogenic clones are uncovered.

In another embodiment, the methods of the present invention provide isolating pathogenic anti-Dsg1 antibodies by non-pathogenic epitope blocking utilized in concert with phage display. In another embodiment, the methods of the present invention provide that blocking to mask non-pathogenic epitopes results in obtaining pathogenic antibody clones. The methods of the present invention further provide isolation of pathogenic anti-Dsg1 scFvs using a non-pathogenic epitope blocking approach. The panning strategy is to target the isolation of pathogenic clones that are putative low abundant clones by blocking non-pathogenic epitopes. The blocking of non-pathogenic epitopes is preformed using a set of previously-isolated non-pathogenic clones.

Using the "non-pathogenic epitope blocking" approach, additional unique clones are isolated. In some instances, pathogenic clones are isolated using this technique. In some instances, the pathogenic clones are encoded by heavy chain genes not previously seen in the set of non-pathogenic anti-Dsg1 antibodies. In another embodiment, the methods of the present invention provide that pathogenic clones are encoded by heavy chain genes VH3-07,VH3-30,or VH3-53. In some instances, the clones derived from heavy chain genes VH3-07 and VH3-30 used multiple light chain genes. In some instances, clones comprising heavy chain genes VH3-07, VH3-30,and VH3-53 produce antibodies that are pathogenic.

In one aspect of the invention, the antibody comprises a heavy chain sequence selected from the amino acid sequence selected from the group consisting of SEQ ID NOs: 216-258, and any combination thereof. In another aspect, the antibody comprises a heavy chain encoded by the nucleic acid sequence selected from the group consisting of SEQ ID NOs: 130-172,and any combination thereof. In another aspect of the invention, the antibody comprises a light chain sequence selected from the amino acid sequence selected from the group consisting of SEQ ID NOs: 173-215,and any combination thereof In another aspect, the antibody comprises a light chain encoded by the nucleic acid sequence selected from the group consisting of SEQ ID NOs: 87-129,and any combination thereof. In another aspect of the invention, the antibody comprises the amino acid sequence selected from the group consisting of SEQ ID NOs: 44-86,and any combination thereof. In another aspect, the antibody comprises the nucleic acid sequence selected from the group consisting of SEQ ID NOs: 1-43,and any combination thereof.

Using the information provided herein, the antibodies of the present invention can be produced recombinantly using standard techniques well known to those of skill in the art. For example, the sequences provided herein can be used to identify and clone appropriate nucleic acid sequences encoding the antibodies. These nucleic acid sequences can then be used to express one or more antibodies. The nucleic acid sequence may be optimized to reflect particular codon "preferences" for various expression systems according to standard methods well known to those of skill in the art.

Using the sequence information provided herein, the nucleic acids may be synthesized according to a number of standard methods known to those of skill in the art. Oligonucleotide synthesis, is preferably carried out on commercially available solid phase oligonucleotide synthesis machines or manually synthesized using the solid phase phosphoramidite triester method described by Beaucage et. al., 1981,Tetrahedron Letts. 22:1859-1862.

Once a nucleic acid encoding an antibody is synthesized, it may be amplified and/or cloned according to standard methods in order to produce recombinant antibodies of the invention. Molecular cloning techniques to achieve these ends are known in the art. A wide variety of cloning and in vitro amplification methods suitable for the construction of recombinant nucleic acids are known to those skilled in the art. Examples of these techniques and instructions sufficient to direct the skilled artisan are found in Berger and Kimmel, Guide to Molecular Cloning Techniques, Methods in Enzymology volume 152 Academic Press, Inc., San Diego, Calif. (Berger); Sambrook et al., 2002 Molecular Cloning. A Laboratory Manual Vol. 1-3, Cold Spring Harbor Laboratory, Cold Spring Harbor Press, NY, (Sambrook). Methods of producing recombinant immunoglobulins are also known in the art. See, Cabilly, U.S. Pat. No. 4,816,567; and Queen et al., 1989 Proc. Nat'l Acad. Sci. USA 86:10029-10033.

Examples of techniques sufficient to direct persons of skill through in vitro amplification methods, including the polymerase chain reaction (PCR), the ligase chain reaction (LCR), and other DNA or RNA polymerase-mediated techniques are found in Berger, Sambrook, and Ausubel, as well as U.S. Pat. Nos. 4,683,202 and 5,426,039.

Once the nucleic acid encoding a desired antibody is isolated and cloned, a skilled artisan may express the recombinant gene(s) in a variety of engineered cells known to those of skill in the art. Examples of such cells include bacteria, yeast, filamentous fungi, insect (especially employing baculoviral vectors), and mammalian cells. It is expected that those of skill in the art are knowledgeable in the numerous expression systems available for expression of the desired antibodies.

For some uses, including in vivo use of antibodies in humans and in vitro detection assays, it may be preferable to use chimeric, hybrid, primatized, humanized, or human antibodies. Methods for producing chimeric and hybrid antibodies are known in the art. See e.g., Morrison, 1985 *Science* 229: 1202-1207; U.S. Pat. Nos. 6,965,024, 5,807,715; 4,816,567; and 4,816,397. Humanized antibodies are antibody molecules from non-human species that bind the desired antigen having one or more complementarity determining regions (CDRs) from the non-human species and framework regions and constant domains from a human immunoglobulin molecule. Often, framework residues in the human framework regions are substituted with the corresponding residue from the CDR donor antibody to alter and in some instances improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089. Antibodies can be humanized using a variety of techniques known in the art including, for example, CDR-grafting and chain shuffling. Humanized antibodies may be generated using any of the methods disclosed in U.S. Pat. Nos. 5,693,762, 5,693,761, 5,585,089, 6,180,370.

Screening for Anti-autoimmune Reagents

The present invention is partly based on the identification of peptides or small molecules that bind a desired autoimmune antibody. In some instances, the autoimmune antibody is a disease associate-pathogenic antibody, for example a pathogentic anti-desmoglein antibody. Accordingly, a peptide that binds to a disease associated-pathogenic antibody is an example of an anti-autoimmune reagent. However, the invention also includes peptides or small molecules that bind to non-pathogenic antibodies.

There are several examples of methods that use peptides or nucleotides to develop libraries of potential receptor, enzyme, or antibody interacting peptides. These libraries have been incorporated into systems that allow the expression of random peptides on the surface of different phage or bacteria. The use of phage display technology to produce and screen libraries of polypeptides for binding to a selected target has been widely used. A basic concept of phage display methods is the establishment of a physical association between DNA encoding a polypeptide to be screened and the target polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means.

In one embodiment, the binding of an anti-autoimmune reagent correlates with $V_H$ gene usage. In one embodiment, PF mAb $V_H$ genes identified by phage display represent feasible targets for therapy. These genes are VH3-07,VH3-30, VH3-53,or the combinations thereof In another embodiment, certain combination of otherwise non-pathogenic anti-Dsg antibodies, still induce pathogenic reaction in the subject. Accordingly, in one embodiment PF mAb $V_H$ target gene for therapy using the compositions and methods provided herein is VH1-18,VH1-08,VH3-09,VH4-b, VH3-66 gene or their combination in other embodiments.

The present invention comprises systems for screening and/or testing the ability of a candidate compound to bind an anti-Dsg1 antibody of the invention. In some instances, a candidate compound that binds pathogenic human monoclonal ScFv anti-Dsg1 antibodies also binds anti-Dsg1 antibodies derived from a PF patient. Preferably, a candidate compound that binds pathogenic human monoclonal ScFv anto-Dsg1 antibodies also binds anti-Dsg1 antibodies in vivo. More preferably, a candidate compound that binds pathogenic human monoclonal ScFv anto-Dsg1 antibodies also binds anti-Dsg1 antibodies in a PF patient. In some instances, the candidate compound inhibits binding of pathogenic antibodies to their epitopes.

The candidate compound of the present invention is a peptide. In another embodiment, the candidate compound of the present invention is a protein. In another embodiment, the candidate compound of the present invention is an inorganic compound. In another embodiment, the candidate compound of the present invention is an organic compound. In another embodiment, the candidate compound of the present invention mimics a Dsg1 pathogenic epitope. In another embodiment, a candidate compound of the present invention comprises a Dsg1 pathogenic epitope.

However, the invention also contemplates peptides and small moleuces that bind to non-pathogenic antibodies. This is because a non-pathogenic can be used in the phage display library screening procedure to identify the corresponding binding molecule, and in some cases non-pathogenic antibodies when used in combination or under certain conditions may prove to cause pathology.

Inhibitors of Anti-desmoglein Pathogenic Antibodies:

The invention provides a composition comprising an anti-autoimmune reagent. The anti-autoimmune reagent includes any agent that is capable of binding to or inhibiting the expression of an autoimmune antibody. In one aspect, the anti-autoimmune reagent is an antibody that binds to an autoantibody. In another aspect, the anti-autoimmune reagent is a peptide or small molcule that binds to an autoantibody. For example, the anti-autoimmune reagent binds to a pathogenic anti-desmoglein antibody.

Binding Function:

The present invention relates to the discovery that inhibition of an anti-desmoglein pathogenic antibody provides a therapeutic benefit. Accordingly, the invention includes an inhibitor of an anti-desmoglein pathogenic antibody. In one aspect, the inhibitor is an agent capable of binding and sequestering an anti-desmoglein pathogenic antibody. In another aspect, the inhibitor can inhibit the function an anti-desmoglein pathogenic autoantibody. In yet another aspect, the inhibitor can inhibit the expression of an anti-desmoglein pathogenic antibody.

In another embodiment, the inhibitor is an anti-autoimmune reagent that is capable of binding to an anti-desmoglein pathogenic antibody. The anti-autoimmune reagent can be an antibody that binds to an anti-desmoglein pathogenic antibody whereby the anti-autoimmune reagent (e.g., an antibody) can be produced by immunizing an animal (i.e., rodents or rabbits) with an immunogen comprising anti-desmoglein pathogenic antibody or any fragment thereof.

In one embodiment, the specific antibody-targeted therapy for pemphigus aims to suppress or eliminate only the anti-Dsg autoantibodies. In another embodiment, the methods described herein target only the pathogenic autoantibodies. In one embodiment, antibodies are targeted by their idiotype. In another embodiment, antibodies are targeted based on their variable region gene usage.

In one embodiment, cloning of human PF mAbs provide novel strategies for direct antibody targeting. In another embodiment treatments using the methods provided herein, are designed based on autoantibody $V_H$ gene usage. In another embodiment, the identification of peptides that specifically bind PF mAbs indicates that the small molecule reagents can also discriminate among PF mAbs based on their $V_H$ gene usage. These small molecule reagents are more practical in one embodiment, than rabbit antibodies against PF mAbs for the development of therapeutic intervention strategies.

Accordingly, the invention provides a method of inhibiting the binding of a autoimmne antibody, for example a pathogenic autoimmune antibody to desmoglein (Dsg), comprising contacting the autoimmune antibodies with a composition comprising an agent capable of inhibiting the expression or function of a variable region of an anti-desmoglein pathogenic autoantibody. In another embodiment, the anti-desmoglein (Dsg) pathogenic autoantibody is an anti-Dsg1 autoantibody, an anti-Dsg3 autoantibody, or an anti-$Dsg_1$ and anti-$Dsg_3$ autoantibody (Anti-$Dsg_{1,3}$ autoantibody), which, in yet another embodiment, is pathognomonic of pemphigus foliaceus (PF).

In another embodiment, provided herein is a method of inhibiting the binding of a pathogenic autoimmune antibody to desmoglein (Dsg), comprising contacting the autoimmune antibodies with a composition comprising an anti-autoimmune reagent capable of inhibiting the binding of a variable region of an anti-desmoglein pathogenic autoantibody. Preferably, the gene encoding the variable region of an anti-desmoglein (anti-Dsg) pathogenic autoantibody, is VH3-07, VH3-30,VH3-53,or the combinations thereof in other embodiments.

In one embodiment, the antibody-targeted agents described in the compositions provided herein and utilized in the methods provided herein, could be coupled to columns as an adjunct for plasmapheresis to improve the efficiency of pathogenic antibody removal from subjects' sera. In another embodiment, the antibody-specific agents described in the compositions provided herein and utilized in the methods provided herein, are linked to B cell superantigens as a method of $V_H$-targeted B-cell deletion. In one embodiment, the methods provided herein offer a safer and more effective treatments for pemphigus. In another embodiment, the $V_H$ gene-targeting approach described hereinabove has implications for the treatment of other genetically restricted antibody-mediated diseases.

Inhibiting Expression:

In one embodiment, the inhibitor used in the compositions provided herein, which are utilized in the methods provided herein, is capable of inhibiting the expression of a nucleotide sequence encoding the heavy chain ($V_H$) of an anti-desmoglein autoantibody. In another embodiment, the nucleotide sequence to be inhibited is selected from the group consisting of the sequence set forth in SEQ ID NOs: 130-172,and any combination thereof In another embodiment, the agent used in the compositions provided herein, which are utilized in the methods provided herein, is capable of inhibiting the expression of a nucleotide sequence encoding the light chain ($V_L$) of an anti-deknoglein autoantibody. In another embodiment, the nucleotide sequence to be inhibited is selected from the group consisting of the sequence set forth in SEQ ID NOs: 87-129,and any combination thereof.

In yet another embodiment, the agent used in the compositions provided herein, which are utilized in the methods provided herein, is capable of inhibiting the expression of a nucleotide sequence encoding an anti-desmoglein autoantibody. In another embodiment, the nucleotide sequence to be inhibited is selected from the group consisting of the sequence set forth in SEQ ID NOs: 1-43,and any combination thereof.

In one embodiment, the nucleotide has at least 85% homology to the nucleotide sequence selected from the group consisting of the sequence set forth in SEQ ID NOs. 1-43, 87-129, 130-172,and any combination thereof. In one embodiment, the terms "homology", "homologue" or "homologous", indicate that the sequence referred to, whether an amino acid sequence, or a nucleic acid sequence, exhibits, in one embodiment at least 70% correspondence with the indicated sequence. In another embodiment, the amino acid sequence or nucleic acid sequence exhibits at least 72% correspondence with the indicated sequence. In another embodiment, the amino acid sequence or nucleic acid sequence exhibits at least 75% correspondence with the indicated sequence. In another embodiment, the amino acid sequence or nucleic acid sequence exhibits at least 80% correspondence with the indicated sequence. In another embodiment, the amino acid sequence or nucleic acid sequence exhibits at least 82% correspondence with the indicated sequence. In another embodiment, the amino acid sequence or nucleic acid sequence exhibits at least 85% correspondence with the indicated sequence. In another embodiment, the amino acid sequence or nucleic acid sequence exhibits at least 87% correspondence with the indicated sequence. In another embodiment, the amino acid sequence or nucleic acid sequence exhibits at least 90% correspondence with the indicated sequence. In another embodiment, the amino acid sequence or nucleic acid sequence exhibits at least 92% correspondence with the indicated sequence. In another embodiment, the amino acid sequence or nucleic acid sequence exhibits at least 95% or more correspondence with the indicated sequence. In another embodiment, the amino acid sequence or nucleic acid sequence exhibits at least 97% correspondence with the indicated sequence. In another embodiment, the amino acid sequence or nucleic acid sequence exhibits at least 99% correspondence with the indicated sequence. In another embodiment, the amino acid sequence or nucleic acid sequence exhibits 95% - 100% correspondence with the indicated sequence. Similarly, as used herein, the reference to a correspondence to a particular sequence includes both direct correspondence, as well as homology to that sequence as herein defined.

In one embodiment, the agent used in the compositions described herein, which are utilized in the methods provided herein, is a siRNA. In another embodiment, the agent capable of inhibiting the expression of the variable region of an anti-desmoglein (anti-Dsg) pathogenic autoantibody is a polyamide. In another embodiment, the agent capable of inhibiting the expression of the variable region of an anti-desmoglein (anti-Dsg) pathogenic autoantibody is a triple-helix-forming agent. In another embodiment, the agent capable of inhibiting the expression of the variable region of an anti-desmoglein (anti-Dsg) pathogenic autoantibody is an antisense RNA. In another embodiment, the agent capable of inhibiting the expression of the variable region of an anti-desmoglein (anti-Dsg) pathogenic autoantibody is a synthetic peptide nucleic acids (PNAs). In another embodiment, the agent capable of inhibiting the expression of the variable region of an anti-desmoglein (anti-Dsg) pathogenic autoantibody is an agRNA. In another embodiment, the agent capable of inhibiting the expression of the variable region of an anti-desmoglein (anti-Dsg) pathogenic autoantibody is a LNA/DNA copolymer. In another embodiment, the agent capable of inhibiting the expression of the variable region of an anti-desmoglein (anti-Dsg) pathogenic autoantibody is a small molecule chemical compounds, or a combination thereof.

In one embodiment, the term "siRNA" refers to RNA interference, which in another embodiment refers to the process of sequence-specific post-transcriptional gene silencing in animals, mediated by short interfering RNAs (siRNAs). In another embodiment, the process of post-transcriptional gene silencing is an evolutionarily-conserved cellular defense mechanism used to prevent the expression of foreign genes. Such protection from foreign gene expression evolved in one embodiment, in response to the production of double-stranded RNAs (dsRNAs) derived from viral infection or in another embodiment, from the random integration of transposon elements into a host genome via a cellular response that specifically destroys homologous single-stranded RNA of viral genomic RNA. In one embodiment, the presence of dsRNA in cells triggers the RNAi response. In one embodiment, the siRNA used in the compositions and methods provided herein interferes with the expression of a heavy chain ($V_H$) of an anti-desmoglein pathogenic autoantibody, encoded by VH3-07,VH3-30,VH3-53,or any combinations thereof.

In one embodiment, the siRNA of the gene encoding the variable region of an anti-desmoglein (anti-Dsg) pathogenic autoantibody described herein exhibits substantial complementarity to its target sequence. In another embodiment, "complementarity" refers to an oligonucleotide has a base sequence containing an at least 15 contiguous base region that is at least 70% complementary, or in another embodiment at least 75% complementary, or in another embodiment at least 80% complementary, or in another embodiment at least 85% complementary, or in another embodiment at least 90% complementary, or in another embodiment at least 95% complementary, or in another embodiment 100% complementary to an-at least 15 contiguous base region present of a target gene sequence (excluding RNA and DNA equivalents).

(Those skilled in the art will readily appreciate modifications that could be made to the hybridization assay conditions at various percentages of complementarity to permit hybridization of the oligonucleotide to the target sequence while preventing unacceptable levels of non-specific hybridization). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In one embodiment oligomeric antisense compounds, particularly oligonucleotides, are used in modulating the function of nucleic acid molecules encoding the variable region of an anti-desmoglein (anti-Dsg) pathogenic autoantibody, ultimately modulating the amount of the pathogenic autoantibody produced. This is accomplished by providing antisense compounds which specifically hybridize with one or more nucleic acids encoding the variable region of an anti-desmoglein (anti-Dsg) pathogenic autoantibody. In one embodiment, the terms "target nucleic acid" and "nucleic acid encoding the variable region of an anti-desmoglein (anti-Dsg) pathogenic autoantibody" encompass DNA encoding the variable region of an anti-desmoglein (anti-Dsg) pathogenic autoantibody, RNA (including pre-mRNA and mRNA) transcribed from such DNA, and also cDNA derived from such RNA. The specific hybridization of an oligomeric compound with its target nucleic acid interferes in another embodiment, with the normal function of the nucleic acid. The modulation of function of a target nucleic acid by compounds which specifically hybridize to it, is referred to in one embodiment as "antisense". In one embodiment, the functions of DNA to be interfered with using the antisense oligonucleotides described herein, which are used in the methods and compositions described herein, include replication and transcription. In another embodiment, functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of the variable region of an anti-desmoglein (anti-Dsg) pathogenic autoantibody. In one embodiment, inhibition of gene expression is preferred and mRNA is a preferred target. In one embodiment, since many genes (including VH3-07 or VH3-30,or the combinations thereof) have multiple transcripts, "inhibition" also includes an alteration in the ratio between gene products, such as alteration of mRNA splice products.

In one embodiment, specific nucleic acids are targeted for antisense. "Targeting" an antisense compound to a particular nucleic acid, in one embodiment, is a multistep process. The process usually begins with the identification of a nucleic acid sequence whose function is to be inhibited. This may be, for example, a cellular gene (or mRNA transcribed from the gene) whose expression is associated with a particular disorder or disease state, or a nucleic acid molecule from an infectious agent. In one embodiment, the target is a nucleic acid molecule encoding the variable region of an anti-desmoglein (anti-Dsg) pathogenic autoantibody. The targeting process also includes in another embodiment, determination of a site or sites within this gene for the antisense interaction to occur such that the desired effect, e.g., inhibition of expression of the protein such as an anti-desmoglein (anti-Dsg) pathogenic autoantibody, will result. In one embodiment, an intragenic site is the region encompassing the translation initiation or termination codon of the open reading frame (ORF) of the gene. Since, the translation initiation codon is in one embodiment 5'-AUG (in transcribed mRNA molecules; 5'-ATG in the corresponding DNA molecule), the translation initiation codon is referred to in one embodiment as the "AUG codon," the "start codon" or the "AUG start codon". In another embodiment, a minority of genes have a translation initiation codon having the RNA sequence 5'-GUG, 5'-UUG or 5'-CUG, and 5'-AUA, 5'-ACG and 5'-CUG and have been shown to function in vivo. Thus, the terms "translation initiation codon" and "start codon" encompasses in other embodiments, many codon sequences, even though the initiator amino acid in each instance is typically methionine (in eukaryotes) or formylmethionine (in prokaryotes). In another embodiment, "start codon" and "translation initiation codon" refer to the codon or codons that are used in vivo to initiate translation of an mRNA molecule transcribed from a gene encoding the variable region of an anti-desmoglein (anti-Dsg) pathogenic autoantibody, regardless of the sequence(s) of such codons.

Antisense compounds are used in one embodiment, as research reagents and diagnostics. In another embodiment, antisense oligonucleotides, which are able to inhibit gene expression, such as the gene encoding the variable region of an anti-desmoglein (anti-Dsg) pathogenic autoantibody, with extreme specificity, are used by those of ordinary skill to elucidate the function of particular genes. Antisense compounds are used in another embodiment, to distinguish between functions of various members of a biological pathway. Antisense modulation is, in one embodiment of the agents described in the methods and compositions described herein, being harnessed for research use.

In one embodiment, the specificity and sensitivity of antisense agents described herein, is also harnessed for therapeutic uses. Antisense oligonucleotides are employed in one embodiment, as therapeutic moieties in the treatment of disease states in animals and man. In one embodiment, antisense oligonucleotides are safely and effectively administered to humans. In one embodiment oligonucleotides are useful therapeutic modalities that can be configured to be useful in treatment regimes of cells, tissues and animals, especially humans.

Treatment

The term "treatment", or "treating" refers to any process, action, application, therapy, or the like, wherein a subject, including a human being, is subjected to medical aid with the object of improving the subject's condition, directly or indirectly. The term "treating" refers also to reducing incidence, or alleviating symptoms, eliminating recurrence, preventing recurrence, preventing incidence, improving symptoms, improving prognosis or combination thereof in other embodiments.

"Treating" embraces in another embodiment, the amelioration of an existing condition. The skilled artisan would understand that treatment does not necessarily result in the complete absence or removal of symptoms. Treatment also embraces palliative effects: that is, those that reduce the likelihood of a subsequent medical condition. The alleviation of a condition that results in a more serious condition is encompassed by this term. Therefore, in one embodiment, the invention provides a method of treating PF, comprising the step of contacting a biological sample of said subject with an effective amount of an agent capable of inhibiting the expression or function of the gene encoding the variable region of an anti-desmoglein (anti-Dsg) pathogenic autoantibody, whereby the inhibition of expression or function that gene or its encoded proteins results in depleting a biological sample from an anti-desmoglein pathogenic antibody.

Accordingly and in one embodiment, provided herein is a method of depleting a biological sample from an anti-desmoglein pathogenic antibody, comprising contacting the sample with an immobile composition comprising an agent capable of binding to a variable region of an anti-desmoglein pathogenic autoantibody; and removing the biological sample without the bound variable region of the heavy chain ($V_H$) of an anti-desmoglein pathogenic autoantibody, thereby depleting the biological sample of anti-desmoglein (Dsg) pathogenic autoantibody. In one embodiment, depletion of the biological sample from an anti-desmoglein pathogenic antibody, is achieved using plsmapheresis.

In another embodiment, provided herein is a method of depleting a biological sample from an anti-desmoglein pathogenic antibody, comprising contacting the sample with an immobile composition comprising an anti-autoimmune reagent capable of binding to a variable region of an anti-desmoglein pathogenic autoantibody; and removing the biological sample without the bound variable region of the heavy chain ($V_H$) of an anti-desmoglein pathogenic autoantibody, thereby depleting the biological sample of anti-desmoglein (Dsg) pathogenic autoantibody. In one embodiment, the heavy chain ($V_H$) of an anti-desmoglein pathogenic autoantibody, is encoded by VH3-07,VH3-30,VH3-53 genes, or the combinations thereof.

In one embodiment, it is desirable to deplete the biological sample from al I anti-Dsg antibodies, whether pathogenic or not. Accordingly and in another embodiment, provided herein is a method of depleting a biological sample from an anti-desmoglein antibody, comprising contacting the sample with an immobile composition comprising an anti-autoimmune reagent capable of binding to a variable region of an anti-desmoglein autoantibody; and removing the biological sample without the bound variable region of the anti-desmoglein autoantibody, thereby depleting the biological sample of anti-desmoglein (Dsg) autoantibody.

In one embodiment, the anti-autoimmune reagents of the invention is useful in removing toxic or unwanted elements, for example, plasma constituents implicated in disease, such as complement or antibodies, from the blood of a patient. The term "plasmapheresis" refers to the separation of a portion of the plasma fraction of the blood from the cellular components thereof. In another embodiment, continuous plasmapheresis is used therapeutically to remove pathologic substances contained in the plasma portion of the blood, such as an anti-Dsg3 autoantibody, or an anti-Dsg, and anti-$Dsg_3$ autoantibody (Anti-$Dsg_{1,3}$ autoantibody) in certain embodiments. In another embodiment, continuous plasmapheresis is used therapeutically to separate the cellular components from the diseased plasma and returning the cellular components to the patient in admixture with a suitable replacement fluid, or in one embodiment, by further fractionating the patient's plasma to remove the unwanted substances, such as an anti-Dsg3 autoantibody, or an anti-$Dsg_1$ and anti-$Dsg_3$ autoantibody (Anti-$Dsg_{1,3}$ autoantibody) in certain embodiments and returning a major portion of the patient's plasma with the depleted cellular components.

In one embodiment, the plasmapheresis used to remove the autoimuune antibodies, is selective plasmapheresis. In another embodiment, the techniques used is selectively removing only the clinically undesirable plasma proteins while leaving the bulk of the remainder of the plasma components in the donor's circulation, thereby enabling extensive plasmapheresis without the need for any plasma replacement. In one embodiment the plasma fraction, after being separated from the corpuscular element fraction, is treated so as to remove one or more selected plasma proteins therefrom, such as a pathogenic antibody. In one embodiment, the protein-depleted plasma fraction is obtained by passing the plasma fraction through an immunoadsorption column to cause adsorption of certain immunoglobulins and/or immune complexes. This technique provides in another embodiment, a high degree of specificity in the profile of proteins removed. In another another embodiment of a selective plasmapheresis technique utilized in conjunction with the methods and compositions provided herein, forced-flow electrophoresis is employed for separating an immunoglobulin-rich fraction from plasma on the basis of differences in electrophoretic mobility.

In one embodiment, the biological sample used in the methods described herein, is blood, sera, plasma or a combination thereof.

In one aspect, the autoantibody and/or other immunologically active elements are removed from the blood by loading an anti-autoimmune reagent that is specific to the autoantibody and/or immunologically active elements onto a solid support or otherwise immobilized on a solid substrate to allow for separation of the autoantibody. When a sample is passed through a solid substrate containing an anti-autoimmune reagent, the anti-autoimmune reagent binds to the corresponding autoantibody, thereby removing the autoantibody from the sample. For example, beads (e.g., magnetic beads) can be coated with an anti-autoimmune reagent. The beads can easily be removed by passing the cultured cells through a magnetic column. Procedures for separation may include magnetic separation, using anti-autoimmune reagent-coated magnetic beads or dynal beads, affinity chromatography, and "panning" with antibody attached to a solid matrix, e.g., plate, or other convenient technique.

Accordingly, the invention provides a method of treating autoimmune conditions of a patient comprising filtering the patient's blood or otherwise separating a plasma constituent from the blood of the present invention and returning the cellular components back to the patient. In one aspect, the method comprises removing autoantibody from the patient's blood using anti-autoimmune reagents of the present invention.

Targeting B-cells:

Autoimmune diseases are a class of diseases associated with a B-cell disorder. Examples include including immune-mediated thrombocytopenias, such as acute idiopathic thrombocytopenic purpura and chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis multiple sclerosis, sarcoidosis, ulcerative colitis, erythema multiforme, IgA nephropathy, polyarteritis nodosa, ankylosing spondylitis, Goodpasture's syndrome, thromboangitis ubiterans, Sjogren's syndrome, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

The most common treatments are corticosteroids and cytotoxic drugs, which can be very toxic. These drugs also suppress the entire immune system which can result in serious infection have adverse affects on the liver and kidneys. The present invention provides a method of targeting B cells using an anti-autoimmune reagent that is capable of binding to an autoantibody.

B-cell clones that bear autoantibody Ig-receptors are present in normal individuals. Autoimmunity results when these B-cells become overactive, and mature to plasma cells that secrete autoantibody. In accordance with the present invention, autoimmune disorders can be treated by administering an anti-autoimmune reagent (e.g., an antibody or polypeptide) that binds to an autoantibody present on a B-cell, such as an anti-desmoglein antibody. In one embodiment, the anti-autoimmune reagent is conjugated with to a therapeutic moiety including, but not limited to an anti-tumor agent, a chemotherapeutic agent, an anti-cell proliferation agent, a drug, a toxin, a therapeutic radioisotope, and any combination thereof.

The present invention contemplates the use of anti-autoimmune reagents for treatment of autoimmune diseases. For example, preferred anti-autoimmune reagents are antibodies or polypeptides that bind to an anti-desmoglein antibody or fragment thereof such as an anti-desmoglein antibody comprising an amino acid sequence represented by SEQ ID NOs: 44-86, 173-215, 216-258 or any combination thereof. Preferably, the anti-desmoglein antibody is pathgenic and is encoded by VH3-07,VH3-30,VH3-53 genes, or the combinations thereof. In a preferred embodiment, the anti-autoimmune reagents are conjugated or fused to a therapeutic moiety. In some instances, the anti-autoimmune reagent is used to deplete the blood or a biological sample of B-cells that express on their surface anti-desmoglein antibodies.

The anti-autoimmune reagents of the invention can be used in combination with other existing therapies in the art. For example, the anti-autoimmune reagents can be administered to mammal, preferably a human, before, concurrently or after administration of other types of therapy. For example, the anti-autoimmune reagent can be co-administered with therapeutics that target against T-cells, plasma cells or macrophages, such as antibodies directed against T-cell epitopes, more particularly against the CD4 epitopes. Gamma globulins also may be co-administered. In some cases, it may be desirable to co-administer immunosupproessive drugs such as corticosteroids and possibly also cytotoxic drugs. In this case, lower doses of the corticosteroids and cytotoxic drugs can be used as compared to the doses used in conventional therapies, thereby reducing the negative side effects of these therapeutics.

Drugs which are known to act on B-cells, plasma cells and/or T-cells are particularly useful in accordance with the present invention, whether conjugated to an anti-autoimmune reagent, or administered as a separate component in combination with the anti-autoimmune reagent. These include methotrexate, phenyl butyrate, bryostatin, cyclophosphamide, etoposide, bleomycin, doxorubicin, carmustine, vincristine, procarbazine, dexamethasone, leucovorin, prednisone, maytansinoids such as DM1,calicheamicin, rapamycin, leflunomide, FK506,immuran, fludarabine, azathiopine, mycophenolate, and cyclosporin. Drugs such as immuran, methotrexate, and fludarabine which act on both B-cells and T-cells are particularly preferred illustrative of toxins which are suitably employed in accordance with the present invention are ricin, abrin, ribonuclease, DNase I, *Staphylococcal* enterotoxin-A, pokeweed antiviral protein, gelonin, diphtheria toxin, *Pseudomonas* exotoxin, *Pseudomonas* endotoxin and RNAses, such as onconase. Other suitable drugs and toxins are known to those of skill in the art.

Cytokine agonists and antagonists may also be used in the therapies according to the present invention. Tumor necrosis factor alpha (TNFα) and interleukin-1 (IL-1) are important in mediating inflammation in rheumatoid arthritis. Accordingly, anti-TNFα reagents, such as infliximab and etanercept (Enbrel), are useful in therapy according to the invention, as well as anti-IL-1 reagents. Other useful secondary therapeutics included IL-2 and GM-CSF, which may be conjugated with the anti-autoimmune reagent.

Diagnostic Tools:

In one embodiment, provided herein is a method of diagnosing pemphigus in a subject, comprising the step of contacting a biological sample of said subject with a composition comprising an anti-autoimmune reagent described herein, for example an antibody that specifically binds to an anti-desmoglein (Dsg) pathogenic autoantibody; and analyzing the biological sample for the presence of antibody-antigen complex, whereby the presence of antibody-antigen complex indicates the subject has or is predisposed to pemphigus.

In another embodiment, the step of contacting a biological sample of said subject with a composition comprising the anti-idiotypic antibody described herein, is affected using a radio-immunoassay (RIA), an enzyme linked immunosorbent assay (ELISA), a western blot, an immunohistochemical analysis, or a combination thereof.

In one embodiment, when using RIA, a labeled anti-idiopathic antibody as described herein is contacted with a sample containing an unknown amount of substrate in varying amounts. The decrease in precipitated counts from the labeled anti-idiotypic antibody is proportional to the amount of anti-Dsg antibodies in the added sample, indicating pemphigus.

In another embodiment, when using ELISA, the anti-idiotypic antibody provided herein, which is coupled to an enzyme is applied and allowed to bind to react with the sample. Presence of the anti-Dsg antibody is then detected and quantitated by a colorimetric reaction employing the enzyme coupled to the anti-idiotypic antibody. In another embodiment, enzymes employed in this method are horseradish peroxidase or in another embodiment alkaline phosphatase. In the dynamic range of response, the amount of anti-Dsg antibodies present in the sample is proportional to the amount of color produced. A substrate standard is employed in one embodiment, to improve quantitative accuracy.

The use of the anti-autoimmune reagents of the present invention are more sensitive in the context of a diagnostic test for pathology of pemphigus because the anti-autoimmune reagents are able to specifically bind to pathogenic antibodies. Prior to the present invention, the diagnostic tests for pemphigus would sometimes result in false positive identification of pemphigus patients because the reagents used by the prior art would sometimes recognized non-pathogenic antibodies.

Administration

In some embodiments, an effective amount of the compositions of the present invention (e.g., anti-idiotypic antibody or otherwise inhibitors of pathogenic PF antibodies) is administered to a mammal, preferably a mammal. In other embodiments, a therapeutically effective amount of the compositions of the present invention are administered to a mammal, preferably a human, for the treatment of a disease or condition.

The term "effective amount" as used herein is defined as the amount of the compositions of the present invention that is necessary to result in a physiological change in the cell or tissue to which it is administered.

The term "therapeutically effective amount" as used herein is defined as the amount of the compositions of the present invention that eliminates, decreases, delays, or minimizes adverse effects of a disease, such as pemphigus. A skilled artisan readily recognizes that in many cases the compositions may not provide a cure but may only provide partial benefit, such as alleviation or improvement of at least one symptom of the disease.

Pharmaceutical compositions comprising the compositions of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries that facilitate processing of the proteins into preparations which can be used pharmaceutically. Proper formulation is dependent upon the route of administration chosen.

For topical administration the proteins of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, inhalation, oral or pulmonary administration.

For injection, the compositions of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents.

Alternatively, the proteins may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the proteins can be readily formulated by combining the proteins with pharmaceutically acceptable carriers well known in the art. Such carriers enable the proteins of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

Alternatively, other pharmaceutical delivery systems may be employed. Liposomes and emulsions are well-known examples of delivery vehicles that may be used to deliver proteins of the invention. Certain organic solvents such as dimethylsulfoxide also may be employed, although usually at the cost of greater toxicity. Additionally, the molecules may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

The compositions of the invention may contain charged side chains or termini. Thus, they may be included in any of the above-described formulations as the free acids or bases or as pharmaceutically acceptable salts. Pharmaceutically acceptable salts are those salts that substantially retain the biologic activity of the free bases and which are prepared by reaction with inorganic acids. Pharmaceutical salts tend to be more soluble in aqueous and other protic solvents than are the corresponding free base forms.

The compositions of the invention will generally be used in an amount effective to achieve the intended purpose. For use to treat or prevent a disease condition, the molecules of the invention, or pharmaceutical compositions thereof; are administered or applied in a therapeutically effective amount.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from about 0.001 to 100 mg/kg/day, preferably from about 0.5 to 1 mg/kg/day and any and all whole or partial integers there between. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of the compositions of the present invention administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs.

The following examples are presented in order to more fully illustrate the preferred embodiments of the invention. They should in no way be construed, however, as limiting the broad scope of the invention.

EXAMPLES

Materials and Methods:
Construction of Phage Library
Separated IgG-λ and IgG-κ phage libraries were constructed from $1 \times 10^7$ mononuclear cells isolated from 50 ml of peripheral blood collected from a PF patient with clinically active disease (Barbas, C. F., III, Burton, D. R., Scott, J. K., and Silverman, G. J. 2001. Phage display: a laboraroty manual. Cold Spring Harbor Laboratory Press, Cold Spring Harbor, N.Y., USA). Briefly, RT-PCR was used to amplify the immunoglobulin variable regions of the heavy (VH) and light chains (VL), and the gene fragments were then cloned into the phagemid vector pComb3X (Scripps Institute, La Jolla, Calif.). The phagemid library was electropolated into XL-1 Blue suppressor strain of E. coli (Stratagene) with superinfection by VCSM13 helper phage (Stratagene). In this system, filamentous phage particles express scFv antibodies (with a carboxy-terminal 6x histidine tag and a hemagglutinin [HA] tag) fused to the pIII bacteriophage coat protein. Recombinant phage were purified from culture supernatants by polyethylene glycol precipitation and resuspended in PBS, pH 7.4 with 1% BSA containing 1 mM $CaCl_2$. The library comprised more than $2 \times 10^8$ independent transformants as determined by titering on E. coli XL1-Blue after transformation. To validate library diversity, the sequences of 14 phage clones from the unpanned library were analyzed. No duplicate sequences and marked heterogeneity in VH and VL gene usage were found, similar to that found in normal human peripheral blood lymphocytes.

Phage Selection Against Dsg1 Absorbed to a Solid Phase
ELISA plates coated with recombinant Dsg1 (MBL) were used to isolate phage clones that express anti-Dsg1 scFv as previously described (Payne et al., 2005 J. Clin. Invest 115: 888-899.). Briefly, four wells were incubated with blocking buffer (50 mM Tris pH 7.5, 150 mM NaCl, 1 mM CaCl2 [TBS-Ca] with 3% skim milk) at room temperature for 1 hour. The phage library was diluted into blocking buffer and was incubated with Dsg1 on the wells for 2 hours at room temperature. After 5 to 10 washes with TBS-Ca containing 0.1% Tween 20, adherent phage were eluted with 76 mM citric acid, pH 2.4, incubated for 10 minutes at room temperature, and then neutralized with 2M unbuffered Tris. The eluted phage were amplified in XL1-Blue E. coli and rescued by superinfection with VCSM13 helper phage. Phage were harvested from bacterial culture supernatant and then re-panned against Dsg1 ELISA plates for three additional rounds. Individual phage clones were isolated from each round of panning and analyzed for the binding to Dsg1 by ELISA using horseradish peroxidase (HRP)-conjugated anti-M13 antibody (GE Healthcare Bio-Sciences). For epitope-blocked panning, the phage library was first mixed with purified recombinant non-pathogenic scFvs (clones 1-18/L1, 1-18/L12, 3-094/O18O8, and 3-093/O12O2) and then incubated on immobilized Dsg1 for 2 hours at room temperature.

Phage Selection Against Mammalian Produced Dsg1 in Solution
cDNA encoding the extracellular region of human Dsg1 fused with the Fc portion of human IgG1 and a histidine tag (6 histidine residues) (Dsg1-IgHis) was subcloned into pcDNA3-1 (Invitrogen). The resultant construct was transiently transfected into 293T cells using jet PEI (Polyplus-transfection Inc.). The recombinant protein was purified from the culture supernatant with Talon metal affinity resin according to manufacturer's protocol (Clontech Laboratories, Inc.)

The PF patient antibody phage library ($2 \times 10^{11}$ colony forming units) was precleared by incubation with the Fc fragment of human IgG (Jackson ImmunoResearch Laboratories, Inc.) which was then removed by protein G magnetic beads (New England Biolabs). The precleared phage library was then incubated with recombinant Dsg1-IgHis at room temperature for 20 min. Phage bound to Dsg1-IgHis were captured by protein G magnetic beads, washed with TBS containing 0.1% Tween 20, then eluted with 0.2 M glycine-HCl, pH 2.2 and immediately neutralized with 1M Tris-HCl, pH 9.1. Eluted phage were amplified in XL1-Blue E. coli followed by superinfection with helper phage as described above. Phage were harvested from bacterial culture supernatant and re-panned against Dsg1-IgHis in solution. Protein G magnetic beads and Protein A magnetic beads (New England Biolabs) were used in alternate rounds of panning to avoid isolation of phage that bound non-specifically to Protein A or G.

Sequence Analysis of scFv Antibodies

Recombinant phagemids were purified with a plasmid preparation system (Qiagen) and the VH and VL inserts were sequenced using pComb3X specific primers previously described (Barbas, C. F., III, Burton, D. R., Scott, J. K., and Silverman, G. J. 2001. Phage display: a laboraroty manual. Cold Spring Harbor Laboratory Press, Cold Spring Harbor, N.Y., USA). The nucleotide sequences were compared with the germline sequences in V Base sequence directory (http://vbase.mrc-cpe.cam.ac.uk/) to determine their germline gene origins and interrelatedness.

Production and Purification of Soluble scFvs

The Top10 F' non-suppressor strain of E. coli (Invitrogen Corp.) was infected with an individual phage clone and soluble scFvs were purified from the bacterial periplasmic space using sucrose shock or Fastbeak (Promega) and Talon metal affinity resin (Clontech Laborarories, Inc.) as previously described (Payne et al., 2005 J. Clin. Invest 115:888-899).

Dsg1 and Dsg3 scFv ELISA

The reactivity of scFv against human Dsg1 and Dsg3 was measured by Dsg1 and Dsg3 ELISA (MBL) using HRP-conjugated anti-HA monoclonal antibody (clone 12CA5, 1:1000 dilution, Roche Diagnostics Corp.) as a secondary antibody as described is Payne et al., 2005 J. Clin. Invest 115:888-899.

Inhibition of scFv Binding by Pemphigus Sera

Inhibition ELISA to block the binding of scFv to Dsg1 by pemphigus sera was performed as previously (Payne et al., 2005 J. Clin. Invest 115:888-899). Briefly, scFvs were used at dilutions that resulted in an OD450 reading of approximately 1.0 in the Dsg1 ELISA in the absence of blocking serum. The diluted scFv, mixed with pemphigus or normal control sera (10 uL), was analyzed by Dsg1 ELISA developed with HRP-conjugate anti-HA antibody. Inhibition was calculated according to the following formula: % inhibition=[1−(OD S/B−OD Sc/B)/(OD S/Bc−OD Sc/Bc)]×100 where S is the scFv being tested, Sc is scFv negative control, B is blocking pemphigus serum and Bc is normal human serum.

Inhibition of PF Sera Binding by scFvs

PF sera were diluted to result in an OD 450 reading of approximately 1.0 in the Dsg1 ELISA without competitors. The diluted PF sera, mixed with scFvs, were analyzed by Dsg1 ELISA developed with HRP-conjugate anti-human Fab antibody. Inhibition was calculated according to the following formula: % inhibition=[1−(OD T/B−OD NB)/(OD T/Bc−OD N/Bc)]×100 where T is the PF sera tested, N is normal control serum, B is blocking monoclonal anti-Dsg1 scFvs, Bc is control scFv (AM3-13).

Epitope mapping by competition ELISA

Extracellular, domain-swapped desmoglein 1 and 3 recombinant molecules were produced by a baculovirus expression system as previously described (Futei et al., 2000 J. Invest Dermatol. 115:829-834.). ScFvs were diluted so that Dsg1 ELISA readings at OD450 were approximately 1.0 in the absence of a competitor. The diluted scFvs were incubated with an excess amount of baculovirus culture supernatant containing the recombinant proteins for 30 minutes at room temperature. Immunoblot analysis confirmed that each culture supernatant contained approximately the same amount of recombinant protein. The mixture was subjected to Dsg1 ELISA (MBL) developed with HRP-anti-HA antibody. Inhibition was calculated using the following formula: Inhibition (%)=[1−(OD competitor−OD blank)/(OD negative−OD blank)]×100;OD competitor is an OD obtained with scFv incubated with culture supernatant with a recombinant baculoprotein; OD negative is an OD obtained with sera incubated with culture supernatant of uninfected High Five insect cells; OD blank is an OD obtained with secondary antibody only. Greater than 40% inhibition was considered positive.

Direct and indirect immunofluorescence

Immunofluorescence for scFvs was performed on human skin, mouse tail or neonatal mouse skin as previously described (Payne et al., 2005 J. Clin. Invest 115:888-899). Binding was detected with rat monoclonal anti-HA antibody (3F10, 1:100 dilution, Roche Diagnostics) followed by Alexa Fluor 568-conjugated anti-rat IgG (1:200 dilution, Invitrogen).

Immunoblotting

The ectodomain of human Dsg1 tagged with an E-tag and a histidine tag (Dsg1-EHis), produced by a baculovirus expression system was used as substrate (Ishii et al., 1997 J. Immunol. 159:2010-2017.). The recombinant proteins were size fractionated by SDS-PAGE and transferred to nitrocellulose membranes. The membranes were incubated with scFvs diluted in PBS/5% milk following by HRP-conjugated anti-HA antibody (1:1000 dilution; Roche Diagnostics) and developed by ECL plus reagent (GE Healthcare Bio-Sciences).

Immunoprecipitation-immunoblotting Bnalysis for Dsg4 Binding

To determine whether anti-Dsg1 scFvs also bind Dsg4, baculovirus-produced recombinant human Dsg4-EHis and human Dsg1-EHis ("EHis" tag defined above) was used (Nagasaka et al., 2004 J. Clin. Invest 114:1484-1492.). Baculovirus-infected insect cell culture supernatants containing recombinant molecules were incubated with scFvs for 30 minutes and then immunoprecipitated with anti-HA agarose (Sigma-Aldrich) at 4° C. for 2 hours with gentle rotation. After washing with TBS-Ca, the immunoprecipitates were resuspended in Laemmli sample buffer, separated by SDS-PAGE, and transferred to nitrocellulose membranes (Bio-Rad Laboratories). Membranes were probed with HRP-conjugated anti-E-tag antibody (1:2000 dilution, GE Healthcare Bio-Sciences).

Neonatal Mouse Injection

Purified scFv (100 uL) were injected subcutaneously along the back into 1-2 day old neonatal C57BU6J mice. The mice were sacrificed at 6 hours and skin was harvested for direct immunofluorescene and for histology.

Human Skin Organ Culture Injection

Specimens were obtained from left over normal skin after excisional surgery. The specimens were trimmed by removing fat tissue and cut into 5 mm diameter pieces. After intradermal injection of 50 uL of purified scFv using an insulin syringe, skin specimens were put on the insert of transwells (Corning) with defined keratinocyte SFM (Invitrogen) containing 1.2 mM CaCl2 in the outer compartment. At 24 hours, the skin was harvested for direct immunofluorescene and for histology.

Example 1

Immunochemical Properties of the Anti-Dsg 1 scFv are Associated with their Heavy-chain Gene Usage ELISA Analysis Representative soluble scFvs were tested for binding to Dsg1 (FIG. 1) and Dsg 3 by ELISA. All scFvs bound Dsg1 as expected, and did not bind Dsg3,except for two 3-07/1e clones (differed from each other only in their light chain VJ recombination) that showed weak binding to Dsg3 at very high concentrations (data not shown). Six VH1-18 clones bound strongly by ELISA, giving an OD450=1 values at concentrations from 0.4 to 2.8 ng/ml (2 clones shown in FIG. 1, light green lines). VH3-09 clones also showed good binding; 9 of 12 clones tested gave OD450=1 values at 0.5-20 ng/ml (i.e. dark green lines in FIG. 1). The VH1-08 and VH3-07 clones showed much weaker binding, and the VH3-30 clone showed intermediate binding (FIG. 1).

Indirect Immunofluorescence on Mouse Tail and Human Skin

Figure 2:
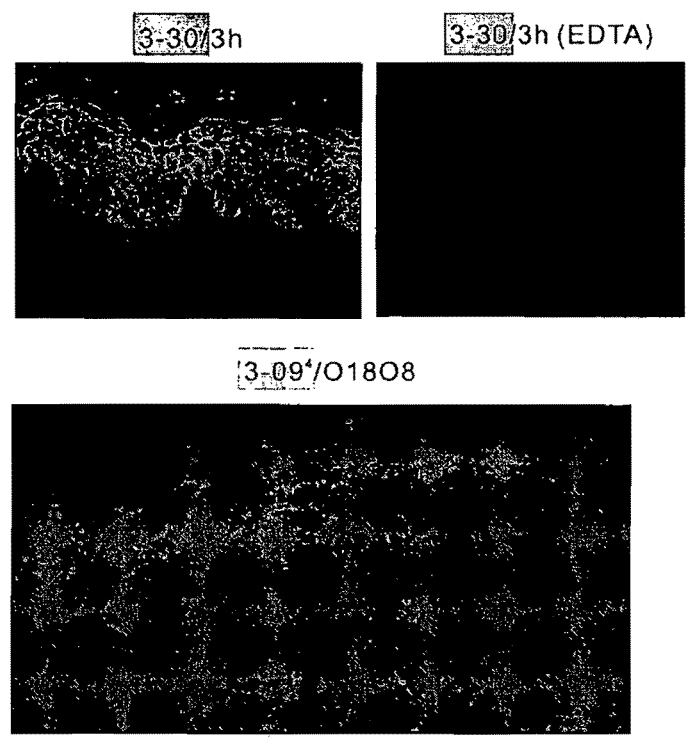
FIG. 2, comprising
Figure 3A:
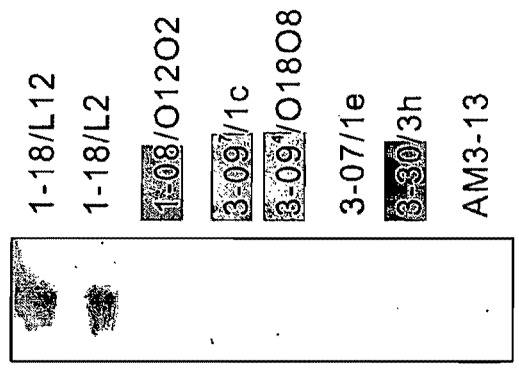
FIGS. 3A and 3B, is a series of images depicting the purified ectodomain of human Dsg1 with an E-tag (Dsg1-EHis), produced by baculovirus that was used as an immunoblot substrate. ScFv heavy chain variable regions encoded by the gene VH1-18, but not other scFvs, bound denatured Dsg1 on immunoblots (FIG. 3A).
Figure 3B:
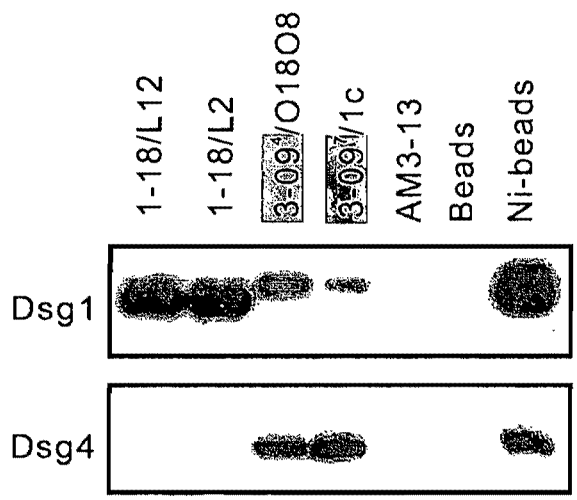
Figure 5A:
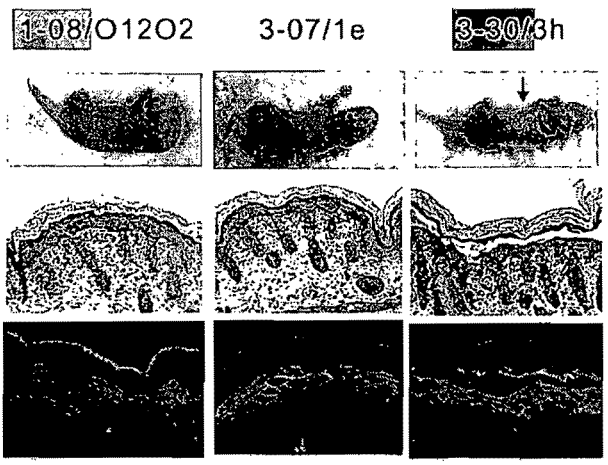
Figure 5B:
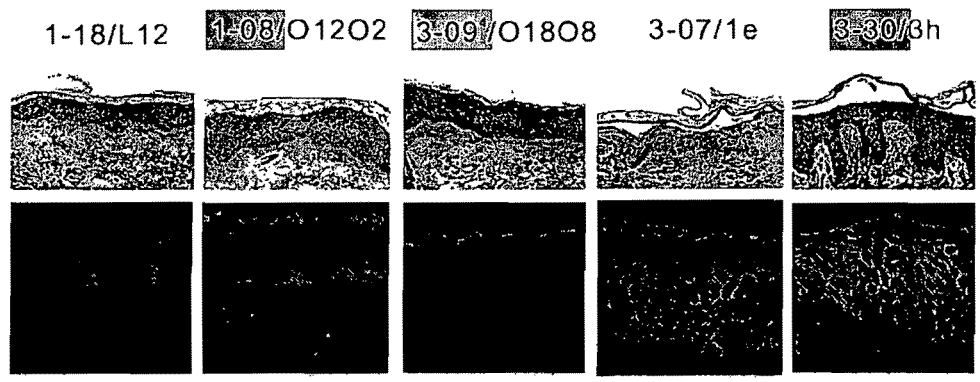

All VH1-18 clones stained the cell surface of keratinocytes throughout human epidermis, stronger in the more superficial epidermis, identical to staining reported with PF serum (Table 1). This pattern was also seen when antibodies were injected into human skin organ culture (FIG. 5B). These VH1-18 antibodies did not stain mouse skin. In contrast, VH3-09 antibodies stained the cell surface of human keratinocytes weakly, if at all, and also did not bind mouse skin. There was a suggestion of some cytoplasmic staining of human epidermis with some of these VH3-09 antibodies, most marked with 3-09$^4$/O18O8 (FIG. 2). The VH3-07 and VH3-30 clones strongly stained the cell surface of both human and mouse epidermis (3-30/3h shown in FIG. 2, also see FIG. 5). The staining with 3-30/3h was eliminated when the human skin was preincubated with EDTA (FIG. 2), suggesting that the antibody binds a calcium-sensitive epitope.

immunoprecipitation experiments using recombinant human Dsg1 produced by baculovirus expression system clones 3-09$^4$/O18O8 and 3-09$^7$/1c immunoprecipitated a Dsg1 polypeptide with a slightly greater apparent molecular weight on SDS PAGE than other clones (FIG. 3B). As it is known that the insect cells transfected with the recombinant baculovirus produce both the proprotein and mature protein forms of Dsg1, this finding suggests that they bind to the proprotein but not the mature protein. Binding to the proprotein was consistent with the cytoplasmic staining seen by indirect immunofluourescence (FIG. 2), because the proprotein is believed to be processed to the mature form as it reaches the cell surface.

Binding of Dsg4

Some pemphigus sera bind Dsg4, and this binding was due to antibodies against Dsg1 that cross react with Dsg4. To determine whether any of the anti-Dsg1 monoclonal antibodies crossreact with Dsg4, scFvs were used to immunoprecipitate recombinant Dsg4 containing a carboxy-terminal E-epitope tag, then identified its presence on an immunoblot stained with anti-E tag antibodies. VH1-18, VH3-07 and VH3-30 antibodies did not bind Dsg4, whereas VH1-08 and VH3-09 antibodies did (Table 1 and FIG. 3B).

TABLE 1

Anti-Dsg1 clones representing each unique heavy chain (VDJ) and their associated light chain genes

| | VH gene | Unique VDJ region[a] | D gene | J gene | VL gene | Name of clone | IIF Human skin | IIF Mouse skin | Dsg1 IB | Dsg4 binding | Patho- genicity | Dsg1 epitope |
|---|---|---|---|---|---|---|---|---|---|---|---|---|
| VH1 | VH1-18 | VDJ1 | D3-10/DXP'1 | JH4b | B3 | 1-18/B3 | + | | + | | | |
| | | | | | L8 | 1-18/L8 | + | — | + | | | |
| | | | | | L1 | 1-18/L1 | + | — | + | | —[b] | 164-401 |
| | | | | | L12 | 1-18/L12 | + | weak + | + | — | — | 164-401 |
| | | | | | L2 | 1-18/L2 | | | | | | |
| | | | | | LFVK431 | 1-18/LFVK431 | + | | + | | | |
| | VH1-08 | VDJ2 | D3-3/DXP4 | JH6b | O12/O2 | 1-08/O12O2 | + | + | — | + | — | 1-161 |
| VH3 | VH3-09 | VDJ3 | D2-2 | JH6b | O12/O2 | 3-09$^3$/O12O2 | weak +[c] | weak + | — | | | |
| | | | | | O18/O8 | 3-09$^3$/O18O8 | | | — | | | |
| | | | | | L11 | 3-09$^3$/L11 | | | | | | |
| | | | | | A30 | 3-09$^3$/A30 | | | | | | |
| | | | | | 1c | 3-09$^3$/1c | | | | | | |
| | | | | | 1e | 3-09$^3$/1e | | | | | | |
| | | | | | 1g | 3-09$^3$/1g | | | | | | |
| | | | | | 6a | 3-09$^3$/6a | | | | | | |
| | | VDJ4 | D3-3/DXP4 | JH3a | O18/O8 | 3-09$^4$/O18O8 | —[d] | weak + | — | + | — | 1-161 |
| | | VDJ5 | | | O18/O8 | 3-09$^5$/O18O8 | + | + | — | — | — | 1-161 |
| | | | | | L11 | 3-09$^5$/L11 | | | | | | |
| | | VDJ6 | | | L12 | 3-09$^6$/L12 | — | | | | | |
| | | | | | O18/O8 | 3-09$^6$/O18O8 | weak + | | | | | |
| | | | | | 1c | 3-09$^6$/1c | | | | | | |
| | | VDJ7 | D3-3/DXP4 | JH3b | O12/O2 | 3-09$^7$/O12O2 | — | | | | | |
| | | | | | 1c | 3-09$^7$/1c | weak + | weak + | — | + | — | 1-161 |
| | | VDJ8 | D3-22/D21-9 | JH4b | L11 | 3-09$^8$/L11 | weak + | | — | | | |
| | | VDJ9 | D2-8/DLR1 | JH2 | L8 | 3-09$^9$/L8 | | | | | | |
| | | | | | L2 | 3-09$^9$/L2 | | | | | | |
| | | VDJ10 | D1-14/DM2 | JH6b | O18/O8 | 3-09$^{10}$/O18O8 | | | | | | |
| | VH3-07 | VDJ11 | D3-10/DXP'1 | JH4b | 1e | 3-07/1e | + | + | — | — | weak +[e] | 1-161 |
| | VH3-30 | VDJ12 | D5-24 | JH4b | 3h | 3-30/3h | + | + | — | — | + | 1-161 |

[a]Each VDJ recombinatory region is defined by a CDR3 (the third complimentary determining region) amino acid sequence. Because of extensive diversity in VDJ gene rearrangements, clones sharing identical VDJ sequences are considered to have arisen from the same B-cell clones.
[b]Intradermal injection into human foreskin grafted SCID mice (ref. 16) was used to test pathogenicity for this clone.
[c]one clone with unique light chain VJ junction also stained epidermal basement membrane.
[d]showed cytoplasmic staining.
[e]one clone with unique 1e VJ junction was negative.
Table abbreviations: IIF, indirect immunofluorescence; IB, immunoblot; Dsg1 epitope defined as amino acid numbers in Dsg1.

Binding to Denatured Dsg1 and to Unprocessed Dsg1 Proprotein

VH1-18 clones bound denatured Dsg1 on immunoblots unlike any of the other clones tested (Table 1 and FIG. 3A). In Epitope Mapping of Anti-Dsg1 Antibodies Four Dsg1/Dsg3 chimeric molecules were used to perform competition assays with various anti-Dsg1 scFvs. As shown in FIG. 4, VH1-18 clones bound to amino acids #164-401, whereas all others mapped to the amino terminus of Dsg1 (amino acids #1-161) (Table 1).

The data presented herein demonstrate, in general, that the properties of the isolated antibodies correlate with heavy chain gene usage, even if the light chains are encoded by a diversity of variable region genes. Overall, the heavy chains of our anti-Dsg1 clones were encoded by only 5 different heavy chain genes belonging to only two heavy chain gene families (VH1 and VH3), whereas light chain gene usage was significantly more promiscuous.

Example 2

Light Chain Suffling Shows that Only Certain Light Chains can Pair with the Restricted Heavy Chains to Allow Dsg1 Binding Although the heavy chain gene usage is generally associated with the immunochemical properties of these scFvs, and the light chain gene usage is much less restricted, light chain shuffling experiments showed that the pairing of light and heavy chains is not entirely random, as only certain light chains allow binding to Dsg1. To demonstrate the light chain contribution to Dsg1 binding, a derivative phage display library was constructed using the heavy chain of scFv 3-098/L11 paired with the entire original light chain repertoire from the PF patient. Analysis of 16 clones from this derivative library before panning showed that none bound to Dsg1 by ELISA, even though all had the VH3-09 heavy chain. The clones did, however, bind an anti-hemagglutinin (HA) tag-coated ELISA plate, showing that the scFv (which is engineered to express the HA tag on its carboxy-terminus) was expressed on the phage surfaces. On the other hand, when this library was panned against Dsg1 to select anti-Dsg1 clones, these clones used the L11, A30 or 1c light chain genes, as were found in the anti-Dsg1 clones isolated from the original libraries. These data suggest that only certain light chains permit Dsg1 binding when paired to this heavy chain.

Example 3

Monovalent, Monoclonal Anti-Dsg1 ScFv can Cause the Pathology of PF

Initially pathogenicity was tested in the neonatal mouse model of pemphigus. Because VH1-18 and VH3-09 clones did not bind well to mouse skin by indirect immunofluorescence, it was believed seemed that theses antibodies would not bind epidermis or induce pathology, which turned out to be the case (Table 1). However, clones 1-08/O12O2 and 3-07/1e did not induce pathology either, even though they did bind mouse epidermis (Table 2, FIG. 5A). Clone 3-30/3h, on the other hand, caused extensive gross blisters with the typical histology and direct immunofluorescence of PF (FIG. 5A).

TABLE 2

Code table for PFl-scFv clones

| VH gene | | Common VDJ | D segment | J segment | VL gene | Original name of clones | name in paper |
|---|---|---|---|---|---|---|---|
| VH1 | VH1-18 | VDJ1 | D3-10/DXP'1 | JH4b | B3 | PF1-2-7 | 1-18/B3 |
| | | | | | L8 | PF1-2-1 | 1-18/L8 |
| | | | | | L1 | PF1-2-5 | 1-18/L1 |
| | | | | | L12 | PF1-2-6 | 1-18/L12 |
| | | | | | | PF1-3-K11 | 1-18/L2 |
| | | | | | LFVK431 | PF1-2-15 | 1-18/LFVK431 |
| | VH1-08 | VDJ2 | D3-3/DXP4 | JH6b | O12/O2 | PF1-2-22 | 1-08/O12O2 |
| VH3 | VH3-9 | VDJ3 | D2-2 | JH6b | O12/O2 | PF1-2-11 | 3-09$^3$/O12O2 |
| | | | | | O18/O8 | PF1-2-17 | 3-09$^3$/O18O8 |
| | | | | | L11 | PF1-29 | 3-09$^3$/L11 |
| | | | | | A30 | PF1-1-35 | 3-09$^3$/A30 |
| | | | | | 1c | PF1-2-L19 | 3-09$^3$/1c |
| | | | | | 1e | PF1-2-L32 | 3-09$^3$/1e |
| | | | | | 1g | PF1-2-L4 | 3-09$^3$/1g |
| | | | | | 6a | PF1-2-L10 | 3-09$^3$/6a |
| | | VDJ4 | D3-3/DXP4 | JH3a | O18/O8 | PF1-2-10 | 3-09$^4$/O18O8 |
| | | VDJ5 | | | O18/O8 | PF1-2-9 | 3-09$^5$/O18O8 |
| | | | | | L11 | PF1-3-K6 | 3-09$^5$/L11 |
| | | VDJ6 | | | L12 | PF1-26 | 3-09$^6$/L12 |
| | | | | | O18/O8 | PF1-22 | 3-09$^6$/O18O8 |
| | | | | | 1c | PF1-2-L02 | 3-09$^6$/1c |
| | | VDJ7 | D3-3/DXP4 | JH3b | O12/O2 | PF1-1-1 | 3-09$^7$/O12O2 |
| | | | | | 1c | PF1-2-3 | 3-09$^7$/1c |
| | | VDJ8 | D3-22/D21-9 | JH4b | L11 | PF1-2-18 | 3-09$^8$/L11 |
| | | VDJ9 | D2-8/DLR1 | JH2 | L8 | PF1-1-7 | 3-09$^9$/L8 |
| | | | | | L2 | PF1-1-19 | 3-09$^9$/L2 |
| | | VDJ10 | D1-14/DM2 | JH6b | O18/O8 | PF1-27 | 3-09$^{10}$/O18O8 |
| | VH3-7 | VDJ11 | D3-10/DXP'1 | JH4b | 1e | PF1-8-2 | 3-07/1e |
| | | | | | 1e | PF1-8-5 | |
| | VH3-30 | VDJ12 | D5-24 | JH4b | 3h | PF1-8-15 | 3-30/3h |

Given the possibility that some monoclonal anti-Dsg1 antibodies might be specific for human rather than mouse pathogenic epitopes, representative scFv clones were tested by injecting them into freshly isolated human skin biopsies, which were then maintained in organ culture for 24 hours. Immunofluorescence of these cultures showed binding of antibodies to the epidermal cell surface (except for VH3-09 antibodies, consistent with their weak binding to the keratinocyte cytoplasm by indirect immunofluorescence), but lo only 3-30/3h caused extensive histologic blisters with features typical of PF, while 3-07/1e caused focal blisters with typical histology (FIG. 5B).

These findings demonstrate that a monovalent, anti-Dsg1 monoclonal antibody that does not bind to Dsg4 can cause the pathology of PF. In addition, one clone (3-07/1e) was specific for a human pathogenic epitope, not shared in the mouse, but one clone (3-30/3h) caused disease in both humans and mice.

Example 4

Figure 6A:
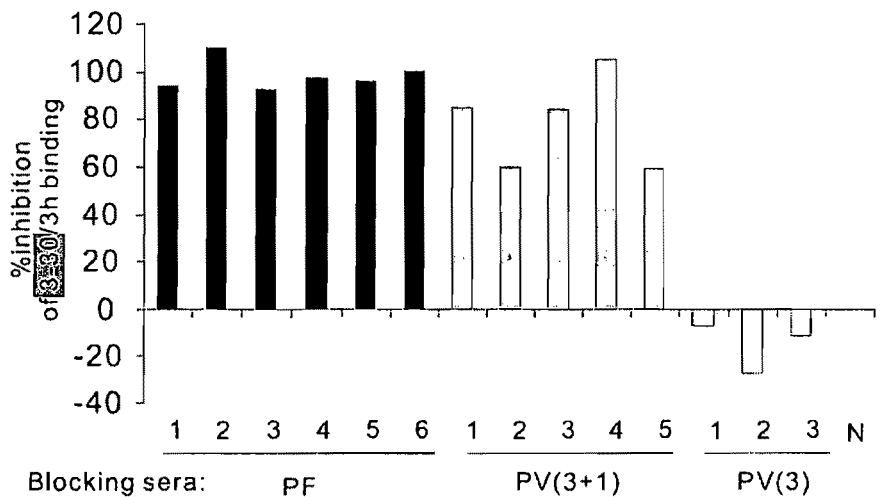

A Common Pathologic Epitope on Dsg1, Defined by scFv 3-30/3H, is Targeted by Multiple PF Sera and PV Sera that Contain Anti-Dsg1 Antibodies ELISA inhibition studies in which patients' sera was used to inhibit the binding of scFv to Dsg1 were used to determine if antibodies from various patients bind at or near the epitopes bound by the scFv (Table 2). Most strikingly, clone 3-30/3h, the most pathogenic scFv, was inhibited by 6/6 PF sera and 5/5 PV sera that contain both anti-Dsg3 and anti-Dsg1 antibodies, but none of 3 PV sera that contain only anti-Dsg3 antibodies (FIG. 6A). It is known that in mucocutaneous PV the anti-Dsg1 antibodies are pathogenic. These results suggest that the pathogenic anti-Dsg1 antibodies in PF and mucocutaneous PV sera inhibit identical or similar epitopes to those defined by scFv 3-30/3h, suggesting that this clone defines an important epitope on Dsg1 that is targeted to cause pathology in many, if not all, PF and mucocutaneous PV patients.

Other anti-Dsg1 clones were inhibited in their binding to Dsg1 by fewer PF and PV patients' sera, suggesting that the epitopes defined by these clones were not as well preserved among patients as was that defined by clone 3-30/3h.

Characterization of the libraries also demonstrate the presence and absence of consensus CDR3 sequences in pathogenic antibodies, respectively. It was observed that a consensus sequence was present by all of the tested pathogenic antibody sequences. However, this sequence was not found in the tested nonpathogenic antibody sequences. The consensus sequence shared among the pathogenic antibodies reside in the CDR3 region of the antibody. The consensus sequence shared among the pathogenic antibodies is D/E-X-X-X-W, wherein X can represent any amino acid. The consensus sequence contains a tryptophan. A conserved tryptophan has been observed in other molecules for example cadherin. Without wishing to be bound by any particular theory, it is believed that cadherin homophilic interaction is dependent on conserved tryptophan residues in the amino terminal binding pocket. Therefore, it is believed that the tryptophan in the CDR3 region plays a role in the antigen-binding characterisitic of the antibody to desmogleins and how the pathogenic antibodies cause a disease state.

Example 5

Figure 6B:
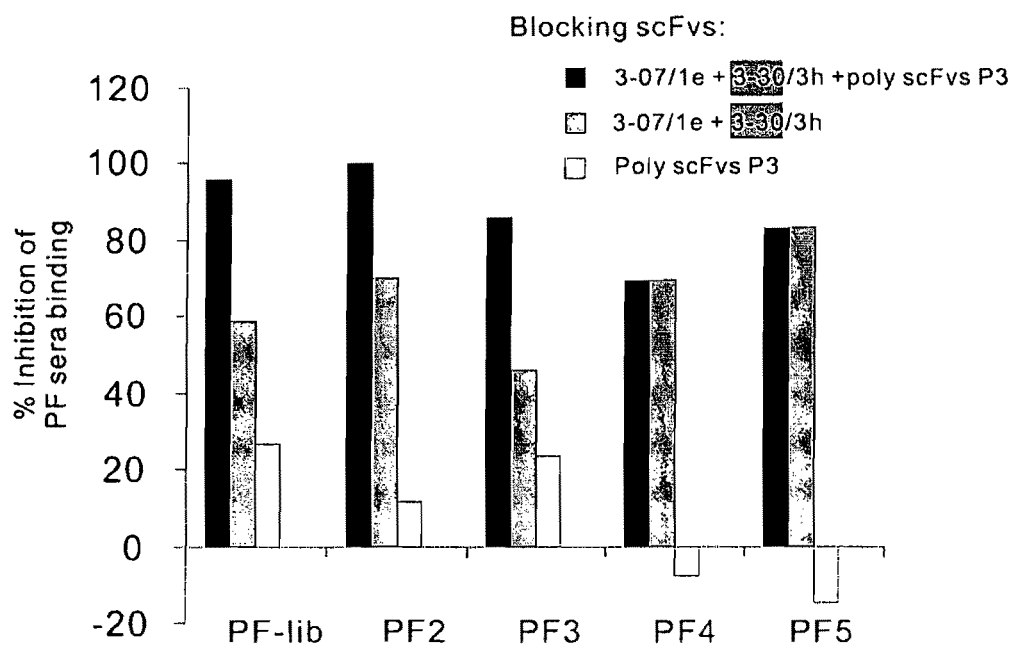

Epitopes Defined by scFvs Isolated from a PF Patient Comprise Major Targets of the Autoantibody Response in Other PF Patients A mixture of non-pathogenic and pathogenic scFvs derived from PF patient I was tested for its ability to block the binding of various PF patient sera to Dsg1. As shown in FIG. 6B, the mixture blocks >90% of Dsg1 binding by the serum from the patient from whom the antibody phage display library was constructed (PF1-lib). This suggests that the isolated scFvs identify nearly all epitopes targeted by serum IgG from PF patient 1. In addition, this combination of scFvs blocks 70-100% of Dsg 1 binding in four other randomly-selected PF patient sera.

Furthermore, significant antibody responses against pathogenic epitopes are found across patients as evidenced by the ability for the two pathogenic scFv clones, 3-30/3h and 3-07/1e, to identify major pathogenic epitopes to which antibodies in many other PF sera bind closely. These two scFvs alone block 60% of binding of the serum from PF patient 1; 3-30/3h alone, the most pathogenic antibody, blocks this serum binding by almost 50%. The combination of 3-30/3h and 3-07/1e block the binding of unrelated PF patients' sera by 46-83%, showing that the epitopes defined by these 2 scFvs are likely involved in many PF patients, and antibodies that bind to them (or nearby) are a major part of the autoantibody response in PF sera.

Example 6

Enzyme-linked Immunosorbaant Assay (ELISA) Analysis of Phage Clones and their scFv

Figure 7:
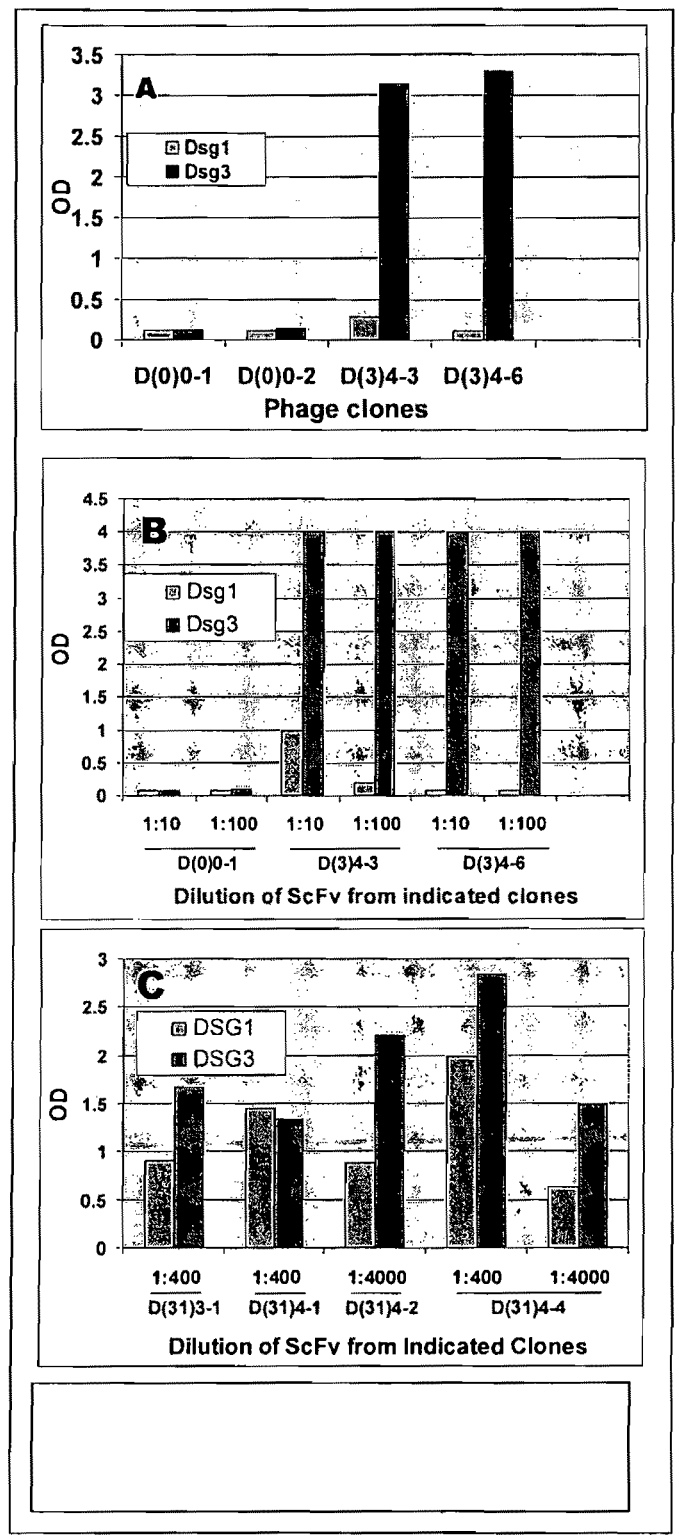

*E. coli* were infected with various clones isolated from the unpanned and panned PV(1) library, and the antibody-expressing phage were used directly for ELISA on Dsg1 and Dsg3. These assays were developed with horseradish peroxidase (HRP) conjugated anti-M13 (i.e. anti-phage antibody). Alternatively, plasmid DNA, derived from phage clones, was expressed in non-suppressor stains of *E. coli* to produce soluble scFv fragments, unlinked to phage. ScFv is essentially the soluble heavy and light chain variable regions (VH and VL), folded into an active antibody binding site, with a 6× His and a hemagglutinin (HA) tag on its carboxy-terminus for purification and detection purposes, respectively. ScFv were used for ELISA on Dsg1 and Dsg3,and detected with HRP-conjugated rat anti-HA tag. Irrelevant phage or scFv were used as controls. Phage panned on Dsg3 (or its scFv) showed positive Dsg3 binding on ELISA. Interestingly, one phage clone, D(3)4-3 showed slight binding to Dsg1. Phage or scFv derived from Dsg3/Dsg1 alternating panning scheme showed binding to both desmogleins by ELISA (FIG. 7).

Example 7

Figure 8:
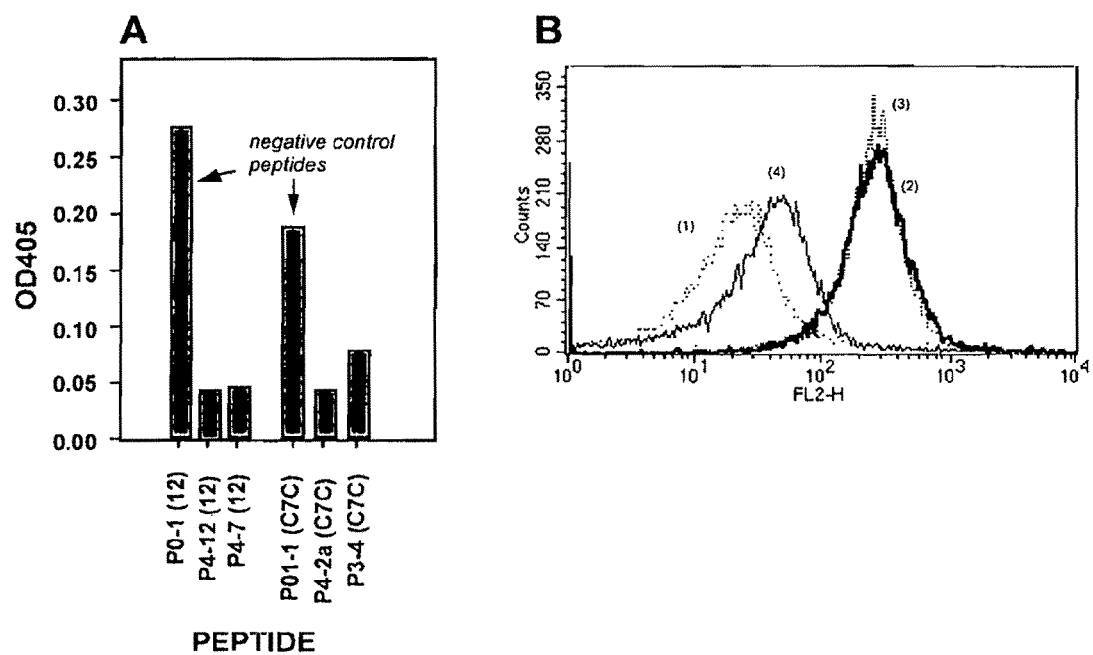
FIG. 8, comprising

Use of a Human Monoclonal Autoantibody to Identify Pathogeneic Epitopes by Peptide Phage Display Pathogenic PF anti-Dsg mAbs are used as targets for the panning of peptide display libraries to isolate peptides that mimic Dsg epitopes and block the binding of anti-Dsg antibodies. To demonstrate the feasibility of this approach, the results of an analogous experiment performed with an autoantibody, H44L4 are presented, isolated from an antibody phage display library derived from an ITP patient. H44L4,a human anti-integrin $\alpha_{2b}\beta_3$ platelet function-inhibiting mAb, was incubated with two commercially-available peptide phage display libraries—a 12-mer linear peptide library and a 7-mer constrained (i.e. cysteines on each end) peptide library. After several rounds of panning, peptides were isolated from both libraries that not only bound to their target (H44L4), but inhibited the binding of the anti-$\alpha_{2b}\beta_3$ autoantibody to $\alpha_{2b}\beta_3$ as assessed by ELISA and flow cytometry with intact platelets. In the case of ITP, these results demonstrate our ability to isolate peptides (using peptide phage display) that block the binding of a human autoantibody (originally derived using antibody phage display) to its autoantigen. Furthermore, these data show that such peptides can mimic conformational epitopes, i.e. epitopes comprising amino acid residues juxtaposed next to each other due to protein folding (FIG. 8).

Peptide Phage Display and Techniques

PhD-12 and PhD-C7C peptide phage display libraries (New England BioLabs) is screened with PF IgG according to manufacturer's instructions, alternating between protein A and protein G magnetic beads (New England BioLabs) for antibody capture. Phage clones are isolated from round 3 of screening for sequencing according to manufacturer's protocols. Unique clones are subsequently characterized by ELISA binding and inhibition assays.

Desirable peptides can be screened using the methods disclosed in PCT/US2008/001023, hereby incorporated herein by reference in their entirety. Briefly, a linear 12-mer and disulfide constrained 7-mer peptide phage display libraries are screened with pathogenic PF antibodies. Pools of phage-displayed peptides from the third round of selection is selected for specific binding to pathogenic PF antibodies by ELISA. Preparations of individual binding phage clones are isolated and their displayed peptide amino acid sequences are deduced by sequencing phage DNA.

Example 8

Using Pathogenic and Non-pathogenic Antibodies to Study the Pathology of Pemphigus Foliaceus The reagents disclosed herein, including pathogenic antibodies for PF should can be valuable to disrupt Dsg1 in keratinocytes. Without wishing to be bound by any particular theory, it is believed that the pathogenic antibodies can be used to study pathways of desmoglein assembly into and disassembly from desmosomes. Targeting desmosomes and associated proteins can be candidates for therapy against skin fragility or susceptibility to blister formation in pemphigus patients.

The pathology of pemphigus foliaceus can be further studied by examining characteristics of desmosome assembly and dissasembly because desmosomes are adhesive junctions that contain transmembrane desmosomal cadherins, desmoglein and desmocollin. Both cadherins bind plakoglobin. Plakoglobin in turn binds desmoplakin, which links to the keratin intermediate filament (KIF) network. Adapter molecules such as plakophilin are believed to serve to increase the lateral adhesive strength of these junctions.

Without wishing to be bound by any particular theory, it is believed that pemphigus foliaceus autoantibodies can act upon non-desmosomal Dsg1, and therefore prevent incorporation of Dsg into the desmosome. Additionally or alternatively, antibodies could bind desmosomal Dsg1, which would be expected to lead to disassembly of Dsg1 from pre-formed desmosomes.

Keratinocytes are exposed to PF monoclonal antibodies at the time of the calcium switch. The effects of PF monoclonal antibody during desmosomal assembly can easily be evaluated by examining the localization of Dsg1 and desmoplakin. Conversely, if the cells are placed in calcium first, and PF monoclonal antibodies are subsequently added, the effects of PF monoclonal antibodies on desmosomal disassembly can similarly be examined by examining the localization of Dsg1 and desmoplakin.

It can also be determined whether the effects of Dsg1 parallel the loss of PF monoclonal antibodies from cell culture supernatants. "Assembly" is evaulated by exposing cells to calcium and PF monoclonal antibodies at the same time. The overall cell architecture of a cell in low and high calcium is represented by the cells shown can be assessed using standard immunohistochemical techniques. Without wishing to be bound by any particular theory, it is believed that cells treated with nonpathogenic antibodies, Dsg1 staining will not disrupted, but in cells treated with pathogenic antibodies, Dsg1 staining will remain diffusely cytoplasmic.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. An isolated anti-desmoglein 1 (Dsg1) antibody or fragment thereof comprising a heavy chain (V$_H$) encoded by the gene selected from the group consisting of VH1-18, VH1-08, VH3-09, VH3-07, VH3-30, VH4-b, VH3-53, VH3-66, and any combination thereof; and a light chain (V$_L$) encoded by the gene selected from the group consisting of A30, B3, L1, L2, L8, L11, L12, LFVK431, O12O2, O18O8, 1c, 1e, 1g, 6a, 3h, and any combination thereof.

2. The antibody or fragment thereof of claim 1, wherein the antibody is pathogenic and comprises a consensus sequence represented by Asp-X-X-X-Trp (SEQ ID NO: 259) or Glu-X-X-X-Trp (SEQ ID NO: 260).

3. The antibody or fragment thereof of claim 1, comprising a heavy chain variable domain comprising the amino acid sequence selected from the group consisting of SEQ ID NOs: 216-258, and any combination thereof.

4. The antibody or fragment thereof of claim 1, comprising a light chain variable domain comprising the amino acid sequence selected from the group consisting of SEQ ID NOs: 173-215, and any combination thereof.

5. The antibody or fragment thereof of claim 1, comprising the amino acid sequence selected from the group consisting of SEQ ID NOs: 44-86, and any combination thereof.

6. The antibody or fragment thereof of claim 1, wherein said antibody or fragment thereof is a single chain Fv (scFv), a Fab, a (Fab')$_2$ or a (scFv')$_2$.

7. A composition comprising an anti-autoimmune antibody, wherein said anti-autoimmune antibody specifically binds to an anti-desmoglein 1 (Dsg1) antibody or fragment thereof comprising a heavy chain (V$_H$) encoded by the gene selected from the group consisting of VH1-18, VH1-08, VH3-09, VH3-07, VH3-30, VH4-b, VH3-53, VH3-66, and any combination thereof; and a light chain ($V_L$) encoded by the gene selected from the group consisting of A30, B3, L1, L2, L8, L11, L12, LFVK431, O12O2, O18O8, 1c, 1e, 1 g, 6a, 3h, and any combination thereof.

8. The composition of claim 7, wherein said anti-autoimmune antibody is selected from the group consisting of, a humanized antibody, a recombinant antibody, and any combination thereof.

9. The composition of claim 7, wherein said antibody or fragment thereof of comprises a heavy chain variable domain comprising the amino acid sequence selected from the group consisting of SEQ ID NOs: 216-258, and any combination thereof.

10. The composition of claim 7, wherein said antibody or fragment thereof of comprises a light chain variable domain comprising the amino acid sequence selected from the group consisting of SEQ ID NOs: 173-215, and any combination thereof.

11. The composition of claim 7, wherein said antibody or fragment thereof of comprises the amino acid sequence selected from the group consisting of SEQ ID NOs: 44-86, and any combination thereof.

12. A method of inhibiting the binding of an anti-desmoglein 1autoantibody or fragment thereof to desmoglein, said method comprising contacting the anti-desmoglein 1 autoantibody or fragment thereof with a composition comprising an anti-autoimmune reagent that specifically binds to an anti-desmoglein 1 autoantibody or fragment thereof comprising a heavy chain ($V_H$) encoded by the gene selected from the group consisting of VH1-18, VH1-08, VH3-09, VH3-07, VH3-30, VH4-b, VH3-53, VH3-66, and an combination thereof; and a light chain ($V_L$) encoded by the gene selected from the group consisting of A30, B3, L1, L2, L8, L11, L12, LFVK431, O12O2, O18O8, 1c, 1e, 1g, 6a, 3h, and any combination thereof.

13. The method of claim 12, wherein said anti-desmoglein 1 antibody or fragment thereof comprises a heavy chain ($V_H$) encoded by the gene selected from the group consisting of VH1-18, VH1-08, VH3-09, VH3-07, VH3-30, VH4-b, VH3-53, VH3-66, and any combination thereof.

14. The method of claim 12, wherein the antibody or fragment thereof of comprises a heavy chain variable domain comprising the amino acid sequence selected from the group consisting of SEQ ID NOs: 216-258, and any combination thereof.

15. The method of claim 12, wherein the antibody or fragment thereof of comprises a light chain variable domain comprising the amino acid sequence selected from the group consisting of SEQ ID NOs: 173-215, and any combination thereof.

16. The method of claim 12, wherein the antibody or fragment thereof of comprises the amino acid sequence selected from the group consisting of SEQ ID NOs: 44-86, and any combination thereof.

17. The method of claim 12, wherein the antibody or fragment thereof is associated with the pathology of pemphigus foliaceus (PF).

* * * * *